(12) United States Patent
    Emery

(10) Patent No.: US 10,420,960 B2
(45) Date of Patent: Sep. 24, 2019

(54) DEVICES AND METHODS FOR MULTI-FOCUS ULTRASOUND THERAPY

(71) Applicant: Ulthera, Inc., Mesa, AZ (US)

(72) Inventor: Charles D. Emery, Gilbert, AZ (US)

(73) Assignee: Ulthera, Inc., Mesa, AZ (US)

( * ) Notice: Subject to any disclaimer, the term of this patent is extended or adjusted under 35 U.S.C. 154(b) by 1417 days.

(21) Appl. No.: 14/193,234

(22) Filed: Feb. 28, 2014

(65) Prior Publication Data
    US 2014/0257145 A1    Sep. 11, 2014

Related U.S. Application Data

(60) Provisional application No. 61/774,785, filed on Mar. 8, 2013.

(51) Int. Cl.
    *A61N 7/00*    (2006.01)
    *A61N 7/02*    (2006.01)
    *A61B 8/00*    (2006.01)
    *A61B 90/00*   (2016.01)

(52) U.S. Cl.
    CPC .............. *A61N 7/00* (2013.01); *A61B 8/4209* (2013.01); *A61N 7/02* (2013.01); *A61B 2090/378* (2016.02); *A61N 2007/0008* (2013.01); *A61N 2007/0034* (2013.01);
    (Continued)

(58) Field of Classification Search
    CPC .......... A61B 2090/378; A61B 8/4209; A61N 2007/0008; A61N 2007/0034; A61N 2007/0052; A61N 2007/0095; A61N 2007/027; A61N 7/00; A61N 7/02
    See application file for complete search history.

(56) References Cited

U.S. PATENT DOCUMENTS

| 2,427,348 A | 9/1947 | Bond et al. |
| 2,792,829 A | 2/1952 | Calosi |
| 3,913,386 A | 10/1975 | Saglio |

(Continued)

FOREIGN PATENT DOCUMENTS

| CN | 104027893 | 9/2014 |
| DE | 4029175 | 3/1992 |

(Continued)

OTHER PUBLICATIONS

Agren, Magnus S. et al., Collagenase in Wound Healing: Effect of Wound Age and Type. The Journal of Investigative Dermatology, vol. 99/No. 6, (Dec. 1992).

(Continued)

*Primary Examiner* — Christopher L Cook
(74) *Attorney, Agent, or Firm* — Knobbe Martens Olson & Bear LLP

(57) ABSTRACT

Embodiments of a dermatological cosmetic treatment and imaging system and method can include use of transducer to simultaneously or substantially simultaneously produce multiple cosmetic treatment zones in tissue. The system can include a hand wand, a removable transducer module, a control module, and/or graphical user interface. In some embodiments, the cosmetic treatment system may be used in cosmetic procedures, including brow lifts, fat reduction, sweat reduction, and treatment of the décolletage. Skin tightening, lifting and amelioration of wrinkles and stretch marks are provided.

15 Claims, 41 Drawing Sheets

(52) U.S. Cl.
CPC ............... *A61N 2007/0052* (2013.01); *A61N 2007/0095* (2013.01); *A61N 2007/027* (2013.01)

(56) References Cited

U.S. PATENT DOCUMENTS

| | | |
|---|---|---|
| 3,965,455 A | 6/1976 | Hurwitz |
| 3,992,925 A | 11/1976 | Perilhou |
| 4,039,312 A | 8/1977 | Patru |
| 4,059,098 A | 11/1977 | Murdock |
| 4,101,795 A | 7/1978 | Fukumoto |
| 4,151,834 A | 5/1979 | Sato et al. |
| 4,166,967 A | 9/1979 | Benes et al. |
| 4,211,948 A | 7/1980 | Smith et al. |
| 4,211,949 A | 7/1980 | Brisken et al. |
| 4,213,344 A | 7/1980 | Rose |
| 4,276,491 A | 6/1981 | Daniel |
| 4,315,514 A | 2/1982 | Drewes et al. |
| 4,325,381 A | 4/1982 | Glenn |
| 4,343,301 A | 8/1982 | Indech |
| 4,372,296 A | 2/1983 | Fahim |
| 4,379,145 A | 4/1983 | Masuho et al. |
| 4,381,007 A | 4/1983 | Doss |
| 4,381,787 A | 5/1983 | Hottinger |
| 4,397,314 A | 8/1983 | Vaguine |
| 4,409,839 A | 10/1983 | Taenzer |
| 4,431,008 A | 2/1984 | Wanner et al. |
| 4,441,486 A | 4/1984 | Pounds |
| 4,452,084 A | 6/1984 | Taenzer |
| 4,460,841 A * | 7/1984 | Smith ............. B06B 1/0622 310/334 |
| 4,484,569 A | 11/1984 | Driller |
| 4,507,582 A | 3/1985 | Glenn |
| 4,513,749 A | 4/1985 | Kino |
| 4,513,750 A | 4/1985 | Heyman et al. |
| 4,527,550 A | 7/1985 | Ruggera et al. |
| 4,528,979 A | 7/1985 | Marchenko |
| 4,534,221 A | 8/1985 | Fife et al. |
| 4,566,459 A | 1/1986 | Umemura et al. |
| 4,567,895 A | 2/1986 | Putzke |
| 4,586,512 A | 5/1986 | Do-Huu |
| 4,601,296 A | 7/1986 | Yerushalmi |
| 4,620,546 A | 11/1986 | Aida et al. |
| 4,637,256 A | 1/1987 | Sugiyama et al. |
| 4,646,756 A | 3/1987 | Watmough |
| 4,663,358 A | 5/1987 | Hyon |
| 4,668,516 A | 5/1987 | Duraffourd et al. |
| 4,672,591 A | 6/1987 | Breimesser et al. |
| 4,680,499 A | 7/1987 | Umemura et al. |
| 4,697,588 A | 10/1987 | Reichenberger |
| 4,754,760 A | 7/1988 | Fukukita et al. |
| 4,757,820 A | 7/1988 | Itoh |
| 4,771,205 A | 9/1988 | Mequio |
| 4,801,459 A | 1/1989 | Liburdy |
| 4,803,625 A | 2/1989 | Fu et al. |
| 4,807,633 A | 2/1989 | Fry |
| 4,817,615 A | 4/1989 | Fukukita et al. |
| 4,858,613 A | 8/1989 | Fry |
| 4,860,732 A | 8/1989 | Hasegawa et al. |
| 4,865,041 A | 9/1989 | Hassler |
| 4,865,042 A | 9/1989 | Umemura |
| 4,867,169 A | 9/1989 | Machida |
| 4,874,562 A | 10/1989 | Hyon |
| 4,875,487 A | 10/1989 | Seppi |
| 4,881,212 A | 11/1989 | Takeuchi |
| 4,891,043 A | 1/1990 | Zeimer et al. |
| 4,893,624 A | 1/1990 | Lele |
| 4,896,673 A | 1/1990 | Rose |
| 4,900,540 A | 2/1990 | Ryan et al. |
| 4,901,729 A | 2/1990 | Saitoh |
| 4,917,096 A | 4/1990 | Englehart |
| 4,973,096 A | 4/1990 | Jaworski |
| 4,932,414 A | 6/1990 | Coleman et al. |
| 4,938,216 A | 7/1990 | Lele |
| 4,938,217 A | 7/1990 | Lele |
| 4,947,046 A | 8/1990 | Kawabata et al. |
| 4,951,653 A | 8/1990 | Fry |
| 4,955,365 A | 9/1990 | Fry |
| 4,958,626 A | 9/1990 | Nambu |
| 4,976,709 A | 12/1990 | Sand |
| 4,979,501 A | 12/1990 | Valchanov |
| 4,992,989 A | 2/1991 | Watanabe et al. |
| 5,012,797 A | 5/1991 | Liang |
| 5,018,508 A | 5/1991 | Fry et al. |
| 5,030,874 A | 7/1991 | Saito et al. |
| 5,036,855 A | 8/1991 | Fry |
| 5,040,537 A | 8/1991 | Katakura |
| 5,054,310 A | 10/1991 | Flynn |
| 5,054,470 A | 10/1991 | Fry |
| 5,054,491 A | 10/1991 | Saito et al. |
| 5,070,879 A | 12/1991 | Herres |
| 5,088,495 A | 2/1992 | Miyagawa |
| 5,115,814 A | 5/1992 | Griffith |
| 5,117,832 A | 6/1992 | Sanghvi |
| 5,123,418 A | 6/1992 | Saurel |
| 5,142,511 A | 8/1992 | Kanai et al. |
| 5,143,063 A | 9/1992 | Fellner |
| 5,143,074 A | 9/1992 | Dory |
| 5,149,319 A | 9/1992 | Unger |
| 5,150,711 A | 9/1992 | Dory |
| 5,150,714 A | 9/1992 | Green |
| 5,152,294 A | 10/1992 | Mochizuki et al. |
| 5,156,144 A | 10/1992 | Iwasaki |
| 5,158,536 A | 10/1992 | Sekins |
| 5,159,931 A | 11/1992 | Pini |
| 5,163,421 A | 11/1992 | Bernstein |
| 5,163,436 A | 11/1992 | Saitoh et al. |
| 5,178,135 A | 1/1993 | Uchiyama et al. |
| 5,190,518 A | 3/1993 | Takasu |
| 5,190,766 A | 3/1993 | Ishihara |
| 5,191,880 A | 3/1993 | McLeod |
| 5,205,287 A | 4/1993 | Erbel et al. |
| 5,209,720 A | 5/1993 | Unger |
| 5,212,671 A | 5/1993 | Fujii et al. |
| 5,215,680 A | 6/1993 | D'Arrigo |
| 5,224,467 A | 7/1993 | Oku |
| 5,230,334 A | 7/1993 | Klopotek |
| 5,230,338 A | 7/1993 | Allen et al. |
| 5,247,924 A | 9/1993 | Suzuki et al. |
| 5,255,681 A | 10/1993 | Ishimura et al. |
| 5,257,970 A | 11/1993 | Dougherty |
| 5,265,614 A | 11/1993 | Hayakawa |
| 5,267,985 A | 12/1993 | Shimada |
| 5,269,297 A | 12/1993 | Weng |
| 5,282,797 A | 2/1994 | Chess |
| 5,295,484 A | 3/1994 | Marcus |
| 5,295,486 A | 3/1994 | Wollschlager et al. |
| 5,304,169 A | 4/1994 | Sand |
| 5,305,756 A | 4/1994 | Entrekin et al. |
| 5,321,520 A | 6/1994 | Inga et al. |
| 5,323,779 A | 6/1994 | Hardy et al. |
| 5,327,895 A | 7/1994 | Hashimoto et al. |
| 5,329,202 A | 7/1994 | Garlick et al. |
| 5,348,016 A | 9/1994 | Unger et al. |
| 5,358,466 A | 10/1994 | Aida et al. |
| 5,360,268 A | 11/1994 | Hayashi |
| 5,370,121 A | 12/1994 | Reichenberger |
| 5,370,122 A | 12/1994 | Kunig et al. |
| 5,371,483 A | 12/1994 | Bhardwaj |
| 5,375,602 A | 12/1994 | Lancee et al. |
| 5,379,773 A | 1/1995 | Hornsby |
| 5,380,280 A | 1/1995 | Peterson |
| 5,380,519 A | 1/1995 | Schneider et al. |
| 5,383,917 A | 1/1995 | Desai et al. |
| 5,391,140 A | 2/1995 | Schaetzle et al. |
| 5,391,197 A | 2/1995 | Burdette et al. |
| 5,392,259 A | 2/1995 | Bolorforosh |
| 5,396,143 A | 3/1995 | Seyed-Bolorforosh et al. |
| 5,398,689 A | 3/1995 | Connor et al. |
| 5,406,503 A | 4/1995 | Williams |
| 5,413,550 A | 5/1995 | Castel |
| 5,417,216 A | 5/1995 | Tanaka |
| 5,419,327 A | 5/1995 | Rohwedder |
| 5,423,220 A | 6/1995 | Finsterwald et al. |

(56) References Cited

U.S. PATENT DOCUMENTS

| | | |
|---|---|---|
| 5,435,311 A | 7/1995 | Umemura |
| 5,438,998 A | 8/1995 | Hanafy |
| 5,443,068 A | 8/1995 | Cline et al. |
| 5,445,611 A | 8/1995 | Eppstein et al. |
| 5,458,596 A | 10/1995 | Lax |
| 5,460,179 A | 10/1995 | Okunuki et al. |
| 5,460,595 A | 10/1995 | Hall et al. |
| 5,469,854 A | 11/1995 | Unger et al. |
| 5,471,488 A | 12/1995 | Fujio |
| 5,472,405 A | 12/1995 | Buchholtz et al. |
| 5,487,388 A | 1/1996 | Rello et al. |
| 5,492,126 A | 2/1996 | Hennige |
| 5,496,256 A | 3/1996 | Bock |
| 5,501,655 A | 3/1996 | Rolt |
| 5,503,152 A | 4/1996 | Oakley et al. |
| 5,503,320 A | 4/1996 | Webster et al. |
| 5,507,790 A | 4/1996 | Weiss |
| 5,511,296 A | 4/1996 | Dias et al. |
| 5,520,188 A | 5/1996 | Hennige |
| 5,522,869 A | 6/1996 | Burdette |
| 5,523,058 A | 6/1996 | Umemura et al. |
| 5,524,620 A | 6/1996 | Rosenchein |
| 5,524,624 A | 6/1996 | Tepper |
| 5,524,625 A | 6/1996 | Okazaki |
| 5,526,624 A | 6/1996 | Berg |
| 5,526,812 A | 6/1996 | Dumoulin et al. |
| 5,526,814 A | 6/1996 | Cline et al. |
| 5,526,815 A | 6/1996 | Granz |
| 5,529,070 A | 6/1996 | Augustine et al. |
| 5,540,235 A | 7/1996 | Wilson |
| 5,558,092 A | 9/1996 | Unger |
| 5,560,362 A | 10/1996 | Sliwa et al. |
| 5,573,497 A | 11/1996 | Chapelon |
| 5,575,291 A | 11/1996 | Hayakawa |
| 5,575,807 A | 11/1996 | Faller |
| 5,577,502 A | 11/1996 | Darrow et al. |
| 5,577,507 A | 11/1996 | Snyder et al. |
| 5,577,991 A | 11/1996 | Akui et al. |
| 5,580,575 A | 12/1996 | Unger et al. |
| 5,643,179 A | 1/1997 | Fujimoto |
| 5,601,526 A | 2/1997 | Chapelon |
| 5,603,323 A | 2/1997 | Pflugrath et al. |
| 5,605,154 A | 2/1997 | Ries et al. |
| 5,609,562 A | 3/1997 | Kaali |
| 5,615,091 A | 3/1997 | Palatnik |
| 5,618,275 A | 4/1997 | Bock |
| 5,620,479 A | 4/1997 | Diederich |
| 5,622,175 A | 4/1997 | Sudol et al. |
| 5,617,858 A | 5/1997 | Taverna et al. |
| 5,638,819 A | 6/1997 | Manwaring et al. |
| 5,644,085 A | 7/1997 | Lorraine et al. |
| 5,647,373 A | 7/1997 | Paltieli |
| 5,655,535 A | 8/1997 | FrIemel et al. |
| 5,655,538 A | 8/1997 | Lorraine |
| 5,657,760 A | 8/1997 | Ying |
| 5,658,328 A | 8/1997 | Johnson |
| 5,660,836 A | 8/1997 | Knowlton |
| 5,662,116 A | 9/1997 | Kondo |
| 5,665,053 A | 9/1997 | Jacobs |
| 5,665,141 A | 9/1997 | Vago |
| 5,671,746 A | 9/1997 | Dreschel et al. |
| 5,673,699 A | 10/1997 | Trahey et al. |
| 5,676,692 A | 10/1997 | Sanghvi |
| 5,685,820 A | 11/1997 | Riek et al. |
| 5,690,608 A | 11/1997 | Watanabe |
| 5,694,936 A | 12/1997 | Fujimoto |
| 5,697,897 A | 12/1997 | Buchholtz |
| 5,701,900 A | 12/1997 | Shehada et al. |
| 5,704,361 A | 1/1998 | Seward et al. |
| 5,706,252 A | 1/1998 | Le Verrier et al. |
| 5,706,564 A | 1/1998 | Rhyne |
| 5,715,823 A | 2/1998 | Wood et al. |
| 5,720,287 A | 2/1998 | Chapelon et al. |
| 5,722,411 A | 3/1998 | Suzuki |
| 5,727,554 A | 3/1998 | Kalend et al. |
| 5,735,280 A | 4/1998 | Sherman et al. |
| 5,743,863 A | 4/1998 | Chapelon |
| 5,746,005 A | 5/1998 | Steinberg |
| 5,746,762 A | 5/1998 | Bass |
| 5,748,767 A | 5/1998 | Raab |
| 5,749,364 A | 5/1998 | Sliwa et al. |
| 5,755,228 A | 5/1998 | Wilson et al. |
| 5,755,753 A | 5/1998 | Knowlton |
| 5,762,066 A | 6/1998 | Law |
| 5,763,886 A | 6/1998 | Schulte |
| 5,769,790 A | 6/1998 | Watkins |
| 5,779,644 A | 7/1998 | Eberle et al. |
| 5,792,058 A | 8/1998 | Lee |
| 5,795,297 A | 8/1998 | Daigle |
| 5,795,311 A | 8/1998 | Wess |
| 5,714,599 A | 9/1998 | Mitragotri et al. |
| 5,810,009 A | 9/1998 | Mine et al. |
| 5,810,888 A | 9/1998 | Fenn |
| 5,814,599 A | 9/1998 | Mitragotri et al. |
| 5,817,013 A | 10/1998 | Ginn et al. |
| 5,817,021 A | 10/1998 | Reichenberger |
| 5,820,564 A | 10/1998 | Slayton |
| 5,823,962 A | 10/1998 | Schaetzle |
| 5,827,204 A | 10/1998 | Grandia et al. |
| 5,839,751 A | 11/1998 | Bonin |
| 5,840,032 A | 11/1998 | Hatfield et al. |
| 5,844,140 A | 12/1998 | Seale |
| 5,853,367 A | 12/1998 | Chalek et al. |
| 5,857,970 A | 1/1999 | Purdy |
| 5,869,751 A | 2/1999 | Bonin |
| 5,871,524 A | 2/1999 | Knowlton |
| 5,873,902 A | 2/1999 | Sanghvi |
| 5,876,341 A | 3/1999 | Wang et al. |
| 5,879,303 A | 3/1999 | Averkiou et al. |
| 5,882,557 A | 3/1999 | Hayakawa |
| 5,891,034 A | 4/1999 | Bucholz |
| 5,895,356 A | 4/1999 | Andrus et al. |
| 5,899,861 A | 5/1999 | Friemel et al. |
| 5,904,659 A | 5/1999 | Duarte |
| 5,919,219 A | 7/1999 | Knowlton |
| 5,923,099 A | 7/1999 | Bilir |
| 5,924,989 A | 7/1999 | Polz |
| 5,928,169 A | 7/1999 | Schatzle et al. |
| 5,931,805 A | 8/1999 | Brisken |
| 5,938,606 A | 8/1999 | Bonnefous |
| 5,938,612 A | 8/1999 | Kline-Schoder |
| 5,948,011 A | 9/1999 | Knowlton |
| 5,957,844 A | 9/1999 | Dekel |
| 5,957,882 A | 9/1999 | Nita et al. |
| 5,957,941 A | 9/1999 | Ream |
| 5,964,707 A | 10/1999 | Fenster et al. |
| 5,967,980 A | 10/1999 | Ferre et al. |
| 5,968,034 A | 10/1999 | Fullmer |
| 5,971,949 A | 10/1999 | Levin |
| 5,977,538 A | 11/1999 | Unger et al. |
| 5,984,881 A | 11/1999 | Ishibashi et al. |
| 5,984,882 A | 11/1999 | Rosenchein |
| 5,990,598 A | 11/1999 | Sudol et al. |
| 5,997,471 A | 12/1999 | Gumb et al. |
| 5,997,497 A | 12/1999 | Nita et al. |
| 5,999,843 A | 12/1999 | Anbar |
| 6,004,262 A | 12/1999 | Putz et al. |
| 6,007,499 A | 12/1999 | Martin et al. |
| 6,013,032 A | 1/2000 | Savord |
| 6,014,473 A | 1/2000 | Hossack et al. |
| 6,016,255 A | 1/2000 | Bolan et al. |
| 6,019,724 A | 2/2000 | Gronningsaeter et al. |
| 6,022,308 A | 2/2000 | Williams |
| 6,022,317 A | 2/2000 | Cruanas et al. |
| 6,022,327 A | 2/2000 | Chang |
| 6,030,374 A | 2/2000 | McDaniel |
| 6,036,646 A | 3/2000 | Barthe |
| 6,039,048 A | 3/2000 | Silberg |
| 6,039,689 A | 3/2000 | Lizzi |
| 6,042,556 A | 3/2000 | Beach |
| 6,049,159 A | 4/2000 | Barthe |
| 6,050,943 A | 4/2000 | Slayton |
| 6,059,727 A | 5/2000 | Fowlkes |
| 6,071,239 A | 6/2000 | Cribbs |

(56) References Cited

U.S. PATENT DOCUMENTS

| | | | |
|---|---|---|---|
| 6,080,108 | A | 6/2000 | Dunham |
| 6,083,148 | A | 7/2000 | Williams |
| 6,086,535 | A | 7/2000 | Ishibashi |
| 6,086,580 | A | 7/2000 | Mordon et al. |
| 6,090,054 | A | 7/2000 | Tagishi |
| 6,093,148 | A | 7/2000 | Fujimoto |
| 6,093,883 | A | 7/2000 | Sanghvi |
| 6,101,407 | A | 8/2000 | Groezinger |
| 6,106,469 | A | 8/2000 | Suzuki et al. |
| 6,113,558 | A | 9/2000 | Rosenchein |
| 6,113,559 | A | 9/2000 | Klopotek |
| 6,120,452 | A | 9/2000 | Barthe |
| 6,123,081 | A | 9/2000 | Durette |
| 6,126,619 | A | 10/2000 | Peterson et al. |
| 6,135,971 | A | 10/2000 | Hutchinson |
| 6,139,499 | A | 10/2000 | Wilk |
| 6,159,150 | A | 12/2000 | Yale et al. |
| 6,171,244 | B1 | 1/2001 | Finger et al. |
| 6,176,840 | B1 | 1/2001 | Nishimura |
| 6,183,426 | B1 | 2/2001 | Akisada |
| 6,183,502 | B1 | 2/2001 | Takeuchi |
| 6,183,773 | B1 | 2/2001 | Anderson |
| 6,190,323 | B1 | 2/2001 | Dias |
| 6,190,336 | B1 | 2/2001 | Duarte |
| 6,193,658 | B1 | 2/2001 | Wendelken |
| 6,198,956 | B1 | 3/2001 | Dunne |
| 6,210,327 | B1 | 4/2001 | Brackett et al. |
| 6,213,948 | B1 | 4/2001 | Barthe |
| 6,216,029 | B1 | 4/2001 | Paltieli |
| 6,233,476 | B1 | 5/2001 | Strommer et al. |
| 6,234,990 | B1 | 5/2001 | Rowe et al. |
| 6,241,753 | B1 | 6/2001 | Knowlton |
| 6,246,898 | B1 | 6/2001 | Vesely et al. |
| 6,251,074 | B1 | 6/2001 | Averkiou et al. |
| 6,251,088 | B1 | 6/2001 | Kaufman et al. |
| 6,268,405 | B1 | 7/2001 | Yao |
| 6,273,864 | B1 | 8/2001 | Duarte |
| 6,280,402 | B1 | 8/2001 | Ishibashi et al. |
| 6,287,257 | B1 | 9/2001 | Matichuk |
| 6,287,304 | B1 | 9/2001 | Eggers et al. |
| 6,296,619 | B1 | 10/2001 | Brisken |
| 6,301,989 | B1 | 10/2001 | Brown et al. |
| 6,307,302 | B1 | 10/2001 | Toda |
| 6,309,355 | B1 | 10/2001 | Cain et al. |
| 6,311,090 | B1 | 10/2001 | Knowlton |
| 6,315,741 | B1 | 11/2001 | Martin |
| 6,322,509 | B1 | 11/2001 | Pan et al. |
| 6,322,532 | B1 | 11/2001 | D'Sa |
| 6,325,540 | B1 | 12/2001 | Lounsberry et al. |
| 6,325,758 | B1 | 12/2001 | Carol et al. |
| 6,325,769 | B1 | 12/2001 | Klopotek |
| 6,325,798 | B1 | 12/2001 | Edwards et al. |
| 6,338,716 | B1 | 1/2002 | Hossack et al. |
| 6,350,276 | B1 | 2/2002 | Knowlton |
| 6,356,780 | B1 | 3/2002 | Licato et al. |
| 6,361,531 | B1 | 3/2002 | Hissong |
| 6,370,411 | B1 | 4/2002 | Osadchy et al. |
| 6,375,672 | B1 | 4/2002 | Aksan |
| 6,377,854 | B1 | 4/2002 | Knowlton |
| 6,377,855 | B1 | 4/2002 | Knowlton |
| 6,381,497 | B1 | 4/2002 | Knowlton |
| 6,381,498 | B1 | 4/2002 | Knowlton |
| 6,387,380 | B1 | 5/2002 | Knowlton |
| 6,390,982 | B1 | 5/2002 | Bova et al. |
| 6,405,090 | B1 | 6/2002 | Knowlton |
| 6,409,720 | B1 | 6/2002 | Hissong |
| 6,413,216 | B1 | 7/2002 | Cain et al. |
| 6,413,253 | B1 | 7/2002 | Koop |
| 6,413,254 | B1 | 7/2002 | Hissong |
| 6,419,648 | B1 | 7/2002 | Vitek |
| 6,423,007 | B2 | 7/2002 | Lizzi et al. |
| 6,425,865 | B1 | 7/2002 | Salcudean |
| 6,425,867 | B1 | 7/2002 | Vaezy |
| 6,425,912 | B1 | 7/2002 | Knowlton |
| 6,428,477 | B1 | 8/2002 | Mason |
| 6,428,532 | B1 | 8/2002 | Doukas |
| 6,430,446 | B1 | 8/2002 | Knowlton |
| 6,432,057 | B1 | 8/2002 | Mazess et al. |
| 6,432,067 | B1 | 8/2002 | Martin |
| 6,432,101 | B1 | 8/2002 | Weber |
| 6,436,061 | B1 | 8/2002 | Costantino |
| 6,438,424 | B1 | 8/2002 | Knowlton |
| 6,440,071 | B1 | 8/2002 | Slayton |
| 6,440,121 | B1 | 8/2002 | Weber |
| 6,443,914 | B1 | 9/2002 | Costantino |
| 6,447,443 | B1 | 9/2002 | Keogh et al. |
| 6,451,013 | B1 | 9/2002 | Bays et al. |
| 6,453,202 | B1 | 9/2002 | Knowlton |
| 6,461,304 | B1 | 10/2002 | Tanaka et al. |
| 6,461,378 | B1 | 10/2002 | Knowlton |
| 6,470,216 | B1 | 10/2002 | Knowlton |
| 6,488,626 | B1 | 12/2002 | Lizzi |
| 6,491,657 | B2 | 12/2002 | Rowe |
| 6,500,121 | B1 | 12/2002 | Slayton |
| 6,500,141 | B1 | 12/2002 | Irion |
| 6,506,171 | B1 * | 1/2003 | Vitek .................. A61H 23/0245 600/439 |
| 6,508,774 | B1 | 1/2003 | Acker |
| 6,511,427 | B1 | 1/2003 | Sliwa, Jr. et al. |
| 6,511,428 | B1 | 1/2003 | Azuma |
| 6,514,244 | B2 | 2/2003 | Pope |
| 6,517,484 | B1 | 2/2003 | Wilk |
| 6,524,250 | B1 | 2/2003 | Weber |
| 6,666,835 | B2 | 3/2003 | Martin |
| 6,540,679 | B2 | 4/2003 | Slayton |
| 6,540,685 | B1 | 4/2003 | Rhoads et al. |
| 6,540,700 | B1 | 4/2003 | Fujimoto et al. |
| 6,547,788 | B1 | 4/2003 | Maguire et al. |
| 6,554,771 | B1 | 4/2003 | Buil et al. |
| 6,569,099 | B1 | 5/2003 | Babaev |
| 6,569,108 | B2 | 5/2003 | Sarvazyan et al. |
| 6,572,552 | B2 | 6/2003 | Fukukita |
| 6,575,956 | B1 | 6/2003 | Brisken et al. |
| 6,595,934 | B1 | 7/2003 | Hissong |
| 6,599,256 | B1 | 7/2003 | Acker |
| 6,605,043 | B1 * | 8/2003 | Dreschel .................. B06B 1/00 600/459 |
| 6,605,080 | B1 | 8/2003 | Altshuler et al. |
| 6,607,498 | B2 | 8/2003 | Eshel |
| 6,618,620 | B1 | 9/2003 | Freundlich et al. |
| 6,623,430 | B1 | 9/2003 | Slayton |
| 6,626,854 | B2 | 9/2003 | Friedman |
| 6,626,855 | B1 | 9/2003 | Weng |
| 6,638,226 | B2 | 10/2003 | He et al. |
| 6,645,145 | B1 | 11/2003 | Dreschel et al. |
| 6,645,150 | B2 | 11/2003 | Angelsen et al. |
| 6,645,162 | B2 | 11/2003 | Friedman |
| 6,662,054 | B2 | 12/2003 | Kreindel |
| 6,663,627 | B2 | 12/2003 | Francischelli |
| 6,665,806 | B1 | 12/2003 | Shimizu |
| 6,669,638 | B1 | 12/2003 | Miller |
| 6,685,639 | B1 | 2/2004 | Wang et al. |
| 6,685,640 | B1 | 2/2004 | Fry |
| 6,692,450 | B1 | 2/2004 | Coleman |
| 6,699,237 | B2 | 3/2004 | Weber |
| 6,716,184 | B2 | 4/2004 | Vaezy et al. |
| 6,719,449 | B1 | 4/2004 | Laughlin |
| 6,719,694 | B1 | 4/2004 | Weng |
| 6,726,627 | B1 | 4/2004 | Lizzi et al. |
| 6,733,449 | B1 | 5/2004 | Krishnamurthy et al. |
| 6,749,624 | B2 | 6/2004 | Knowlton |
| 6,772,490 | B2 | 8/2004 | Toda |
| 6,773,409 | B2 | 8/2004 | Truckai et al. |
| 6,775,404 | B1 | 8/2004 | Pagoulatos et al. |
| 6,790,187 | B2 | 9/2004 | Thompson et al. |
| 6,824,516 | B2 | 11/2004 | Batten et al. |
| 6,825,176 | B2 | 11/2004 | White et al. |
| 6,835,940 | B2 | 12/2004 | Morikawa et al. |
| 6,846,290 | B2 | 1/2005 | Lizzi et al. |
| 6,875,176 | B2 | 4/2005 | Mourad et al. |
| 6,882,884 | B1 | 4/2005 | Mosk et al. |
| 6,887,239 | B2 | 5/2005 | Elstrom |
| 6,889,089 | B2 | 5/2005 | Behl |
| 6,896,657 | B2 | 5/2005 | Willis |

(56) References Cited

U.S. PATENT DOCUMENTS

| | | |
|---|---|---|
| 6,902,536 B2 | 6/2005 | Manna |
| 6,905,466 B2 | 6/2005 | Salgo |
| 6,918,907 B2 | 7/2005 | Kelly |
| 6,920,883 B2 | 7/2005 | Bessette |
| 6,921,371 B2 | 7/2005 | Wilson |
| 6,932,771 B2 | 8/2005 | Whitmore |
| 6,932,814 B2 | 8/2005 | Wood |
| 6,936,044 B2 | 8/2005 | McDaniel |
| 6,936,046 B2 | 8/2005 | Hissong |
| 6,945,937 B2 | 9/2005 | Culp et al. |
| 6,948,843 B2 | 9/2005 | Laugham et al. |
| 6,953,941 B2 | 10/2005 | Nakano et al. |
| 6,958,043 B2 | 10/2005 | Hissong |
| 6,971,994 B1 | 12/2005 | Young et al. |
| 6,974,417 B2 | 12/2005 | Lockwood |
| 6,976,492 B2 | 12/2005 | Ingle |
| 6,992,305 B2 | 1/2006 | Maezawa et al. |
| 6,997,923 B2 | 2/2006 | Anderson |
| 7,006,874 B2 | 2/2006 | Knowlton |
| 7,020,528 B2 | 3/2006 | Neev |
| 7,022,089 B2 | 4/2006 | Ooba |
| 7,058,440 B2 | 6/2006 | Heuscher et al. |
| 7,063,666 B2 | 6/2006 | Weng |
| 7,070,565 B2 | 7/2006 | Vaezy et al. |
| 7,074,218 B2 | 7/2006 | Washington et al. |
| 7,094,252 B2 | 8/2006 | Koop |
| 7,108,663 B2 | 9/2006 | Talish et al. |
| 7,115,123 B2 | 10/2006 | Knowlton |
| 7,122,029 B2 | 10/2006 | Koop et al. |
| 7,142,905 B2 | 11/2006 | Slayton |
| 7,165,451 B1 | 1/2007 | Brooks et al. |
| 7,179,238 B2 | 2/2007 | Hissong |
| 7,189,230 B2 | 3/2007 | Knowlton |
| 7,229,411 B2 | 6/2007 | Slayton |
| 7,235,592 B2 | 6/2007 | Muratoglu |
| 7,258,674 B2 | 8/2007 | Cribbs |
| 7,273,459 B2 | 9/2007 | Desilets |
| 7,294,125 B2 | 11/2007 | Phalen et al. |
| 7,297,117 B2 | 11/2007 | Trucco |
| 7,303,555 B2 | 12/2007 | Makin et al. |
| 7,311,679 B2 | 12/2007 | Desilets et al. |
| 7,327,071 B2 | 2/2008 | Nishiyama et al. |
| 7,331,951 B2 | 2/2008 | Eshel et al. |
| 7,332,985 B2 | 2/2008 | Larson et al. |
| 7,338,434 B1 | 3/2008 | Haarstad et al. |
| 7,347,855 B2 | 3/2008 | Eshel |
| RE40,403 E | 6/2008 | Cho et al. |
| 7,393,325 B2 | 7/2008 | Barthe |
| 7,398,116 B2 | 7/2008 | Edwards |
| 7,399,279 B2 | 7/2008 | Abend et al. |
| 7,491,171 B2 | 2/2009 | Barthe et al. |
| 7,507,235 B2 | 3/2009 | Keogh et al. |
| 7,510,536 B2 | 3/2009 | Foley et al. |
| 7,517,315 B2 | 4/2009 | Willis |
| 7,530,356 B2 | 5/2009 | Slayton |
| 7,530,958 B2 | 5/2009 | Slayton |
| 7,532,201 B2 | 5/2009 | Quistgaard et al. |
| 7,571,336 B2 | 8/2009 | Barthe |
| 7,601,120 B2 | 10/2009 | Moilanen et al. |
| 7,615,015 B2 | 11/2009 | Coleman |
| 7,615,016 B2 | 11/2009 | Barthe |
| 7,631,611 B1 | 12/2009 | Dick et al. |
| 7,652,411 B2 | 1/2010 | Crunkilton et al. |
| 7,662,114 B2 | 2/2010 | Seip et al. |
| 7,674,257 B2 | 3/2010 | Pless et al. |
| 7,686,763 B2 | 3/2010 | Vaezy et al. |
| 7,713,203 B2 | 3/2010 | Lacoste et al. |
| 7,694,406 B2 | 4/2010 | Wildes et al. |
| 7,695,437 B2 | 4/2010 | Quistgaard et al. |
| 7,727,156 B2 | 6/2010 | Angelsen et al. |
| 7,758,524 B2 | 7/2010 | Barthe |
| 7,766,848 B2 | 8/2010 | Desilets et al. |
| 7,789,841 B2 | 9/2010 | Huckle et al. |
| 7,806,839 B2 | 10/2010 | Mast et al. |
| 7,815,570 B2 | 10/2010 | Eshel et al. |
| 7,819,826 B2 | 10/2010 | Diederich et al. |
| 7,828,734 B2 | 10/2010 | Azhari et al. |
| 7,824,348 B2 | 11/2010 | Barthe |
| 7,833,162 B2 | 11/2010 | Hasegawa et al. |
| 7,841,984 B2 | 11/2010 | Cribbs et al. |
| 7,846,096 B2 | 12/2010 | Mast et al. |
| 7,857,773 B2 | 12/2010 | Desilets et al. |
| 7,875,023 B2 | 1/2011 | Eshel et al. |
| 7,901,359 B2 | 3/2011 | Mandrusov et al. |
| 7,905,007 B2 | 3/2011 | Calisti et al. |
| 7,905,844 B2 | 3/2011 | Desilets et al. |
| 7,914,453 B2 | 3/2011 | Slayton et al. |
| 7,914,469 B2 | 3/2011 | Torbati |
| 7,955,281 B2 | 6/2011 | Pedersen et al. |
| 7,967,764 B2 | 6/2011 | Lidgren et al. |
| 7,967,839 B2 | 6/2011 | Flock et al. |
| 7,955,262 B2 | 7/2011 | Rosenberg |
| 7,993,289 B2 | 8/2011 | Quistgaard et al. |
| 8,057,465 B2 | 9/2011 | Sliwa, Jr. et al. |
| 8,057,389 B2 | 11/2011 | Barthe et al. |
| 8,066,641 B2 | 11/2011 | Barthe et al. |
| 8,123,707 B2 | 2/2012 | Huckle et al. |
| 8,128,618 B2 | 3/2012 | Gliklich et al. |
| 8,133,180 B2 | 3/2012 | Slayton et al. |
| 8,133,191 B2 | 3/2012 | Rosenberg et al. |
| 8,142,200 B2 | 3/2012 | Crunkilton et al. |
| 8,152,904 B2 | 4/2012 | Slobodzian et al. |
| 8,162,858 B2 | 4/2012 | Manna et al. |
| 8,166,332 B2 | 4/2012 | Barthe et al. |
| 8,182,428 B2 | 5/2012 | Angelsen et al. |
| 8,197,409 B2 | 6/2012 | Foley et al. |
| 8,206,299 B2 | 6/2012 | Foley et al. |
| 8,208,346 B2 | 6/2012 | Crunkilton |
| 8,211,017 B2 | 7/2012 | Foley et al. |
| 8,262,591 B2 | 9/2012 | Pedersen et al. |
| 8,262,650 B2 | 9/2012 | Zanelli et al. |
| 8,264,126 B2 | 9/2012 | Toda et al. |
| 8,273,037 B2 | 9/2012 | Kreindel et al. |
| 8,282,554 B2 | 10/2012 | Makin et al. |
| 8,292,835 B1 | 10/2012 | Cimino |
| 8,298,163 B1 | 10/2012 | Cimino |
| 8,333,700 B1 | 12/2012 | Barthe et al. |
| 8,334,637 B2 | 12/2012 | Crunkilton et al. |
| 8,337,407 B2 | 12/2012 | Quistgaard et al. |
| 8,343,051 B2 | 1/2013 | Desilets et al. |
| 8,454,540 B2 | 1/2013 | Eshel et al. |
| 8,366,622 B2 | 2/2013 | Slayton et al. |
| 8,398,549 B2 | 3/2013 | Palmeri et al. |
| 8,409,097 B2 | 4/2013 | Slayton et al. |
| 8,425,435 B2 | 4/2013 | Wing et al. |
| 8,388,535 B2 | 5/2013 | Weng et al. |
| 8,444,562 B2 | 5/2013 | Barthe et al. |
| 8,460,193 B2 | 6/2013 | Barthe et al. |
| 8,480,585 B2 | 7/2013 | Slayton et al. |
| 8,486,001 B2 | 7/2013 | Weyant |
| 8,506,486 B2 | 8/2013 | Slayton et al. |
| 8,512,250 B2 | 8/2013 | Quistgaard et al. |
| 8,523,775 B2 | 9/2013 | Barthe et al. |
| 8,523,849 B2 | 9/2013 | Liu et al. |
| 8,535,228 B2 | 9/2013 | Slayton et al. |
| 8,570,837 B2 | 10/2013 | Toda et al. |
| 8,573,392 B2 | 11/2013 | Bennett et al. |
| 8,583,211 B2 | 11/2013 | Salomir et al. |
| 8,585,618 B2 | 11/2013 | Hunziker et al. |
| 8,604,672 B2 | 12/2013 | Toda et al. |
| 8,622,937 B2 | 1/2014 | Weng et al. |
| 8,636,665 B2 | 1/2014 | Slayton et al. |
| 8,640,193 B2 | 1/2014 | Shigeeda |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,708,935 B2 | 4/2014 | Barthe et al. |
| 8,715,186 B2 | 5/2014 | Slayton et al. |
| 8,726,781 B2 | 5/2014 | Eckhoff et al. |
| 8,728,071 B2 | 5/2014 | Lischinsky et al. |
| 8,753,295 B2 | 6/2014 | Thierman |

(56) References Cited

U.S. PATENT DOCUMENTS

| | | |
|---|---|---|
| 8,758,253 B2 | 6/2014 | Sano et al. |
| 8,836,203 B2 | 9/2014 | Nobles et al. |
| 8,857,438 B2 | 10/2014 | Barthe et al. |
| 8,858,471 B2 | 10/2014 | Barthe et al. |
| 8,915,853 B2 | 12/2014 | Barthe et al. |
| 8,915,854 B2 | 12/2014 | Slayton et al. |
| 8,915,870 B2 | 12/2014 | Barthe et al. |
| 8,920,320 B2 | 12/2014 | Stecco et al. |
| 8,920,324 B2 | 12/2014 | Slayton et al. |
| 8,926,533 B2 | 1/2015 | Bockenstedt et al. |
| 8,932,224 B2 | 1/2015 | Barthe et al. |
| 8,932,238 B2 | 1/2015 | Wing et al. |
| 8,968,205 B2 | 3/2015 | Zeng et al. |
| 9,011,336 B2 | 4/2015 | Slayton et al. |
| 9,039,617 B2 | 5/2015 | Slayton et al. |
| 9,039,619 B2 | 5/2015 | Barthe et al. |
| 9,050,116 B2 | 6/2015 | Homer |
| 9,095,697 B2 | 8/2015 | Barthe et al. |
| 9,107,798 B2 | 8/2015 | Azhari et al. |
| 9,114,247 B2 | 8/2015 | Barthe et al. |
| 9,180,314 B2 | 11/2015 | Desilets et al. |
| 9,216,276 B2 | 12/2015 | Slayton et al. |
| 9,220,915 B2 | 12/2015 | Liu et al. |
| 9,272,162 B2 | 3/2016 | Slayton et al. |
| 9,283,409 B2 | 3/2016 | Slayton et al. |
| 9,283,410 B2 | 3/2016 | Slayton et al. |
| 9,295,607 B2 | 3/2016 | Rosenberg |
| 9,308,390 B2 | 4/2016 | Youngquist |
| 9,308,391 B2 | 4/2016 | Liu et al. |
| 9,314,650 B2 | 4/2016 | Rosenberg et al. |
| 9,320,537 B2 | 4/2016 | Slayton et al. |
| 9,345,910 B2 | 5/2016 | Slayton et al. |
| 9,421,029 B2 | 8/2016 | Barthe et al. |
| 9,427,600 B2 | 8/2016 | Barthe et al. |
| 9,427,601 B2 | 8/2016 | Barthe et al. |
| 9,433,803 B2 | 9/2016 | Lin et al. |
| 9,440,093 B2 | 9/2016 | Homer |
| 9,440,096 B2 | 9/2016 | Barthe et al. |
| 9,492,645 B2 | 11/2016 | Zhou et al. |
| 9,492,686 B2 | 11/2016 | Da Silva |
| 9,498,651 B2 | 11/2016 | Sapozhnikov et al. |
| 9,510,802 B2 | 12/2016 | Barthe et al. |
| 9,522,290 B2 | 12/2016 | Slayton et al. |
| 9,532,832 B2 | 1/2017 | Ron Edoute et al. |
| 9,533,174 B2 | 1/2017 | Barthe et al. |
| 9,533,175 B2 | 1/2017 | Slayton et al. |
| 9,545,529 B2 | 1/2017 | Britva et al. |
| 9,566,454 B2 | 2/2017 | Barthe et al. |
| 9,623,267 B2 | 4/2017 | Ulric et al. |
| 9,694,211 B2 | 7/2017 | Barthe et al. |
| 9,694,212 B2 | 7/2017 | Barthe et al. |
| 9,700,340 B2 | 7/2017 | Barthe et al. |
| 9,707,412 B2 | 7/2017 | Slayton et al. |
| 9,710,607 B2 | 7/2017 | Ramdas et al. |
| 9,713,731 B2 | 7/2017 | Slayton et al. |
| 9,802,063 B2 | 10/2017 | Barthe et al. |
| 9,827,449 B2 | 11/2017 | Barthe et al. |
| 9,827,450 B2 | 11/2017 | Slayton et al. |
| 9,833,639 B2 | 12/2017 | Slayton et al. |
| 9,833,640 B2 | 12/2017 | Barthe et al. |
| 9,895,560 B2 | 2/2018 | Barthe et al. |
| 9,907,535 B2 | 3/2018 | Barthe et al. |
| 9,919,167 B2 | 3/2018 | Domankevitz |
| 9,974,982 B2 | 5/2018 | Slayton et al. |
| 1,001,072 A1 | 7/2018 | Slayton et al. |
| 1,004,618 A1 | 8/2018 | Barthe et al. |
| 2001/0009997 A1 | 7/2001 | Pope |
| 2001/0009999 A1 | 7/2001 | Kaufman et al. |
| 2001/0014780 A1 | 8/2001 | Martin |
| 2001/0014819 A1 | 8/2001 | Ingle |
| 2001/0031922 A1 | 10/2001 | Weng |
| 2001/0039380 A1 | 11/2001 | Larson et al. |
| 2001/0041880 A1 | 11/2001 | Brisken |
| 2002/0000763 A1 | 1/2002 | Jones |
| 2002/0002345 A1 | 1/2002 | Marlinghaus |
| 2002/0040199 A1 | 4/2002 | Klopotek |
| 2002/0040442 A1 | 4/2002 | Ishidera |
| 2002/0055702 A1 | 5/2002 | Atala |
| 2002/0062077 A1 | 5/2002 | Emmenegger |
| 2002/0062142 A1 | 5/2002 | Knowlton |
| 2002/0072691 A1 | 6/2002 | Thompson et al. |
| 2002/0082528 A1 | 6/2002 | Friedman |
| 2002/0082529 A1 | 6/2002 | Suorsa et al. |
| 2002/0082589 A1 | 6/2002 | Friedman |
| 2002/0087080 A1 | 7/2002 | Slayton |
| 2002/0095143 A1 | 7/2002 | Key |
| 2002/0099094 A1 | 7/2002 | Anderson |
| 2002/0115917 A1 | 8/2002 | Honda et al. |
| 2002/0128639 A1 | 8/2002 | Pless et al. |
| 2002/0128648 A1 | 9/2002 | Weber |
| 2002/0143252 A1 | 10/2002 | Dunne et al. |
| 2002/0156400 A1 | 10/2002 | Babaev |
| 2002/0161357 A1 | 10/2002 | Anderson |
| 2002/0165529 A1 | 11/2002 | Danek |
| 2002/0168049 A1 | 11/2002 | Schriever |
| 2002/0169394 A1 | 11/2002 | Eppstein et al. |
| 2002/0169442 A1 | 11/2002 | Neev |
| 2002/0173721 A1 | 11/2002 | Grunwald et al. |
| 2002/0193784 A1 | 12/2002 | McHale et al. |
| 2002/0193831 A1 | 12/2002 | Smith |
| 2003/0009153 A1 | 1/2003 | Brisken et al. |
| 2003/0014039 A1 | 1/2003 | Barzell et al. |
| 2003/0018255 A1 | 1/2003 | Martin |
| 2003/0018270 A1 | 1/2003 | Makin et al. |
| 2003/0023283 A1 | 1/2003 | McDaniel |
| 2003/0028111 A1 | 2/2003 | Vaezy et al. |
| 2003/0028113 A1 | 2/2003 | Gilbert et al. |
| 2003/0032900 A1 | 2/2003 | Ella |
| 2003/0036706 A1 | 2/2003 | Slayton |
| 2003/0040739 A1 | 2/2003 | Koop |
| 2003/0050678 A1 | 3/2003 | Sierra |
| 2003/0055308 A1 | 3/2003 | Friemel et al. |
| 2003/0055417 A1 | 3/2003 | Truckai et al. |
| 2003/0060736 A1 | 3/2003 | Martin et al. |
| 2003/0040442 A1 | 4/2003 | Ishidera |
| 2003/0065313 A1 | 4/2003 | Koop |
| 2003/0066708 A1 | 4/2003 | Allison et al. |
| 2003/0073907 A1 | 4/2003 | Taylor |
| 2003/0074023 A1 | 4/2003 | Kaplan |
| 2003/0083536 A1 | 5/2003 | Eshel |
| 2003/0092988 A1 | 5/2003 | Makin |
| 2003/0097071 A1 | 5/2003 | Halmann et al. |
| 2003/0099383 A1 | 5/2003 | Lefebvre |
| 2003/0125629 A1 | 7/2003 | Ustuner |
| 2003/0135135 A1 | 7/2003 | Miwa et al. |
| 2003/0139790 A1 | 7/2003 | Ingle et al. |
| 2003/0149366 A1 | 8/2003 | Stringer et al. |
| 2003/0153961 A1 | 8/2003 | Babaev |
| 2003/0171678 A1 | 9/2003 | Batten et al. |
| 2003/0171701 A1 | 9/2003 | Babaev |
| 2003/0176790 A1 | 9/2003 | Slayton |
| 2003/0191396 A1 | 10/2003 | Sanghvi |
| 2003/0199794 A1 | 10/2003 | Sakurai et al. |
| 2003/0200481 A1 | 10/2003 | Stanley |
| 2003/0212129 A1 | 11/2003 | Liu et al. |
| 2003/0212351 A1 | 11/2003 | Hissong |
| 2003/0212393 A1 | 11/2003 | Knowlton |
| 2003/0216648 A1 | 11/2003 | Lizzi et al. |
| 2003/0216795 A1 | 11/2003 | Harth |
| 2003/0220536 A1 | 11/2003 | Hissong |
| 2003/0220585 A1 | 11/2003 | Hissong |
| 2003/0229331 A1 | 12/2003 | Brisken et al. |
| 2003/0233085 A1 | 12/2003 | Giammarusti |
| 2003/0236487 A1 | 12/2003 | Knowlton |
| 2004/0000316 A1 | 1/2004 | Knowlton |
| 2004/0001809 A1 | 1/2004 | Brisken |
| 2004/0002658 A1 | 1/2004 | Marian, Jr. |
| 2004/0002705 A1 | 1/2004 | Knowlton |
| 2004/0010222 A1 | 1/2004 | Nunomura et al. |
| 2004/0015079 A1 | 1/2004 | Berger et al. |
| 2004/0015106 A1 | 1/2004 | Coleman |
| 2004/0030227 A1 | 2/2004 | Littrup |
| 2004/0030268 A1 | 2/2004 | Weng et al. |
| 2004/0039312 A1 | 2/2004 | Hillstead |

(56) References Cited

U.S. PATENT DOCUMENTS

| | | |
|---|---|---|
| 2004/0039418 A1 | 2/2004 | Elstrom |
| 2004/0041563 A1 | 3/2004 | Lewin et al. |
| 2004/0041880 A1 | 3/2004 | Ikeda et al. |
| 2004/0042168 A1 | 3/2004 | Yang et al. |
| 2004/0044375 A1 | 3/2004 | Diederich et al. |
| 2004/0049134 A1 | 3/2004 | Tosaya et al. |
| 2004/0049734 A1 | 3/2004 | Tosaya et al. |
| 2004/0059266 A1 | 3/2004 | Fry |
| 2004/0068186 A1 | 4/2004 | Ishida et al. |
| 2004/0073079 A1 | 4/2004 | Altshuler et al. |
| 2004/0073113 A1 | 4/2004 | Salgo |
| 2004/0073115 A1 | 4/2004 | Horzewski et al. |
| 2004/0073116 A1 | 4/2004 | Smith |
| 2004/0073204 A1 | 4/2004 | Ryan et al. |
| 2004/0077977 A1 | 4/2004 | Ella et al. |
| 2004/0082857 A1 | 4/2004 | Schonenberger |
| 2004/0082859 A1 | 4/2004 | Schaer |
| 2004/0102697 A1 | 5/2004 | Evron |
| 2004/0105559 A1 | 6/2004 | Aylward et al. |
| 2004/0106867 A1 | 6/2004 | Eshel et al. |
| 2004/0122323 A1 | 6/2004 | Vortman et al. |
| 2004/0122493 A1 | 6/2004 | Ishibashi et al. |
| 2004/0143297 A1 | 7/2004 | Ramsey |
| 2004/0152982 A1 | 8/2004 | Hwang et al. |
| 2004/0158150 A1 | 8/2004 | Rabiner et al. |
| 2004/0186535 A1 | 9/2004 | Knowlton |
| 2004/0189155 A1 | 9/2004 | Funakubo |
| 2004/0206365 A1 | 10/2004 | Knowlton |
| 2004/0210214 A1 | 10/2004 | Knowlton |
| 2004/0217675 A1 | 11/2004 | Desilets |
| 2004/0249318 A1 | 12/2004 | Tanaka |
| 2004/0254620 A1 | 12/2004 | Lacoste |
| 2004/0267252 A1 | 12/2004 | Washington |
| 2005/0033201 A1 | 2/2005 | Takahashi |
| 2005/0033316 A1 | 2/2005 | Kertz |
| 2005/0038340 A1 | 2/2005 | Vaezy et al. |
| 2005/0055018 A1 | 3/2005 | Kreindel |
| 2005/0055073 A1 | 3/2005 | Weber |
| 2005/0061834 A1 | 3/2005 | Garcia et al. |
| 2005/0070961 A1 | 3/2005 | Maki |
| 2005/0074407 A1 | 4/2005 | Smith |
| 2005/0080469 A1 | 4/2005 | Larson |
| 2005/0085731 A1 | 4/2005 | Miller et al. |
| 2005/0091770 A1 | 5/2005 | Mourad et al. |
| 2005/0096542 A1 | 5/2005 | Weng et al. |
| 2005/0104690 A1 | 5/2005 | Larson et al. |
| 2005/0113689 A1 | 5/2005 | Gritzky |
| 2005/0131302 A1 | 6/2005 | Poland |
| 2005/0137656 A1 | 6/2005 | Malak |
| 2005/0143677 A1 | 6/2005 | Young et al. |
| 2005/0154313 A1 | 7/2005 | Desilets |
| 2005/0154314 A1 | 7/2005 | Quistgaard |
| 2005/0154332 A1 | 7/2005 | Zanelli |
| 2005/0154431 A1 | 7/2005 | Quistgaard |
| 2005/0187495 A1 | 8/2005 | Quistgaard |
| 2005/0191252 A1 | 9/2005 | Mitsui |
| 2005/0193451 A1 | 9/2005 | Quistgaard |
| 2005/0193820 A1 | 9/2005 | Sheljaskow et al. |
| 2005/0197681 A1 | 9/2005 | Barolet et al. |
| 2005/0228281 A1 | 10/2005 | Nefos |
| 2005/0240127 A1 | 10/2005 | Seip et al. |
| 2005/0240170 A1 | 10/2005 | Zhang et al. |
| 2005/0251120 A1 | 11/2005 | Anderson et al. |
| 2005/0251125 A1 | 11/2005 | Pless et al. |
| 2005/0256406 A1 | 11/2005 | Barthe |
| 2005/0261584 A1 | 11/2005 | Eshel |
| 2005/0261585 A1 | 11/2005 | Makin et al. |
| 2005/0267454 A1 | 12/2005 | Hissong |
| 2005/0288748 A1 | 12/2005 | Li et al. |
| 2006/0004306 A1 | 1/2006 | Altshuler |
| 2006/0020260 A1 | 1/2006 | Dover et al. |
| 2006/0025756 A1 | 2/2006 | Francischelli |
| 2006/0042201 A1 | 3/2006 | Curry |
| 2006/0058664 A1 | 3/2006 | Barthe |
| 2006/0058671 A1 | 3/2006 | Vitek et al. |
| 2006/0058707 A1 | 3/2006 | Barthe |
| 2006/0058712 A1 | 3/2006 | Altshuler et al. |
| 2006/0074309 A1 | 4/2006 | Bonnefous |
| 2006/0074313 A1 | 4/2006 | Slayton |
| 2006/0074314 A1 | 4/2006 | Slayton |
| 2006/0074355 A1 | 4/2006 | Slayton |
| 2006/0079816 A1 | 4/2006 | Barthe |
| 2006/0079868 A1 | 4/2006 | Makin |
| 2006/0084891 A1 | 4/2006 | Barthe |
| 2006/0089632 A1 | 4/2006 | Barthe |
| 2006/0089688 A1 | 4/2006 | Panescu |
| 2006/0094988 A1 | 5/2006 | Tosaya |
| 2006/0111744 A1 | 5/2006 | Makin |
| 2006/0116583 A1 | 6/2006 | Ogasawara et al. |
| 2006/0116671 A1 | 6/2006 | Slayton |
| 2006/0122508 A1 | 6/2006 | Slayton |
| 2006/0122509 A1 | 6/2006 | Desilets |
| 2006/0161062 A1 | 7/2006 | Arditi et al. |
| 2006/0184069 A1 | 8/2006 | Vaitekunas |
| 2006/0184071 A1 | 8/2006 | Klopotek |
| 2006/0189972 A1 | 8/2006 | Grossman |
| 2006/0206105 A1 | 9/2006 | Chopra |
| 2006/0224090 A1 | 10/2006 | Ostrovsky et al. |
| 2006/0229514 A1 | 10/2006 | Wiener |
| 2006/0241440 A1 | 10/2006 | Eshel |
| 2006/0241442 A1 | 10/2006 | Barthe |
| 2006/0241470 A1 | 10/2006 | Novak et al. |
| 2006/0241576 A1 | 10/2006 | Diederich et al. |
| 2006/0250046 A1 | 11/2006 | Koizumi et al. |
| 2006/0282691 A1 | 12/2006 | Barthe |
| 2006/0291710 A1 | 12/2006 | Wang et al. |
| 2007/0016039 A1 | 1/2007 | Vortman et al. |
| 2007/0032784 A1 | 2/2007 | Gliklich |
| 2007/0035201 A1 | 2/2007 | Desilets |
| 2007/0055154 A1 | 3/2007 | Torbati |
| 2007/0055155 A1 | 3/2007 | Owen et al. |
| 2007/0055156 A1 | 3/2007 | Desilets |
| 2007/0065420 A1 | 3/2007 | Johnson |
| 2007/0083120 A1 | 4/2007 | Cain et al. |
| 2007/0087060 A1 | 4/2007 | Dietrich |
| 2007/0088245 A1 | 4/2007 | Babaev et al. |
| 2007/0088346 A1 | 4/2007 | Mirizzi et al. |
| 2007/0161902 A1 | 7/2007 | Dan |
| 2007/0166357 A1 | 7/2007 | Shaffer et al. |
| 2007/0167709 A1 | 7/2007 | Slayton |
| 2007/0208253 A1 | 9/2007 | Slayton |
| 2007/0219604 A1 | 9/2007 | Yaroslaysky et al. |
| 2007/0219605 A1 | 9/2007 | Yaroslaysky et al. |
| 2007/0238994 A1 | 10/2007 | Stecco et al. |
| 2007/0239075 A1 | 10/2007 | Rosenberg |
| 2007/0239077 A1 | 10/2007 | Azhari et al. |
| 2007/0239079 A1 | 10/2007 | Manstein et al. |
| 2007/0239142 A1 | 10/2007 | Altshuler |
| 2008/0015435 A1 | 1/2008 | Cribbs et al. |
| 2008/0027328 A1 | 1/2008 | Klopotek |
| 2008/0033458 A1 | 2/2008 | McLean et al. |
| 2008/0039724 A1 | 2/2008 | Seip et al. |
| 2008/0071255 A1 | 3/2008 | Barthe |
| 2008/0086054 A1 | 4/2008 | Slayton |
| 2008/0086056 A1 | 4/2008 | Chang et al. |
| 2008/0097214 A1 | 4/2008 | Meyers et al. |
| 2008/0097253 A1 | 4/2008 | Pedersen et al. |
| 2008/0114251 A1 | 5/2008 | Weymer et al. |
| 2008/0139943 A1 | 6/2008 | Deng et al. |
| 2008/0139974 A1 | 6/2008 | Da Silva |
| 2008/0146970 A1 | 6/2008 | Litman et al. |
| 2008/0167556 A1 | 7/2008 | Thompson |
| 2008/0183077 A1 | 7/2008 | Moreau-Gobard et al. |
| 2008/0183110 A1 | 7/2008 | Davenport et al. |
| 2008/0188745 A1 | 8/2008 | Chen et al. |
| 2008/0194964 A1 | 8/2008 | Randall et al. |
| 2008/0195000 A1 | 8/2008 | Spooner et al. |
| 2008/0200810 A1 | 8/2008 | Buchalter |
| 2008/0200813 A1 | 8/2008 | Quistgaard |
| 2008/0214966 A1 | 9/2008 | Slayton |
| 2008/0214988 A1 | 9/2008 | Altshuler et al. |
| 2008/0221491 A1* | 9/2008 | Slayton .............. A61N 7/00 601/3 |
| 2008/0223379 A1 | 9/2008 | Stuker et al. |

(56) References Cited

U.S. PATENT DOCUMENTS

| | | |
|---|---|---|
| 2008/0242991 A1 | 10/2008 | Moon et al. |
| 2008/0243035 A1 | 10/2008 | Crunkilton |
| 2008/0269608 A1 | 10/2008 | Anderson et al. |
| 2008/0275342 A1 | 11/2008 | Barthe |
| 2008/0281206 A1 | 11/2008 | Bartlett et al. |
| 2008/0281236 A1 | 11/2008 | Eshel et al. |
| 2008/0281237 A1 | 11/2008 | Slayton |
| 2008/0281255 A1 | 11/2008 | Slayton |
| 2008/0294073 A1 | 11/2008 | Barthe |
| 2008/0319356 A1 | 12/2008 | Cain |
| 2009/0005680 A1 | 1/2009 | Jones et al. |
| 2009/0012394 A1 | 1/2009 | Hobelsberger et al. |
| 2009/0043198 A1 | 2/2009 | Milner et al. |
| 2009/0043293 A1 | 2/2009 | Pankratov et al. |
| 2009/0048514 A1 | 2/2009 | Azhari et al. |
| 2009/0069677 A1 | 3/2009 | Chen et al. |
| 2009/0093737 A1 | 4/2009 | Chomas et al. |
| 2009/0156969 A1 | 6/2009 | Santangelo |
| 2009/0163807 A1 | 6/2009 | Sliwa |
| 2009/0171252 A1 | 7/2009 | Bockenstedt et al. |
| 2009/0177122 A1 | 7/2009 | Peterson |
| 2009/0177123 A1 | 7/2009 | Peterson |
| 2009/0182231 A1 | 7/2009 | Barthe et al. |
| 2009/0198157 A1 | 8/2009 | Babaev et al. |
| 2009/0216159 A1 | 8/2009 | Slayton et al. |
| 2009/0226424 A1 | 9/2009 | Hsu |
| 2009/0227910 A1 | 9/2009 | Pedersen et al. |
| 2009/0230823 A1 | 9/2009 | Kushculey et al. |
| 2009/0253988 A1 | 10/2009 | Slayton et al. |
| 2009/0281463 A1 | 11/2009 | Chapelon et al. |
| 2009/0312693 A1 | 12/2009 | Thapliyal et al. |
| 2009/0318909 A1 | 12/2009 | Debenedictis et al. |
| 2009/0326420 A1 | 12/2009 | Moonen et al. |
| 2010/0011236 A1 | 1/2010 | Barthe et al. |
| 2010/0022919 A1 | 1/2010 | Peterson |
| 2010/0022921 A1 | 1/2010 | Seip et al. |
| 2010/0022922 A1 | 1/2010 | Barthe et al. |
| 2010/0030076 A1* | 2/2010 | Vortman ............ A61N 7/02 600/439 |
| 2010/0042020 A1 | 2/2010 | Ben-Ezra |
| 2010/0049178 A1 | 2/2010 | Deem et al. |
| 2010/0056925 A1 | 3/2010 | Zhang et al. |
| 2010/0100014 A1 | 4/2010 | Eshel et al. |
| 2010/0113983 A1 | 5/2010 | Heckerman et al. |
| 2010/0130891 A1 | 5/2010 | Taggart et al. |
| 2010/0160782 A1 | 6/2010 | Slayton et al. |
| 2010/0160837 A1 | 6/2010 | Hunziker et al. |
| 2010/0168576 A1 | 7/2010 | Poland et al. |
| 2010/0191120 A1 | 7/2010 | Kraus et al. |
| 2010/0241035 A1 | 9/2010 | Barthe et al. |
| 2010/0249602 A1 | 9/2010 | Buckley et al. |
| 2010/0249669 A1 | 9/2010 | Ulric et al. |
| 2010/0256489 A1 | 10/2010 | Pedersen et al. |
| 2010/0274161 A1 | 10/2010 | Azhari et al. |
| 2010/0280420 A1 | 11/2010 | Barthe et al. |
| 2010/0286518 A1 | 11/2010 | Lee et al. |
| 2010/0312150 A1 | 12/2010 | Douglas et al. |
| 2011/0040171 A1 | 2/2011 | Foley et al. |
| 2011/0040190 A1 | 2/2011 | Jahnke et al. |
| 2011/0040213 A1 | 2/2011 | Dietz et al. |
| 2011/0040214 A1 | 2/2011 | Foley et al. |
| 2011/0066084 A1 | 3/2011 | Desilets et al. |
| 2011/0077514 A1 | 3/2011 | Ulric et al. |
| 2011/0087099 A1 | 4/2011 | Eshel et al. |
| 2011/0087255 A1 | 4/2011 | McCormack et al. |
| 2011/0112405 A1 | 5/2011 | Barthe et al. |
| 2011/0144490 A1 | 6/2011 | Davis et al. |
| 2011/0178444 A1 | 7/2011 | Slayton et al. |
| 2011/0178541 A1 | 7/2011 | Azhari |
| 2011/0190745 A1 | 8/2011 | Uebelhoer et al. |
| 2011/0201976 A1 | 8/2011 | Sanghvi et al. |
| 2011/0251524 A1 | 10/2011 | Azhari et al. |
| 2011/0251527 A1 | 10/2011 | Kushculey et al. |
| 2011/0270137 A1 | 11/2011 | Goren et al. |
| 2011/0319793 A1 | 12/2011 | Henrik et al. |
| 2011/0319794 A1 | 12/2011 | Gertner |
| 2012/0004549 A1 | 1/2012 | Barthe et al. |
| 2012/0016239 A1 | 1/2012 | Barthe et al. |
| 2012/0029353 A1 | 2/2012 | Slayton et al. |
| 2012/0035473 A1 | 2/2012 | Sanghvi et al. |
| 2012/0035475 A1 | 2/2012 | Barthe et al. |
| 2012/0035476 A1 | 2/2012 | Barthe et al. |
| 2012/0046547 A1 | 2/2012 | Barthe et al. |
| 2012/0053458 A1 | 3/2012 | Barthe et al. |
| 2012/0059288 A1 | 3/2012 | Barthe et al. |
| 2012/0111339 A1 | 5/2012 | Barthe et al. |
| 2012/0123304 A1 | 5/2012 | Rybyanets et al. |
| 2012/0136280 A1 | 5/2012 | Rosenberg et al. |
| 2012/0136282 A1 | 5/2012 | Rosenberg et al. |
| 2012/0143056 A1 | 6/2012 | Slayton et al. |
| 2012/0143100 A1 | 6/2012 | Jeong et al. |
| 2012/0165668 A1 | 6/2012 | Slayton et al. |
| 2012/0165848 A1 | 6/2012 | Slayton et al. |
| 2012/0191019 A1 | 7/2012 | Desilets et al. |
| 2012/0191020 A1 | 7/2012 | Vitek et al. |
| 2012/0197120 A1 | 8/2012 | Makin et al. |
| 2012/0197121 A1 | 8/2012 | Slayton et al. |
| 2012/0209150 A1 | 8/2012 | Zeng et al. |
| 2012/0215105 A1 | 8/2012 | Slayton et al. |
| 2012/0271202 A1 | 10/2012 | Wisdom |
| 2012/0271294 A1 | 10/2012 | Barthe et al. |
| 2012/0296240 A1 | 11/2012 | Azhari et al. |
| 2012/0302883 A1 | 11/2012 | Kong et al. |
| 2012/0316426 A1 | 12/2012 | Foley et al. |
| 2012/0330197 A1 | 12/2012 | Makin et al. |
| 2012/0330222 A1 | 12/2012 | Makin et al. |
| 2012/0330223 A1 | 12/2012 | Makin et al. |
| 2012/0330283 A1 | 12/2012 | Hyde et al. |
| 2012/0330284 A1 | 12/2012 | Hyde et al. |
| 2013/0012755 A1 | 1/2013 | Slayton |
| 2013/0012816 A1 | 1/2013 | Slayton et al. |
| 2013/0012838 A1 | 1/2013 | Jaeger et al. |
| 2013/0012842 A1 | 1/2013 | Barthe |
| 2013/0018285 A1 | 1/2013 | Park et al. |
| 2013/0018286 A1 | 1/2013 | Slayton et al. |
| 2013/0046209 A1 | 2/2013 | Slayton et al. |
| 2013/0051178 A1 | 2/2013 | Rybyanets |
| 2013/0060170 A1 | 3/2013 | Lee et al. |
| 2013/0066208 A1 | 3/2013 | Barthe et al. |
| 2013/0066237 A1 | 3/2013 | Smotrich et al. |
| 2013/0072826 A1 | 3/2013 | Slayton et al. |
| 2013/0073001 A1* | 3/2013 | Campbell ............ A61N 1/0476 607/50 |
| 2013/0096471 A1 | 4/2013 | Slayton et al. |
| 2013/0190659 A1 | 7/2013 | Slayton et al. |
| 2013/0211293 A1 | 8/2013 | Auboiroux et al. |
| 2013/0225994 A1 | 8/2013 | Hsu et al. |
| 2013/0268032 A1 | 10/2013 | Neev |
| 2013/0274603 A1 | 10/2013 | Barthe et al. |
| 2013/0281853 A1 | 10/2013 | Slayton et al. |
| 2013/0281891 A1 | 10/2013 | Slayton et al. |
| 2013/0296697 A1 | 11/2013 | Slayton et al. |
| 2013/0296700 A1 | 11/2013 | Slayton et al. |
| 2013/0296743 A1 | 11/2013 | Lee et al. |
| 2013/0303904 A1 | 11/2013 | Barthe et al. |
| 2013/0303905 A1 | 11/2013 | Barthe et al. |
| 2013/0310714 A1 | 11/2013 | Eshel et al. |
| 2013/0310863 A1 | 11/2013 | Makin et al. |
| 2013/0345562 A1 | 12/2013 | Barthe et al. |
| 2014/0024974 A1 | 1/2014 | Slayton et al. |
| 2014/0050054 A1 | 2/2014 | Toda et al. |
| 2014/0081300 A1 | 3/2014 | Melodelima et al. |
| 2014/0082907 A1 | 3/2014 | Barthe et al. |
| 2014/0117814 A1 | 5/2014 | Toda et al. |
| 2014/0142430 A1 | 5/2014 | Slayton et al. |
| 2014/0148834 A1 | 5/2014 | Barthe et al. |
| 2014/0180174 A1 | 6/2014 | Slayton et al. |
| 2014/0187944 A1 | 7/2014 | Slayton et al. |
| 2014/0188015 A1 | 7/2014 | Slayton et al. |
| 2014/0188145 A1 | 7/2014 | Slayton et al. |
| 2014/0194723 A1 | 7/2014 | Herzog et al. |
| 2014/0208856 A1 | 7/2014 | Schmid |
| 2014/0221823 A1 | 8/2014 | Keogh et al. |
| 2014/0236049 A1 | 8/2014 | Barthe et al. |

(56) References Cited

U.S. PATENT DOCUMENTS

| | | |
|---|---|---|
| 2014/0236061 A1 | 8/2014 | Lee et al. |
| 2014/0243713 A1 | 8/2014 | Slayton et al. |
| 2014/0276055 A1 | 9/2014 | Barthe et al. |
| 2015/0000674 A1 | 1/2015 | Barthe et al. |
| 2015/0025420 A1 | 1/2015 | Slayton et al. |
| 2015/0080723 A1 | 3/2015 | Barthe et al. |
| 2015/0080771 A1 | 3/2015 | Barthe et al. |
| 2015/0080874 A1 | 3/2015 | Slayton et al. |
| 2015/0088182 A1 | 3/2015 | Slayton et al. |
| 2015/0141734 A1 | 5/2015 | Chapelon et al. |
| 2015/0164734 A1 | 6/2015 | Slayton et al. |
| 2015/0165238 A1 | 6/2015 | Slayton et al. |
| 2015/0165243 A1 | 6/2015 | Slayton et al. |
| 2015/0174388 A1 | 6/2015 | Slayton |
| 2015/0202468 A1 | 7/2015 | Slayton et al. |
| 2015/0217141 A1 | 8/2015 | Barthe et al. |
| 2015/0238258 A1 | 8/2015 | Palero et al. |
| 2015/0321026 A1 | 11/2015 | Branson et al. |
| 2015/0360058 A1 | 12/2015 | Barthe et al. |
| 2015/0374333 A1 | 12/2015 | Barthe et al. |
| 2015/0375014 A1 | 12/2015 | Slayton et al. |
| 2016/0001097 A1 | 1/2016 | Cho et al. |
| 2016/0016015 A1 | 1/2016 | Slayton et al. |
| 2016/0027994 A1 | 1/2016 | Toda et al. |
| 2016/0151618 A1 | 6/2016 | Powers et al. |
| 2016/0175619 A1 | 6/2016 | Lee et al. |
| 2016/0206335 A1 | 7/2016 | Slayton |
| 2016/0206341 A1 | 7/2016 | Slayton |
| 2016/0256675 A1 | 9/2016 | Slayton |
| 2016/0296769 A1 | 10/2016 | Barthe et al. |
| 2016/0361571 A1 | 12/2016 | Bernabei |
| 2016/0361572 A1 | 12/2016 | Slayton |
| 2017/0028227 A1 | 2/2017 | Emery et al. |
| 2017/0043190 A1 | 2/2017 | Barthe et al. |
| 2017/0050019 A1 | 2/2017 | Ron Edoute et al. |
| 2017/0080257 A1 | 3/2017 | Paunescu et al. |
| 2017/0100585 A1 | 4/2017 | Hall et al. |
| 2017/0136263 A1 | 5/2017 | Reil |
| 2017/0209201 A1 | 7/2017 | Slayton et al. |
| 2017/0304654 A1 | 10/2017 | Blanche et al. |
| 2018/0001113 A1 | 1/2018 | Streeter |
| 2018/0015308 A1 | 1/2018 | Reed et al. |
| 2018/0043147 A1 | 2/2018 | Slayton |
| 2018/0099162 A1 | 4/2018 | Bernabei |
| 2018/0099163 A1 | 4/2018 | Bernabei |
| 2018/0272156 A1 | 9/2018 | Slayton et al. |
| 2018/0272157 A1 | 9/2018 | Barthe et al. |
| 2018/0272158 A1 | 9/2018 | Barthe et al. |
| 2018/0272159 A1 | 9/2018 | Slayton et al. |

FOREIGN PATENT DOCUMENTS

| | | |
|---|---|---|
| DE | 10140064 | 3/2003 |
| DE | 10219297 | 11/2003 |
| DE | 10219217 | 12/2004 |
| DE | 20314479 | 12/2004 |
| EP | 0142215 | 5/1984 |
| EP | 0344773 | 12/1989 |
| EP | 1479412 | 11/1991 |
| EP | 0473553 | 4/1992 |
| EP | 670147 | 2/1995 |
| EP | 0661029 | 7/1995 |
| EP | 724894 | 2/1996 |
| EP | 763371 | 11/1996 |
| EP | 1044038 | 10/2000 |
| EP | 1050322 | 11/2000 |
| EP | 1234566 | 8/2002 |
| EP | 1262160 | 12/2002 |
| EP | 1283690 | 2/2003 |
| EP | 0659387 | 4/2003 |
| EP | 1374944 | 1/2004 |
| EP | 1028660 | 1/2008 |
| EP | 1874241 | 1/2008 |
| EP | 1362223 | 5/2008 |
| EP | 1750804 | 7/2008 |
| EP | 1811901 | 4/2009 |
| EP | 1785164 | 8/2009 |
| EP | 2230904 | 9/2010 |
| EP | 1501331 | 6/2011 |
| EP | 2066405 | 11/2011 |
| EP | 2474050 | 7/2012 |
| EP | 2709726 | 11/2015 |
| EP | 1538980 | 1/2017 |
| EP | 2897547 | 11/2017 |
| FR | 2532851 | 9/1983 |
| FR | 2685872 | 1/1992 |
| FR | 2672486 | 8/1992 |
| FR | 2703254 | 3/1994 |
| GB | 2113099 | 8/1983 |
| IL | 102516 | 1/1996 |
| IL | 112369 | 8/1999 |
| IL | 120079 | 3/2001 |
| JP | 63036171 | 2/1988 |
| JP | 03048299 | 3/1991 |
| JP | 3123559 | 5/1991 |
| JP | 03136642 | 6/1991 |
| JP | 4089058 | 3/1992 |
| JP | 4-150847 | 5/1992 |
| JP | 04150847 | 5/1992 |
| JP | 7080087 | 3/1995 |
| JP | 07505793 | 6/1995 |
| JP | 2007505793 | 6/1995 |
| JP | 7184907 | 7/1995 |
| JP | 7222782 | 8/1995 |
| JP | 09047458 | 2/1997 |
| JP | 9108288 | 4/1997 |
| JP | 9503926 | 4/1997 |
| JP | 11-505440 | 5/1999 |
| JP | 11123226 | 5/1999 |
| JP | 11-506636 | 6/1999 |
| JP | 10248850 | 9/1999 |
| JP | 2000126310 | 5/2000 |
| JP | 2000166940 | 6/2000 |
| JP | 2000233009 | 8/2000 |
| JP | 2001170068 | 6/2001 |
| JP | 2002-505596 | 2/2002 |
| JP | 2002078764 | 3/2002 |
| JP | 2002515786 | 5/2002 |
| JP | 2002521118 | 7/2002 |
| JP | 2002-537939 | 11/2002 |
| JP | 2003050298 | 7/2003 |
| JP | 2003204982 | 7/2003 |
| JP | 2004-504898 | 2/2004 |
| JP | 2004-507280 | 3/2004 |
| JP | 2004-509671 | 4/2004 |
| JP | 2004-512856 | 4/2004 |
| JP | 2004-147719 | 5/2004 |
| JP | 2005503388 | 2/2005 |
| JP | 2005527336 | 9/2005 |
| JP | 2005323213 | 11/2005 |
| JP | 2006520247 | 9/2006 |
| JP | 2008515559 | 5/2008 |
| JP | 2009518126 | 5/2009 |
| JP | 2010517695 | 5/2010 |
| KR | 1020010024871 | 3/2001 |
| KR | 100400870 | 10/2003 |
| KR | 20060121267 | 11/2006 |
| KR | 1020060113930 | 11/2006 |
| KR | 1020070065332 | 6/2007 |
| KR | 1020070070161 | 7/2007 |
| KR | 1020070098856 | 10/2007 |
| KR | 1020070104878 | 10/2007 |
| KR | 1020070114105 | 11/2007 |
| KR | 1020000059516 | 4/2012 |
| KR | 10-2013-0124598 | 11/2013 |
| KR | 10-1365946 | 2/2014 |
| TW | 386883 | 9/2000 |
| TW | 201208734 A | 3/2012 |
| WO | WO93/12742 | 7/1993 |
| WO | WO95/24159 | 9/1995 |
| WO | WO 96/25888 | 8/1996 |
| WO | WO96/34568 | 11/1996 |
| WO | WO 96/39079 | 12/1996 |
| WO | WO 9735518 | 10/1997 |

(56) References Cited

FOREIGN PATENT DOCUMENTS

| | | |
|---|---|---|
| WO | WO 9832379 | 7/1998 |
| WO | WO 9852465 | 11/1998 |
| WO | WO 9933520 | 7/1999 |
| WO | WO 9949788 | 10/1999 |
| WO | WO 200006032 | 2/2000 |
| WO | WO 0015300 | 3/2000 |
| WO | WO 0021612 | 4/2000 |
| WO | WO 0053113 | 9/2000 |
| WO | WO 0128623 | 4/2001 |
| WO | WO01/045550 | 6/2001 |
| WO | WO01/080709 | 11/2001 |
| WO | WO 0182777 | 11/2001 |
| WO | WO 0182778 | 11/2001 |
| WO | WO 0187161 | 11/2001 |
| WO | WO 2001087161 | 11/2001 |
| WO | WO 02/09812 | 2/2002 |
| WO | WO02/015768 | 2/2002 |
| WO | WO 0209813 | 2/2002 |
| WO | WO 0224050 | 3/2002 |
| WO | WO 02092168 | 11/2002 |
| WO | WO 03/053266 | 7/2003 |
| WO | WO 03065347 | 8/2003 |
| WO | WO 03070105 | 8/2003 |
| WO | WO 03077833 | 9/2003 |
| WO | WO 2002054018 | 9/2003 |
| WO | WO 03086215 | 10/2003 |
| WO | WO 03/096883 | 11/2003 |
| WO | WO 03/099382 | 12/2003 |
| WO | WO 03099177 | 12/2003 |
| WO | WO 03101530 | 12/2003 |
| WO | WO 2004000116 | 12/2003 |
| WO | WO 2004080147 | 9/2004 |
| WO | WO 2004110558 | 12/2004 |
| WO | WO 2005011804 | 2/2005 |
| WO | WO 2005065408 | 7/2005 |
| WO | WO2005065409 | 7/2005 |
| WO | WO 2005090978 | 9/2005 |
| WO | WO 2005113068 | 12/2005 |
| WO | WO 2006036870 | 4/2006 |
| WO | WO 2006042163 | 4/2006 |
| WO | WO 2006042168 | 4/2006 |
| WO | WO 2006042201 | 4/2006 |
| WO | WO 2006065671 | 6/2006 |
| WO | WO 2006082573 | 8/2006 |
| WO | WO2006104568 | 10/2006 |
| WO | WO 2007067563 | 6/2007 |
| WO | WO 2008036622 | 3/2008 |
| WO | WO 2008036479 | 11/2008 |
| WO | WO 2009013729 | 1/2009 |
| WO | WO2009/149390 | 10/2009 |
| WO | WO 2008144274 | 1/2010 |
| WO | WO 2012134645 | 1/2013 |
| WO | WO2013048912 | 4/2013 |
| WO | WO2013178830 | 12/2013 |
| WO | WO 2014045216 | 3/2014 |
| WO | WO2014/055708 | 4/2014 |
| WO | WO 2014057388 | 4/2014 |
| WO | WO2014127091 | 8/2014 |
| WO | WO2015160708 | 10/2015 |
| WO | WO2016054155 | 4/2016 |
| WO | WO2017127328 | 7/2017 |
| WO | WO2017149506 | 9/2017 |
| WO | WO2017165595 | 9/2017 |
| WO | WO2017212489 | 12/2017 |
| WO | WO2018035012 | 2/2018 |

OTHER PUBLICATIONS

Alam, M., "The future of noninvasive procedural dermatology". Semin Cutan Med Surg. Mar. 2013; 32(1):59-61.
Alam, M., et al., "Ultrasound tightening of facial and neck skin: a rater-blinded prospective cohort study". J Am Acad Dermatol, 2010. 62(2): p. 262-9.
Alexiades-Armenakas, M., "Ultrasound Technologies for Dermatologic Techniques". J Drugs Derm. 2014. 12 (11): p. 1305.
Alster, T.S., et. al., "Noninvasive lifting of arm, thigh, and knee skin with transcutaneousintense focused ultrasound". Dermatol Surg, 2012. 38(5): p. 754-9.
Arosarena, O., "Options and Challenges for Facial Rejuvenation in Patients With Higher Fitzpatrick Skin Phototypes". JAMA Facial Plastic Surgery, 2015.
Bozec, Laurent et al., Thermal Denaturation Studies of Collagen by Microthermal Analysis and Atomic Force Microscopy, Biophysical Journal, vol. 101, pp. 228-236. (Jul. 2001).
Brobst, R.W., et. al., "Noninvasive Treatment of the Neck". Facial Plast Surg Clin North Am, 2014. 22(2): p. 191-202.
Brobst, R.W., et., al., "Ulthera: initial and six month results". Facial Plast Surg Clin North Am, 2012. 20(2): p. 163-76.
Casabona, G., et. al., "Microfocused Ultrasound With Visualization and Fillers for Increased Neocollagenesis: Clinical and Histological Evaluation". Dermatol Surg 2014;40:S194-S198.
Chan, N.P., et al.,"Safety study of transcutaneous focused ultrasound for non-invasive skin tightening in Asians". Lasers Surg Med, 2011. 43(5): p. 366-75.
Chapelon et al., "Effects of Cavitation In The High Intensity Therapeutic Ultrasound", Ultrasonics Symposium—1357 (1991).
Chapelon, et al., "Thresholds for Tissue Ablation by Focused Ultrasound" (1990).
Dayan, S.H., et al., "Prospective, Multi-Center, Pivotal Trial Evaluating the Safety and Effectiveness of Micro-Focused Ultrasound with Visualization (MFU-V) for Improvement in Lines and Wrinkles of the Décolletage". Plast Reconstr Surg. Oct. 2014; 134(4 Suppl 1):123-4.
Dierickx, Christine C., "The Role of Deep Heating for Noninvasive Skin Rejuvenation" Lasers in Surgery and Medicine 38:799-807 (2006).
Dobke, M.K., et al., "Tissue restructuring by energy-based surgical tools". Clin Plast Surg, 2012. 39(4): p. 399-408.
Dong, Yuan-Lin et al., "Effect of Ibuprofen on the Inflammatory Response to Surgical Wounds" The Journal of Trauma, vol. 35, No. 3. (1993).
Dvivedi, Sanjay, et al. "Effect of Ibuprofen and diclofenac sodium on experimental wound healing" Indian Journal of Experimental Biology, vol. 35, pp. 1243-1245. (Nov. 1997).
Fabi, S.G., "Microfocused Ultrasound With Visualization for Skin Tightening and Lifting: My Experience and a Review of the Literature". Dermatol Surg. Dec. 2014; 40 Suppl 12:S164-7.
Fabi, S.G., "Noninvasive skin tightening: focus on new ultrasound techniques". Clin Cosmet Investig Dermatol. Feb. 5, 2015; 8:47-52.
Fabi, S.G., et. al., "A prospective multicenter pilot study of the safety and efficacy of microfocused ultrasound with visualization for improving lines and wrinkles of the décolleté". Dermatol Surg. Mar. 2015; 41(3):327-35.
Fabi, S.G., et. al., "Evaluation of microfocused ultrasound with visualization for lifting, tightening, and wrinkle reduction of the decolletage". J Am Acad Dermatol, 2013. 69(6): p. 965-71.
Fabi, S.G., et. al., "Future directions in cutaneous laser surgery". Dermatol Clin, 2014. 32(1): p. 61-9.
Fabi, S.G., et. al., "Retrospective Evaluation of Micro-focused Ultrasound for Lifting and Tightening the Face and Neck". Dermatol Surg, 2014.
Friedmann D.P., "Comments on evaluation of microfocused ultrasound system for improving skin laxity and tightening in the lower face". Aesthet Surg J. Mar. 2015;35(3):NP81-2.
Friedmann, D.P., et. al., "Combination of intense pulsed light, Sculptra, and Ultherapy for treatment of the aging face". J Cosmet Dermatol, 2014. 13(2): p. 109-18.
Fujimoto, et al., "A New Cavitation Suppression Technique for Local Ablation Using High-Intensity Focused Ultrasound" Ultrasonics Symposium—1629 (1995).
Gold, M.H., et. al., "Use of Micro-Focused Ultrasound with Visualization to Lift and Tighten Lax Knee Skin". J Cosmet Laser Ther, 2014: p. 1-15.
Goldberg, D.J., et. al., "Safety and Efficacy of Microfocused Ultrasound to Lift, Tighten, and Smooth the Buttocks". Dermatol Surg 2014; 40:1113-1117.

(56) References Cited

OTHER PUBLICATIONS

Greene, R.M., et al., "Skin tightening technologies". Facial Plast Surg. Feb. 2014; 30(1):62-7.
Greenhalgh, David G., "Wound healing and diabetes mellitus" Clinics in Plastic Surgery 30; 37-45. (2003).
Guo, S. et al., "Factors Affecting Wound Healing" Critical Reviews in Oral Biology & Medicine, J Dent Res 89(3), pp. 219-229. (2010).
Hantash, Basil M. et al., "Bipolar Fractional Radiofrequency Treatment Induces Neoelastogenesis and Neocollagenesis" Lasers in Surgery and Medicine 41:1-9 (2009).
Hantash, Basil M. et al., "In Vivo Histological Evaluation of a Novel Ablative Fractional Resurfacing Device" Lasers in Surgery and Medicine 39:96-107 (2007).
Harris, M.O., "Safety of Microfocused Ultrasound With Visualization in Patients With Fitzpatrick Skin Phototypes III to VI". JAMA Facial Plast. Surg, 2015.
Hart, et. al., "Current Concepts in the Use of PLLA:Clinical Synergy Noted with Combined Use of Microfocused Ultrasound and Poly-l-Lactic Acid on the Face, Neck, and Décolletage". Amer. Soc. Plast. Surg. 2015. 136; 180-187S.
Hitchcock, T.M . et. al., "Review of the safety profile for microfocused ultrasound with Visualization". Journal of Cosmetic Dermatology, 13, 329-335. (2014).
Hynynen et al., Temperature Distributions During Local Ultrasound Induced Hyperthermia In Vivo, Ultrasonics Symposium—745 (1982).
Jeong, K.H., et al., "Neurologic complication associated with intense focused ultrasound". J Cosmet Laser Ther, 2013.
Kim, H.J., et al., "Coagulation and ablation patterns of high-intensity focused ultrasound on a tissue mimicking phantom and cadaveric skin". Laser Med Sci. Sep. 4, 2015.
Kornstein, A.N., "Ulthera for silicone lip correction". Plast Reconstr Surg, 2012. 129(6): p. 1014e-1015e.
Kornstein, A.N., "Ultherapy shrinks nasal skin after rhinoplasty following failure of conservative measures". Plast Reconstr Surg, 2013. 131(4): p. 664e-6e.
Krischak, G.D., et al., "The effects of non-steroidal anti-inflammatory drug application on incisional wound healing in rats" Journal of Wound Care, vol. 6, No. 2, (Feb. 2007).
Laubach, H.J., et. al., "Confined Thermal Damage with Intense Ultrasound (IUS)" [abstr.] American Society for Laser Medicine and Surgery Abstracts, p. 15 #43 (Apr. 2006).
Laubach, H.J., et. al., "Intense focused ultrasound: evaluation of a new treatment modality for precise microcoagulation within the skin". Dermatol Surg, 2008. 34(5): p. 727-34.
Lee, H.J., et. al., "The efficacy and safety of intense focused ultrasound in the treatment of enlarged facial pores in Asian skin". J Dermatolog Treat, 2014.
Lee, H.S., et al., "Multiple Pass Ultrasound Tightening of Skin Laxity of the Lower Face and Neck". Dermatol Surg, 2011.
Lin, Sung-Jan, et al., "Monitoring the thermally induced structural transitions of collagen by use of second-harmonic generation microscopy" Optics Letters, vol. 30, No. 6, (Mar. 15, 2005).
MacGregor J.L., et. al., "Microfocused Ultrasound for Skin Tightening". Semin Cutan Med Surg 32:18-25. (2013).
Meshkinpour, Azin, et al., "Treatment of Hypertrophic Scars and Keloids With a Radiofrequency Device: A Study of Collagen Effects" Lasers in Surgery and Medicine 37:343-349 (2005).
Minkis, K., et. al., "Ultrasound skin tightening". Dermatol Clin, 2014. 32(1): p. 71-7.
Mosser, David M. et al., "Exploring the full spectrum of macrophage activation" Nat Rev Immunol; 8(12): 958-969. (Dec. 2008).
Murota, Sei-Itsu, et al., "Stimulatory Effect of Prostaglandins on the Production of Hexosamine-Containing Substances by Cultured Fibroblasts (3) Induction of Hyaluronic Acid Synthetase by Prostaglandin" Department of Pharmacology, Tokyo Metropolitan Institute of Gerontology, Itabashiku, Tokyo-173, Japan. (Nov. 1977, vol. 14, No. 5).
Murota, Sei-Itsu, et al., "The Stimulatory Effect of Prostaglandins on Production of Hexosamine-Containing Substances by Cultured Fibroblasts" Department of Pharmacology, Tokyo Metropolitan Institute of Gerontology, Itabashiku, Tokyo-173, Japan. (Aug. 1976, vol. 12, No. 2).
Nestor, M.S. et. al., "Safety and Efficacy of Micro-focused Ultrasound Plus Visualization for the Treatment of Axillary Hyperhidrosis". J Clin Aesthet Dermatol, 2014. 7(4): p. 14-21.
Oni, G., et. al. "Response to 'comments on evaluation of microfocused ultrasound system for improving skin laxity and tightening in the lower face'". Aesthet Surg J. Mar. 2015;35(3):NP83-4.
Oni, G., et. al., "Evaluation of a Microfocused Ultrasound System for Improving Skin Laxity and Tightening in the Lower Face". Aesthet Surg J, 2014. 38:861-868.
Pak, C.S., et. al., "Safety and Efficacy of Ulthera in the Rejuvenation of Aging Lower Eyelids: A Pivotal Clinical Trial". Aesthetic Plast Surg, 2014.
Pritzker, R.N., et. al., "Updates in noninvasive and minimally invasive skin tightening". Semin Cutan Med Surg. Dec. 2014;33(4):182-7.
Pritzker, R.N., et. al., "Comparison of different technologies for noninvasive skin tightening". Journal of Cosmetic Dermatology, 13, 315-323. (2014).
Rappolee, Daniel A., et al., "Wound Macrophages Express TGF and Other Growth Factors in Vivo: Analysis by mRNA Phenotyping" Science, vol. 241, No. 4866 (Aug. 1988).
Rokhsar, C., et. al., "Safety and efficacy of microfocused ultrasound in tightening of lax elbow skin". Dermatol Surg. 2015; 41(7):821-6.
Rosenberg, Carol S. "Wound Healing in the Patient with Diabetes Mellitus" Nursing Clinics of North America, vol. 25, No. 1, (Mar. 1990).
Sabet-Peyman, E.J. et. al., "Complications Using Intense Ultrasound Therapy to TreatDeep Dermal Facial Skin and Subcutaneous Tissues". Dermatol Surg 2014; 40:1108-1112.
Sandulache, Vlad C. et al., "Prostaglandin E2 inhibition of keloid fibroblast migration, contraction, and transforming growth factor (TGF)—B1-induced collagen synthesis" Wound Rep Reg 15 122-133, 2007. (2007).
Sasaki, G.H. et. al., "Clinical Efficacy and Safety of Focused-Image Ultrasonography: A 2-Year Experience". Aesthet Surg J, 2012.
Sasaki, G.H. et. al., "Microfocused Ultrasound for Nonablative Skin and Subdermal Tightening to the Periorbitum and Body Sites: Preliminary Report on Eighty-Two Patients". Journal of Cosmetics, Dermatological Sciences and Applications, 2012, 2, 108-116.
Sklar, L.R., et. al., "Use of transcutaneous ultrasound for lipolysis and skin tightening: a review". Aesthetic Plast Surg, 2014. 38(2): p. 429-41.
Suh, D.H., et. al., "A intense-focused ultrasound tightening for the treatment of infraorbital laxity". J Cosmet Laser Ther, 2012. 14(6): p. 290-5.
Suh, D.H., et. al., "Comparative histometric analysis of the effects of high-intensity focused ultrasound and radiofrequency on skin". J Cosmet Laser Ther. Mar. 24, 2015:1-7.
Suh, D.H., et. al., "Intense Focused Ultrasound Tightening in Asian Skin: Clinical and Pathologic Results" American Society for Dermatologic Surgery, Inc.; 37:1595-1602. (2011).
Suh, D.H., et. al., "Intense focused ultrasound tightening in asian skin: clinical and pathologic results". Dermatol Surg, 2011. 37(11): p. 1595-602.
Verhofstad, Michiel H.J. et al., "Collagen Synthesis in rat skin and ileum fibroblasts is affected differently by diabetes-related factors" Int. J. Exp. Path. (1998), 79, 321-328.
Weiss, M., "Commentary: noninvasive skin tightening: ultrasound and other technologies: where are we in 2011?" Dermatol Surg, 2012. 38(1): p. 28-30.
White, W. M., et al., "Selective Transcutaneous Delivery of Energy to Facial Subdermal Tissues Using the Ultrasound Therapy System" [abstr]. American Society for Laser Medicine and Surgery Abstracts, p. 37 #113 (Apr. 2006).
White, W. Matthew, et al., "Selective Transcutaneous Delivery of Energy to Porcine Soft Tissues Using Intense Ultrasound (IUS)" Lasers in Surgery and Medicine 40:67-75 (2008).

(56) References Cited

OTHER PUBLICATIONS

Woodward, J.A., et. al. "Safety and Efficacy of Combining Microfocused Ultrasound With Fractional CO2 Laser Resurfacing for Lifting and Tightening the Face and Neck". Dermatol Surg, Dec. 2014 40:S190-S193.
Zelickson, Brian D. et al., "Histological and Ultrastructural Evaluation of the Effects of a Radiofrequency-Based Nonablative Dermal Remodeling Device, A Pilot Study" Arch Dermatol, vol. 140, (Feb. 2004).
U.S. Appl. No. 12/996,616, filed Jan. 12, 2011, Hand Wand for Ultrasonic Cosmetic Treatment and Imaging.
U.S. Appl. No. 13/245,822, filed Sep. 26, 2011, System and Method for Cosmetic Treatment.
U.S. Appl. No. 13/245,852, filed Sep. 26, 2011, Systems for Cosmetic Treatment.
U.S. Appl. No. 13/245,864, filed Sep. 27, 2011, Methods for Non-Invasive Cosmetic Treatment of the Eye Region.
U.S. Appl. No. 13/246,117, filed Sep. 27, 2011, Methods for Non-Invasive Lifting and Tightening of the Lower Face and Neck.
U.S. Appl. No. 13/246,112, filed Sep. 27, 2011, Tissue Imaging and Treatment Method.
U.S. Appl. No. 14/193,234, filed Feb. 28, 2014, Devices and Methods for Multi-Focus Ultrasound Therapy.
U.S. Appl. No. 08/950,353, filed Oct. 14, 1997, Imaging, Therapy and Temperature Monitoring Ultrasonic System.
U.S. Appl. No. 09/502,174, filed Feb. 10, 2000, Imaging, Therapy and Temperature Monitoring Ultrasonic System.
U.S. Appl. No. 10/193,419, filed Jul. 10, 2002, Imaging, Therapy and Temperature Monitoring Ultrasonic System.
U.S. Appl. No. 10/944,499, filed Sep. 16, 2004, Method and System for Ultrasound Treatment With a Multi-Directional Transducer.
U.S. Appl. No. 11/163,177, filed Oct. 7, 2005, Method and System for Treating Acne and Sebaceous Glands.
U.S. Appl. No. 10/950,112, filed Sep. 24, 2004, Method and System for Combined Ultrasound Treatment.
U.S. Appl. No. 11/163,178, filed Oct. 7, 2005, Method and System for Treating Stretch Marks.
U.S. Appl. No. 11/245,999, filed Oct. 6, 2005, System and Method for Ultra-High Frequency Ultrasound Treatment.
U.S. Appl. No. 10/944,500, filed Sep. 16, 2004, System and Method for Variable Depth Ultrasound Treatment.
U.S. Appl. No. 11/744,655, filed May 4, 2007, Imaging, Therapy and Temperature Monitoring Ultrasonic System.
U.S. Appl. No. 12/135,962, filed Jun. 9, 2008, Method and System for Ultrasound Treatment With a Multi-Directional Transducer.
U.S. Appl. No. 12/792,934, filed Jun. 3, 2010, System and Method for Ultra-High Frequency Ultrasound Treatment.
U.S. Appl. No. 12/834,754, filed Jul. 12, 2010, System and Method for Variable Depth Ultrasound Treatment.
U.S. Appl. No. 11/126,760, filed May 11, 2005, Method and System for Three-Dimensional Scanning and Imaging.
U.S. Appl. No. 13/564,552, filed Aug. 1, 2012, Method and System for Controlled Scanning, Imaging and/or Therapy.
U.S. Appl. No. 12/437,726, filed May 8, 2009 Method and System for Combined Ultrasound Treatment.
U.S. Appl. No. 11/163,148, filed Oct. 6, 2005, Method and System for Controlled Thermal Injury of Human Superficial Tissue.
U.S. Appl. No. 13/444,688, filed Apr. 11, 2012, Customized Cosmetic Treatment.
U.S. Appl. No. 11/163,152, filed Oct. 6, 2005, Method and System for Treatment of Sweat Glands.
U.S. Appl. No. 13/444,485, filed Apr. 11, 2012, Methods for Treatment of Sweat Glands.
U.S. Appl. No. 13/603,159, filed Sep. 4, 2012, Methods for Treatment of Hyperhidrosis.
U.S. Appl. No. 13/603,279, filed Sep. 4, 2012, Energy Based Hyperhidrosis Treatment.
U.S. Appl. No. 13/950,728, filed Jul. 25, 2013, Energy Based Hyperhidrosis Treatment.
U.S. Appl. No. 11/163,151, filed Oct. 6, 2005, Method and System for Noninvasive Face Lifts and Deep Tissue Tightening.
U.S. Appl. No. 13/444,336, filed Apr. 11, 2012, Treatment of Sub-Dermal Regions for Cosmetic Effects.
U.S. Appl. No. 13/679,430, filed Nov. 16, 2012, Ultrasound Treatment of Sub-Dermal Tissue for Cosmetic Effects.
U.S. Appl. No. 13/924,376, filed Jun. 21, 2013, Noninvasive Tissue Tightening for Cosmetic Effects.
U.S. Appl. No. 13/924,355, filed Jun. 21, 2013, Noninvasive Aesthetic Treatment for Tightening Tissue.
U.S. Appl. No. 13/924,323, filed Jun. 21, 2013, Energy-Based Tissue Tightening.
U.S. Appl. No. 14/200,852, filed Mar. 7, 2014, Noninvasive Tissue Tightening System.
U.S. Appl. No. 14/200,961, filed Mar. 7, 2014, Energy-Based Tissue Tightening System.
U.S. Appl. No. 12/028,636, filed Feb. 8, 2008, Method and System for Noninvasive Face Lifts and Deep Tissue Tightening.
U.S. Appl. No. 13/964,820, filed Aug. 12, 2013, Methods for Noninvasive Skin Tightening.
U.S. Appl. No. 14/201,256, filed Mar. 7, 2014, System for Noninvasive Skin Tightening.
U.S. Appl. No. 11/163,150, filed Oct. 6, 2005, Method and System for Photoaged Tissue.
U.S. Appl. No. 13/230,498, filed Sep. 12, 2011, Method and System for Photoaged Tissue.
U.S. Appl. No. 14/169,709, filed Jan. 31, 2014, Methods for Treating Skin Laxity.
U.S. Appl. No. 11/163,176, filed Oct. 7, 2005, Method and System for Treating Blood Vessel Disorders.
U.S. Appl. No. 13/601,742, filed Aug. 31, 2012, Method and System for Treating Blood Vessel Disorders.
U.S. Appl. No. 12/574,512, filed Oct. 6, 2009, Method and System for Treating Stretch Marks.
U.S. Appl. No. 11/857,989, filed Sep. 19, 2007, Method and System for Treating Muscle, Tendon, Ligament and Cartilage Tissue.
U.S. Appl. No. 13/494,856, filed Jun. 12, 2012, Method and System for Treating Muscle, Tendon, Ligament and Cartilage Tissue.
U.S. Appl. No. 13/835,635, filed Mar. 15, 2013, Methods for Face and Neck Lifts.
U.S. Appl. No. 13/965,741, filed Aug. 13, 2013, Methods for Preheating Tissue for Cosmetic Treatment of the Face and Body.
U.S. Appl. No. 12/954,484, filed Nov. 24, 2010, Methods and Systems for Generating Thermal Bubbles for Improved Ultrasound Imaging and Therapy.
U.S. Appl. No. 12/350,383, filed Jan. 8, 2009, Method and System for Treating Acne and Sebaceous Glands.
U.S. Appl. No. 12/116,845, filed May 7, 2008, Method and System for Combined Energy Profile.
U.S. Appl. No. 08/766,083, filed Dec. 16, 1996, Method and Apparatus for Surface Ultrasound Imaging.
U.S. Appl. No. 09/113,227, filed Jul. 10, 1998, Method and Apparatus for Three Dimensional Ultrasound Imaging.
U.S. Appl. No. 08/944,261, filed Oct. 6, 1997, Wideband Acoustic Transducer.
U.S. Appl. No. 09/434,078, filed Nov. 5, 1999, Method and Apparatus for Three Dimensional Ultrasound Imaging.
U.S. Appl. No. 09/523,890, filed Mar. 13, 2000, Method and Apparatus for Three Dimensional Ultrasound Imaging.
U.S. Appl. No. 09/419,543, filed Oct. 18, 1999, Peripheral Ultrasound Imaging System.
U.S. Appl. No. 09/750,816, filed Dec. 28, 2000, Visual Imaging System for Ultrasonic Probe.
U.S. Appl. No. 10/358,110, filed Feb. 4, 2003, Visual Imaging System for Ultrasonic Probe.
U.S. Appl. No. 11/380,161, filed Apr. 25, 2006, Method and System for Enhancing Computer Peripheral Safety.
U.S. Appl. No. 11/554,272, filed Oct. 30, 2006, Visual Imaging System for Ultrasonic Probe.
U.S. Appl. No. 13/071,298, filed Mar. 24, 2011, Visual Imaging System for Ultrasonic Probe.
U.S. Appl. No. 13/854,936, filed Mar. 25, 2013, Visual Imaging System for Ultrasonic Probe.

(56) References Cited

OTHER PUBLICATIONS

U.S. Appl. No. 12/509,254, filed Jul. 24, 2009, Method and System for Enhancing Computer Peripheral Safety.
U.S. Appl. No. 13/453,847, filed Apr. 23, 2012, Method and System for Enhancing Computer Peripheral Safety.
U.S. Appl. No. 11/528,794, filed Oct. 4, 2006, Ultrasound System and Method for Imaging and/or Measuring Displacement of Moving Tissue and Fluid.
U.S. Appl. No. 09/502,175, filed Feb. 10, 2000, Method and Apparatus for Safely Delivering Medicants to a Region of Tissue, Using Imaging, Therapy and Temperature Monitoring.
U.S. Appl. No. 08/943,728, filed Oct. 3, 1997, Method and Apparatus for Safely Delivering Medicants to a Region of Tissue Using Ultrasound.
U.S. Appl. No. 12/415,945, filed Mar. 31, 2009, Method and System for Noninvasive Mastopexy.
U.S. Appl. No. 11/163,155, filed Oct. 6, 2005, Method and System for Noninvasive Mastopexy.
U.S. Appl. No. 11/163,154, filed Oct. 6, 2005, Method and System for Treatment of Cellulite.
U.S. Appl. No. 13/356,405, filed Jan. 23, 2012, Method and System for Treatment of Cellulite.
U.S. Appl. No. 13/789,562, filed Mar. 7, 2013, Method and System for Ultrasound Treatment of Fat.
U.S. Appl. No. 14/164,598, filed Jan. 27, 2013, Method for Fat and Cellulite Reduction.
U.S. Appl. No. 11/738,682, filed Apr. 23, 2007, Method and System for Non-Ablative Acne Treatment and Prevention.
U.S. Appl. No. 12/116,810, filed May 7, 2008, Methods and Systems for Modulating Medicants Using Acoustic Energy.
U.S. Appl. No. 12/116,828, filed May 7, 2008, Methods and Systems for Coupling and Focusing Acoustic Energy Using a Coupler Member.
U.S. Appl. No. 12/646,609, filed Dec. 23, 2009, Methods and System for Fat Reduction and/or Cellulite Treatment.
U.S. Appl. No. 14/192,520, filed Feb. 27, 2014, Energy Based Fat Reduction.
U.S. Appl. No. 13/291,312, filed Nov. 11, 2011, Devices and Methods for Acoustic Shielding.
U.S. Appl. No. 13/136,538, filed Aug. 2, 2011, Systems and Methods for Treating Acute and/or Chronic Injuries in Soft Tissue.
U.S. Appl. No. 13/136,542, filed Aug. 2, 2011, System and Method for Treating Cartilage.
U.S. Appl. No. 13/163,541, filed Aug. 2, 2011, Methods and Systems for Treating Plantar Fascia.
U.S. Appl. No. 13/136,544, filed Aug. 2, 2011, Systems and Methods for Ultrasound Treatment.
U.S. Appl. No. 13/547,023, filed Jul. 11, 2012, Systems and Methods for Coupling an Ultrasound Source to Tissue.
U.S. Appl. No. 13/545,931, filed Jul. 10, 2012, Methods and Systems for Controlling Acoustic Energy Deposition Into a Medium.
U.S. Appl. No. 13/545,953, filed Jul. 10, 2012, Systems and Methods for Accelerating Healing of Implanted Material and/or Native Tissue.
U.S. Appl. No. 13/547,011, filed Jul. 11, 2012, Systems and Methods for Monitoring and Controlling Ultrasound Power Output and Stability.
U.S. Appl. No. 13/545,954, filed Jul. 10, 2012, Systems and Methods for Improving an Outside Appearance of Skin Using Ultrasound As an Energy Source.
U.S. Appl. No. 13/545,945, filed Jul. 10, 2012, Systems and Methods for Treating Injuries to Joints and Connective Tissue.
U.S. Appl. No. 13/863,249, filed Apr. 15, 2013, Systems for Cosmetic Treatment.
U.S. Appl. No. 13/863,281, filed Apr. 15, 2013, Methods for Non-invasive Cosmetic Treatment.
U.S. Appl. No. 14/225,189, filed Mar. 25, 2014, Reflective Ultrasound Technology for Dermatological Treatments.
A Validated Photonumeric Cellulite Severity Scale; Hexsel et al; J Eur Acad Dermatol Venereol. May 2009;23(5):523-8, 6 pages.
Delon Martin, C., et al, "Venous Thrombosis Generation by Means of High-Intensity Focused Ultrasound" Ultrasound in Med. & Biol., vol. 21, No. 1, pp. 113-119 (1995).
Microfocused Ultrasound with Visualization and Calcium Hydroxylapatite for Improving Skin Laxity and Cellulite Appearance; Casabona et al.; Plast Reconstr Surg Glob Open. Jul. 25, 2017;5(7):e1388, 8 pages.
Microfocused Ultrasound With Visualization and Fillers for Increased Neocollagenesis: Clinical and Histological Evaluation;I Casabona et al.; Dermatol Surg. Dec. 2014; 40 Suppl 12:S194-8, 5 pages.
Decision on Institution of Inter Partes Review in Re U.S. Pat. No. 6,113,559; IPR2016-01459; 20 pages [011] (Dated Jan. 23, 2017).
DERMAFOCUS Response to Institution of Inter Partes Review in Re U.S. Pat. No. 6,113,559; IPR2016-01459; 73 pages [018] (Dated Apr. 26, 2017).
DERMAFOCUS Exhibit List in Re U.S. Pat. No. 6,113,559; IPR2016-01459; 5 pages [019] (Dated Apr. 26, 2017).
DERMAFOCUS Exhibit 2002, Declaration of Mark Palmeri, in Re U.S. Pat. No. 6,113,559; IPR2016-01459; 136 pages (Filed Apr. 26, 2017).
DERMAFOCUS Exhibit 2003, Deposition of Dr. Mark Schafer, in Re U.S. Pat. No. 6,113,559; IPR2016-01459; 327 pages (Filed Apr. 26, 2017).
DERMAFOCUS Exhibit 2004, Amendment No. 4 to Ulthera Form S-1, in Re U.S. Pat. No. 6,113,559; IPR2016-01459; 308 pages (Filed Apr. 26, 2017).
DERMAFOCUS Exhibit 2005, Excerpt from Churchill Livingstone, Gray's Anatomy (38th ed. 1995), in Re U.S. Pat. No. 6,113,559; IPR2016-01459; 7 pages (Filed Apr. 26, 2017).
DERMAFOCUS Exhibit 2006, Bo Eklof et al., "Revision of the CEAP Classification for Chronic Venous Disorders: Consensus Statement," ACTA FAC MED NAISS, vol. 25, No. 1 (2008), 3-10 in Re U.S. Pat. No. 6,113,559; IPR2016-01459; 7 pages (Filed Apr. 26, 2017).
DERMAFOCUS Exhibit 2007, WebMD, "Varicose Veins and Spider Veins" downloaded from http://www.webmd.com/skin-problems-andtreatments/guide/varicose-spider-veins#1 in Re.U.S. Pat. No. 6,113,559; IPR2016-01459; 3 pages (Filed Apr. 26, 2017).
DERMAFOCUS Exhibit 2008, John M. Porter et al, "Reporting Standards in Venous Disease: An Update," Journal of Vascular Surgery, vol. 21, No. 4 (1995), 635-645 in Re U.S. Pat. No. 6,113,559; IPR2016-01459; 11 pages (Filed Apr. 26, 2017).
DERMAFOCUS Exhibit 2009, Kullervo Hynynen, "Review of Ultrasound Therapy," 1997 Ultrasonics Symposium (1997), 1305-1313, in Re U.S. Pat. No. 6,113,559; IPR2016-01459; 9 pages (Filed Apr. 26, 2017).
DERMAFOCUS Exhibit 2010, A.G. Visioli et al, "Preliminary Results of a Phase I Dose Escalation Clinical Trial Using Focused Ultrasound in the Treatment of Localised Tumours," European Journal of Ultrasound, vol. 9 (1999), 11-18, in Re U.S. Pat. No. 6,113,559; IPR2016-01459; 8 pages (Filed Apr. 26, 2017).
DERMAFOCUS Exhibit 2011, U.S. Pat. No. 5,143,063, issued on Sep. 1,1992, Fellner, in Re U.S. Pat. No. 6,113,559; IPR2016-01459; 6 pages (Filed Apr. 26, 2017).
DERMAFOCUS Exhibit 2012, Hugh G. Beebe et al, "Consensus Statement: Classification and Grading of Chronic Venous Disease in the Lower Limbs," European Journal of Vascular and Endovascular Surgery, vol. 12 (1996), 487-492, in Re U.S. Pat. No. 6,113,559; IPR2016-01459; 6 pages (Filed Apr. 26, 2017).
DERMAFOCUS Exhibit 2013, Excerpt from Mosby's Medical Dictionary (3rd ed. 1990), in Re U.S. Pat. No. 6,113,559; IPR2016-01459; 4 pages (Filed Apr. 26, 2017).
DERMAFOCUS Exhibit 2014, Excerpt from Miller-Keane Encyclopedia & Dictionary of Medicine, Nursing, & Allied Health (5th ed. 1992), in Re U.S. Pat. No. 6,113,559; IPR2016-01459; 6 pages (Filed Apr. 26, 2017).
DERMAFOCUS Exhibit 2015, David J. Tibbs et al, Varicose Veins, Venous Disorders, and Lymphatic Problems in the Lower Limbs (1997), Chapter 4: Clinical Patterns of Venous Disorder I, 47-67, in Re U.S. Pat. No. 6,113,559; IPR2016-01459; 24 pages (Filed Apr. 26, 2017).
DERMAFOCUS Exhibit 2016, Mitchel P. Goldman et al, Varicose Veins and Telangiectasias (2nd ed. 1999), Chapter 22: Treatment of

(56) References Cited

OTHER PUBLICATIONS

Leg Telangiectasias with Laser and High-Intensity Pulsed Light, 470-497, in Re U.S. Pat. No. 6,113,559; IPR2016-01459; 31 pages (Filed Apr. 26, 2017).
DERMAFOCUS Exhibit 2017, Email from Anderson to Klopotek dated May 25, 2004, in Re U.S. Pat. No. 6,113,559; IPR2016-01459; 1 page (Filed Apr. 26, 2017).
DERMAFOCUS Exhibit 2018, List of Klopotek Patents, in Re U.S. Pat. No. 6,113,559; IPR2016-01459; 411 pages (Filed Apr. 26, 2017).
DERMAFOCUS Exhibit 2019, Declaration of Peter Klopotek Civil Action 15-cv-654-SLR, dated Nov. 2, 2016, in Re U.S. Pat. No. 6,113,559; IPR2016-01459; 1 page (Filed Apr. 26, 2017).
DERMAFOCUS Exhibit 2020, "Our Technology," downloaded from http://jobs.ulthera.com/about on Apr. 10, 2017, in Re U.S. Pat. No. 6,113,559; IPR2016-01459; 4 pages (Filed Apr. 26, 2017).
DERMAFOCUS Exhibit 2021, C. Damianou and K. Hynynen, "Focal Spacing and Near-Field Heating During Pulsed High Temperature Ultrasound Therapy," Ultrasound in Medicine & Biology, vol. 19, No. 9 (1993), 777-787, in Re U.S. Pat. No. 6,113,559; IPR2016-01459; 11 pages (Filed Apr. 26, 2017).
DERMAFOCUS Exhibit 2022, Excerpt from Mosby's Medical Dictionary (5th ed. 1997), in Re U.S. Pat. No. 6,113,559; IPR2016-01459; 5 pages (Filed Apr. 26, 2017).
DERMAFOCUS Exhibit 2023, Excerpt from Miller-Keane Encyclopedia & Dictionary of Medicine, Nursing, & Allied Health (6th ed. 1997), in Re U.S. Pat. No. 6,113,559; IPR2016-01459; 7 pages (Filed Apr. 26, 2017).
DERMAFOCUS Exhibit 2024, Excerpt from Stedman's Concise Medical Dictionary (3 rd ed. 1997), in Re U.S. Pat. No. 6,113,559; IPR2016-01459; 4 pages (Filed Apr. 26, 2017).
DERMAFOCUS Exhibit 2025, Excerpt from Taber's Cyclopedic Medical Dictionary (18th ed. 1997), in Re U.S. Pat. No. 6,113,559; IPR2016-01459; 9 pages (Filed Apr. 26, 2017).
DERMAFOCUS Exhibit 2026, Bo Eklof et al, "Revision of the CEAP Classification for Chronic Venous Disorders: Consensus Statement," Journal ofVascular Surgery, vol. 40, No. 6 (2004), 1248-1252.el, in Re U.S. Pat. No. 6,113,559; IPR2016-01459; 6 pages (Filed Apr. 26, 2017).
Ulthera, Inc., Reply in Support of Petition for Inter Partes Review in Re U.S. Pat. No. 6,113,559; IPR2016-01459; 33 pages (Filed Aug. 2, 2017).
ULTHERA Exhibit 1022, Use of the Argon and Carbon Dioxide Lasers for Treatment of Superficial Venous Varicosities of the Lower Extremity, D. Apfelberg et al., Lasers in Surgery and Medicine, vol. 4.3, pp. 221-231 (1984) (filed Aug. 2, 2017 in re IPR2016-01459).
ULTHERA Exhibit 1023, 532-Nanometer Green Laser Beam Treatment of Superficial Varicosities of the Lower Extremities, T. Smith et al., Lasers in Surgery and Medicine, vol. 8.2, pp. 130-134 (1988) (filed Aug. 2, 2017 in re IPR2016-01459).
ULTHERA Exhibit 1024, Deposition Transcript of Dr. Mark Palmeri on Jul. 11, 2017 (filed Aug. 2, 2017 in re IPR2016-01459).
ULTHERA Exhibit 1025, Ulthera Oral Proceeding Demonstrative Slides (filed Oct. 2, 2017 in re IPR2016-01459).
DERMAFOCUS Exhibit 2027, DermaFocus Oral Proceeding Demonstrative Slides (filed Oct. 2, 2017 in re IPR2016-01459).
PTAB Record of Oral Hearing held Oct. 4, 2017 in Re U.S. Pat. No. 6,113,559; IPR2016-01459; 67 pages (PTAB Document sent to Ulthera on Nov. 1, 2017).
Ulthera, Inc., Petition for Inter Partes Review filed Jul. 19, 2016 in Re U.S. Pat. No. 6,113,559; IPR2016-01459; 63 pages.
ULTHERA Exhibit 1001, U.S. Pat. No. 6,113,559 to Klopotek, filed Jul. 19, 2016 in re IPR2016-01459.
ULTHERA Exhibit 1002, Patent file history of U.S. Pat. No. 6,113,559 Klopotek.
ULTHERA Exhibit 1003, Declaration of Expert Witness Mark E. Schafer, Ph.D.
ULTHERA Exhibit 1004, Curriculum Vitae of Mark E. Schafer, Ph.D.
ULTHERA Exhibit 1005, International PCT Publication WO96/34568 Knowlton.
ULTHERA Exhibit 1006, French Patent No. 2,672,486, Technomed patent.
ULTHERA Exhibit 1007, English translation of French Patent No. 2,672,486, Technomed.
ULTHERA Exhibit 1008, International PCT Publication WO93/12742, Technomed PCT.
ULTHERA Exhibit 1009, English translation of International PCT Publication WO93/12742, Technomed PCT.
ULTHERA Exhibit 1010, U.S. Pat. No. 5,601,526, which claims priority to Technomed PCT.
ULTHERA Exhibit 1011, Patent file history for European Patent Application No. 98964890.2, Klopotek.
ULTHERA Exhibit 1012, Translator Declaration.
ULTHERA Exhibit 1013, U.S. Pat. No. 5,230,334 to Klopotek.
ULTHERA Exhibit 1014, U.S. Pat. No. 5,755,753 to Knowlton.
ULTHERA Exhibit 1015, Excerpts from The American Medical Association Encyclopedia of Medicine (1989).
ULTHERA Exhibit 1016, The Simultaneous Study of Light Emissions and Shock Waves Produced by Cavitation Bubbles, G. Gimenez, J. Acoust. Soc. Am. 71(4), Apr. 1982, pp. 839-847.
ULTHERA Exhibit 1017, Excerpts from Gray's Anatomy (1995).
ULTHERA Exhibit 1018, Anatomy of the Superficial Venous System, Comjen G.M., Dermatol. Surg., 1995; 21:35-45.
ULTHERA Exhibit 1019, Section 2.6 from Ultrasonics Theory and Application, by G.L. Gooberman (Hart Publishing Co., 1969).
ULTHERA Exhibit 1020, Deep Local Hyperthermia for Cancer Therapy: External Electromagnetic and Ultrasound Techniques, A.Y. Cheung and A. Neyzari, Cancer Research (Suppl.), vol. 44, pp. 4736-4744 (1984).
Calderhead et al., "One Mechanism Behind LED Photo-Therapy for Wound Healing and Skin Rejuvenation: Key Role of the Mast Cell" Laser Therapy 17.3: 141-148 (2008).
Carruthers et al., "Consensus Recommendations for Combined Aesthetic Interventions in the Face Using Botulinum Toxin, Fillers,and Energy-Based Devices" Dermatol Surg 2016 (pp. 1-12).
Final Written Decision of Inter Partes Review in Re U.S. Pat. No. 6,113,559; IPR2016-01459; 37 pages [030] (Entered Jan. 19, 2018).
Ulthera, Inc., Petitioner Notice of Appeal to Federal Circuit 2018-1542 re: IPR2016-01459; 4 pages from [001] (no appendices) (Filed Feb. 9, 2018).
Federal Circuit Order Granting Ulthera Motion to Remand, re: 2018-1542; 4 pages [022] (Dated May 25, 2018).
MICROCHIP microlD 125 kHz EFID System Design Guide, Microchip Technology Inc. (2004).
Alster, Tinas S., Tanzi, Elizabeth L., "Cellulite Treatment using a Novel Combination Radiofrequency, Infrared Light, and Mechanical Tissue Manipulation Device," Journal of Cosmetic & Laser Therapy, Jun. 2005, vol. 7, Issue 2, pp. 81-85.
Arthur et al., "Non-invasive estimation of hyperthermia temperatures with ultrasound," Int. J. Hyperthermia, Sep. 2005, 21(6), pp. 589-600.
Barthe et al., "Ultrasound therapy system and ablation results utilizing miniature imaging/therapy arrays," Ultrasonics Symposium, 2004 IEEE, Aug. 23, 2004, pp. 1792-1795, vol. 3.
Chen, L. et al., "Effect of Blood Perfusion on the ablation of liver parenchyma with high intensity focused ultrasound," Phys. Med. Biol; 38:1661-1673; 1993b.
Coon, Joshua et al., "Protein identification using sequential ion/ion reactions and tandem mass spectrometry" Proceedings of the National Academy of Sciences of the USA, vol. 102, No. 27, Jul. 27, 2005, pp. 9463-9468.
Corry, Peter M., et al., "Human Cancer Treatment with Ultrasound", IEEE Transactions on Sonics and Ultrasonics, vol. SU-31, No. 5, Sep. 1984, pp. 444, 456.
Damianou et al., "Application of the Thermal Dose Concept for Predicting the Necrosed Tissue Volume During Ultrasound Surgery," 1993 IEEE Ultrasound Symposium, pp. 1199-1202.
Daum, et al., Design and Evaluation of a Feedback Based Phased Array System for Ultrasound Surgery, IEEE Transactions on Ultrasonics, Ferroelectrics, and Frequency Control, vol. 45, No. 2, Mar. 1998, pp. 431-438.

(56) References Cited

OTHER PUBLICATIONS

Davis, Brian J., et al., "An Acoustic Phase Shift Technique for the Non-Invasive Measurement of Temperature Changes in Tissues", 1985 Ultrasonics Symposium, pp. 921-924.

Decision of the Korean Intellectual Property Tribunal dated Jun. 28, 2013 regarding Korean Patent No. 10-1142108, which is related to the pending application and/or an application identified in the Table on pp. 2-5 of the Information Disclosure Statement herein (English translation, English translation certification, and Korean decision included).

Fry, W.J. et al., "Production of Focal Destructive Lesions in the Central Nervous System with Ultrasound," J. Neurosurg., 11:471-478; 1954.

Gliklich et al., Clinical Pilot Study of Intense Ultrasound therapy to Deep Dermal Facial Skin and Subcutaneous Tissues, Arch Facial Plastic Surgery, Mar. 1, 2007, vol. 9, No. 1.

Haar, G.R. et al., "Tissue Destruction with Focused Ultrasound in Vivo," Eur. Urol. 23 (suppl. 1):8-11; 1993.

Hassan et al., "Structure and Applications of Poly(vinyl alcohol) Hydrogels Produced by Conventional Crosslinking or by Freezing/Thawing Methods," advanced in Polymer Science, 2000, pp. 37-65, vol. 153.

Hassan et al., "Structure and Morphology of Freeze/Thawed PVA Hydrogels," Macromolecules, Mar. 11, 2000, pp. 2472-2479, vol. 33, No. 7.

Husseini et al, "The Role of Cavitation in Acoustically Activated Drug Delivery," J. Control Release, Oct. 3, 2005, pp. 253-261, vol. 107(2).

Husseini et al. "Investigating the mechanism of acoustically activated uptake of drugs from Pluronic micelles," BMD Cancer 2002, 2:20k, Aug. 30, 2002, pp. 1-6.

Jeffers et al., "Evaluation of the Effect of Cavitation Activity on Drug-Ultrasound Synergisms," 1993 IEEE Ultrasonics Symposium, pp. 925-928.

Jenne, J., et al., "Temperature Mapping for High Energy US-Therapy", 1994 Ultrasonics Symposium, pp. 1879-1882.

Johnson, S.A., et al., "Non-Intrusive Measurement of Microwave and Ultrasound-Induced Hyperthermia by Acoustic Temperature Tomography", Ultrasonics Symposium Proceedings, pp. 977-982. (1977).

Madersbacher, S. et al., "Tissue Ablation in Benign Prostatic Hyperplasia with High Intensity Focused Ultrasound," Dur. Urol., 23 (suppl. 1):39-43; 1993.

Makin et al, "B-Scan Imaging and Thermal Lesion Monitoring Using Miniaturized Dual-Functionality Ultrasound Arrays," Ultrasonics Symposium, 2004 IEEE, Aug. 23, 2004, pp. 1788-1791, vol. 3.

Makin et al, "Confirmed Bulk Ablation and Therapy Monitoring Using Intracorporeal Image-Treat Ultrasound Arrays," 4th International Symposium on Therapeutic Ultrasound, Sep. 19, 2004.

Makin et al., "Miniaturized Ultrasound Arrays for Interstitial Ablation and Imaging," UltraSound Med. Biol. 2005, Nov. 1, 2005, pp. 1539-1550, vol. 31(11).

Manohar et al, "Photoacoustic mammography laboratory prototype: imaging of breast tissue phantoms," Journal of Biomedical Optics, Nov./Dec. 2004, pp. 1172-1181, vol. 9, No. 6.

Mast et al, "Bulk Ablation of Soft Tissue with Intense Ultrasound; Modeling and Experiments," J. Acoust. Soc. Am., Oct. 1, 2005, pp. 2715-2724, vol. 118(4).

Mitragotri, S., "Healing sound: the use of ultrasound in drug delivery and other therapeutic applications," Nature Reviews; Drug Delivery, pp. 255-260, vol. 4 (Mar. 2005).

Paradossi et al., "Poly(vinyl alcohol) as versatile biomaterial for potential biomedical applications," Journal of Materials Science: Materials in Medicine, 2003, pp. 687-691, vol. 14.

Reid, Gavin, et al., "Tandem Mass spectrometry of ribonuclease A and B: N-linked glycosylation site analysis of whole protein ions," Analytical Chemistry. Feb. 1, 2002, vol. 74, No. 3, pp. 577-583.

Righetti et al, "Elastographic Characterization of HIFU-Induced Lesions in Canine Livers," 1999, Ultrasound in Med & Bio, vol. 25, No. 7, pp. 1099-1113.

Saad et al., "Ultrasound-Enhanced Effects of Adriamycin Against Murine Tumors," Ultrasound in Med. & Biol. vol. 18, No. 8, pp. 715-723 (1992).

Sanghvi, N.T., et al., "Transrectal Ablation of Prostrate Tissue Using Focused Ultrasound," 1993 Ultrasonics Symposium, IEEE, pp. 1207-1210.

Sassen, Sander, "ATI's R520 architecture, the new king of the hill?" http://www.hardwareanalysis.com/content/article/1813, Sep. 16, 2005, 2 pages.

Seip, Ralf, et al., "Noninvasive Detection of Thermal Effects Due to Highly Focused Ultrasonic Fields," IEEE Symposium, pp. 1229-1232, vol. 2, Oct. 3-Nov. 1993.

Seip, Ralf, et al., "Noninvasive Estimation of Tissue Temperature Response to Heating Fields Using Diagnostic Ultrasound," IEEE Transactions on Biomedical Engineering, vol. 42, No. 8, Aug. 1995, pp. 828-839.

Simon et al., "Applications of Lipid-Coated Microbubble Ultrasonic Contrast to Tumor Therapy," Ultrasound in Med. & Biol. vol. 19, No. 2, pp. 123-125 (1993).

Smith, Nadine Barrie, et al., "Non-invasive In Vivo Temperature Mapping of Ultrasound Heating Using Magnetic Resonance Techniques", 1994 Ultrasonics Symposium, pp. 1829-1832, vol. 3.

Surry et al., "Poly(vinyl alcohol) cryogel phantoms for use in ultrasound and MR imaging," Phys. Med. Biol., Dec. 6, 2004, pp. 5529-5546, vol. 49.

Syka J. E. P. et al., "Peptide and Protein Sequence Analysis by Electron Transfer Dissociation Mass Spectrometry," Proceedings of the National Academy of Sciences of USA, National Academy of Science, Washington, DC, vol. 101, No. 26, Jun. 29, 2004, pp. 9528-9533.

Talbert, D. G., "An Add-On Modification for Linear Array Real-Time Ultrasound Scanners to Produce 3D Displays," UTS Int'l 1977 Brighton, England (Jun. 28-30, 1977) pp. 57-67.

Tata et al., "Interaction of Ultrasound and Model Membrane Systems: Analyses and Predictions," American Chemical Society, Phys. Chem. 1992, 96, pp. 3548-3555.

Ueno, S., et al., "Ultrasound Thermometry in Hyperthermia", 1990 Ultrasonic Symposium, pp. 1645-1652.

Wang, H., et al., "Limits on Focused Ultrasound for Deep Hyperthermia", 1994 Ultrasonic Symposium, Nov. 1-4, 1994, pp. 1869-1872, vol. 3.

Wasson, Scott, "NVIDIA's GeForce 7800 GTX graphics processor Power MADD," http://techreport.com/reviews/2005q2/geforce-7800gtx/index.x?pg=1, Jun. 22, 2005, 4 pages.

White et al "Selective Creating of Thermal Injury Zones in the Superficial Musculoaponeurotic System Using Intense Ultrasound Therapy," Arch Facial Plastic Surgery, Jan./Feb. 2007, vol. 9, No. 1.

* cited by examiner

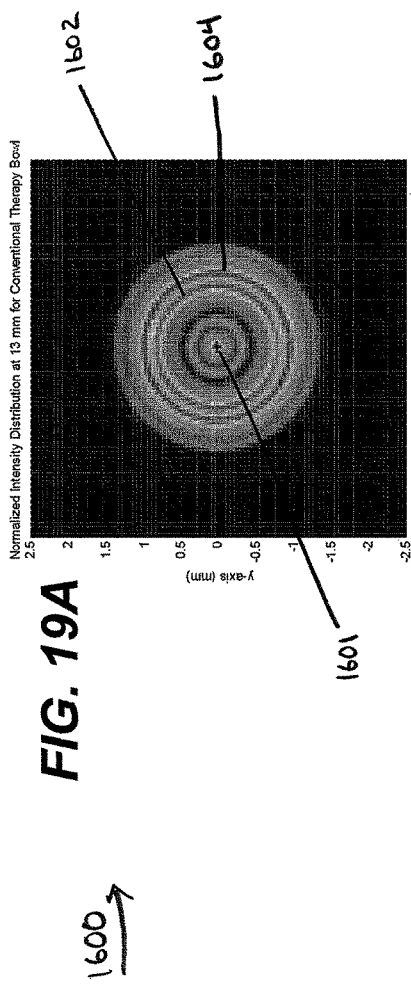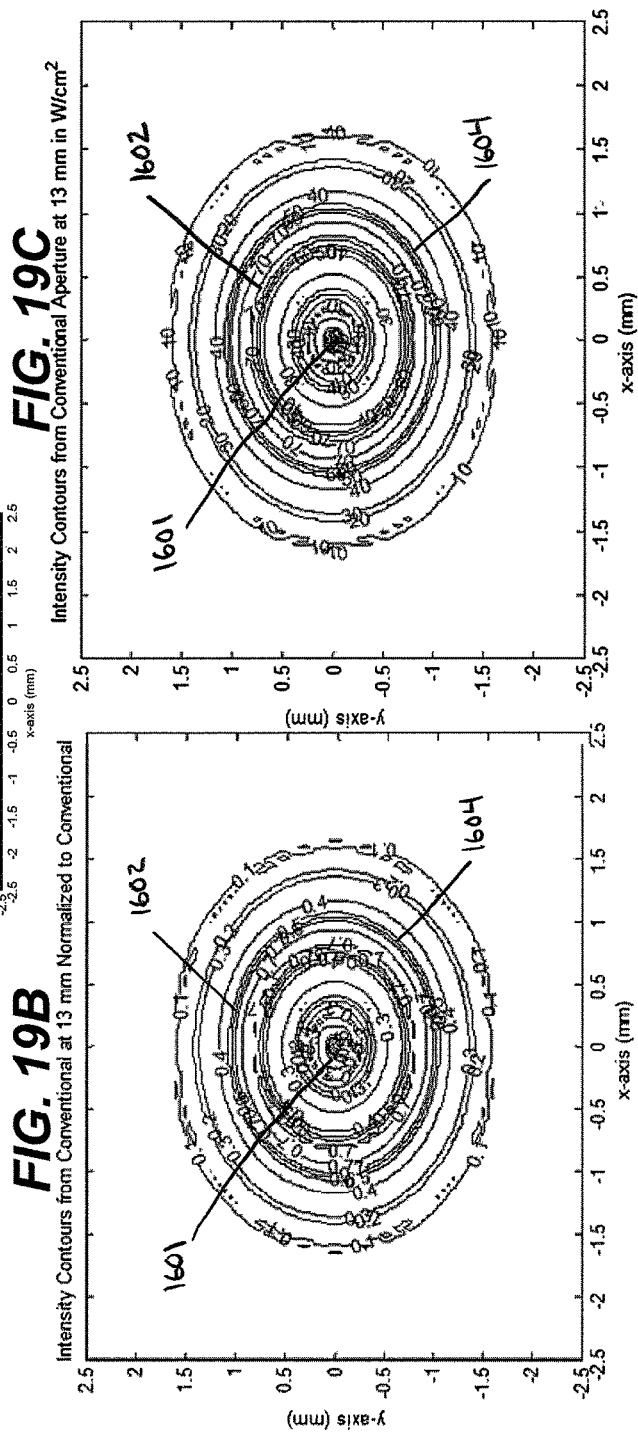
FIG. 19A
FIG. 19B
FIG. 19C

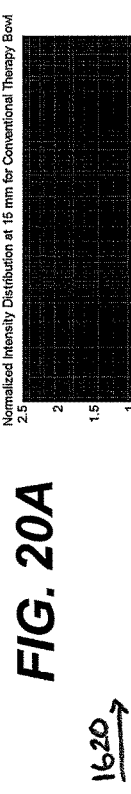
FIG. 20A
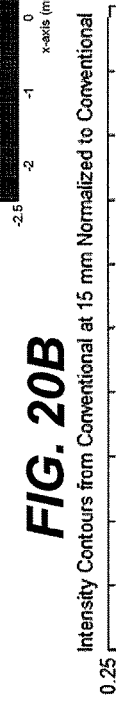
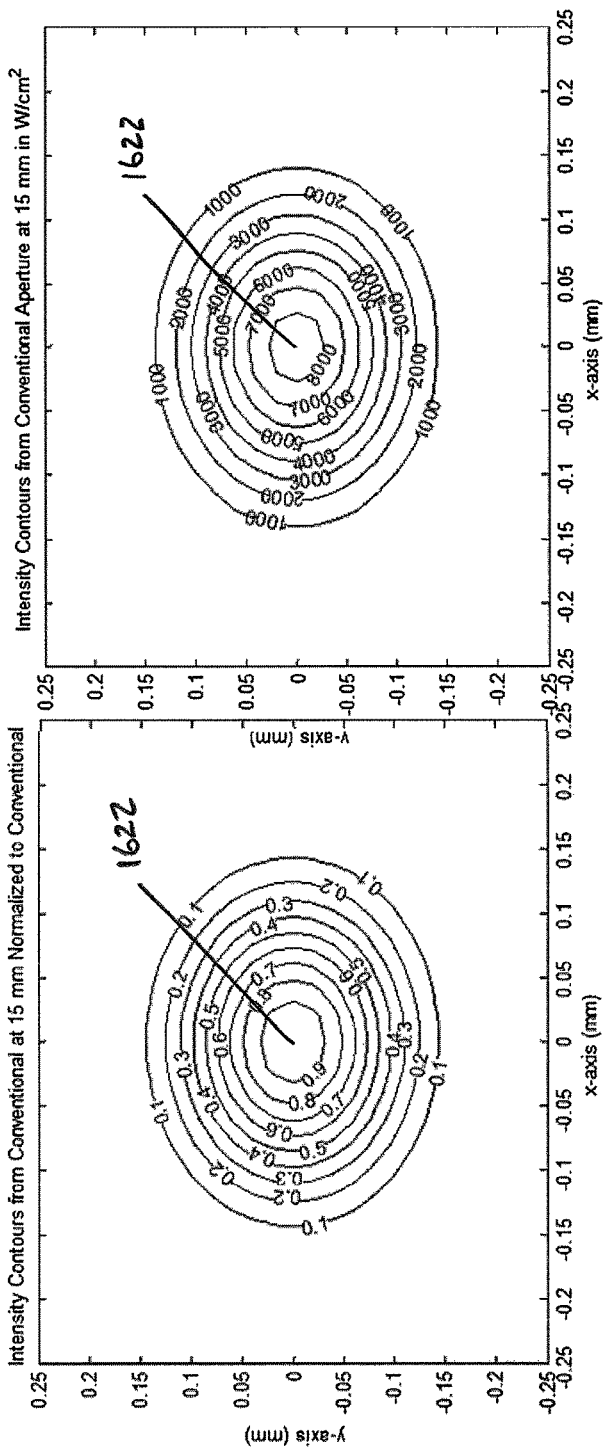

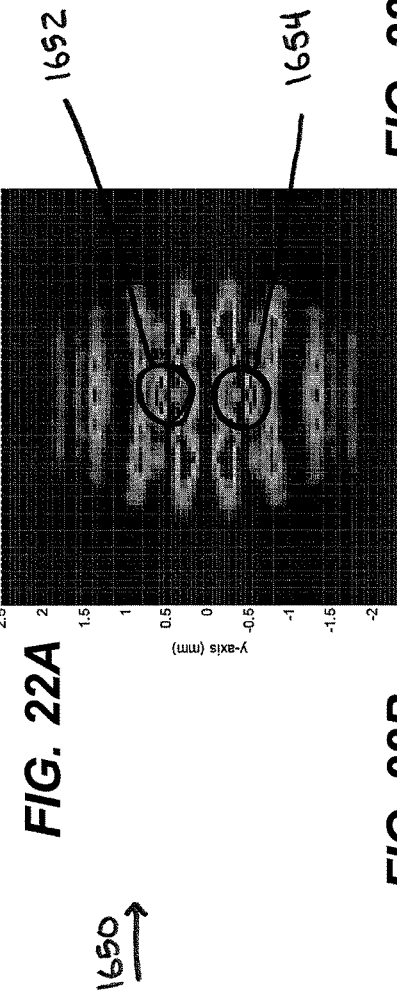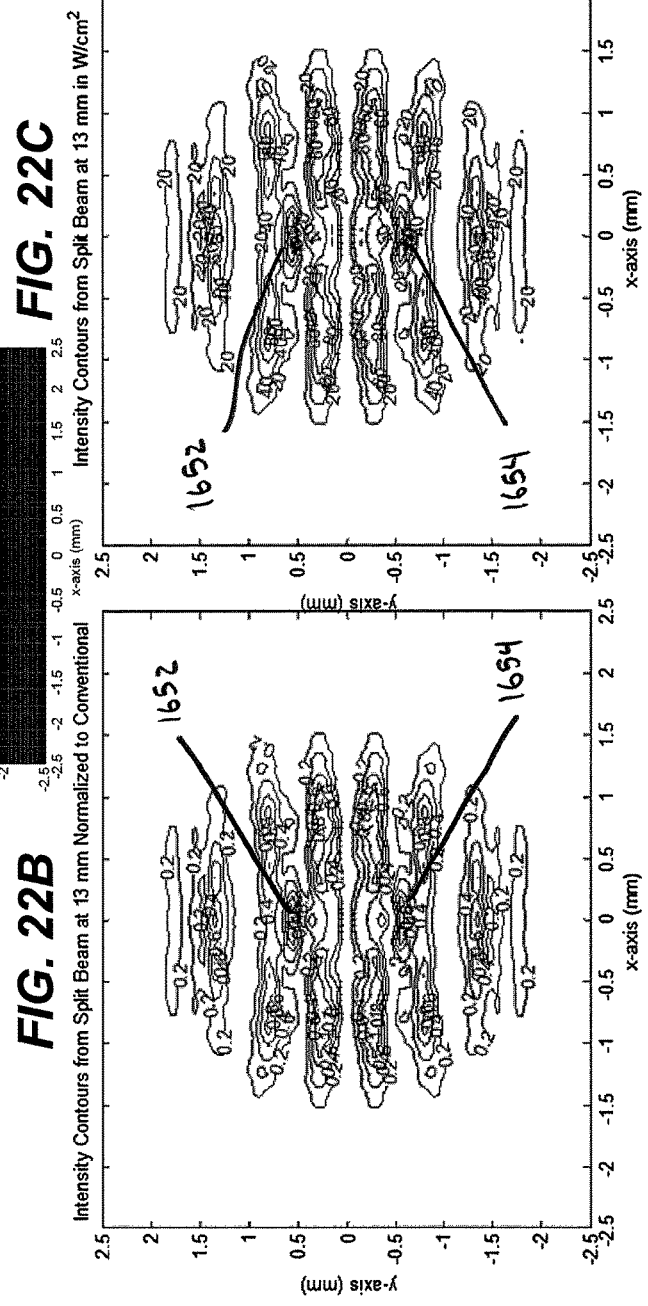
FIG. 22A
FIG. 22B
FIG. 22C

| STATE | TIME | APERTURE GROUP | | | | | | | |
|---|---|---|---|---|---|---|---|---|---|
| | | A | B | C | D | E | F | G | H |
| S1 | T1 | +1 | +1 | +1 | +1 | -1 | -1 | -1 | -1 |
| S2 | T2 | -1 | +1 | +1 | +1 | +1 | -1 | -1 | -1 |
| S3 | T3 | -1 | -1 | +1 | +1 | +1 | +1 | -1 | -1 |
| S4 | T4 | -1 | -1 | -1 | +1 | +1 | +1 | +1 | -1 |
| S5 | T5 | -1 | +1 | -1 | -1 | -1 | +1 | +1 | +1 |
| S6 | T6 | +1 | +1 | +1 | -1 | -1 | -1 | +1 | +1 |
| S7 | T7 | +1 | +1 | +1 | +1 | -1 | -1 | -1 | +1 |
| S8 | T8 | +1 | -1 | -1 | +1 | +1 | +1 | -1 | -1 |
| S1 | T9 | -1 | -1 | -1 | -1 | +1 | +1 | +1 | -1 |
| S2 | T10 | -1 | +1 | -1 | -1 | -1 | +1 | +1 | -1 |
| S3 | T11 | -1 | +1 | +1 | +1 | +1 | -1 | -1 | +1 |
| S4 | T12 | +1 | -1 | -1 | +1 | +1 | +1 | +1 | +1 |
| S5 | T13 | +1 | +1 | +1 | -1 | -1 | -1 | +1 | +1 |
| S6 | T14 | +1 | +1 | +1 | +1 | -1 | -1 | +1 | +1 |
| S7 | T15 | . | . | . | . | . | . | . | . |
| S8 | T16 | . | . | . | . | . | . | . | . |
| . | . | . | . | . | . | . | . | . | . |
| Sn | Tn | TBD | TBD | TBD | TBD | TBD | TBD | TBD | TBD |

| STATE | TIME | APERTURE GROUP ||||||||
|---|---|---|---|---|---|---|---|---|---|
| | | A | B | C | D | E | F | G | H |
| S1 | T1 | +1 | 0 | -1 | 0 | +1 | 0 | -1 | 0 |
| S2 | T2 | 0 | +1 | 0 | -1 | 0 | +1 | 0 | -1 |
| S3 | T3 | -1 | 0 | +1 | 0 | -1 | 0 | +1 | 0 |
| S4 | T4 | 0 | -1 | 0 | +1 | 0 | -1 | 0 | +1 |
| S1 | T5 | +1 | 0 | -1 | 0 | +1 | 0 | -1 | 0 |
| S2 | T6 | 0 | +1 | 0 | -1 | 0 | +1 | 0 | -1 |
| S3 | T7 | -1 | 0 | +1 | 0 | -1 | 0 | +1 | 0 |
| S4 | T8 | 0 | -1 | 0 | +1 | 0 | -1 | 0 | +1 |
| S1 | T9 | +1 | 0 | -1 | 0 | +1 | 0 | -1 | 0 |
| S2 | T10 | 0 | +1 | 0 | -1 | 0 | +1 | 0 | -1 |
| S3 | T11 | -1 | 0 | +1 | 0 | -1 | 0 | +1 | 0 |
| S4 | T12 | 0 | -1 | 0 | +1 | 0 | -1 | 0 | +1 |
| S1 | T13 | +1 | 0 | -1 | 0 | +1 | 0 | -1 | 0 |
| S2 | T14 | 0 | +1 | 0 | -1 | 0 | +1 | 0 | -1 |
| S3 | T15 | -1 | 0 | +1 | 0 | -1 | 0 | +1 | 0 |
| S4 | T16 | 0 | -1 | 0 | +1 | 0 | -1 | 0 | +1 |
| . | . | . | . | . | . | . | . | . | . |
| . | . | . | . | . | . | . | . | . | . |
| . | . | . | . | . | . | . | . | . | . |
| Sn | Tn | TBD | TBD | TBD | TBD | TBD | TBD | TBD | TBD |

| STATE | TIME | APERTURE GROUP ||||||||
| | | A | B | C | D | E | F | G | H |
|---|---|---|---|---|---|---|---|---|---|
| S1 | T1 | +0.5 | +1 | +1 | +0.5 | -0.5 | -1 | -1 | -0.5 |
| S2 | T2 | -0.5 | +0.5 | +1 | +1 | +0.5 | -0.5 | -1 | -1 |
| S3 | T3 | -1 | -0.5 | +0.5 | +1 | +1 | +0.5 | -0.5 | -1 |
| S4 | T4 | -1 | -1 | -0.5 | +0.5 | +1 | +1 | +0.5 | -0.5 |
| S5 | T5 | -0.5 | -1 | -1 | -0.5 | +0.5 | +1 | +1 | +0.5 |
| S6 | T6 | +0.5 | -0.5 | -1 | -1 | -0.5 | +0.5 | +1 | +1 |
| S7 | T7 | +1 | +0.5 | -0.5 | -1 | -1 | -0.5 | +0.5 | +1 |
| S8 | T8 | +1 | +1 | +0.5 | -0.5 | -1 | -1 | -0.5 | +0.5 |
| S1 | T9 | +0.5 | +1 | +1 | +0.5 | -0.5 | -1 | -1 | -0.5 |
| S2 | T10 | -0.5 | +0.5 | +1 | +1 | +0.5 | -0.5 | -1 | -1 |
| S3 | T11 | -1 | -0.5 | +0.5 | +1 | +1 | +0.5 | -0.5 | -1 |
| S4 | T12 | -1 | -1 | -0.5 | +0.5 | +1 | +1 | +0.5 | -0.5 |
| S5 | T13 | -0.5 | -1 | -1 | -0.5 | +0.5 | +1 | +1 | +0.5 |
| S6 | T14 | +0.5 | -0.5 | -1 | -1 | -0.5 | +0.5 | +1 | +1 |
| S7 | T15 | +1 | +0.5 | -0.5 | -1 | -1 | -0.5 | +0.5 | +1 |
| S8 | T16 | +1 | +1 | +0.5 | -0.5 | -1 | -1 | -0.5 | +0.5 |
| . | . | . | . | . | . | . | . | . | . |
| . | . | . | . | . | . | . | . | . | . |
| . | . | . | . | . | . | . | . | . | . |
| Sn | Tn | TBD | TBD | TBD | TBD | TBD | TBD | TBD | TBD |

*FIG. 29B*

DEVICES AND METHODS FOR MULTI-FOCUS ULTRASOUND THERAPY

CROSS-REFERENCE TO RELATED APPLICATIONS

This application claims the benefit of priority from U.S. Provisional Application No. 61/774,785 filed Mar. 8, 2013, which is incorporated in its entirety by reference, herein. Any and all priority claims identified in the Application Data Sheet, or any correction thereto, are hereby incorporated by reference under 37 CFR 1.57.

FIELD

Several embodiments of the present invention generally relate to noninvasive energy-based treatments to achieve cosmetic effects. For example, some embodiments generally relate to devices, systems and methods for providing multiple ultrasound treatment points or focus zones for performing various treatment and/or imaging procedures safely and effectively. Some embodiments relate to splitting an ultrasound therapy beam to two, three, four, or more focal zones for performing various treatment and/or imaging procedures with modulated and/or multiphasing. Some embodiments relate to splitting an ultrasound therapy beam to two, three, four, or more focal zones for performing various treatment and/or imaging procedures with poling techniques. Devices and methods of directing ultrasound therapy to multiple focus points in cosmetic and/or medical procedures are provided in several embodiments.

DESCRIPTION OF THE RELATED ART

Many cosmetic procedures involve invasive procedures that may require invasive surgery. Patients not only have to endure weeks of recovery time, but also are frequently required to undergo risky anesthetic procedures for aesthetic treatments.

SUMMARY

Although energy-based treatments have been disclosed for cosmetic and medical purposes, no procedures are known to Applicant, other that Applicant's own work, that successfully achieve an aesthetic effect using targeted and precise ultrasound to cause a visible and effective cosmetic result via a thermal pathway by splitting an ultrasound therapy beam to two, three, four, or more focal zones for performing various treatment and/or imaging procedures.

In several embodiments disclosed herein, non-invasive ultrasound is used to achieve one or more of the following effects: a face lift, a brow lift, a chin lift, an eye treatment, a wrinkle reduction, a scar reduction, a burn treatment, a tattoo removal, a vein removal, a vein reduction, a treatment on a sweat gland, a treatment of hyperhidrosis, a sun spot removal, an acne treatment, a pimple reduction. Treatment of the décolletage is provided in several embodiments. In another embodiment, the device may be used on adipose tissue (e.g., fat). In another embodiment the system, device and/or method may be applied in the genital area (e.g., vaginal rejuvenation and/or vaginal tightening, such as for tightening the supportive tissue of the vagina).

In accordance with various embodiments, a cosmetic ultrasound treatment system and/or method can non-invasively produce single or multiple cosmetic treatment zones and/or thermal coagulation points where ultrasound is focused in one or more locations in a region of treatment in tissue under a skin surface. Some systems and methods provide cosmetic treatment at different locations in tissue, such as at different depths, heights, widths, and/or positions. In one embodiment, a method and system comprise a multiple depth transducer system configured for providing ultrasound treatment to more than one region of interest, such as between at least two of a deep treatment region of interest, a superficial region of interest, and/or a subcutaneous region of interest. In one embodiment, a method and system comprise a transducer system configured for providing ultrasound treatment to more than one region of interest, such as between at least two points in various locations (e.g., at a fixed or variable depth, height, width, orientation, etc.) in a region of interest in tissue. Some embodiments can split a beam to focus at two, three, four, or more focal points (e.g., multiple focal points, multi-focal points) for cosmetic treatment zones and/or for imaging in a region of interest in tissue. Position of the focal points can be positioned axially, laterally, or otherwise within the tissue. Some embodiments can be configured for spatial control, such as by the location of a focus point, changing the distance from a transducer to a reflecting surface, and/or changing the angles of energy focused or unfocused to the region of interest, and/or configured for temporal control, such as by controlling changes in the frequency, drive amplitude and timing of the transducer. In some embodiments the position of multiple treatment zones or focal points with poling, phasic poling, biphasic poling, and/or multi-phasic poling. In some embodiments the position of multiple treatment zones or focal points with phasing, such as in one embodiment, electrical phasing. As a result, changes in the location of the treatment region, the number, shape, size and/or volume of treatment zones or lesions in a region of interest, as well as the thermal conditions, can be dynamically controlled over time.

In accordance with various embodiments, a cosmetic ultrasound treatment system and/or method can create multiple cosmetic treatment zones using one or more of phase modulation, poling, nonlinear acoustics, and/or Fourier transforms to create any spatial periodic pattern with one or multiple ultrasound portions. In one embodiment, a system simultaneously or sequentially delivers single or multiple treatment zones using poling at a ceramic level. In one embodiment, a poling pattern is function of focal depth and frequency, and the use of odd or even functions. In one embodiment, a process can be used in two or more dimensions to create any spatial periodic pattern. In one embodiment, an ultrasound beam is split axially and laterally to significantly reduce treatment time through the use of non-linear acoustics and Fourier transforms. In one embodiment, modulation from a system and amplitude modulation from a ceramic or a transducer can be used to place multiple treatments zones in tissue, either sequentially or simultaneously.

In one embodiment, an aesthetic imaging and treatment system includes an ultrasonic probe that includes an ultrasound transducer configured to apply ultrasonic therapy to tissue at a plurality of locations at a focal depth with at least one of the group consisting of amplitude modulation poling and phase shifting. In one embodiment, the system includes a control module coupled to the ultrasonic probe for controlling the ultrasound transducer.

In various embodiments, the plurality of locations are positioned in a substantially linear sequence within a cosmetic treatment zone. In one embodiment, a first set of locations is positioned within a first cosmetic treatment zone and a second set of locations is positioned within a second cosmetic treatment zone, the first zone being different from the second zone. In one embodiment, the first cosmetic treatment zone includes a substantially linear sequence of the first set of locations and the second cosmetic treatment zone includes a substantially linear sequence of the second set of locations. In one embodiment, the ultrasound transducer is configured to apply ultrasonic therapy using amplitude modulation whereby a plurality of portions of the ultrasound transducer are configured to emit ultrasonic therapy at a plurality of amplitudes of acoustic intensity, wherein a first amplitude is different than a second amplitude. In one embodiment, the ultrasound transducer is configured to apply ultrasonic therapy phase shifting whereby a plurality of portions of the ultrasound transducer are configured to emit ultrasonic therapy at a plurality of phases of acoustic intensity, wherein a first phase is different than a second phase. In one embodiment, the ultrasound transducer is configured to apply ultrasonic therapy using amplitude modulation whereby a plurality of portions of the ultrasound transducer are configured to emit ultrasonic therapy at a plurality of amplitudes of acoustic intensity, wherein a first amplitude is different than a second amplitude, and apply ultrasonic therapy phase shifting whereby a plurality of portions of the ultrasound transducer are configured to emit ultrasonic therapy at a plurality of phases of acoustic intensity, wherein a first phase is different than a second phase. In one embodiment, the plurality of phases includes discrete phase values. In one embodiment, the ultrasound transducer includes piezoelectric material and the plurality of portions of the ultrasound transducer are configured to create a plurality of corresponding piezoelectric material variations in response to an electric field applied to the ultrasound transducer. In one embodiment, the plurality of piezoelectric material variations include at least one of expansion of the piezoelectric material and contraction of the piezoelectric material. In one embodiment, at least one portion of the ultrasonic transducer is configured to emit ultrasonic therapy at two or more amplitudes of acoustic intensity, and wherein the amplitude of ultrasonic therapy emitted by the at least one portion of the piezoelectric varies over time. In one embodiment, the system also includes a movement mechanism configured to be programmed to provide variable spacing between the plurality of individual cosmetic treatment zones. In one embodiment, a sequence of individual cosmetic treatment zones has a treatment spacing in a range from about 0.01 mm to about 25 mm. In various embodiments, the ultrasonic treatment is at least one of a face lift, a brow lift, a chin lift, an eye treatment, a wrinkle reduction, a scar reduction, a burn treatment, a tattoo removal, a skin tightening, a vein removal, a vein reduction, a treatment on a sweat gland, a treatment of hyperhidrosis, a sun spot removal, a fat treatment, a vaginal rejuvenation, and an acne treatment. In one embodiment, the ultrasonic transducer is configured to provide an acoustic power of the ultrasonic therapy in a range of between about 1 W to about 100 W and a frequency of about 1 MHz to about 10 MHz to thermally heat the tissue to cause coagulation.

In one embodiment, an aesthetic imaging and treatment system for use in cosmetic treatment includes: an ultrasonic probe and a control module. The ultrasonic probe includes a first switch operably controlling an ultrasonic imaging function for providing an ultrasonic imaging, a second switch operably controlling an ultrasonic treatment function for providing an ultrasonic treatment, and a movement mechanism configured to direct ultrasonic treatment in at least one sequence of individual thermal cosmetic treatment zones. In one embodiment, the system also includes a transducer module. In one embodiment, the transducer module is configured for both ultrasonic imaging and ultrasonic treatment. In one embodiment, the transducer module is configured for coupling to the ultrasonic probe. In one embodiment, the transducer module includes an ultrasound transducer configured to apply ultrasonic therapy to tissue at a plurality of locations at a focal depth. In one embodiment, the transducer module is configured to be operably coupled to at least one of the first switch, the second switch and the movement mechanism. In one embodiment, the control module includes a processor and a display for controlling the transducer module.

In various embodiments, the plurality of locations are positioned in a substantially linear sequence within a cosmetic treatment zone. In one embodiment, a first set of locations is positioned within a first cosmetic treatment zone and a second set of locations is positioned within a second cosmetic treatment zone, the first zone being different from the second zone. In one embodiment, the first cosmetic treatment zone includes a substantially linear sequence of the first set of locations and the second cosmetic treatment zone includes a substantially linear sequence of the second set of locations. In one embodiment, the transducer module is configured to apply ultrasonic therapy using amplitude modulation whereby a plurality of portions of the transducer module are configured to emit ultrasonic therapy at a plurality of amplitudes of acoustic intensity, wherein a first amplitude is different than a second amplitude. In one embodiment, the transducer module is configured to apply ultrasonic therapy phase shifting whereby a plurality of portions of the transducer module are configured to emit ultrasonic therapy at a plurality of phases of acoustic intensity, wherein a first phase is different than a second phase. In one embodiment, the transducer module is configured to apply ultrasonic therapy using amplitude modulation whereby a plurality of portions of the transducer module are configured to emit ultrasonic therapy at a plurality of amplitudes of acoustic intensity, wherein a first amplitude is different than a second amplitude. In one embodiment, the transducer module is configured to apply ultrasonic therapy phase shifting whereby a plurality of portions of the transducer module are configured to emit ultrasonic therapy at a plurality of phases of acoustic intensity, wherein a first phase is different than a second phase. In one embodiment, the plurality of phases includes discrete phase values. In one embodiment, the transducer module is configured to the transducer module includes piezoelectric material and the plurality of portions of the transducer module are configured to create a plurality of corresponding piezoelectric material variations in response to an electric field applied to the transducer module. In one embodiment, the plurality of piezoelectric material variations include at least one of expansion of the material and contraction of the material. In one embodiment, at least one portion of the transducer module is configured to emit ultrasonic therapy at two or more amplitudes of acoustic intensity, and wherein the amplitude of ultrasonic therapy emitted by the at least one portion of the transducer module varies over time. In one embodiment, the movement mechanism is configured to be programmed to provide variable spacing between a plurality of individual thermal cosmetic treatment zones. In one embodiment, a sequence of individual thermal cosmetic treatment zones has a treatment spacing in a range from about 0.01 mm to about 25 mm. In one embodiment, the first and second switches include user operated buttons or keys. In one embodiment, at least one of the first switch and the second switch is activated by the control module. In one embodiment, the treatment function is at least one of a face lift, a brow lift, a chin lift, an eye treatment, a wrinkle reduction, a scar reduction, a burn treatment, a tattoo removal, a skin tightening, a vein removal, a vein reduction, a treatment on a sweat gland, a treatment of hyperhidrosis, a sun spot removal, a fat treatment, a vaginal rejuvenation, and an acne treatment. In one embodiment, the transducer module is configured to provide an acoustic power of the ultrasonic therapy in a range of between about 1 W to about 100 W and a frequency of about 1 MHz to about 10 MHz to thermally heat the tissue to cause coagulation.

In one embodiment, a treatment system includes a controlling device operably controlling an ultrasonic treatment function for providing an ultrasonic treatment and a hand wand configured to direct ultrasonic treatment in a sequence of individual thermal cosmetic treatment zones. In one embodiment, the hand wand includes a transducer configured to apply ultrasonic therapy to tissue at a location at a focal depth, the location positioned within a thermal cosmetic treatment zone, wherein the transducer is further configured to apply ultrasonic therapy to tissue at a plurality of locations at the focal depth.

In one embodiment, a method of performing a cosmetic procedure includes coupling a transducer module with an ultrasonic probe, wherein the ultrasonic probe includes a first switch to control acoustic imaging, wherein the ultrasonic probe includes a second switch to control acoustic therapy for causing a plurality of individual cosmetic treatment zones, wherein the ultrasonic probe includes a movement mechanism to provide desired spacing between the individual cosmetic treatment zones. In one embodiment, the method includes contacting the transducer module with a subject's skin surface. In one embodiment, the method includes activating the first switch on the ultrasonic probe to acoustically image, with the transducer module, a region below the skin surface. In one embodiment, the method includes activating the second switch on the ultrasonic probe to acoustically treat, with the transducer module, the region below the skin surface in a desired sequence of individual cosmetic treatment zones that is controlled by the movement mechanism, wherein the transducer module includes an ultrasound transducer configured to apply ultrasonic therapy to tissue at a plurality of locations at a focal depth.

In one embodiment, a treatment system includes a controlling device operably controlling an ultrasonic treatment function for providing an ultrasonic treatment, and a hand wand configured to direct ultrasonic treatment in a sequence of individual thermal cosmetic treatment zones. In one embodiment, the hand wand includes a transducer configured to apply ultrasonic therapy to tissue at a plurality of locations at a focal depth.

In one embodiment, the use of an aesthetic imaging and treatment system is for the non-invasive cosmetic treatment of skin.

In accordance with various embodiments, an aesthetic ultrasound treatment system for creating multiple focus points with an ultrasound transducer includes an ultrasonic probe comprising an ultrasound transducer configured to apply ultrasonic therapy to tissue at a plurality of locations at a focal depth with at least one of the group consisting of amplitude modulation poling and phase shifting, and a control module coupled to the ultrasonic probe for controlling the ultrasound transducer.

In one embodiment, the ultrasound transducer comprises a single ultrasound transduction element. In one embodiment, the plurality of locations are positioned in a substantially linear sequence within a cosmetic treatment zone. In one embodiment, a first set of locations is positioned within a first cosmetic treatment zone and a second set of locations is positioned within a second cosmetic treatment zone, the first zone being different from the second zone. In one embodiment, the first cosmetic treatment zone comprises a substantially linear sequence of the first set of locations and the second cosmetic treatment zone comprises a substantially linear sequence of the second set of locations.

In one embodiment, the ultrasound transducer is configured to apply ultrasonic therapy using amplitude modulation whereby a plurality of portions of the ultrasound transducer are configured to emit ultrasonic therapy at a plurality of amplitudes of acoustic intensity, wherein a first amplitude is different than a second amplitude. In one embodiment, the ultrasound transducer is configured to apply ultrasonic therapy phase shifting whereby a plurality of portions of the ultrasound transducer are configured to emit ultrasonic therapy at a plurality of phases of acoustic intensity, wherein a first phase is different than a second phase. In one embodiment, the ultrasound transducer is configured to apply ultrasonic therapy using amplitude modulation whereby a plurality of portions of the ultrasound transducer are configured to emit ultrasonic therapy at a plurality of amplitudes of acoustic intensity, wherein a first amplitude is different than a second amplitude, and apply ultrasonic therapy phase shifting whereby a plurality of portions of the ultrasound transducer are configured to emit ultrasonic therapy at a plurality of phases of acoustic intensity, wherein a first phase is different than a second phase. In one embodiment, the plurality of phases comprises discrete phase values. In one embodiment, the ultrasound transducer comprises piezoelectric material and the plurality of portions of the ultrasound transducer are configured to create a plurality of corresponding piezoelectric material variations in response to an electric field applied to the ultrasound transducer. In one embodiment, the plurality of piezoelectric material variations comprise at least one of expansion of the piezoelectric material and contraction of the piezoelectric material. In one embodiment, at least one portion of the ultrasonic transducer is configured to emit ultrasonic therapy at two or more amplitudes of acoustic intensity, and wherein the amplitude of ultrasonic therapy emitted by the at least one portion of the piezoelectric varies over time.

In one embodiment, the system further includes a movement mechanism configured to be programmed to provide variable spacing between the plurality of individual cosmetic treatment zones. In one embodiment, a sequence of individual cosmetic treatment zones has a treatment spacing in a range from about 0.01 mm to about 25 mm.

In various embodiments, the ultrasonic treatment is at least one of a face lift, a brow lift, a chin lift, an eye treatment, a wrinkle reduction, a scar reduction, a burn treatment, a tattoo removal, a skin tightening, a vein removal, a vein reduction, a treatment on a sweat gland, a treatment of hyperhidrosis, a sun spot removal, a fat treatment, a vaginal rejuvenation, and an acne treatment.

In one embodiment, the ultrasonic transducer is configured to provide an acoustic power of the ultrasonic therapy in a range of between about 1 W to about 100 W and a frequency of about 1 MHz to about 10 MHz to thermally heat the tissue to cause coagulation.

In accordance with various embodiments, an aesthetic treatment system for use in cosmetic treatment for creating multiple focal points with an ultrasound transducer includes an ultrasonic probe that includes a first switch operably controlling an ultrasonic imaging function for providing an ultrasonic imaging, a second switch operably controlling an ultrasonic treatment function for providing an ultrasonic treatment, and a movement mechanism configured to direct ultrasonic treatment in at least one sequence of individual thermal cosmetic treatment zones. The system includes a transducer module configured to apply ultrasonic therapy with at least one of the group consisting of amplitude modulation poling and phase shifting, wherein the transducer module is configured for both ultrasonic imaging and ultrasonic treatment, wherein the transducer module is configured for coupling to the ultrasonic probe, wherein the transducer module comprises an ultrasound transducer configured to apply ultrasonic therapy to tissue at a plurality of locations at a focal depth, wherein the transducer module is configured to be operably coupled to at least one of the first switch, the second switch and the movement mechanism, and a control module, wherein the control module comprises a processor and a display for controlling the transducer module.

In one embodiment, the plurality of locations are positioned in a substantially linear sequence within a cosmetic treatment zone. In one embodiment, a first set of locations is positioned within a first cosmetic treatment zone and a second set of locations is positioned within a second cosmetic treatment zone, the first zone being different from the second zone. In one embodiment, the first cosmetic treatment zone comprises a substantially linear sequence of the first set of locations and the second cosmetic treatment zone comprises a substantially linear sequence of the second set of locations.

In one embodiment, the transducer module is configured to apply ultrasonic therapy using amplitude modulation whereby a plurality of portions of the transducer module are configured to emit ultrasonic therapy at a plurality of amplitudes of acoustic intensity, wherein a first amplitude is different than a second amplitude. In one embodiment, the transducer module is configured to apply ultrasonic therapy phase shifting whereby a plurality of portions of the transducer module are configured to emit ultrasonic therapy at a plurality of phases of acoustic intensity, wherein a first phase is different than a second phase. In one embodiment, the transducer module is configured to apply ultrasonic therapy using amplitude modulation whereby a plurality of portions of the transducer module are configured to emit ultrasonic therapy at a plurality of amplitudes of acoustic intensity, wherein a first amplitude is different than a second amplitude, and apply ultrasonic therapy phase shifting whereby a plurality of portions of the transducer module are configured to emit ultrasonic therapy at a plurality of phases of acoustic intensity, wherein a first phase is different than a second phase. In one embodiment, the plurality of phases comprises discrete phase values. In one embodiment, the transducer module comprises piezoelectric material and the plurality of portions of the transducer module are configured to create a plurality of corresponding piezoelectric material variations in response to an electric field applied to the transducer module. In one embodiment, the plurality of piezoelectric material variations comprise at least one of expansion of the material and contraction of the material. In one embodiment, at least one portion of the transducer module is configured to emit ultrasonic therapy at two or more amplitudes of acoustic intensity, and wherein the amplitude of ultrasonic therapy emitted by the at least one portion of the transducer module varies over time.

In one embodiment, the movement mechanism is configured to be programmed to provide variable spacing between a plurality of individual thermal cosmetic treatment zones.

In one embodiment, a sequence of individual thermal cosmetic treatment zones has a treatment spacing in a range from about 0.01 mm to about 25 mm. In one embodiment, the first and second switches comprises user operated buttons or keys. In one embodiment, at least one of the first switch and the second switch is activated by the control module.

In one embodiment, the treatment function is at least one of a face lift, a brow lift, a chin lift, an eye treatment, a wrinkle reduction, a scar reduction, a burn treatment, a tattoo removal, a skin tightening, a vein removal, a vein reduction, a treatment on a sweat gland, a treatment of hyperhidrosis, a sun spot removal, a fat treatment, a vaginal rejuvenation, and an acne treatment.

In one embodiment, the transducer module is configured to provide an acoustic power of the ultrasonic therapy in a range of between about 1 W to about 100 W and a frequency of about 1 MHz to about 10 MHz to thermally heat the tissue to cause coagulation.

In accordance with various embodiments, a treatment system includes a controlling device operably controlling an ultrasonic treatment function for providing an ultrasonic treatment, and a hand wand configured to direct ultrasonic treatment in a sequence of individual thermal cosmetic treatment zones. The hand wand includes a transducer configured to apply ultrasonic therapy to tissue at a location at a focal depth, the location positioned within a thermal cosmetic treatment zone, wherein the transducer is further configured to apply ultrasonic therapy to tissue at a plurality of locations at the focal depth.

In accordance with various embodiments, a method of performing a noninvasive cosmetic procedure on the skin by creating multiple focal points with a single transducer includes coupling a transducer module with an ultrasonic probe, wherein the ultrasonic probe comprises a first switch to control acoustic imaging, wherein the ultrasonic probe comprises a second switch to control acoustic therapy for causing a plurality of individual cosmetic treatment zones, wherein the ultrasonic probe comprises a movement mechanism to provide desired spacing between the individual cosmetic treatment zones, contacting the transducer module with a subject's skin surface, activating the first switch on the ultrasonic probe to acoustically image, with the transducer module, a region below the skin surface, and activating the second switch on the ultrasonic probe to acoustically treat, with the transducer module, the region below the skin surface in a desired sequence of individual cosmetic treatment zones that is controlled by the movement mechanism, wherein the transducer module comprises a single ultrasound transducer configured to apply ultrasonic therapy to tissue at a plurality of locations at a focal depth.

In accordance with various embodiments, an aesthetic treatment system for creating multiple focal points in tissue with an ultrasound transducer includes a controlling device operably controlling an ultrasonic treatment function for providing an ultrasonic treatment, and a hand wand configured to direct ultrasonic treatment in a sequence of individual thermal cosmetic treatment zones. The hand wand includes a transducer configured to apply ultrasonic therapy to tissue at a plurality of locations at a focal depth. In accordance with various embodiments, the use of an aesthetic treatment system is for the non-invasive cosmetic treatment of skin.

In accordance with various embodiments, an aesthetic ultrasound treatment system for creating multiple focus points with an ultrasound transducer includes an ultrasonic probe comprising an ultrasound transducer configured to apply ultrasonic therapy to tissue at a plurality of locations at a focal depth with at least one of the group consisting of amplitude modulation poling and phase shifting, and a control module coupled to the ultrasonic probe for controlling the ultrasound transducer. In one embodiment, the ultrasound transducer is configured to apply ultrasonic therapy using amplitude modulation whereby a plurality of portions of the ultrasound transducer are configured to emit ultrasonic therapy at a plurality of amplitudes of acoustic intensity, wherein a first amplitude is different than a second amplitude. In one embodiment, the ultrasound transducer is configured to apply ultrasonic therapy phase shifting whereby a plurality of portions of the ultrasound transducer are configured to emit ultrasonic therapy at a plurality of phases of acoustic intensity, wherein a first phase is different than a second phase. In one embodiment, the ultrasound transducer is configured to apply ultrasonic therapy using amplitude modulation whereby a plurality of portions of the ultrasound transducer are configured to emit ultrasonic therapy at a plurality of amplitudes of acoustic intensity, wherein a first amplitude is different than a second amplitude, and apply ultrasonic therapy phase shifting whereby a plurality of portions of the ultrasound transducer are configured to emit ultrasonic therapy at a plurality of phases of acoustic intensity, wherein a first phase is different than a second phase. In one embodiment, the plurality of phases comprises discrete phase values. In one embodiment, the ultrasound transducer comprises piezoelectric material and the plurality of portions of the ultrasound transducer are configured to create a plurality of corresponding piezoelectric material variations in response to an electric field applied to the ultrasound transducer. In one embodiment, the plurality of piezoelectric material variations comprise at least one of expansion of the piezoelectric material and contraction of the piezoelectric material. In one embodiment, at least one portion of the ultrasonic transducer is configured to emit ultrasonic therapy at two or more amplitudes of acoustic intensity, and wherein the amplitude of ultrasonic therapy emitted by the at least one portion of the piezoelectric varies over time. In various embodiments, the ultrasonic treatment is at least one of a face lift, a brow lift, a chin lift, an eye treatment, a wrinkle reduction, a scar reduction, a burn treatment, a tattoo removal, a skin tightening, a vein removal, a vein reduction, a treatment on a sweat gland, a treatment of hyperhidrosis, a sun spot removal, a fat treatment, a vaginal rejuvenation, and an acne treatment.

In accordance with various embodiments, an aesthetic treatment system for use in cosmetic treatment for creating multiple focal points with an ultrasound transducer includes an ultrasonic probe that includes a first switch operably controlling an ultrasonic imaging function for providing an ultrasonic imaging, a second switch operably controlling an ultrasonic treatment function for providing an ultrasonic treatment, and a movement mechanism configured to direct ultrasonic treatment in at least one sequence of individual thermal cosmetic treatment zones. The system includes a transducer module configured to apply ultrasonic therapy with at least one of the group consisting of amplitude modulation poling and phase shifting, wherein the transducer module is configured for both ultrasonic imaging and ultrasonic treatment, wherein the transducer module is configured for coupling to the ultrasonic probe, wherein the transducer module comprises an ultrasound transducer configured to apply ultrasonic therapy to tissue at a plurality of locations at a focal depth, wherein the transducer module is configured to be operably coupled to at least one of the first switch, the second switch and the movement mechanism, and a control module, wherein the control module comprises a processor and a display for controlling the transducer module. In one embodiment, the ultrasound module comprises a single ultrasound transducer. In one embodiment, the ultrasound module comprises a single ultrasound transduction element. In one embodiment, the ultrasound module comprises a single ultrasound transducer comprising a single transduction element. In one embodiment, the plurality of locations are positioned in a substantially linear sequence within a cosmetic treatment zone. In one embodiment, a first set of locations is positioned within a first cosmetic treatment zone and a second set of locations is positioned within a second cosmetic treatment zone, the first zone being different from the second zone. In one embodiment, the first cosmetic treatment zone comprises a substantially linear sequence of the first set of locations and the second cosmetic treatment zone comprises a substantially linear sequence of the second set of locations. In one embodiment, the transducer module is configured to apply ultrasonic therapy using amplitude modulation whereby a plurality of portions of the transducer module are configured to emit ultrasonic therapy at a plurality of amplitudes of acoustic intensity, wherein a first amplitude is different than a second amplitude. In one embodiment, the transducer module is configured to apply ultrasonic therapy phase shifting whereby a plurality of portions of the transducer module are configured to emit ultrasonic therapy at a plurality of phases of acoustic intensity, wherein a first phase is different than a second phase. In one embodiment, the transducer module is configured to apply ultrasonic therapy using amplitude modulation whereby a plurality of portions of the transducer module are configured to emit ultrasonic therapy at a plurality of amplitudes of acoustic intensity, wherein a first amplitude is different than a second amplitude, and apply ultrasonic therapy phase shifting whereby a plurality of portions of the transducer module are configured to emit ultrasonic therapy at a plurality of phases of acoustic intensity, wherein a first phase is different than a second phase. In one embodiment, the plurality of phases comprises discrete phase values. In one embodiment, the transducer module comprises piezoelectric material and the plurality of portions of the transducer module are configured to create a plurality of corresponding piezoelectric material variations in response to an electric field applied to the transducer module. In one embodiment, the plurality of piezoelectric material variations comprise at least one of expansion of the material and contraction of the material. In one embodiment, at least one portion of the transducer module is configured to emit ultrasonic therapy at two or more amplitudes of acoustic intensity, and wherein the amplitude of ultrasonic therapy emitted by the at least one portion of the transducer module varies over time. In one embodiment, the movement mechanism is configured to be programmed to provide variable spacing between a plurality of individual thermal cosmetic treatment zones. In one embodiment, a sequence of individual thermal cosmetic treatment zones has a treatment spacing in a range from about 0.01 mm to about 25 mm. In one embodiment, the first and second switches comprises user operated buttons or keys. In one embodiment, at least one of the first switch and the second switch is activated by the control module. In one embodiment, the treatment function is at least one of a face lift, a brow lift, a chin lift, an eye treatment, a wrinkle reduction, a scar reduction, a burn treatment, a tattoo removal, a skin tightening, a vein removal, a vein reduction, a treatment on a sweat gland, a treatment of hyperhidrosis, a sun spot removal, a fat treatment, a vaginal rejuvenation, and an acne treatment.

In one embodiment, an aesthetic imaging and treatment system for use in cosmetic treatment includes an ultrasonic probe configured for ultrasonic imaging and ultrasonic treatment of tissue at a plurality of locations at a focal depth. In one embodiment, the probe includes a transducer module configured for coupling to the ultrasonic probe, wherein the transducer module comprises an ultrasound transducer configured to apply an ultrasonic therapy to tissue at the plurality of locations at the focal depth. In one embodiment, a first switch operably controlling an ultrasonic imaging function for providing an ultrasonic imaging. In one embodiment, a second switch operably controlling an ultrasonic treatment function for providing the ultrasonic therapy. In one embodiment, a movement mechanism is configured to direct ultrasonic treatment in at least one sequence of individual thermal cosmetic treatment zones, wherein the transducer module is configured to be operably coupled to at least one of the first switch, the second switch and the movement mechanism. In one embodiment, the control module comprises a processor and a display for controlling the transducer module. In one embodiment, the module is removable. For example, some non-limiting embodiments transducers can be configured for a tissue depth of 1.5 mm, 3 mm, 4.5 mm, 6 mm, less than 3 mm, between 1.5 mm and 3 mm, between 1.5 mm and 4.5 mm, more than more than 4.5 mm, more than 6 mm, and anywhere in the ranges of 0.1 mm-3 mm, 0.1 mm-4.5 mm, 0.1 mm-25 mm, 0.1 mm-100 mm, and any depths therein.

In various embodiments, the plurality of locations are positioned in a substantially linear sequence within a cosmetic treatment zone. In one embodiment, a first set of locations is positioned within a first cosmetic treatment zone and a second set of locations is positioned within a second cosmetic treatment zone, the first zone being different from the second zone. In one embodiment, the first cosmetic treatment zone comprises a substantially linear sequence of the first set of locations and the second cosmetic treatment zone comprises a substantially linear sequence of the second set of locations. In one embodiment, the transducer module is configured to apply ultrasonic therapy using amplitude modulation whereby the transducer module comprises a plurality of portions that are configured to emit ultrasonic therapy at a plurality of amplitudes of acoustic intensity, wherein a first amplitude is different than a second amplitude. In one embodiment, the transducer module is configured to apply ultrasonic therapy phase shifting whereby the transducer module comprises a plurality of portions that are configured to emit ultrasonic therapy at a plurality of phases of acoustic intensity, wherein a first phase is different than a second phase.

In one embodiment, a movement mechanism is a motion mechanism. In various embodiments, a movement mechanism is configured to move a transducer within a module or a probe. In one embodiment, a transducer is held by a transducer holder. In one embodiment, the transducer holder includes a sleeve which is moved along motion constraining bearings, such as linear bearings, namely, a bar (or shaft) to ensure a repeatable linear movement of the transducer. In one embodiment, sleeve is a spline bushing which prevents rotation about a spline shaft, but any guide to maintain the path of motion is appropriate.

In one embodiment, the transducer holder is driven by a motion mechanism, which may be located in a hand wand or in a module, or in a probe. In one embodiment, a motion mechanism 400 includes any one or more of a scotch yoke, a movement member, and a magnetic coupling. In one embodiment, the magnetic coupling helps move the transducer. One benefit of a motion mechanism is that it provides for a more efficient, accurate and precise use of an ultrasound transducer, for imaging and/or therapy purposes. One advantage this type of motion mechanism has over conventional fixed arrays of multiple transducers fixed in space in a housing is that the fixed arrays are a fixed distance apart.

By placing transducer on a track (e.g., such as a linear track) under controller control, embodiments of the system and device provide for adaptability and flexibility in addition to efficiency, accuracy and precision. Real time and near real time adjustments can be made to imaging and treatment positioning along the controlled motion by the motion mechanism. In addition to the ability to select nearly any resolution based on the incremental adjustments made possible by the motion mechanism, adjustments can be made if imaging detects abnormalities or conditions meriting a change in treatment spacing and targeting. In one embodiment, one or more sensors may be included in the module. In one embodiment, one or more sensors may be included in the module to ensure that a mechanical coupling between the movement member and the transducer holder is indeed coupled. In one embodiment, an encoder may be positioned on top of the transducer holder and a sensor may be located in a portion of the module, or vice versa (swapped).

In various embodiments the sensor is a magnetic sensor, such as a giant magnetoresistive effect (GMR) or Hall Effect sensor, and the encoder a magnet, collection of magnets, or multi-pole magnetic strip. The sensor may be positioned as a transducer module home position. In one embodiment, the sensor is a contact pressure sensor. In one embodiment, the sensor is a contact pressure sensor on a surface of the device to sense the position of the device or the transducer on the patient. In various embodiments, the sensor can be used to map the position of the device or a component in the device in one, two, or threes dimensions. In one embodiment the sensor is configured to sense the position, angle, tilt, orientation, placement, elevation, or other relationship between the device (or a component therein) and the patient. In one embodiment, the sensor comprises an optical sensor. In one embodiment, the sensor comprises a roller ball sensor. In one embodiment, the sensor is configured to map a position in one, two and/or three dimensions to compute a distance between areas or lines of treatment on the skin or tissue on a patient.

Motion mechanism can be any motion mechanism that may be found to be useful for movement of the transducer. Other embodiments of motion mechanisms useful herein can include worm gears and the like. In various embodiments, the motion mechanism is located in a module 200. In various embodiments, the motion mechanism can provide for linear, rotational, multi-dimensional motion or actuation, and the motion can include any collection of points and/or orientations in space. Various embodiments for motion can be used in accordance with several embodiments, including but not limited to rectilinear, circular, elliptical, arc-like, spiral, a collection of one or more points in space, or any other 1-D, 2-D, or 3-D positional and attitudinal motional embodiments. The speed of the motion mechanism may be fixed or may be adjustably controlled by a user. One embodiment, a speed of the motion mechanism for an image sequence may be different than that for a treatment sequence. In one embodiment, the speed of the motion mechanism is controllable by a controller.

In various embodiments, the transducer module is configured to apply ultrasonic therapy using amplitude modulation whereby the transducer module comprises a plurality of portions that are configured to emit ultrasonic therapy at a plurality of amplitudes of acoustic intensity, wherein a first amplitude is different than a second amplitude, and apply ultrasonic therapy phase shifting whereby the transducer module comprises a plurality of portions that are configured to emit ultrasonic therapy at a plurality of phases of acoustic intensity, wherein a first phase is different than a second phase.

In one embodiment, the plurality of phases comprises discrete phase values. In one embodiment, the transducer module comprises piezoelectric material and the plurality of portions of the transducer module are configured to create a plurality of corresponding piezoelectric material variations in response to an electric field applied to the transducer module. In one embodiment, the plurality of piezoelectric material variations comprise at least one of expansion of the material and contraction of the material. In one embodiment, the transducer module comprises at least one portion that is configured to emit ultrasonic therapy at two or more amplitudes of acoustic intensity, and wherein the amplitude of ultrasonic therapy emitted by the at least one portion of the transducer module varies over time.

In one embodiment, the movement mechanism is configured to be programmed to provide variable spacing between a plurality of individual thermal cosmetic treatment zones. In one embodiment, a sequence of individual thermal cosmetic treatment zones has a treatment spacing in a range from about 0.01 mm to about 25 mm (e.g., 1 mm, 1.5 mm, 2 mm, 1-5 mm). In one embodiment, the first and second switches comprise user operated buttons or keys. In one embodiment, at least one of the first switch and the second switch is activated by the control module.

In various embodiments, the treatment function is at least one of a face lift, a brow lift, a chin lift, an eye treatment, a wrinkle reduction, a scar reduction, a burn treatment, a tattoo removal, a skin tightening, a vein removal, a vein reduction, a treatment on a sweat gland, a treatment of hyperhidrosis, a sun spot removal, a fat treatment, a vaginal rejuvenation, and an acne treatment. In one embodiment, the transducer module is configured to provide an acoustic power of the ultrasonic therapy in a range of between about 1 W to about 100 W (e.g., 5-40 W, 10-50 W, 25-35 W) and a frequency of about 1 MHz to about 10 MHz to thermally heat the tissue to cause coagulation. In one embodiment, the acoustic power can be from a range of 1 W to about 100 W in a frequency range from about 1 MHz to about 12 MHz (e.g., 4 MHz, 7 MHz, 10 MHz, 4-10 MHz), or from about 10 W to about 50 W at a frequency range from about 3 MHz to about 8 MHz. In one embodiment, the acoustic power and frequencies are about 40 W at about 4.3 MHz and about 30 W at about 7.5 MHz. An acoustic energy produced by this acoustic power can be between about 0.01 joule ("J") to about 10 J or about 2 J to about 5 J. In one embodiment, the acoustic energy is in a range less than about 3 J.

In various embodiments, a multi-focus ultrasound treatment system includes a controlling device operably controlling an ultrasonic treatment function for providing an ultrasonic treatment and a hand wand configured to direct ultrasonic treatment in a sequence of individual thermal cosmetic treatment zones. The hand wand includes a transducer configured to apply ultrasonic therapy to tissue at a location at a focal depth, the location positioned within a thermal cosmetic treatment zone, wherein the transducer is further configured to apply ultrasonic therapy to tissue simultaneously at a plurality of locations at the focal depth.

In various embodiments, an aesthetic imaging and multi-focus treatment system includes an ultrasonic probe comprising an ultrasound transducer configured to apply ultrasonic therapy to tissue at a plurality of locations at a focal depth with at least one of the group consisting of amplitude modulation poling and phase shifting, and a control module coupled to the ultrasonic probe for controlling the ultrasound transducer. In one embodiment, the plurality of locations are positioned in a substantially linear sequence within a cosmetic treatment zone. In one embodiment, a first set of locations is positioned within a first cosmetic treatment zone and a second set of locations is positioned within a second cosmetic treatment zone, the first zone being different from the second zone. In one embodiment, the first cosmetic treatment zone comprises a substantially linear sequence of the first set of locations and the second cosmetic treatment zone comprises a substantially linear sequence of the second set of locations. In one embodiment, the ultrasound transducer is configured to apply ultrasonic therapy using amplitude modulation whereby the ultrasound transducer comprises a plurality of portions that are configured to emit ultrasonic therapy at a plurality of amplitudes of acoustic intensity, wherein a first amplitude is different than a second amplitude. In one embodiment, the ultrasound transducer is configured to apply ultrasonic therapy phase shifting whereby the ultrasound transducer comprises a plurality of portions that are configured to emit ultrasonic therapy at a plurality of phases of acoustic intensity, wherein a first phase is different than a second phase. In one embodiment, the ultrasound transducer is configured to apply ultrasonic therapy using amplitude modulation whereby the ultrasound transducer comprises a plurality of portions that are configured to emit ultrasonic therapy at a plurality of amplitudes of acoustic intensity, wherein a first amplitude is different than a second amplitude, and apply ultrasonic therapy phase shifting whereby the ultrasound transducer comprises a plurality of portions that are configured to emit ultrasonic therapy at a plurality of phases of acoustic intensity, wherein a first phase is different than a second phase. In one embodiment, the plurality of phases comprises discrete phase values.

In one embodiment, the ultrasound transducer comprises piezoelectric material and the plurality of portions of the ultrasound transducer are configured to create a plurality of corresponding piezoelectric material variations in response to an electric field applied to the ultrasound transducer. In one embodiment, the plurality of piezoelectric material variations comprise at least one of expansion of the piezoelectric material and contraction of the piezoelectric material. In one embodiment, the ultrasonic transducer comprises at least one portion that is configured to emit ultrasonic therapy at two or more amplitudes of acoustic intensity, and wherein the amplitude of ultrasonic therapy emitted by the at least one portion of the piezoelectric varies over time. In one embodiment, the system also includes a movement mechanism configured to be programmed to provide variable spacing between the plurality of individual cosmetic treatment zones. In one embodiment, a sequence of individual cosmetic treatment zones has a treatment spacing in a range from about 0.01 mm to about 25 mm. In one embodiment, the ultrasonic treatment is at least one of a face lift, a brow lift, a chin lift, an eye treatment, a wrinkle reduction, a scar reduction, a burn treatment, a tattoo removal, a skin tightening, a vein removal, a vein reduction, a treatment on a sweat gland, a treatment of hyperhidrosis, a sun spot removal, a fat treatment, a vaginal rejuvenation, and an acne treatment. In one embodiment, the ultrasonic transducer is configured to provide an acoustic power of the ultrasonic therapy in a range of between about 1 W to about 100 W and a frequency of about 1 MHz to about 10 MHz to thermally heat the tissue to cause coagulation.

In various embodiments, a treatment system includes a controlling device operably controlling an ultrasonic treatment function for providing an ultrasonic treatment, and a hand wand configured to direct ultrasonic treatment in a sequence of individual thermal cosmetic treatment zones. In one embodiment, the hand wand includes a transducer configured to simultaneously apply ultrasonic therapy to tissue at a plurality of locations at a focal depth.

In various embodiments, a system of performing a cosmetic procedure that is not performed by a doctor, includes an ultrasonic probe comprising a transducer module. In one embodiment, the transducer module comprises an ultrasound transducer configured to apply ultrasonic therapy to tissue at a plurality of locations at a focal depth with at least one of the group consisting of amplitude modulation poling and phase shifting. In one embodiment, the ultrasonic probe comprises a first switch to control acoustic imaging, the ultrasonic probe comprises a second switch to control acoustic therapy for causing a plurality of individual cosmetic treatment zones, and the ultrasonic probe comprises a movement mechanism to provide desired spacing between the individual cosmetic treatment zones.

In various embodiments, aesthetic imaging and treatment system for use in cosmetic treatment, includes an ultrasonic probe. In one embodiment, a transducer module includes an ultrasound transducer configured to apply ultrasonic therapy through an aperture in an acoustically transparent member to form a thermal coagulation point (TCP) at a focal depth in tissue. In one embodiment, a first switch operably controls an ultrasonic imaging function for providing an ultrasonic imaging, a second switch operably controls an ultrasonic treatment function for providing an ultrasonic treatment, and a movement mechanism is configured to direct ultrasonic treatment in at least one sequence of individual thermal cosmetic treatment zones. In various embodiments, the transducer module is configured for both ultrasonic imaging and ultrasonic treatment, the transducer module is configured for coupling to the ultrasonic probe, the transducer module is configured to be operably coupled to at least one of the first switch, the second switch and the movement mechanism. In one embodiment, a control module comprises a processor and a display for controlling the transducer module.

In one embodiment, the plurality of locations are positioned in a substantially linear sequence within a cosmetic treatment zone. In one embodiment, a first set of locations is positioned within a first cosmetic treatment zone and a second set of locations is positioned within a second cosmetic treatment zone, the first zone being different from the second zone. In one embodiment, the first cosmetic treatment zone comprises a substantially linear sequence of the first set of locations and the second cosmetic treatment zone comprises a substantially linear sequence of the second set of locations. In one embodiment, the movement mechanism is configured to provide fixed spacing between a plurality of individual thermal cosmetic treatment zones. In one embodiment, a sequence of individual thermal cosmetic treatment zones has a treatment spacing in a range from about 0.01 mm to about 25 mm. In one embodiment, the first and second switches comprises user operated buttons or keys. In one embodiment, the treatment function is at least one of a face lift, a brow lift, a chin lift, an eye treatment, a wrinkle reduction, a scar reduction, a burn treatment, a tattoo removal, a skin tightening, a vein removal, a vein reduction, a treatment on a sweat gland, a treatment of hyperhidrosis, a sun spot removal, a fat treatment, a vaginal rejuvenation, and an acne treatment. In one embodiment, the transducer module is configured to provide an acoustic power of the ultrasonic therapy in a range of between about 1 W to about 100 W and a frequency of about 1 MHz to about 10 MHz to thermally heat the tissue to cause coagulation.

In various embodiments, a cosmetic treatment system includes a controlling device operably controlling an ultrasonic treatment function for providing an ultrasonic treatment to different depths below a skin surface, and a hand wand configured to direct ultrasonic treatment at two or more focal depths below the skin surface, the hand wand configured to connect at least two interchangeable transducer modules configured to apply the ultrasonic treatment to said two or more focal depths below the skin surface, wherein each of the transducer modules is configured to create one or more sequences of thermal coagulation points (TCPs).

In one embodiment, the system also includes an imaging transducer configured to provide images of at least one depth below the skin surface. In one embodiment, the system also includes a movement mechanism to place the sequence of individual discrete lesions in a linear sequence. In one embodiment, the transducer modules comprise at least one transducer module that is configured to provide ultrasound therapy in a range of between about 1 W to about 100 W and a frequency of about 1 MHz to about 10 MHz. In one embodiment, the transducer modules comprises one transducer module that is configured to provide therapy at a depth of 3 mm. In one embodiment, the transducer modules comprise one transducer module that is configured to provide therapy at a depth of 4.5 mm.

In one embodiment, the at least two interchangeable transducer modules comprise a first interchangeable transducer module that is configured to treat at a first focal depth below the skin surface with a first therapeutic transduction element, wherein the at least two interchangeable transducer modules comprise a second interchangeable transducer module that is configured to treat at a second focal depth below the skin surface with a second therapeutic transduction element, wherein the hand wand is configured to connect to one of the first interchangeable transducer module and the second interchangeable transducer module at a time, wherein the system further comprises a display to show a first image of the first focal depth below the skin surface and a second image of the second focal depth below the skin surface.

In one embodiment, the hand wand is configured to connect to one of the at least two interchangeable transducer modules at a time, the at least two interchangeable transducer modules comprise a first module that is configured to treat at a first focal depth below the skin surface with a single first ultrasound therapy element, and a second module that is configured to treat at a second focal depth below the skin surface with a single second ultrasound therapy element. In one embodiment, the creation of the one or more sequences of thermal coagulation points (TCPs) comprises the creation of multiple linear sequences of thermal coagulation points (TCPs).

In one embodiment, an imaging transducer is configured to provide images of at least one depth below the skin surface, wherein the individual thermal cosmetic treatment zones are individual discrete lesions, and further comprising a movement mechanism to place the sequence of individual discrete lesions in a linear sequence, wherein the transducer modules comprise at least one transducer module that is configured to provide ultrasound therapy in a range of between about 1 W to about 100 W and a frequency of about 1 MHz to about 10 MHz, wherein the transducer modules comprise one transducer module that is configured to provide therapy at a depth of 3 mm or 4.5 mm, and wherein the treatment function is at least one of a face lift, a brow lift, a chin lift, an eye treatment, a wrinkle reduction, a scar reduction, a burn treatment, a tattoo removal, a skin tightening, a vein removal, a vein reduction, a treatment on a sweat gland, a treatment of hyperhidrosis, a sun spot removal, a fat treatment, a vaginal rejuvenation, and an acne treatment.

In several of the embodiments described herein, the procedure is entirely cosmetic and not a medical act. For example, in one embodiment, the methods described herein need not be performed by a doctor, but at a spa or other aesthetic institute. In some embodiments, a system can be used for the non-invasive cosmetic treatment of skin.

The methods summarized above and set forth in further detail below describe certain actions taken by a practitioner; however, it should be understood that they can also include the instruction of those actions by another party. Thus, actions such as "coupling a transducer module with an ultrasonic probe" include "instructing the coupling of a transducer module with an ultrasonic probe."

Further, areas of applicability will become apparent from the description provided herein. It should be understood that the description and specific examples are intended for purposes of illustration only and are not intended to limit the scope of the embodiments disclosed herein.

BRIEF DESCRIPTION OF THE DRAWINGS

The drawings described herein are for illustration purposes only and are not intended to limit the scope of the present disclosure in any way. Embodiments of the present invention will become more fully understood from the detailed description and the accompanying drawings wherein:

FIGS. 19A-19C are plots of an intensity distribution before focus according to an embodiment of the present invention.

FIGS. 20A-20C are plots an intensity distribution at focus according to an embodiment of the present invention.

FIGS. 22A-22C are plots of an intensity distribution from an amplitude modulated aperture before focus according to an embodiment of the present invention.

FIG. 27B is a state transition table of the schematic of FIG. 27A according to an embodiment of the present invention.

FIG. 28B is a state transition table of the schematic of FIG. 28A according to an embodiment of the present invention.

FIG. 29B is a state transition table of the schematic of FIG. 29A according to an embodiment of the present invention.

DETAILED DESCRIPTION

Figure 1:
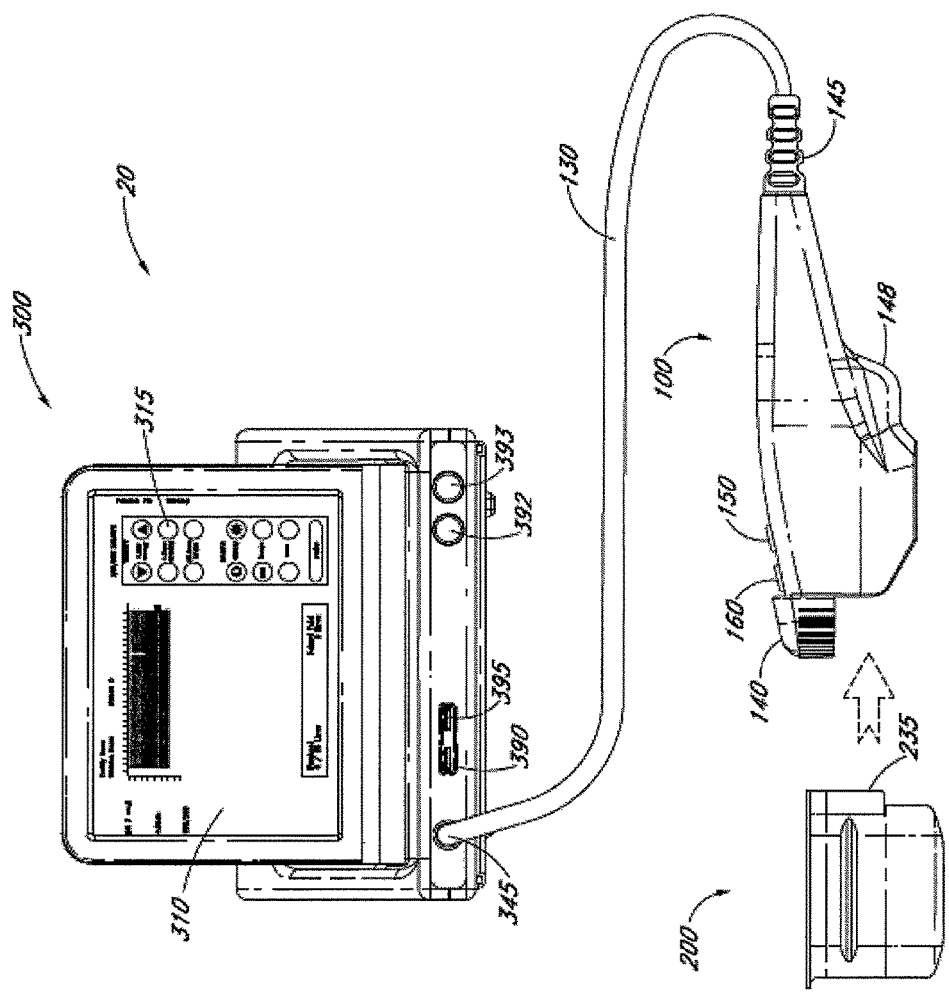
FIG. 1 is a schematic illustration of an ultrasound system according to various embodiments of the present invention.

The following description sets forth examples of embodiments, and is not intended to limit the present invention or its teachings, applications, or uses thereof. It should be understood that throughout the drawings, corresponding reference numerals indicate like or corresponding parts and features. The description of specific examples indicated in various embodiments of the present invention are intended for purposes of illustration only and are not intended to limit the scope of the invention disclosed herein. Moreover, recitation of multiple embodiments having stated features is not intended to exclude other embodiments having additional features or other embodiments incorporating different combinations of the stated features. Further, features in one embodiment (such as in one figure) may be combined with descriptions (and figures) of other embodiments.

In various embodiments, systems and methods for ultrasound treatment of tissue are configured to provide cosmetic treatment. In various embodiments, tissue below or even at a skin surface such as epidermis, dermis, fascia, muscle, fat, and superficial muscular aponeurotic system ("SMAS"), are treated non-invasively with ultrasound energy. The ultrasound energy can be focused at one or more treatment points, can be unfocused and/or defocused, and can be applied to a region of interest containing at least one of epidermis, dermis, hypodermis, fascia, muscle, fat and SMAS to achieve a cosmetic and/or therapeutic effect. In various embodiments, systems and/or methods provide non-invasive dermatological treatment to tissue through thermal treatment, coagulation, ablation, and/or tightening. In several embodiments disclosed herein, non-invasive ultrasound is used to achieve one or more of the following effects: a face lift, a brow lift, a chin lift, an eye treatment, a wrinkle reduction, a scar reduction, a burn treatment, a tattoo removal, a vein removal, a vein reduction, a treatment on a sweat gland, a treatment of hyperhidrosis, sun spot removal, an acne treatment, and a pimple removal. In one embodiment, fat reduction is achieved. In one embodiment, décolletage is treated. In some embodiments, two, three or more beneficial effects are achieved during the same treatment session, and may be achieved simultaneously. In another embodiment, the device may be used on adipose tissue (e.g., fat). In another embodiment the system, device and/or method may be applied in the genital area (e.g., a vagina for vaginal rejuvenation and/or vaginal tightening, such as for tightening the supportive tissue of the vagina).

Various embodiments of the present invention relate to devices or methods of controlling the delivery of energy to tissue. In various embodiments, various forms of energy can include acoustic, ultrasound, light, laser, radio-frequency (RF), microwave, electromagnetic, radiation, thermal, cryogenic, electron beam, photon-based, magnetic, magnetic resonance, and/or other energy forms. Various embodiments of the present invention relate to devices or methods of splitting an ultrasonic energy beam into multiple beams. In various embodiments, devices or methods can be used to alter the delivery of ultrasound acoustic energy in any procedures such as, but not limited to, therapeutic ultrasound, diagnostic ultrasound, non-destructive testing (NDT) using ultrasound, ultrasonic welding, any application that involves coupling mechanical waves to an object, and other procedures. Generally, with therapeutic ultrasound, a tissue effect is achieved by concentrating the acoustic energy using focusing techniques from the aperture. In some instances, high intensity focused ultrasound (HIFU) is used for therapeutic purposes in this manner. In one embodiment, a tissue effect created by application of therapeutic ultrasound at a particular depth to can be referred to as creation of a thermal coagulation point (TCP). It is through creation of TCPs at particular positions that thermal and/or mechanical ablation of tissue can occur non-invasively or remotely.

In one embodiment, TCPs can be created in a linear or substantially linear zone or sequence, with each individual TCP separated from neighboring TCPs by a treatment spacing. In one embodiment, multiple sequences of TCPs can be created in a treatment region. For example, TCPs can be formed along a first linear sequence and a second linear sequence separated by a treatment distance from the first linear sequence. Although treatment with therapeutic ultrasound can be administered through creation of individual TCPs in a sequence and sequences of individual TCPs, it may be desirable to reduce treatment time and corresponding risk of pain and/or discomfort experienced by a patient. Therapy time can be reduced by forming multiple TCPs simultaneously, nearly simultaneously, or sequentially. In some embodiments, a treatment time can be reduced 10%, 20%, 25%, 30%, 35%, 40%, 4%, 50%, 55%, 60%, 65%, 70%, 75%, 80% or more by creating multiple TCPs.

Various embodiments of the present invention address potential challenges posed by administration of ultrasound therapy. In various embodiments, time for effecting the formation of TCPs for a desired cosmetic and/or therapeutic treatment for a desired clinical approach at a target tissue is reduced. In various embodiments, target tissue is, but is not limited to, any of skin, eyelids, eye lash, eye brow, caruncula *lacrimalis*, crow's feet, wrinkles, eye, nose, mouth, tongue, teeth, gums, ears, brain, heart, lungs, ribs, abdomen, stomach, liver, kidneys, uterus, breast, vagina, prostrate, testicles, glands, thyroid glands, internal organs, hair, muscle, bone, ligaments, cartilage, fat, fat labuli, adipose tissue, subcutaneous tissue, implanted tissue, an implanted organ, lymphoid, a tumor, a cyst, an abscess, or a portion of a nerve, or any combination thereof.

In some embodiments, amplitude modulation and/or discrete phasing techniques can be applied to an aperture configured to emit ultrasonic energy. This can cause splitting of an ultrasonic beam emitted by the aperture into multiple beams, which may simultaneously, substantially simultaneously, or sequentially deliver ultrasonic energy to multiple locations or focal points. In some embodiments, amplitude modulation can be combined with techniques configured to change modulation states of an aperture in order to reduce intensity of ultrasonic energy delivered to tissues located before and/or after focal points. In various embodiments, therapy time can be reduced by 1-24%, 1-26%, 1-39%, 1-50%, or more than 50%.

Various embodiments of ultrasound treatment and imaging devices are described in U.S. application Ser. No. 12/996,616, which published as U.S. Publication No. 2011-0112405 A1 on May 12, 2011, which is a U.S. National Phase under 35 U.S.C. § 371 of International Application No. PCT/US2009/046475, filed on Jun. 5, 2009 and published in English on Dec. 10, 2009, which claims the benefit of priority from U.S. Provisional No. 61/059,477 filed Jun. 6, 2008, each of which is incorporated in its entirety by reference, herein.

System Overview

With reference to the illustration in FIG. 1, an embodiment of an ultrasound system 20 includes a hand wand 100, module 200, and a controller 300. The hand wand 100 can be coupled to the controller 300 by an interface 130, which may be a wired or wireless interface. The interface 130 can be coupled to the hand wand 100 by a connector 145. The distal end of the interface 130 can be connected to a controller connector on a circuit 345. In one embodiment, the interface 130 can transmit controllable power from the controller 300 to the hand wand 100.

In various embodiments, the controller 300 can be configured for operation with the hand wand 100 and the module 200, as well as the overall ultrasound system 20 functionality. In various embodiments, multiple controllers 300, 300', 300", etc. can be configured for operation with multiple hand wands 100, 100', 100", etc. and or multiple modules 200, 200', 200", etc. The controller 300 can include an interactive graphical display 310, which can include a touchscreen monitor and Graphic User Interface (GUI) that allows the user to interact with the ultrasound system 20. As is illustrated, the graphical display 315 includes a touchscreen interface 315. In various embodiments, the display 310 sets and displays the operating conditions, including equipment activation status, treatment parameters, system messages and prompts, and ultrasound images. In various embodiments, the controller 300 can be configured to include, for example, a microprocessor with software and input/output devices, systems and devices for controlling electronic and/or mechanical scanning and/or multiplexing of transducers and/or multiplexing of transducer modules, a system for power delivery, systems for monitoring, systems for sensing the spatial position of the probe and/or transducers and/or multiplexing of transducer modules, and/or systems for handling user input and recording treatment results, among others. In various embodiments, the controller 300 can include a system processor and various analog and/or digital control logic, such as one or more of microcontrollers, microprocessors, field-programmable gate arrays, computer boards, and associated components, including firmware and control software, which may be capable of interfacing with user controls and interfacing circuits as well as input/output circuits and systems for communications, displays, interfacing, storage, documentation, and other useful functions. System software running on the system process may be configured to control all initialization, timing, level setting, monitoring, safety monitoring, and all other ultrasound system functions for accomplishing user-defined treatment objectives. Further, the controller 300 can include various input/output modules, such as switches, buttons, etc., that may also be suitably configured to control operation of the ultrasound system 20.

As is illustrated in FIG. 1, in one embodiment, the controller 300 can include one or more data ports 390. In various embodiments, the data ports 390 can be a USB port, Bluetooth port, IrDA port, parallel port, serial port, and the like. The data ports 390 can be located on the front, side, and/or back of the controller 300, and can be used for accessing storage devices, printing devices, computing devices, etc. The ultrasound system 20 can include a lock 395. In one embodiment, in order to operate the ultrasound system 20, the lock 395 should be unlocked so that a power switch 393 may be activated. In one embodiment, the lock 395 can be connectable to the controller 300 via a data port 390 (e.g., a USB port). The lock 395 could be unlocked by inserting into the data port 390 an access key (e.g., USB access key), a hardware dongle, or the like. The controller 300 can include an emergency stop button 392, which can be readily accessible for emergency deactivation.

In one embodiment, the hand wand 100 includes one or more finger activated controllers or switches, such as 150 and 160. In one embodiment, the hand wand 100 can include a removable module 200. In other embodiments, the module 200 may be non-removable. The module 200 can be mechanically coupled to the hand wand 100 using a latch or coupler 140. An interface guide 235 can be used for assisting the coupling of the module 200 to the hand wand 100. The module 200 can include one or more ultrasound transducers. In some embodiments, an ultrasound transducer includes one or more ultrasound elements. The module 200 can include one or more ultrasound elements. The hand wand 100 can include imaging-only modules, treatment-only modules, imaging-and-treatment modules, and the like. In one embodiment, the control module 300 can be coupled to the hand wand 100 via the interface 130, and the graphic user interface 310 can be configured for controlling the module 200. In one embodiment, the control module 300 can provide power to the hand wand 100. In one embodiment, the hand wand 100 can include a power source. In one embodiment, the switch 150 can be configured for controlling a tissue imaging function and the switch 160 can be configured for controlling a tissue treatment function In one embodiment, the module 200 can be coupled to the hand wand 100. The module 200 can emit and receive energy, such as ultrasonic energy. The module 200 can be electronically coupled to the hand wand 100 and such coupling may include an interface which is in communication with the controller 300. In one embodiment, the interface guide 235 can be configured to provide electronic communication between the module 200 and the hand wand 100. The module 200 can comprise various probe and/or transducer configurations. For example, the module 200 can be configured for a combined dual-mode imaging/therapy transducer, coupled or co-housed imaging/therapy transducers, separate therapy and imaging probes, and the like. In one embodiment, when the module 200 is inserted into or connected to the hand wand 100, the controller 300 automatically detects it and updates the interactive graphical display 310.

Figure 2:
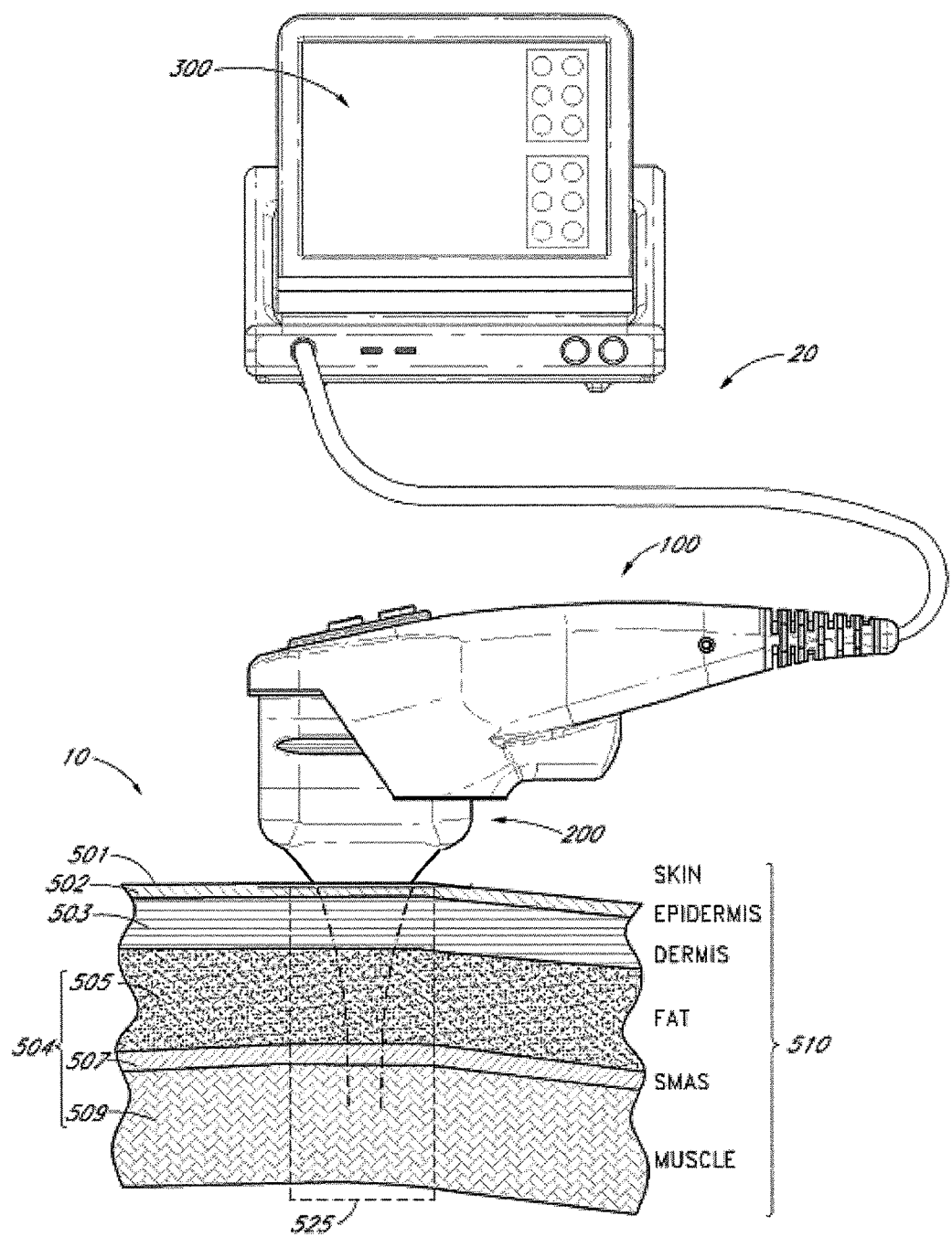
FIG. 2 is a schematic illustration of an ultrasound system coupled to a region of interest according to various embodiments of the present invention.

In various embodiments, tissue below or even at a skin surface such as epidermis, dermis, hypodermis, fascia, and superficial muscular aponeurotic system ("SMAS"), and/or muscle are treated non-invasively with ultrasound energy. Tissue may also include blood vessels and/or nerves. The ultrasound energy can be focused, unfocused or defocused and applied to a region of interest containing at least one of epidermis, dermis, hypodermis, fascia, and SMAS to achieve a therapeutic effect. FIG. 2 is a schematic illustration of the ultrasound system 20 coupled to a region of interest 10. In various embodiments, tissue layers of the region of interest 10 can be at any part of the body of a subject. In one embodiment, the tissue layers are in the head and face region of the subject. The cross-sectional portion of the tissue of the region of interest 10 includes a skin surface 501, an epidermal layer 502, a dermal layer 503, a fat layer 505, a superficial muscular aponeurotic system 507 (hereinafter "SMAS 507"), and a muscle layer 509. The tissue can also include the hypodermis 504, which can include any tissue below the dermal layer 503. The combination of these layers in total may be known as subcutaneous tissue 510. Also illustrated in FIG. 2 is a treatment zone 525 which is below the surface 501. In one embodiment, the surface 501 can be a surface of the skin of a subject 500. Although an embodiment directed to therapy at a tissue layer may be used herein as an example, the system can be applied to any tissue in the body. In various embodiments, the system and/or methods may be used on muscles (or other tissue) of the face, neck, head, arms, legs, or any other location in the body.

Figure 3:
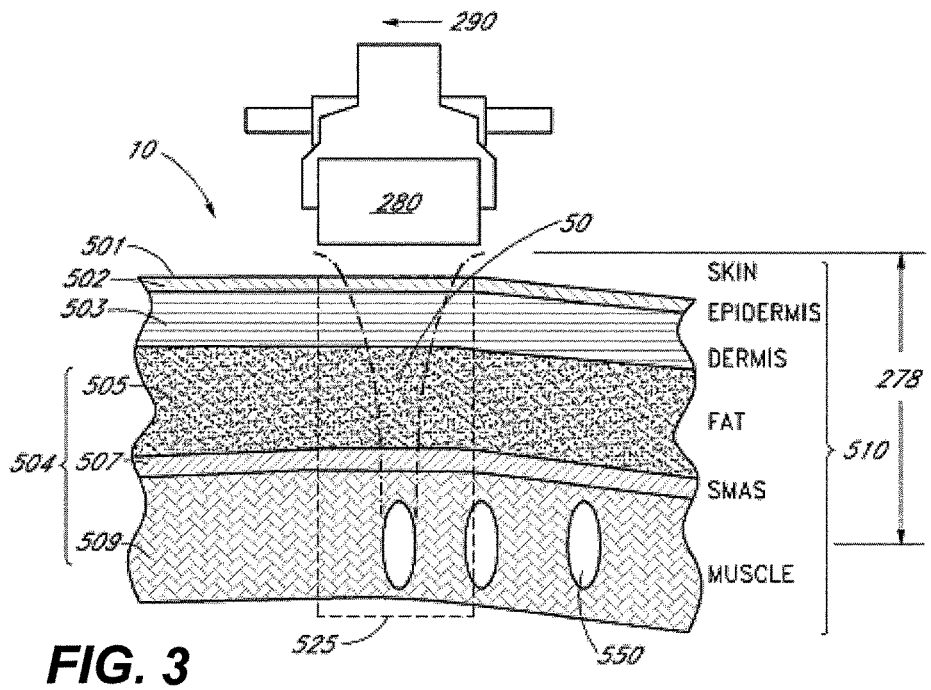
FIG. 3 is a schematic partial cut away illustration of a portion of a transducer according to various embodiments of the present invention.

With reference to the illustration in FIG. 2, an embodiment of the ultrasound system 20 includes the hand wand 100, the module 200, and the controller 300. In one embodiment, the module 200 includes a transducer 280. FIG. 3 illustrates an embodiment of an ultrasound system 20 with a transducer 280 configured to treat tissue at a focal depth 278. In one embodiment, the focal depth 278 is a distance between the transducer 280 and the target tissue for treatment. In one embodiment, a focal depth 278 is fixed for a given transducer 280. In one embodiment, a focal depth 278 is variable for a given transducer 280.

Figure 4:
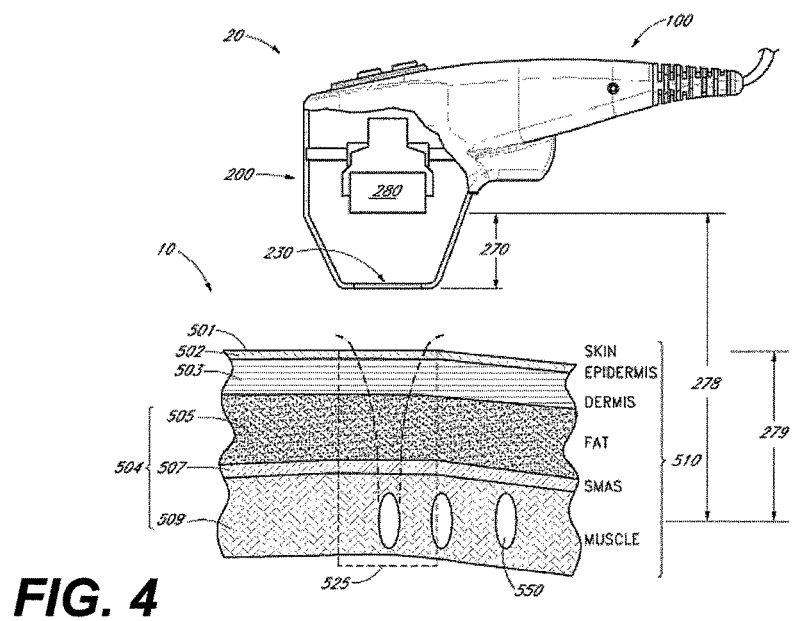
FIG. 4 is a partial cut away side view of an ultrasound system according to various embodiments of the present invention.

With reference to the illustration in FIG. 4, the module 200 can include a transducer 280 which can emit energy through an acoustically transparent member 230. In various embodiments, a depth may refer to the focal depth 278. In one embodiment, the transducer 280 can have an offset distance 270, which is the distance between the transducer 280 and a surface of the acoustically transparent member 230. In one embodiment, the focal depth 278 of a transducer 280 is a fixed distance from the transducer. In one embodiment, a transducer 280 may have a fixed offset distance 270 from the transducer to the acoustically transparent member 230. In one embodiment, an acoustically transparent member 230 is configured at a position on the module 200 or the ultrasound system 20 for contacting the skin surface 501. In various embodiments, the focal depth 278 exceeds the offset distance 270 by an amount to correspond to treatment at a target area located at a tissue depth 279 below a skin surface 501. In various embodiments, when the ultrasound system 20 placed in physical contact with the skin surface 501, the tissue depth 279 is a distance between the acoustically transparent member 230 and the target area, measured as the distance from the portion of the hand wand 100 or module 200 surface that contacts skin (with or without an acoustic coupling gel, medium, etc.) and the depth in tissue from that skin surface contact point to the target area. In one embodiment, the focal depth 278 can correspond to the sum of an offset distance 270 (as measured to the surface of the acoustically transparent member 230 in contact with a coupling medium and/or skin 501) in addition to a tissue depth 279 under the skin surface 501 to the target region. In various embodiments, the acoustically transparent member 230 is not used.

Coupling components can comprise various substances, materials, and/or devices to facilitate coupling of the transducer 280 or module 200 to a region of interest. For example, coupling components can comprise an acoustic coupling system configured for acoustic coupling of ultrasound energy and signals. Acoustic coupling system with possible connections such as manifolds may be utilized to couple sound into the region of interest, provide liquid- or fluid-filled lens focusing. The coupling system may facilitate such coupling through use of one or more coupling media, including air, gases, water, liquids, fluids, gels, solids, non-gels, and/or any combination thereof, or any other medium that allows for signals to be transmitted between the transducer 280 and a region of interest. In one embodiment one or more coupling media is provided inside a transducer. In one embodiment a fluid-filled module 200 contains one or more coupling media inside a housing. In one embodiment a fluid-filled module 200 contains one or more coupling media inside a sealed housing, which is separable from a dry portion of an ultrasonic device. In various embodiments, a coupling medium is used to transmit ultrasound energy between one or more devices and tissue with a transmission efficiency of 100%, 99% or more, 98% or more, 95% or more, 90% or more, 80% or more, 75% or more, 60% or more, 50% or more, 40% or more, 30% or more, 25% or more, 20% or more, 10% or more, and/or 5% or more.

In various embodiments, the transducer 280 can image and treat a region of interest at any suitable tissue depths 279. In one embodiment, the transducer module 280 can provide an acoustic power in a range of about 1 W or less, between about 1 W to about 100 W, and more than about 100 W. In one embodiment, the transducer module 280 can provide an acoustic power at a frequency of about 1 MHz or less, between about 1 MHz to about 10 MHz, and more than about 10 MHz. In one embodiment, the module 200 has a focal depth 278 for a treatment at a tissue depth 279 of about 4.5 mm below the skin surface 501. Some non-limiting embodiments of transducers 280 or modules 200 can be configured for delivering ultrasonic energy at a tissue depth of 3 mm, 4.5 mm, 6 mm, less than 3 mm, between 3 mm and 4.5 mm, between 4.5 mm and 6 mm, more than more than 4.5 mm, more than 6 mm, etc., and anywhere in the ranges of 0-3 mm, 0-4.5 mm, 0-6 mm, 0-25 mm, 0-100 mm, etc. and any depths therein. In one embodiment, the ultrasound system 20 is provided with two or more transducer modules 280. For example, a first transducer module can apply treatment at a first tissue depth (e.g., about 4.5 mm) and a second transducer module can apply treatment at a second tissue depth (e.g., of about 3 mm), and a third transducer module can apply treatment at a third tissue depth (e.g., of about 1.5-2 mm). In one embodiment, at least some or all transducer modules can be configured to apply treatment at substantially same depths.

In various embodiments, changing the number of focus point locations (e.g., such as with a tissue depth 279) for an ultrasonic procedure can be advantageous because it permits treatment of a patient at varied tissue depths even if the focal depth 278 of a transducer 270 is fixed. This can provide synergistic results and maximizing the clinical results of a single treatment session. For example, treatment at multiple depths under a single surface region permits a larger overall volume of tissue treatment, which results in enhanced collagen formation and tightening. Additionally, treatment at different depths affects different types of tissue, thereby producing different clinical effects that together provide an enhanced overall cosmetic result. For example, superficial treatment may reduce the visibility of wrinkles and deeper treatment may induce formation of more collagen growth. Likewise, treatment at various locations at the same or different depths can improve a treatment.

Although treatment of a subject at different locations in one session may be advantageous in some embodiments, sequential treatment over time may be beneficial in other embodiments. For example, a subject may be treated under the same surface region at one depth in time one, a second depth in time two, etc. In various embodiments, the time can be on the order of nanoseconds, microseconds, milliseconds, seconds, minutes, hours, days, weeks, months, or other time periods. The new collagen produced by the first treatment may be more sensitive to subsequent treatments, which may be desired for some indications. Alternatively, multiple depth treatment under the same surface region in a single session may be advantageous because treatment at one depth may synergistically enhance or supplement treatment at another depth (due to, for example, enhanced blood flow, stimulation of growth factors, hormonal stimulation, etc.). In several embodiments, different transducer modules provide treatment at different depths. In one embodiment, a single transducer module can be adjusted or controlled for varied depths. Safety features to minimize the risk that an incorrect depth will be selected can be used in conjunction with the single module system.

In several embodiments, a method of treating the lower face and neck area (e.g., the submental area) is provided. In several embodiments, a method of treating (e.g., softening) mentolabial folds is provided. In other embodiments, a method of treating the eye region is provided. Upper lid laxity improvement and periorbital lines and texture improvement will be achieved by several embodiments by treating at variable depths. By treating at varied locations in a single treatment session, optimal clinical effects (e.g., softening, tightening) can be achieved. In several embodiments, the treatment methods described herein are non-invasive cosmetic procedures. In some embodiments, the methods can be used in conjunction with invasive procedures, such as surgical facelifts or liposuction, where skin tightening is desired. In various embodiments, the methods can be applied to any part of the body.

In one embodiment, a transducer module permits a treatment sequence at a fixed depth at or below the skin surface. In one embodiment, a transducer module permits a treatment sequence at a fixed depth below the dermal layer. In several embodiments, the transducer module comprises a movement mechanism configured to direct ultrasonic treatment in a sequence of individual thermal lesions (hereinafter "thermal coagulation points" or "TCPs") at a fixed focal depth. In one embodiment, the linear sequence of individual TCPs has a treatment spacing in a range from about 0.01 mm to about 25 mm. For example, the spacing can be 1.1 mm or less, 1.5 mm or more, between about 1.1 mm and about 1.5 mm, etc. In one embodiment, the individual TCPs are discrete. In one embodiment, the individual TCPs are overlapping. In one embodiment, the movement mechanism is configured to be programmed to provide variable spacing between the individual TCPs. In several embodiments, a transducer module comprises a movement mechanism configured to direct ultrasonic treatment in a sequence so that TCPs are formed in linear or substantially linear sequences separated by a treatment distance. For example, a transducer module can be configured to form TCPs along a first linear sequence and a second linear sequence separated by a treatment distance from the first linear sequence. In one embodiment, treatment distance between adjacent linear sequences of individual TCPs is in a range from about 0.01 mm to about 25 mm. For example, the treatment distance can be 2 mm or less, 3 mm or more, between about 2 mm and about 3 mm, etc. In several embodiments, a transducer module can comprise one or more movement mechanisms configured to direct ultrasonic treatment in a sequence so that TCPs are formed in linear or substantially linear sequences of individual thermal lesions separated by a treatment distance from other linear sequences. In one embodiment, the treatment distance separating linear or substantially linear TCPs sequences is the same or substantially the same. In one embodiment, the treatment distance separating linear or substantially linear TCPs sequences is different or substantially different for various adjacent pairs of linear TCPs sequences.

In one embodiment, first and second removable transducer modules are provided. In one embodiment, each of the first and second transducer modules are configured for both ultrasonic imaging and ultrasonic treatment. In one embodiment, a transducer module is configured for treatment only. In one embodiment, an imaging transducer may be attached to a handle of a probe or a hand wand. The first and second transducer modules are configured for interchangeable coupling to a hand wand. The first transducer module is configured to apply ultrasonic therapy to a first layer of tissue, while the second transducer module is configured to apply ultrasonic therapy to a second layer of tissue. The second layer of tissue is at a different depth than the first layer of tissue.

As illustrated in FIG. 3, in various embodiments, delivery of emitted energy 50 at a suitable focal depth 278, distribution, timing, and energy level is provided by the module 200 through controlled operation by the control system 300 to achieve the desired therapeutic effect of controlled thermal injury to treat at least one of the epidermis layer 502, dermis layer 503, fat layer 505, the SMAS layer 507, the muscle layer 509, and/or the hypodermis 504. FIG. 3 illustrates one embodiment of a depth that corresponds to a depth for treating muscle. In various embodiments, the depth can correspond to any tissue, tissue layer, skin, epidermis, dermis, hypodermis, fat, SMAS, muscle, blood vessel, nerve, or other tissue. During operation, the module 200 and/or the transducer 280 can also be mechanically and/or electronically scanned along the surface 501 to treat an extended area. Before, during, and after the delivery of ultrasound energy 50 to at least one of the epidermis layer 502, dermis layer 503, hypodermis 504, fat layer 505, the SMAS layer 507 and/or the muscle layer 509, monitoring of the treatment area and surrounding structures can be provided to plan and assess the results and/or provide feedback to the controller 300 and the user via a graphical interface 310.

In one embodiment, an ultrasound system 20 generates ultrasound energy which is directed to and focused below the surface 501. This controlled and focused ultrasound energy 50 creates the thermal coagulation point or zone (TCP) 550. In one embodiment, the ultrasound energy 50 creates a void in subcutaneous tissue 510. In various embodiments, the emitted energy 50 targets the tissue below the surface 501 which cuts, ablates, coagulates, microablates, manipulates, and/or causes a lesion 550 in the tissue portion 10 below the surface 501 at a specified focal depth 278. In one embodiment, during the treatment sequence, the transducer 280 moves in a direction denoted by the arrow marked 290 at specified intervals 295 to create a series of treatment zones 254 each of which receives an emitted energy 50 to create one or more TCPs 550.

In various embodiments, transducer modules can comprise one or more transduction elements. The transduction elements can comprise a piezoelectrically active material, such as lead zirconante titanate (PZT), or any other piezoelectrically active material, such as a piezoelectric ceramic, crystal, plastic, and/or composite materials, as well as lithium niobate, lead titanate, barium titanate, and/or lead metaniobate. In various embodiments, in addition to, or instead of, a piezoelectrically active material, transducer modules can comprise any other materials configured for generating radiation and/or acoustical energy. In various embodiments, transducer modules can be configured to operate at different frequencies and treatment depths. Transducer properties can be defined by an outer diameter ("OD") and focal length ($F_L$). In one embodiment, a transducer can be configured to have OD=19 mm and $F_L$=15 mm. In other embodiments, other suitable values of OD and $F_L$ can be used, such as OD of less than about 19 mm, greater than about 19 mm, etc. and $F_L$ of less than about 15 mm, greater than about 15 mm, etc. Transducer modules can be configured to apply ultrasonic energy at different target tissue depths. As described above, in several embodiments, transducer modules comprise movement mechanisms configured to direct ultrasonic treatment in a linear or substantial liner sequence of individual TCPs with a treatment spacing between individual TCPs. For example, treatment spacing can be about 1.1 mm, 1.5 mm, etc. In several embodiments, transducer modules can further comprise movement mechanisms configured to direct ultrasonic treatment in a sequence so that TCPs are formed in linear or substantially linear sequences separated by a treatment spacing. For example, a transducer module can be configured to form TCPs along a first linear sequence and a second linear sequence separated by treatment spacing between about 2 mm and 3 mm from the first linear sequence. In one embodiment, a user can manually move the transducer modules across the surface of a treatment area so that adjacent linear sequences of TCPs are created. In one embodiment, a movement mechanism can automatically move the transducer modules across the surface of a treatment area so that adjacent linear sequences of TCPs are created.

In various embodiments, treatment advantageously can be delivered at a faster rate and with improved accuracy. This in turn can reduce treatment time and decrease pain experienced by a subject. Further, efficiency can be increased if variance is reduced in a treatment spacing between linear or substantially linear sequences of TCPs. In one embodiment, a system uses a transducer configured to produce a single focus treatment point. In one embodiment, the transducer can be mechanically moved along a line to create a linear sequence of TCPs. For example, Table 1 provides an estimate of time for creating a linear sequence of TCPs and an estimate of time for moving between linear sequences of TCPs according to one embodiment. It can be seen that time for creating a linear sequence of TCPs and time for moving between linear sequences of TCPs are nearly equivalent.

TABLE 1

| Time Metric | Time (in msec) | Percentage of Total Time |
| --- | --- | --- |
| Time for creating a linear sequence | 2.9 | 48 |
| Time for moving between linear sequences | 3.2 | 52 |
| Total Time | 6.1 | 100 |

In various embodiments, therapeutic treatment advantageously can be delivered at a faster rate and with improved accuracy by using a transducer configured to deliver multiple focus points, or TCPs. This in turn can reduce treatment time and decrease pain experienced by a subject. In several embodiments, treatment time is reduced if time for creating a linear sequence of TCPs and time for moving between linear sequences of TCPs are reduced by emitting TCPs at multiple locations from a single transducer.

Therapy Delivery Using Amplitude Modulation

Aperture Spatial Frequency Analysis and Fourier Transform

In various embodiments, spatial frequency analysis techniques based on Fourier analysis and Fourier optics can be used to increase efficiency of therapeutic treatment. When a system that has an impulse response h(t) is excited by a stimulus x(t), the relationship between the input x(t) and output y(t) is related by the convolution function as follows:

$$y(t) = x(t) * h(t) = \int_{-\infty}^{\infty} x(\tau) h(t-\tau) d\tau \quad (1)$$

In various embodiments, Fourier transform can be applied to compute the convolution of equation (1). Continuous one-dimensional Fourier transform can be defined as:

$$Y(f) = F(y(t)) = \int_{-\infty}^{\infty} y(t) e^{-j2\pi ft} dt \quad (2)$$

Here f is frequency, t is time. It can be shown that convolution in the time domain is equivalent to multiplication in the frequency domain:

$$F(x(t) * h(t)) = X(f) H(f) = Y(f) \quad (3)$$

In various embodiments, the Fraunhofer approximation can be used for deriving a relationship between a transducer opening or aperture and a resulting ultrasonic beam response. Derivation of the Fraunhofer approximation is described in Joseph Goodman, *Introduction to Fourier Optics* (3d ed. 2004), which is incorporated in its entirety by reference, herein. According to the Fraunhofer approximation, a far-field complex amplitude pattern produced by a complex aperture is equal to a two-dimensional Fourier transform of the aperture amplitude and phase. In several embodiments, this relationship in optics can be extended to ultrasound since linear wave equations can be used to represent both light propagation and sound propagation. In the case of optics and/or ultrasound, the two-dimensional Fourier transform can determine a sound wave pressure amplitude distribution at the focus of a transducer.

In various embodiments, a Huygens-Fresnel integral determines an amplitude in the pressure field $U(P_0)$ from an aperture by integrating the effect (both amplitude and phase) from each resonator or transducer on a surface $\Sigma$. It is expressed as:

$$U(P_0) = \int\int_{\Sigma} h(P_0, P_1) U(P_1) ds \quad (4a)$$

$$h(P_0, P_1) = \frac{1}{j\lambda} \frac{e^{(jkr_{01})}}{r_{01}} \cos(\vec{n}, \vec{r_{01}}) \quad (4b)$$

where k is a wave number expressed as $2\pi/\lambda$, $r_{01}$ is a distance from an aperture to the screen in a field, n is a directional vector from the aperture, $U(P_1)$ is the pressure field in the aperture, and $U(P_0)$ is the pressure field in the screen.

In various embodiments, following assumption are used to lead to an approximation that the amplitude in the pressure field $U(P_0)$ is a two-dimensional Fourier transform of $U(P_1)$. First, at small angles, the cosine function of the angle between n and $r_{01}$ is 1. This leads to the following simplifications:

$$\cos(\vec{n}, \vec{r_{01}}) \approx 1$$

$$r_{01} \approx z$$

$$h(x_0, y_0; x_1, y_1) \approx \frac{1}{j\lambda} e^{jkr_{01}}$$

where z represents depth. Second, Fresnel approximation of the distance $r_{01}$ can be expressed, using a binomial expansion, as:

$$r_{01} = \frac{e^{jkz}}{z} e^{\left[\frac{jk}{2z}((x_1-x_0)^2 + (y_1-y_0)^2)\right]}$$

Third, it can be assumed that the observation plane is much greater than the dimensions of the aperture as follows:

$$z \gg \frac{k(x_1^2 + y_1^2)_{max}}{2}$$

If these assumptions are applied to equations (4a) and (4b), then the amplitude in the field can be expressed as:

$$U(x_0, y_0) \approx \frac{e^{jkz}e^{\left[\frac{jk}{2z}(x_0^2+y_0^2)\right]}}{j\lambda z}\int\int_{-\infty}^{\infty} U(x_1, y_1)e^{-\frac{j2\pi}{\lambda z}(x_0 x_1 + y_0 y_1)}dx_1 dy_1 \quad (5)$$

Equation (5) includes a quadratic phase term on the outside of the integral which does not affect the overall magnitude. Comparing equation (5) to equation (2) reveals a similarity in the arguments inside the integral. In particular, instead of a one dimensional function y(t) evaluated at frequencies f, a two dimensional function $U(x_1,y_1)$ is evaluated at spatial frequencies given as:

$$f_x = \frac{x_0}{\lambda z} \quad (5a)$$

$$f_y = \frac{y_0}{\lambda z} \quad (5b)$$

Because the integral of equation (5) is the two-dimensional Fourier transform, equation (5) can be rewritten as:

$$U(x_0, y_0) \approx \frac{e^{jkz}e^{\left[\frac{jk}{2z}(x_0^2+y_0^2)\right]}}{j\lambda z} F_{x_1}F_{y_1}(U(x_1, y_1)) \quad (6)$$

In various embodiments, the amplitude and phase functions in the aperture $U(x_1,y_1)$ are separable into two functions, namely a function of $x_1$ and a function of $y_1$ respectively.

$$U(x_1,y_1)=g(x_1)h(y_1) \quad (7)$$

Applying equation (7) to equation (6) leads to further simplification:

$$U(x_0, y_0) \approx \frac{e^{jkz}e^{\left[\frac{jk}{2z}(x_0^2+y_0^2)\right]}}{j\lambda z} F_{x_1}(g(x_1))F_{y_1}(h(y_1)) \quad (8)$$

Equation (8) demonstrates that a response of the aperture in the field for a separable two-dimensional function is the multiplication of two one-dimensional Fourier transforms in $x_1$ and $y_1$ directions. It can be further shown that equations (6) and (8) hold for a focused system with the exception that spatial frequency arguments change as is expressed in equations (9a) and (9b). For a focused system, the variable z which represents depth can be replaced with $z_f$ which represents a focal distance.

$$f_x = \frac{x_0}{\lambda z_f} \quad (9a)$$

$$f_y = \frac{y_0}{\lambda z_f} \quad (9b)$$

In various embodiments, Fourier optics and Fourier transform identities (some of which are listed in Table 2, below) can be used for ultrasound transducers in order to determine the intensity distribution corresponding to a transducer design. For example, Fourier transform of a rectangle rect (ax) is a sinc function. As another example, Fourier transform of a two dimensional circle of uniform amplitude is a first order Bessel function which can be represented as $J_1$.

TABLE 2

| | Aperture Function | Fourier Transform |
|---|---|---|
| 1 | rect(ax) | $\frac{1}{|a|}\text{sinc}\left(\frac{\xi}{a}\right)$ |
| 2 | $\delta(x)$ | 1 |
| 3 | cos(ax) | $\frac{\delta\left(\xi - \frac{a}{2\pi}\right) + \delta\left(\xi + \frac{a}{2\pi}\right)}{2}$ |
| 4 | sin(ax) | $\frac{\delta\left(\xi - \frac{a}{2\pi}\right) - \delta\left(\xi + \frac{a}{2\pi}\right)}{2j}$ |
| 5 (two-dimensional transform pair) | $\text{circ}(\sqrt{x^2 + y^2})$ | $\frac{J_1\left(2\pi\sqrt{\xi_x^2 + \xi_y^2}\right)}{\sqrt{\xi_x^2 + \xi_y^2}}$ |
| 6 | f(x) * g(x) | $F(\xi)G(\xi)$ |
| 7 | f(x)g(x) | $F(\xi) * G(\xi)$ |

In several embodiments, an ultrasound transducer can have a rectangular aperture of suitable dimensions and focal length. In several embodiments, an ultrasound transducer can have a circular aperture with suitable dimensions and focal length. In one embodiment, a transducer can have a circular aperture with an outer radius of approximately 9.5 mm, an inner diameter of approximately 2 mm, and focal length of approximately 15 mm. The aperture of a circular transducer may be described as:

$$f(x, y) = \text{circ}\left(\frac{r}{a}\right) - \text{circ}\left(\frac{r}{b}\right) \quad (10a)$$

$$r = \sqrt{x^2 + y^2} \quad (10b)$$

For example, a can be approximately 9.5 mm and b can be approximately 2 mm. Applying Fourier transform to equation (10a) can provide an estimate of the sound wave pressure distribution at the focus.

$$F_{x,y}(f(x, y)) = F(\xi_x, \xi_y) = \frac{aJ_1\left(2\pi a\sqrt{\xi_x^2 + \xi_y^2}\right)}{\sqrt{\xi_x^2 + \xi_y^2}} - \frac{bJ_1\left(2\pi b\sqrt{\xi_x^2 + \xi_y^2}\right)}{\sqrt{\xi_x^2 + \xi_y^2}} \quad (11)$$

where $\xi_x$ and $\xi_y$ are same as $f_x$ and $f_y$ of equations (9a) and (9b). Equation (11) demonstrates that the sound wave pressure distribution of a transducer with a circular aperture is a first order Bessel function. In one embodiment, a substantial majority of the energy is concentrated at the focus (e.g., 15 mm away from the aperture). The width of a main ultrasonic beam and the distribution of energy away from the main beam can be expressed as a function of the operating frequency as is expressed in equations (9a) and (9b).

In various embodiments, two identical or nearly identical beams could be created at the focus if the aperture was modulated (e.g., multiplied) by a correct function. In one embodiment, a cosine function can be applied to a circular aperture as follows:

$$g(x, y) = \cos(cx)\left(circ\left(\frac{r}{a}\right) - circ\left(\frac{r}{b}\right)\right) \quad (12)$$

An energy distribution or beam response at the focus of the modulated aperture of equation (12) is the convolution of the Fourier transform of the two functions of the aperture:

$$G(\xi_x, \xi_y) = \left(\frac{\delta\left(\xi_x - \frac{c}{2\pi}\right) + \delta\left(\xi_x + \frac{c}{2\pi}\right)}{2}\right) * F(\xi_x, \xi_y) \quad (13)$$

Equation (13) can be simplified into the summation of two separate functions applying the Fourier Transform identity for a Dirac delta function (e.g., identity 2 in Table 2):

$$G(\xi_x, \xi_y) = \frac{1}{2}\left(F\left(\xi_x - \frac{c}{2\pi}, \xi_y\right) + F\left(\xi_x + \frac{c}{2\pi}, \xi_y\right)\right) \quad (14)$$

Equation (14) shows that two beams appearing at the focus are spatially shifted by $$\pm \frac{c}{2\pi}$$

n-modulated beam. In several embodiments, one or more other modulation functions, such as sine function, can be used to achieve a desired beam response. In several embodiments, aperture can be modulated such that more than two foci are created. For example, three, four, five, etc. foci can be created. In several embodiments, aperture can be modulated such that foci are created sequentially or substantially sequentially rather than simultaneously.

In several embodiments, therapy transducer modules comprise movement mechanisms configured to direct ultrasonic treatment in a linear or substantial liner sequence of individual TCPs with a treatment spacing between individual TCPs. For example, treatment spacing can be about 1.1 mm, 1.5 mm, etc. In several embodiments, transducer modules can further comprise movement mechanisms configured to direct ultrasonic treatment in a sequence so that TCPs are formed in linear or substantially linear sequences separated by a treatment spacing. For example, a transducer module can be configured to form TCPs along a first linear sequence and a second linear sequence separated by treatment spacing between about 2 mm and 3 mm from the first linear sequence. According to equation (14), a simultaneous or substantially simultaneous split in the ultrasonic beam may be achieved at the focus (or before the focus) if the aperture is modulated by a cosine and/or sine function of a desired spatial frequency. In one embodiment, two simultaneous or nearly simultaneous focused beams separated by about 1.1 mm treatment spacing can be created in a linear or substantially linear sequence. At 7 MHz frequency of ultrasound, the wavelength λ of ultrasound wave in water is approximately 0.220 mm. Accordingly, spatial frequencies $\xi_x$ and $\xi_y$ at the focus are represented as:

$$\xi_x = \frac{x_0}{15*0.220} - \frac{x_0}{3.3} \quad (15a)$$

$$\xi_y = \frac{y_0}{15*0.220} - \frac{y_0}{3.3} \quad (15b)$$

In order to place two foci separated by about 1.1 mm, then the spatial frequency for modulating the aperture is calculated as follows. Using identities 3 and 4 in Table 2, the Fourier transformation of a sine or cosine function is a Dirac delta function with the argument:

$$\arg = \frac{x_0}{3.3} - \frac{k_x}{2\pi} \quad (16a)$$

In one embodiment, equation (16a) can solved for $k_x$ when argument is 0:

$$k_x = \frac{2\pi x_0}{3.3} \quad (16b)$$

Further, $x_o$ can be replaced by half of the separation distance (e.g., 1.1 mm):

$$k_x = \frac{2\pi \frac{s}{2}}{z_f \lambda} = \frac{2\pi \frac{1.1}{2}}{3.3} = 1.04 \text{ mm}^{-1} \quad (16c)$$

In several embodiments, a transducer with circular aperture emitting ultrasonic energy at various operating frequencies can be modulated by a sine and/or cosine functions at spatial frequencies listed in Table 3. Modulated aperture of the transducer can produce a simultaneously or substantially simultaneously split beam with two foci having different separation distances, as is indicated in Table 3. In one embodiment, the transducer can have OD of about 19 mm and a focal length of about 15 mm.

TABLE 3

| | Separation Distance Between Foci | | | |
|---|---|---|---|---|
| Ultrasound Frequency | 1.1 mm | 1.5 mm | 2 mm | 3 mm |
| 4 MHz | 0.60 | 0.82 | 1.09 | 1.63 |
| 7 MHz | 1.04 | 1.43 | 1.90 | 2.86 |
| 10 MHz | 1.50 | 2.04 | 2.72 | 3.08 |

As is shown in Table 3, in several embodiments, a spatial frequency of an aperture modulation function increases as the ultrasonic operating frequency increases for a given foci separation distance. In addition, the spatial frequency increases as the desired foci separation distance increases.

In one embodiment, higher spatial frequency can result in amplitude transitions in the aperture occurring more rapidly. Due to transducer processing limitations, rapid amplitude variations in the aperture can make the aperture less efficient as there may be a variance in an amount of sound pressure produced by different parts of the aperture. In one embodiment, using spatial frequencies to simultaneously or nearly simultaneously split the beam can reduce the overall focal gain of each beam. As is shown in equation (14), a field pressure at the focus of each beam is reduced by a factor of two in comparison with an unmodulated beam. In one embodiment, the sound pressure or ultrasound intensity from the aperture can be increased to obtain similar or substantially similar intensities at the focal plane. However, in one embodiment, increasing the pressure at the aperture may not be limited by system and/or transducer processing limitations. In one embodiment, an increase in the pressure at the aperture can increase the overall intensity in the near field, which may increase the possibility of excessively heating treatment area tissue(s) that is located before focus. In one embodiment, the possibility of additional heating of the pre-focal tissue(s) may be limited or eliminated by using a lower ultrasound treatment frequency.

In one embodiment, applying aperture modulation function as is shown in equation (12) results in two simultaneous or substantially simultaneous ultrasound beams at the focus. In various embodiments, ultrasound beam can be split multiple times, such as three, four, five, etc. times, such that multiple simultaneous or nearly simultaneous beams are created. In one embodiment, four equally spaced beams along one dimension can be generated by modulating or multiplying the aperture by two separate spatial frequencies:

$$g(x, y) = (\cos(cx) + \cos(dx))\left(circ\left(\frac{r}{a}\right) - circ\left(\frac{r}{b}\right)\right) \quad (17a)$$

$$G(\xi_x, \xi_y) = \frac{1}{2}\left(F\left(\xi_x - \frac{c}{2\pi}, \xi_y\right) + F\left(\xi_x + \frac{c}{2\pi}, \xi_y\right) + F\left(\xi_x - \frac{d}{2\pi}, \xi_y\right) + F\left(\xi_x + \frac{d}{2\pi}, \xi_y\right)\right) \quad (17b)$$

As is shown in equation (17b), unmodulated beam at the focus can be created at four different locations along the x-axis. In one embodiment, a constant or DC term, C1, may be added to the amplitude modulation function to maintain placement of energy at the original focal location:

$$g(x, y) = (\cos(cx) + \cos(dx) + C_1)\left(circ\left(\frac{r}{a}\right) - circ\left(\frac{r}{b}\right)\right) \quad (18a)$$

$$G(\xi_x, \xi_y) = \frac{1}{2}\left(F\left(\xi_x - \frac{c}{2\pi}, \xi_y\right) + F\left(\xi_x + \frac{c}{2\pi}, \xi_y\right) + F\left(\xi_x - \frac{d}{2\pi}, \xi_y\right) + F\left(\xi_x + \frac{d}{2\pi}, \xi_y\right)\right) + C_1 F(\xi_x, \xi_y) \quad (18b)$$

In one embodiment, aperture modulation of equations (17) and (18), whereby the beam can be placed at multiple locations simultaneously or nearly simultaneously, may be have limited applicability due to system, material, and/or tissue limitations. In one embodiment, due to the possibility of heating treatment area tissue(s) located before focus, the frequency of ultrasound therapy may be adjusted, such as lowered, in order to limit and/or eliminate such possibility. In one embodiment, nonlinear techniques can be applied at the focus in order to limit and/or eliminate the possibility of heating of the pre-focal tissue(s). In one embodiment, the sound pressure or ultrasound intensity from the aperture can be increased to obtain similar or substantially similar intensities at the focal plane.

In various embodiments, as is shown in equation (7), if the amplitude and phase functions at the aperture are separable, the two-dimensional Fourier transform of a sound pressure function $U(x_1, y_1)$ can be expressed as a product of one-dimensional Fourier transform of two functions in x and y, which is shown in equation (8). In various embodiments, it may be advantageous to create multiple TCPs in a linear or substantially linear sequence as well as to create multiple linear sequences simultaneously or nearly simultaneously. As is shown in Table 1, in one embodiment, if two TCPs are created simultaneously or substantially simultaneously in a linear sequence, but linear sequences are created sequentially, overall treatment time may be reduced by about 24%. In one embodiment, if four TCPs are created simultaneously or substantially simultaneously in a linear sequence, but linear sequences are created sequentially, overall treatment time may be reduced by about 39%. In one embodiment, if two TCPs are created simultaneously or substantially simultaneously along with two linear sequences, overall treatment time may be reduced by about 50%.

Multiple Beam Splitting in Two Dimensions

In several embodiments, four TCPs can be created, such as two each in two linear or substantially linear sequences, using the following aperture amplitude modulation function:

$$g(x, y) = \cos(cx)\cos(dy)\left(circ\left(\frac{r}{a}\right) - circ\left(\frac{r}{b}\right)\right) \quad (19a)$$

The Fourier transform of this function is:

$$G(\xi_x, \xi_y) = \frac{1}{4}\left(F\left(\xi_x - \frac{c}{2\pi}, \xi_y - \frac{d}{2\pi}\right) + F\left(\xi_x + \frac{c}{2\pi}, \xi_y - \frac{d}{2\pi}\right) + F\left(\xi_x - \frac{c}{2\pi}, \xi_y + \frac{d}{2\pi}\right) + F\left(\xi_x + \frac{c}{2\pi}, \xi_y + \frac{d}{2\pi}\right)\right) \quad (19b)$$

As is shown in equations (19a) and (19b), the beam can be modulated into two linear sequences, with each sequence having two foci. In one embodiment, the linear sequences may be orthogonal. In one embodiment, the linear sequences may not be orthogonal. Because the Fourier transform is multiplied by ¼ in equation (19b), the amplitude of the beam or the intensity is further reduced as compared with beam split in into two foci (e.g., as is shown in equation (14)). In one embodiment, due to the possibility of heating treatment area tissue(s) that is located before focus, the frequency of ultrasound therapy may be adjusted, such as lowered, in order to limit and/or eliminate possibility of excessive heating of tissue(s) located before the focus. In several embodiments, modulation can be applied so that linear or substantially linear sequences of TCPs are created sequentially or substantially sequentially.

In various embodiments, as is shown in equations (12) through (14), cosine and/or sine amplitude modulation across a transducer with having a circular aperture creates two separate beams shifted by a spatial frequency of the cosine and/or sine modulation function. In various embodiments, modulation function can be spatially or phase shifted as follows:

$$g_{shift}(x, y) = \cos(cx - \theta)\left(circ\left(\frac{r}{a}\right) - circ\left(\frac{r}{b}\right)\right) \quad (20a)$$

$$G_{shift}(\xi_x, \xi_y) = \frac{1}{2}e^{j2\pi\xi_x\theta}\left(F\left(\xi_x - \frac{c}{2\pi}, \xi_y\right) + F\left(\xi_x + \frac{c}{2\pi}, \xi_y\right)\right) \quad (20a)$$

In one embodiment, the amplitude caused by the shift is the same as that in equation (14). In one embodiment, although spatial shift (e.g., by angle θ) does not change the overall amplitude at the focus, the phase is modified. In several embodiments, modification of the phase may be advantageous for reducing a peak intensity before the focus. In several embodiments, an aperture can be designed so that near field or pre-focal heating of the tissue(s) is substantially minimized while intensity at the focus or focal gain is substantially maximized.

Therapy Delivery Using Phase Shifting

In various embodiments, the beam may be split axially. It may be advantageous to analyze such axial split through an analysis of time delays and application of discrete phasing. In several embodiments, splitting the beam axially in x and/or y direction can be combined with planar or two-dimensional amplitude modulation of the aperture (e.g., such as that shown in equations (19a) and (19b)), which may result in splitting the beam in two or three dimensions. In several embodiments, beam can be shifted by using phase tilting at the aperture, which can be substantially equivalent to spatial shifting. In several embodiments, phase tilting can be performed using the following Fourier transform pair:

$$e^{jax} = \cos(ax) + j\sin(ax) \tag{21a}$$

$$F(e^{jax}) = \delta\left(\xi - \frac{a}{2\pi}\right) \tag{21b}$$

In one embodiment, this function describes an aperture which is only phase modulated since the magnitude of the exponential term is one. In one embodiment, each spatial location has an element that is under a different phase which can be expressed as the ratio of the imaginary (sine) and real (cosine) parts as follows:

$$\theta(x) = \tan^{-1}\left(\frac{\sin(ax)}{\cos(ax)}\right) \tag{22}$$

Equation (22) expresses the phase differences spatially.

In various embodiments, time delays associated with the propagation of ultrasound waves can be used to describe the phase shift or tilt for focusing the beam. In one embodiment, a transducer aperture can be a focused circular bowl having the following geometry:

$$r^2 + (z - z_f)^2 = z_f^2 \tag{23a}$$

$$r^2 = x^2 + y^2 \tag{23b}$$

Equations (23a) and (23b) describe a circular bowl that is centered at the bowl apex with a focal length zf. In one embodiment, the focus can be moved from (0, 0, zf) to a spatial point P0 which is located at (x0, y0, z0). The distance to this new spatial point P0 from any point on the bowl can be expressed as:

$$d = \sqrt{(x_1 - x_0)^2 + (y_1 - y_0)^2 + (z_1 - z_0)^2} \tag{24}$$

where (x1, y1, z1) are points on the bowl aperture that is defined by equations (23a) and (23b). In one embodiment, in order to determine the actual time to the target P0, then the speed of sound c (343.2 m/s) can be divided into a propagation distance d as follows:

$$t = \frac{\sqrt{(x_1 - x_0)^2 + (y_1 - y_0)^2 + (z_1 - z_0)^2}}{c} \tag{25}$$

In one embodiment, in order to obtain a desired constructive interference associated with propagation of delayed ultrasound waves at the focus, equation (25) can be used to calculate the relative time delay to another part of the aperture. In one embodiment, this can be accomplished by subtracting equation (25) by the minimum time delay. The remaining time is the extra time for ultrasound waves emitted by other parts of the aperture to arrive at the new spatial point $P_0$.

Figure 5A:
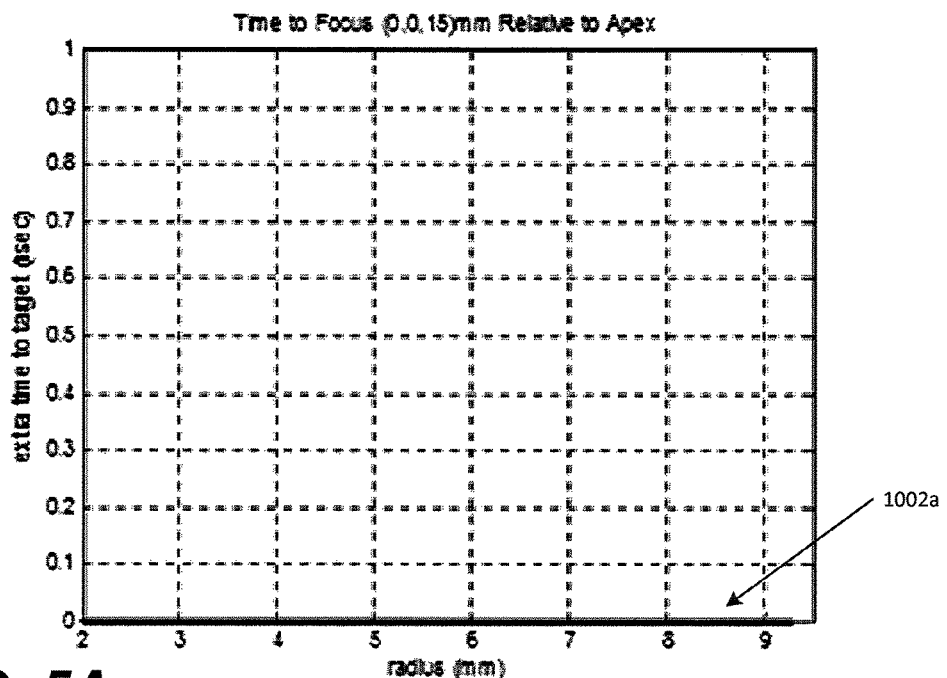
FIGS. 5A-5D are plots illustrating time delays for reaching a focal point for various transducers according to several embodiments of the present invention.
Figure 5B:
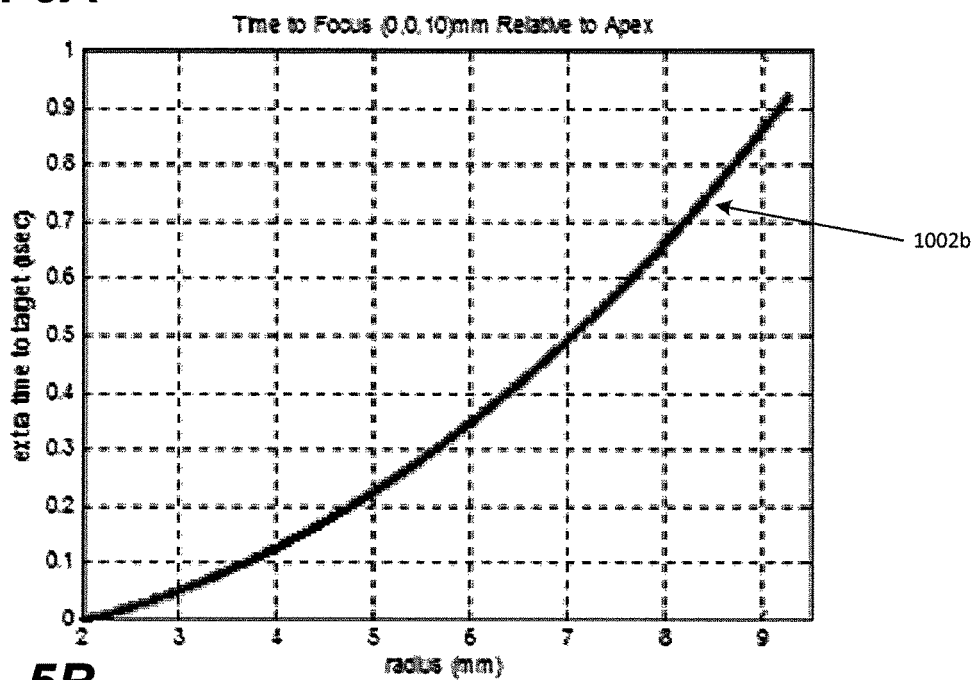
Figure 5C:
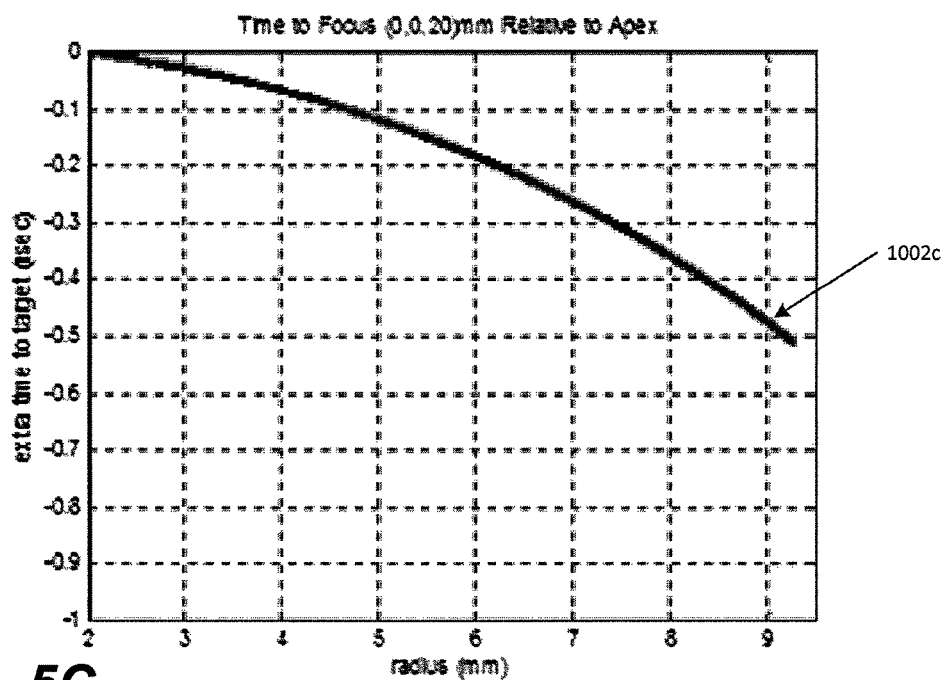
Figure 5D:
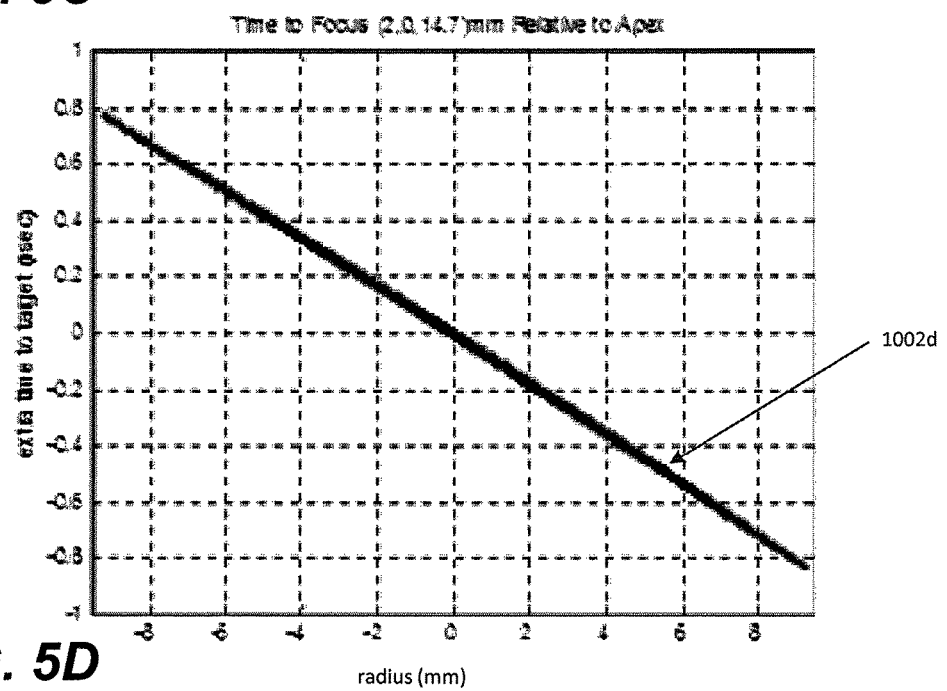

In several embodiments, a focus point of (0, 0, 15 mm) can be moved to a different focus point $P_0$. Relative time delays to new focus points $P_0$ relative to the center or apex of the aperture bowl (as expressed in radial distance) can be calculated using equation (25) and are illustrated in FIGS. 5A-5D for a transducer having geometry of outer diameter (OD)=19 mm, inner diameter (ID)=4 mm, and distance to focus ($F_L$)=15 mm. Other embodiments can use other dimensions, the present examples illustrate one non-limiting embodiment. Other dimensions are contemplated. FIG. 5A illustrates the relative time delay 1002a (in microseconds) for sound energy travelling from a spatial point on the aperture to reach a target focus point $P_0$=(0, 0, 15 mm) in relation to varying radial locations on the bowl aperture according to one embodiment. As expected, the delay illustrated in FIG. 5A is zero since the target point is the same as the focal point, and the focus point has not changed. FIG. 5B illustrates the relative time delay 1002b (in microseconds) for sound energy travelling from a spatial point on the aperture to reach a target focus point $P_0$=(0, 0, 10 mm) in relation to varying radial locations on the bowl aperture according to one embodiment. As is illustrated, the radial position starts at 2 mm due to a hole in the center of the transducer bowl. In one embodiment, an imaging element can be placed in the hole. Time to the target point $P_0$=(0, 0, 10 mm) increases as the radial position on the bowl increases. FIG. 5C illustrates the relative time delay 1002c (in microseconds) for sound energy travelling from a spatial point on the aperture to reach a target point $P_0$=(0, 0, 20 mm) in relation to varying radial locations on the bowl aperture according to one embodiment. As is illustrated, if the focus is shifted to $P_0$=(0, 0, 20) mm, time to the target decreases as the radial position on the bowl increases. FIG. 5D illustrates the relative time delay 1002d (in microseconds) for sound energy travelling from a spatial point on the aperture to reach a target focus point $P_0$=(2 mm, 0, 14.7 mm) in relation to varying radial locations on the bowl aperture according to one embodiment. In one embodiment, the total distance from the apex to the target point $P_0$=(2 mm, 0, 14.7 mm) is about 15 mm. As is illustrated, if the focus is shifted to $P_0$=(2 mm, 0, 14.7 mm), time to the target is linearly dependent on the x coordinate of the position on the bowl. Time to the target is less for positions having positive x relative to the apex and greater for positions having negative x relative to the apex. Positions having x coordinates between about −2 mm and about 2 mm occur outside of the inner diameter of the bowl (e.g., where an imaging element can be located).

FIGS. 5A-5D illustrate time delays for propagation of sound from various points on the aperture for constructively placing the sound energy at the focus according to several embodiments. A negative time relative to zero implies that it takes less time for energy from that point to reach a new focus point. A positive time relative to zero implies that it takes more time for energy to reach a new focus point. In one embodiment, if appropriate time delays could be placed on individual points of the bowl, the time delays can be controlled to obtain constructive interference at the new focus. In one embodiment, for transducers comprising piezoelectrically active material, moving the focus from a mechanical focus (0, 0, $z_f$) to a new focus point $P_0$ can changes the distances that resonators on the aperture should travel (due to expansion and/or contraction of the material) to create constructive interference at the focus $P_0$. These distances can be converted to time delays by dividing by the distances by the speed of sound. In one embodiment, if time delays for the resonators on the surface of the aperture are known, additional time delays to reach the focus $P_0$ could be accounted for such that desired pressure intensity at the focus $P_0$ can be achieved.

In various embodiments, ultrasound wave of a suitable frequency can be directed to a target area. In one embodiment, a transducer comprising piezoelectrically active material can be electrically excited by a continuous wave signal of a suitable operational frequency to achieve a suitable therapy frequency. In various embodiments of transducers, the operational frequency can be about 4 MHz, about 7 MHz, about 10 MHz, less than about 4 MHz (e.g., between about 20 KHz and about 4 MHz), between about 4 MHz and about 7 MHz, greater than about 10 MHz, etc. In one embodiment, the continuous wave signal can be on or active for a period of between about 20 msec to 30 msec. This in turn can imply that the aperture is excited by between about 80,000 cycles to about 300,000 cycles of the excitation signal. In one embodiment, other suitable periods of the excitation signal being active can be used, such as for example, less than about 20 msec, greater than about 30 msec, and the like. In one embodiment, a short duration of the excitation signal being active can make it unnecessary to obtain constructive interference at the focus. This can be a result of time delays for propagation of an ultrasonic wave from different points of the aperture to a focus point $P_o$ being greater than the duration of the excitation signal being active. In one embodiment, it may be sufficient to modify phases corresponding to aperture locations based on the operational frequency without controlling the time delays for obtaining constructive interference. In one embodiment, phases corresponding to aperture locations may be modified and, additionally, time delays for obtaining constructive interference at a new focus point may be controlled.

Figure 6A:
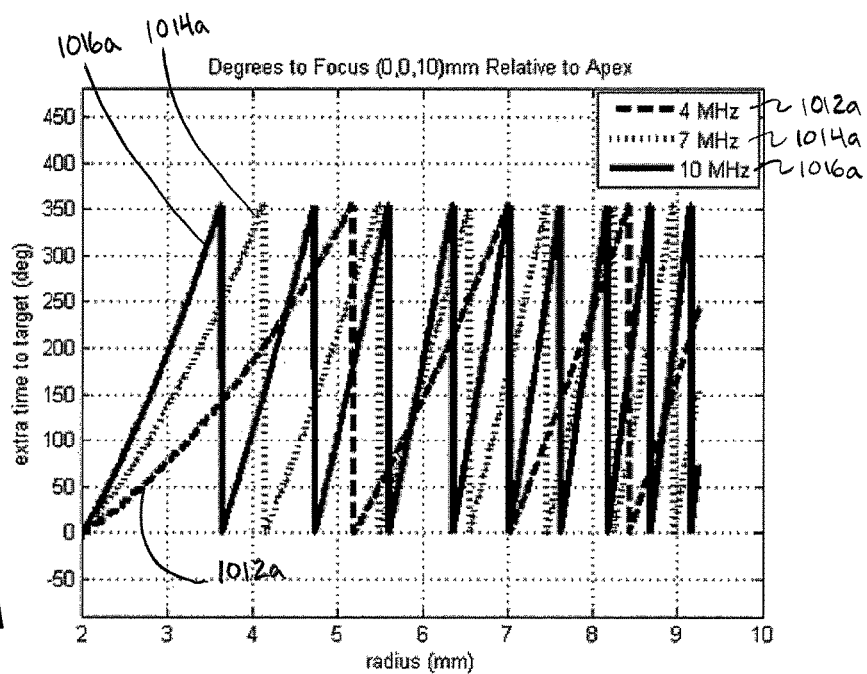
FIGS. 6A-6C are plots illustrating phase delays for reaching a focal point for various transducers according to several embodiments of the present invention.
Figure 6B:
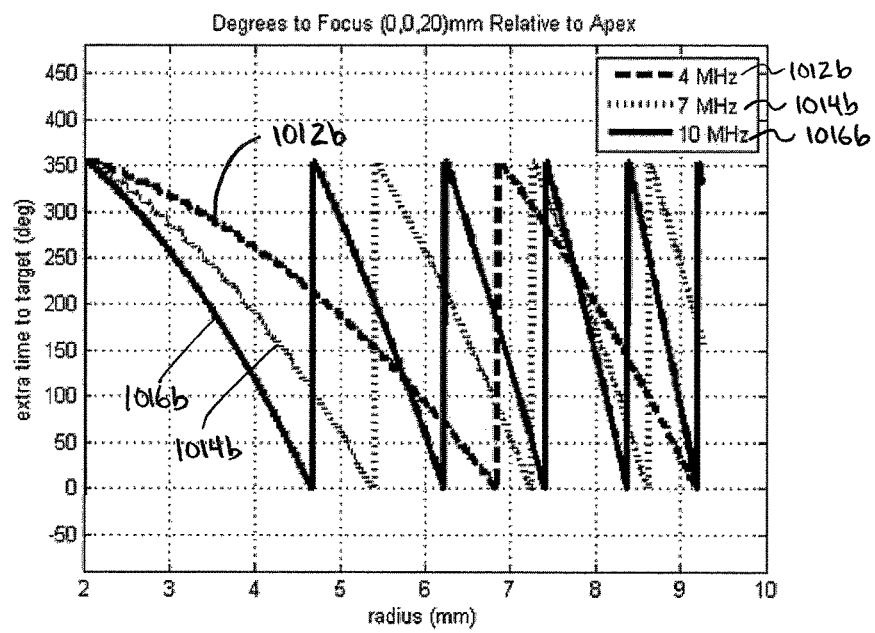
Figure 6C:
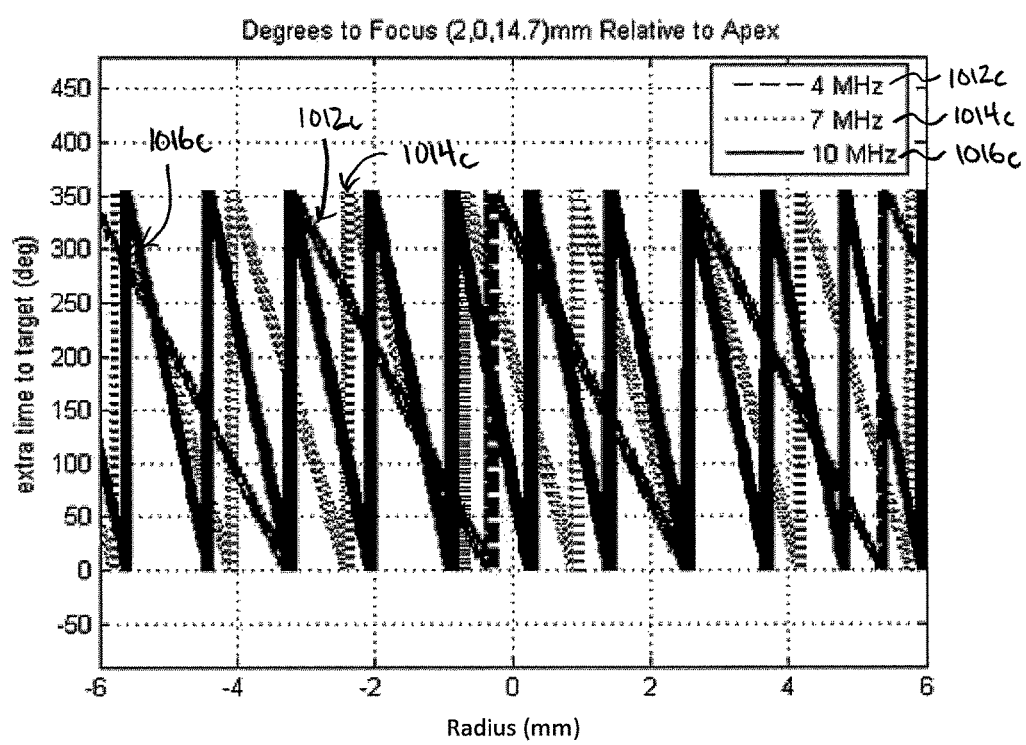

FIGS. 6A-6C illustrate phase delays associated with propagation of sound to focus relative to the apex of an aperture according to several embodiments. In one embodiment, phase delays are associated with time delays. FIG. 6A illustrates the relative phase delays 1012a, 1014a, and 1016a (in degrees) for sound energy travelling from a spatial point on the aperture to reach a target focus point $P_0$=(0, 0, 10 mm) in relation to varying radial locations on the bowl aperture according to one embodiment. Curve 1012a corresponds to an excitation signal of about 4 MHz, curve 1014a corresponds to an excitation signal of about 7 MHz, and curve 1016a corresponds to an excitation signal of about 10 MHz. FIG. 6B illustrates the relative phase delays 1012b, 1014b, and 1016b (in degrees) for sound energy travelling from a spatial point on the aperture to reach a target focus point $P_0$=(0, 0, 20 mm) in relation to varying radial locations on the bowl aperture according to one embodiment. Curve 1012b corresponds to an excitation signal of about 4 MHz, curve 1014b corresponds to an excitation signal of about 7 MHz, and curve 1016b corresponds to an excitation signal of about 10 MHz. FIG. 6C illustrates the relative phase delays 1012c, 1014c, and 1016c (in degrees) for sound energy travelling from a spatial point on the aperture to reach a target focus point $P_0$=(2 mm, 0, 14.7 mm) in relation to varying radial locations on the bowl aperture according to one embodiment. Curve 1012c corresponds to an excitation signal of about 4 MHz, curve 1014c corresponds to an excitation signal of about 7 MHz, and curve 1016c corresponds to an excitation signal of about 10 MHz. As is illustrated in FIGS. 6A-6C, in one embodiment, whether the aperture attempts to focus shallow, deep, or laterally, which can be related to the operational frequency, is related to a number of discontinuities in the phase delay. The number of discontinuities over a given length increases with the operational frequency of the excitation signal. In one embodiment, as is explained below, manufacturing and system limitations may increase the number of discontinuities. In one embodiment, as is illustrated in FIG. 6B, the rate of phase delay transitions increases toward the edge of the transducer (e.g., right part of the graph) regardless of whether the transducer is used to focus deep or shallow. In one embodiment, as is illustrated in FIG. 6C, the rate of phase delay transitions is substantially constant when a transducer is used to tilt the beam. FIGS. 5B-5D and FIGS. 6A-6C illustrate additional time and phase to a focus point from a point on a transducer bowl. In one embodiment, the additional time and/or phase can be reduced or eliminated by placing an opposite of the time and/or phase delay at appropriate transducer locations.

Therapy Delivery Using Discrete Phase Shifting

In one embodiment, delay and/or phase quantization can affect the precision that is used to represent time and/or phase delays. In other words, the discrete delay and/or discrete phase can be used. In one embodiment, a precision of time and/or phase delays can be limited by system parameters, such as a system clock and/or number of bits available for representing the delay. In one embodiment, other system parameters can instead or further limit the precision. In one embodiment, phase delays are equally spaced around the unit circle (360°). In one embodiment, phase delays can aperiodic or unequally spaced around the unit circle. Table 4 shows phase quantization levels according to several embodiments. Additional numbers of levels (greater than 8) can be used in several embodiments. As is shown in Table 4 two phases (N=2), 0° and 180°, can represent a minimum level of phase control for changing the focus point of an ultrasound beam according to one embodiment.

TABLE 4

| Number of levels (N) | Phases (degrees) |
| --- | --- |
| 2 | 0, 180 |
| 3 | 0, 120, 240 |
| 4 | 0, 90, 180, 270 |
| 5 | 0, 72, 144, 216, 288 |
| 6 | 0, 60, 120, 180, 240, 300 |
| 7 | 0, 51, 103, 154, 206, 257, 309 |
| 8 | 0, 45, 90, 135, 180, 225, 270, 315 |

Figure 7A:
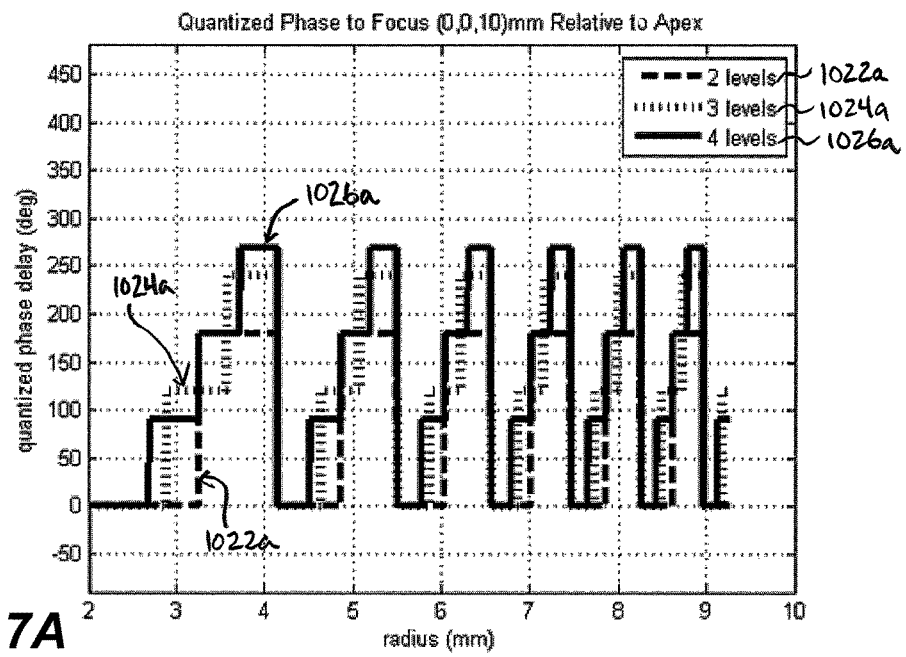
FIGS. 7A-7C are plots illustrating quantized phase delays for reaching a focal point for various transducers according to several embodiments of the present invention.
Figure 7B:
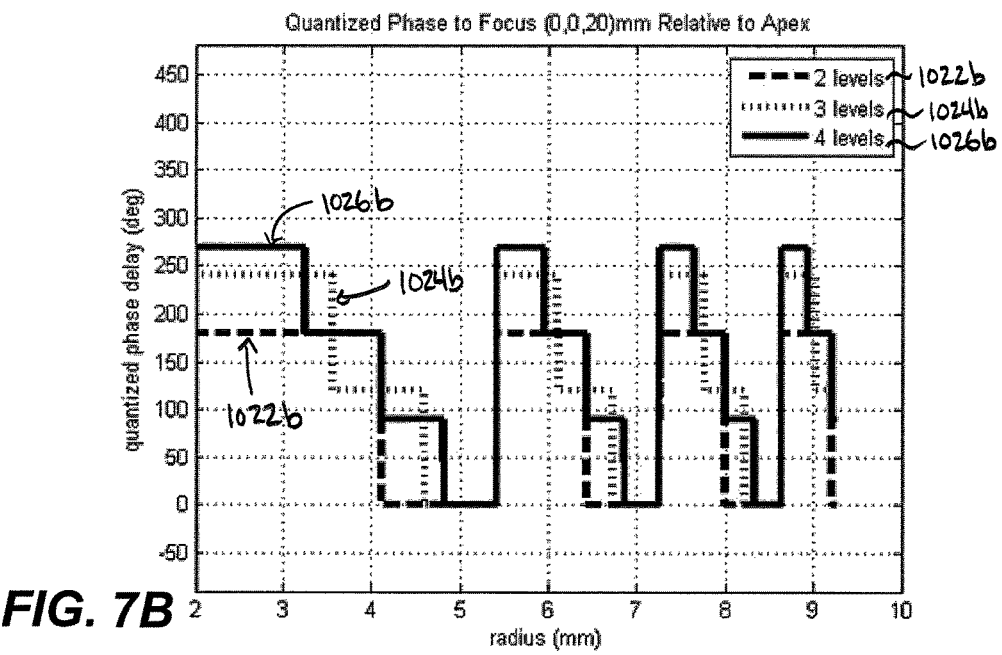
Figure 7C:
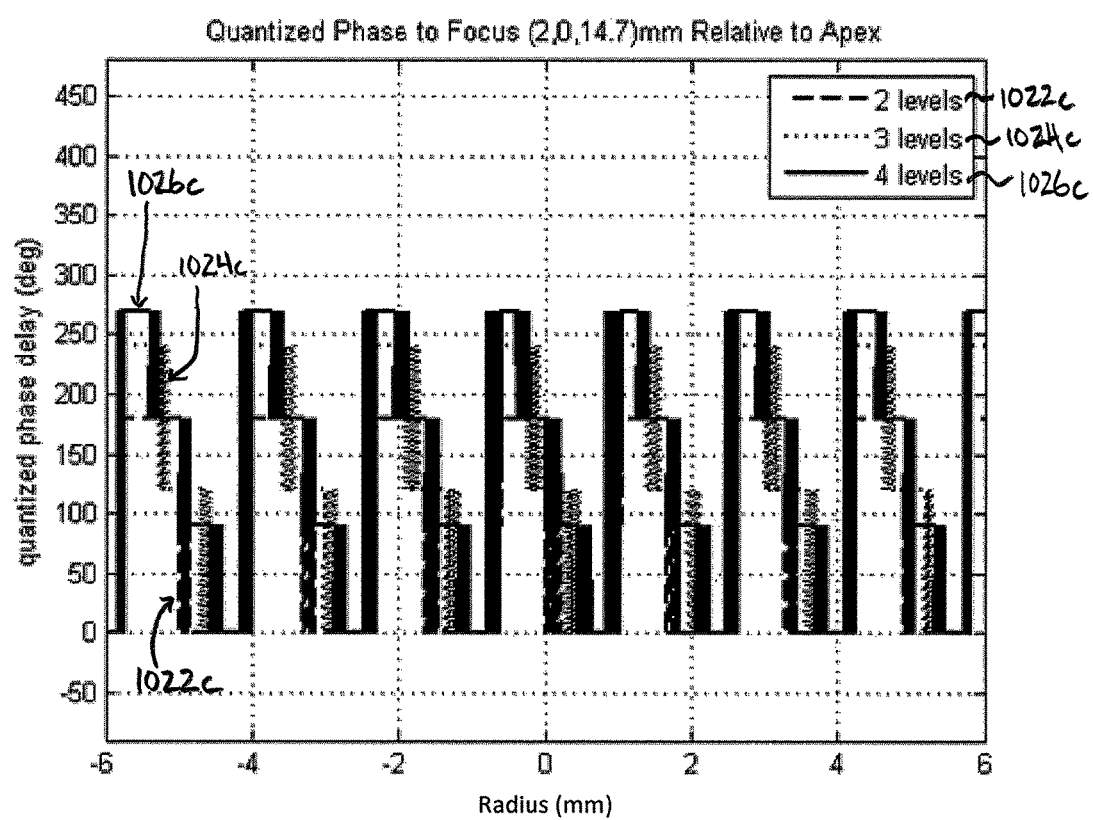

FIGS. 7A-7C illustrate discrete or quantized phase delays for various quantization levels, where phase delays are associated with propagation of sound to focus relative to the apex of an aperture according to several embodiments. FIGS. 7A-7C illustrate sound propagation at an operational frequency of about 7 MHz. FIG. 7A illustrates the relative quantized phase delays 1022a, 1024a, and 1026a (in degrees) for sound energy travelling from a spatial point on the aperture to reach a target focus point P0=(0, 0, 10 mm) in relation to varying radial locations on the bowl aperture according to one embodiment. Curve 1022a corresponds to two phase quantization levels, curve 1024a corresponds to three phase quantization levels, and curve 1026a corresponds to four phase quantization levels. FIG. 7B illustrates the relative quantized phase delays 1022b, 1024b, and 1026b (in degrees) for sound energy travelling from a spatial point on the aperture to reach a target focus point P0=(0, 0, 20 mm) in relation to varying radial locations on the bowl aperture according to one embodiment. Curve 1022b corresponds to two phase quantization levels, curve 1024b corresponds to three phase quantization levels, and curve 1026b corresponds to four phase quantization levels. FIG. 7C illustrates the relative quantized phase delays 1022c, 1024c, and 1026c (in degrees) for sound energy travelling from a spatial point on the aperture to reach a target focus point P0=(2 mm, 0, 14.7 mm) in relation to varying radial locations on the bowl aperture according to one embodiment. Curve 1022c corresponds to two phase quantization levels, curve 1024c corresponds to three phase quantization levels, and curve 1026c corresponds to four phase quantization levels. In several embodiments, as the number of quantization levels increases as is shown in FIGS. 7A-7C (e.g., curves 1026a, 1026b, and 1026c), quantized phase delay patterns in the one embodiment with a frequency of 7 MHz become substantially similar to unquantized phase delay patterns shown in FIGS. 6A-6C (e.g., curves 1014a, 1014b, and 1014c).

In one embodiment with reference to curve 1022c of FIG. 7C (two-level phase quantization), demonstrates that when a focused beam is steered 2 mm and −2 mm, a resulting phase delay pattern is substantially similar with transition from 0° to 180° occurring at substantially same spatial frequency. There is a slight spatial shift in the phase delay pattern. Since the phase delay pattern is substantially similar at 2 mm and −2 mm, in one embodiment, acoustic intensity distribution at the focus may have a peak at both foci locations simultaneously. In one embodiment, if the phase quantization is two levels, a phase solution for a specific focus will also be a solution for another location. In one embodiment, this result can be similar for modification of the focus along the beam axis. If the phase quantization is two levels, then a solution for one focus can also be a solution for another focus.

Figure 8A:
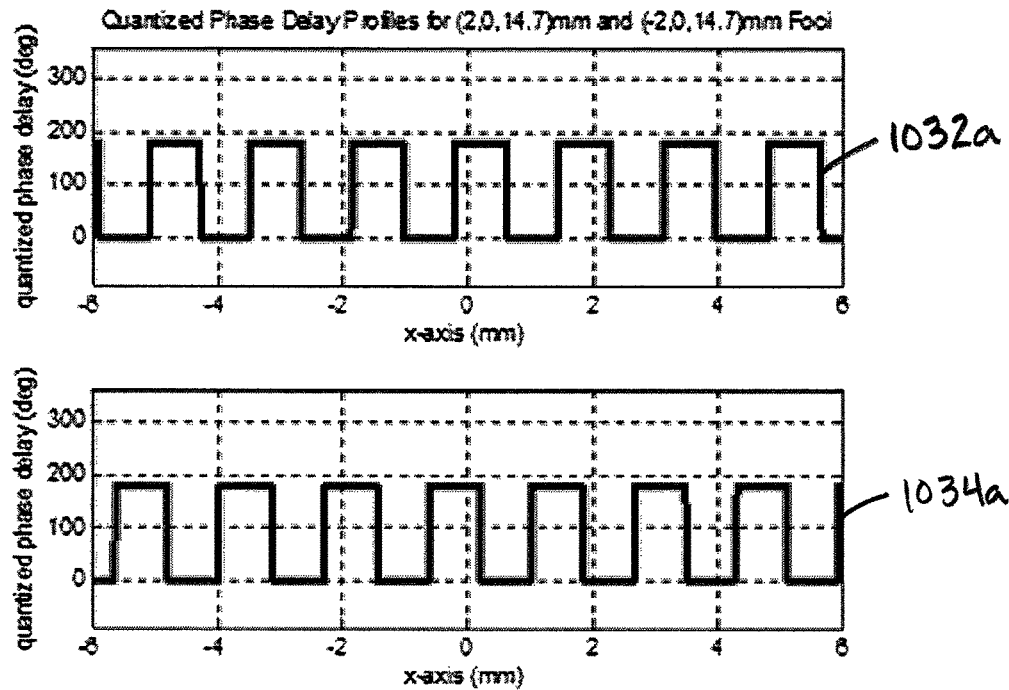
FIGS. 8A-8B are plots illustrating quantized phase delay profiles for reaching a focal point for various transducers according to several embodiments of the present invention.

FIG. 8A illustrates discrete or quantized phase delays associated with propagation of sound, at an operational frequency of about 7 MHz, to focus relative to the apex of an aperture according to several embodiments. FIG. 8A illustrates the relative phase delays 1032a and 1034a (in degrees) for sound energy travelling from a spatial point on the aperture to reach target focus points (2 mm, 0, 14.7 mm) and (−2 mm, 0, 14.7 mm) respectively. Curves 1032a and 1034a are shown in relation to varying radial locations on the bowl aperture according to one embodiment. In one embodiment, the quantization level of two is shown in FIG. 8A. As shown in FIG. 8A, quantized phase delay patterns for the two foci are substantially similar.

Figure 8B:
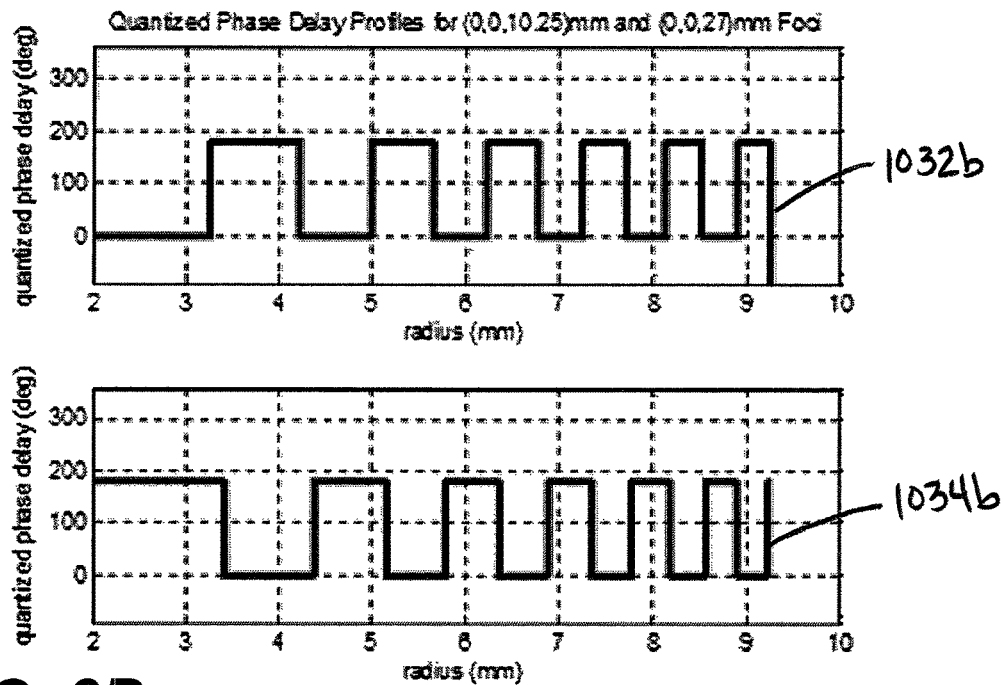

FIG. 8B illustrates discrete or quantized phase delays associated with propagation of sound, at an operational frequency of about 7 MHz, to focus relative to the apex of an aperture according to several embodiments. FIG. 8B illustrates the relative phase delays 1032b and 1034b (in degrees) for sound energy travelling from a spatial point on the aperture to reach target focus points (0, 0, 10.25 mm) and (0, 0, 27 mm) respectively. Curves 1032b and 1034b are shown in relation to varying radial locations on the bowl aperture according to one embodiment. In one embodiment, the quantization level of two is shown in FIG. 8B. As shown in FIG. 8B, quantized phase delay patterns for the two foci are substantially 180° out of phase.

In various embodiments, continuous or discrete amplitude modulation at an aperture and/or continuous or discrete phase delays to focus an ultrasound beam can be used. In one embodiment, it may be advantageous to provide a mechanical focal point rather than using aperture amplitude modulation and/or phase control in a flat aperture because the focal gain associated with mechanical focus may be preferable. In one embodiment, complexity of aperture or system design may be reduced if a mechanical focus can be created and modulation and/or phase delay techniques can be applied to the mechanical focus. One advantage can be a reduction in a number of discrete phase transitions for focusing the beam at a new focal point. Another advantage can be that a distance between different discrete phase levels can be increased when the aperture is already mechanical focused, which may result in using fewer quantization levels, such as two, three, four, etc.

In various embodiments, fabrication methods, including piezoelectric material poling and/or discrete system phasing, can be used to manufacture transducers configured to split or focus an ultrasound beam in two and/or three dimensions from a mechanical focus. The following lists several non-limiting examples of transducer designs. In various embodiments, other transducer designs can be manufactured using the disclosed methods.

Multi-Focal Energy Delivery Using Transducer Poling

In several embodiments, a transducer can comprise piezoelectric material. Piezoceramic material can be poled at elevated temperatures and high electric fields to create a net dipole moment in the material. A net dipole moment can allow the piezoceramic material to have a piezoelectric effect that causes either material contraction or expansion when an electric field is placed across a whole or part of the material in the direction of the dipole moment. In one embodiment, parts of a transducer, such as a transduction element, can be treated to have different poling moment features. In one embodiment, a single transduction element can be treated to have one, two, or more poling features. In one embodiment, a single transduction element can be treated to have one pole. In another embodiment, parts of an element can be treated with one pole, and non-treated parts of the element can have a second pole. In one embodiment, a poling treatment can be painted on a transduction element.

Figure 9:
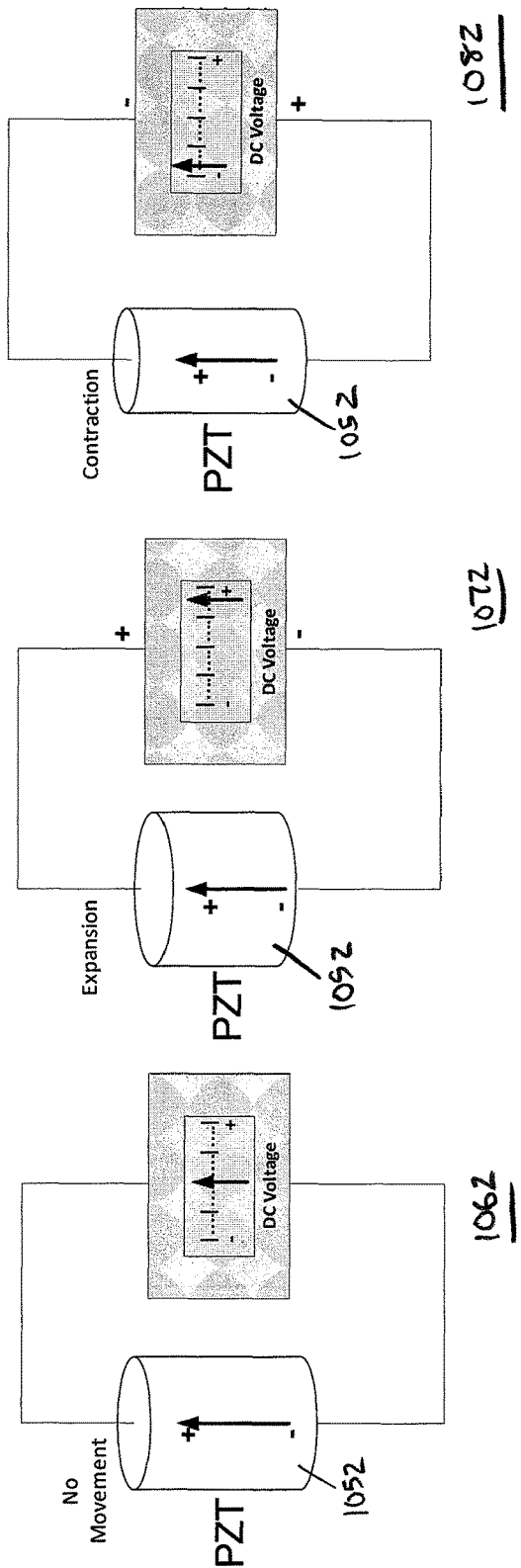
FIG. 9 is a schematic illustration of characteristics of poled piezoelectric material according to an embodiment of the present invention.

FIG. 9 shows a schematic diagram of a poled piezoceramic material and resulting behavior when a voltage is applied according to one embodiment. In one embodiment, a transducer can comprise PZT 1052 piezoceramic material. The arrow shown in the PZT material 1052 is a net dipole moment. In one embodiment, if a voltage is placed across the PZT material 1052 such that the electric field is in the opposite or substantially opposite direction of the dipole moment (as is shown in 1082), then the material contracts. In one embodiment, if a voltage is placed across the PZT material 1052 such that the electric field is in the same or substantially same direction as the dipole moment (as is shown in 1072), then the material expands. In one embodiment, the PZT material 1052 does not expand or contract when no voltage is applied across the material, as is shown in 1062.

Figure 10A:
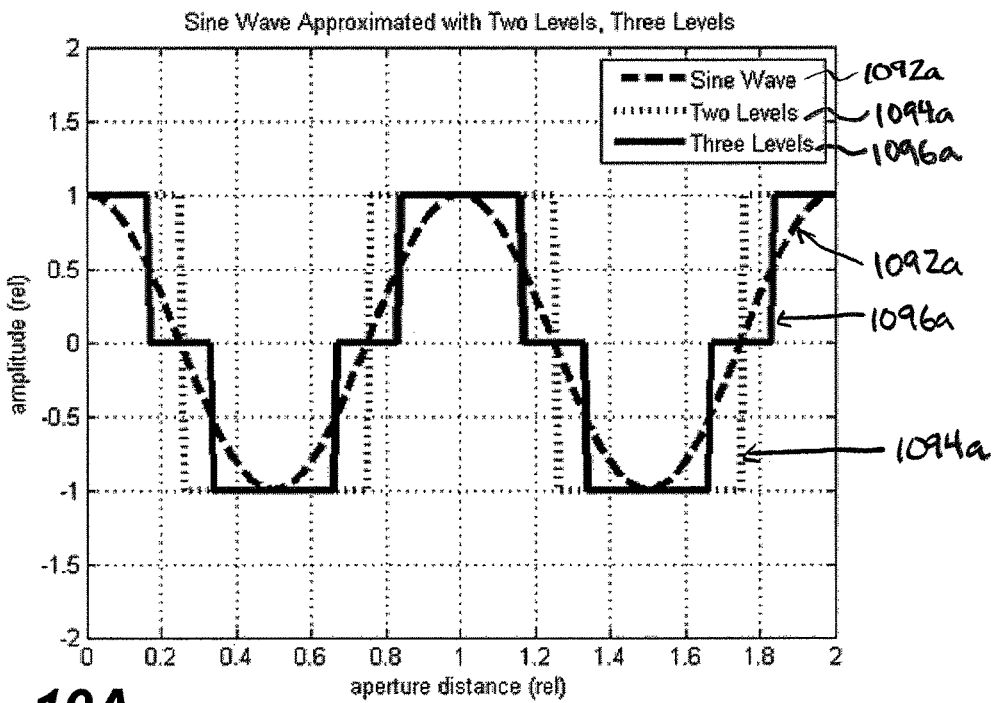
FIGS. 10A-10B are plots illustrating approximations of amplitude modulation according to several embodiments of the present invention.
Figure 10B:
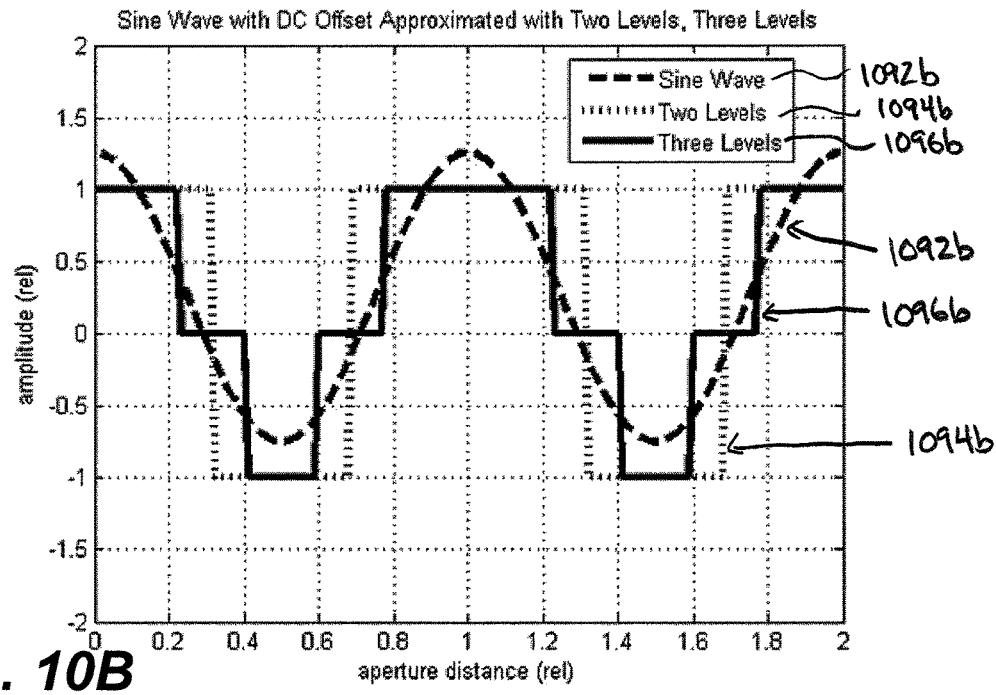

In several embodiments, piezoelectric material poling can be used to implement aperture amplitude modulation. In one embodiment, two level modulation can be equivalent to two level phase quantization. As is shown in equations (12)-(14), an ultrasonic beam emitted by a transducer aperture can be modulated to appear at two (or more) locations in a focal plane shifted by a distance that is related to the spatial frequency of a modulation function (e.g., cosine and/or sine function). In one embodiment, poling direction may be used to modify the amplitude modulation at the aperture, and to approximate cosine and/or sine amplitude modulation. As is shown in FIG. 9, in one embodiment, poling or applying voltage across the whole or part of the material can provide three levels of amplitude modulation: −1 (contraction of the material), 1 (expansion of the material), and 0 (no change to the shape of the material). FIGS. 10A-10B illustrate approximations of amplitude modulation using two and three levels of poling according to several embodiments. FIG. 10A illustrates approximations of amplitude modulation using a sine function according to one embodiment. The x-axis represents relative distance with respect to an apex of the aperture and the y-axis represents amplitude of the modulation function. Curve 1092*a* illustrates the modulation function (e.g., sine function), curve 1094*a* illustrates approximation using two levels of poling (e.g., ±1), and curve 1096*a* illustrates approximation using three levels of poling (e.g., ±1 and 0). FIG. 10B illustrates approximations of amplitude modulation using a sine function with DC offset of 0.25 according to one embodiment. The x-axis represents relative distance with respect to an apex of the aperture and the y-axis represents amplitude of the modulation function. Curve 1092*b* illustrates the modulation function (e.g., sine function), curve 1094*b* illustrates approximation using two levels of poling (e.g., ±1), and curve 1096*b* illustrates approximation using three levels of poling (e.g., ±1 and 0). In one embodiment, as is illustrated in FIG. 10B, the width of a positive poled region (having amplitude of 1) is greater than the width of a negative poled region (having amplitude of −1) so that a mean amplitude is substantially equal to the DC offset (e.g., 0.25). The limitation of two or three levels limits the achievable DC offset between −1 and 1. In several embodiments, more than three levels of poling can be used for amplitude modulation.

In one embodiment, in order to quantify the energy distribution at the focus, then the square wave can be represented in terms of a function that has a related Fourier transform pair. The Fourier series expansion for a square wave of period c is:

$$f_{square}\left(\frac{x}{c}\right) = \frac{4}{\pi}\sum_{n=1}^{\infty}\frac{\sin(2\pi(2n-1)ct)}{(2n-1)} = \frac{4}{\pi}\left(\sin(2\pi ct) + \frac{1}{3}\sin(2\pi 3ct) + \frac{1}{5}\sin(2\pi 5ct) + \ldots\right)$$ (25)

In one embodiment, a circular aperture with amplitude modulation described in equation (25) can be described as:

$$f_{aperture}(x, y) = f_{square}\left(\frac{x}{c}\right)\left(circ\left(\frac{r}{a}\right) - circ\left(\frac{r}{b}\right)\right)$$ (26a)

The Fourier transform of this function is:

$$F_{x,y}(f_{aperture}(x, y)) = \left[\frac{4}{\pi}\sum_{n=1}^{\infty}\frac{\delta(\xi_x - (2n-1)c) - \delta(\xi_x + (2n-1)c)}{2f(2n-1)}\right] * F(\xi_x, \xi_y)$$ (26b)

Equation (26b) may be simplified as follows:

$$F_{x,y}(f_{aperture}(x, y)) = \left[\frac{4}{\pi}\sum_{n=1}^{\infty}\frac{F(\xi_x - (2n-1)c, \xi_y) - F(\xi_x + (2n-1)c, \xi_y)}{2j(2n-1)}\right]$$ (26c)

In one embodiment, sound wave pressure in the focal plane includes repeating patterns of the main beam at multiple spatial locations separated by a distance of 2c between each beam. The repeating patterns can be decreasing in the amplitude.

Figure 11A:
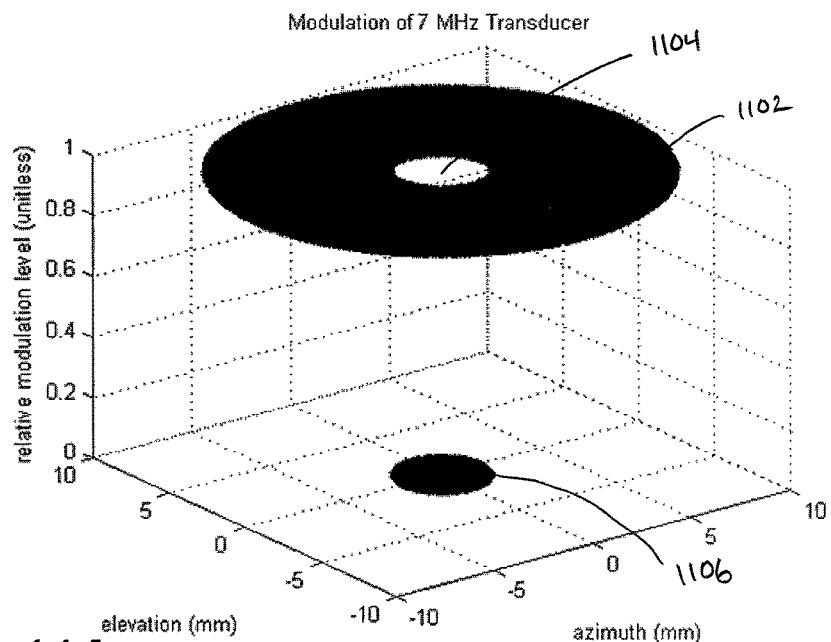
FIGS. 11A-11H are schematic illustrations and plots illustrating modulation functions and corresponding intensity distributions according to several embodiments of the present invention.
Figure 11B:
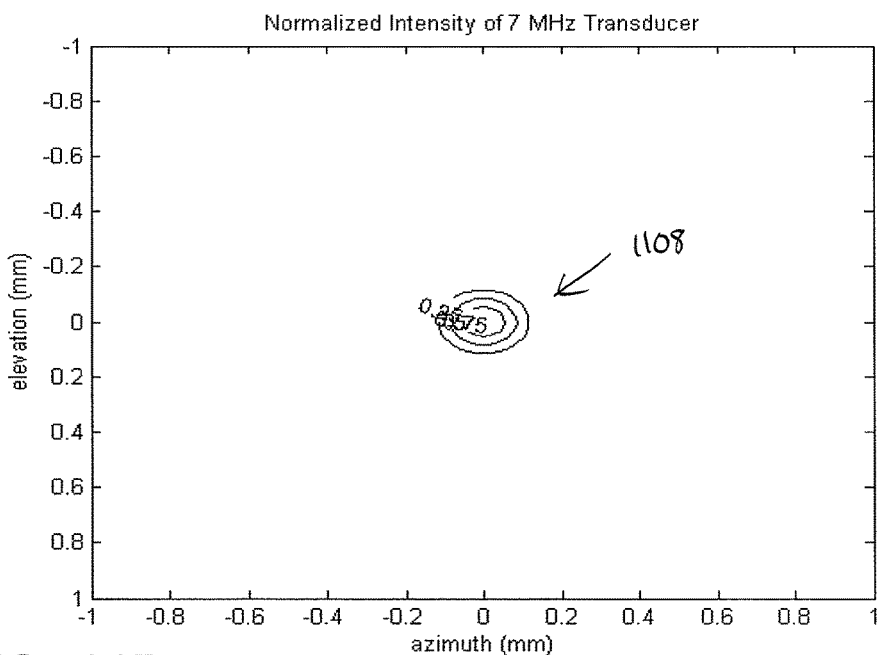
Figure 11C:
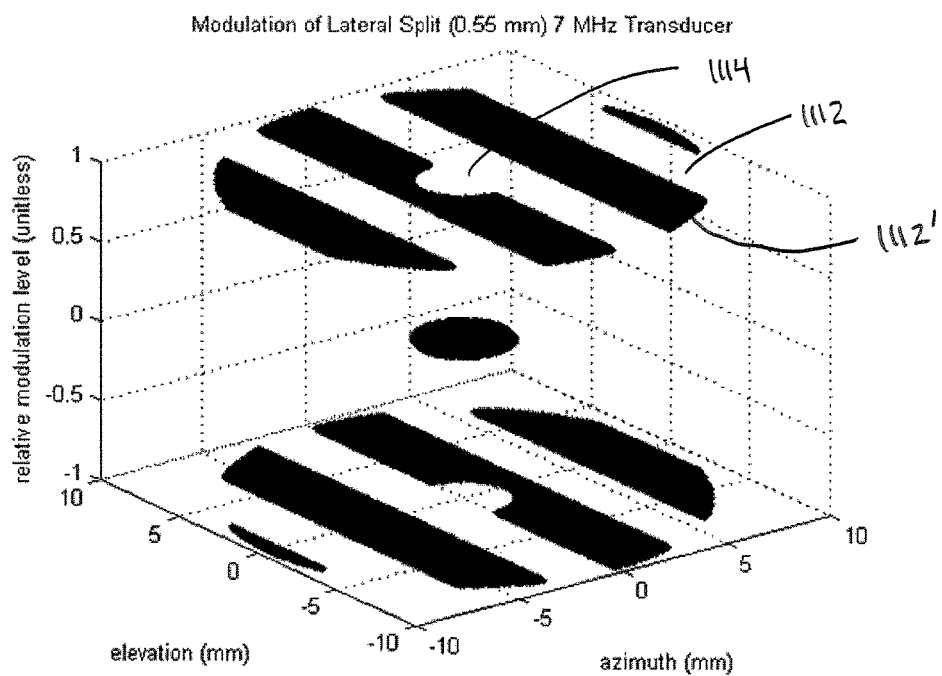
Figure 11D:
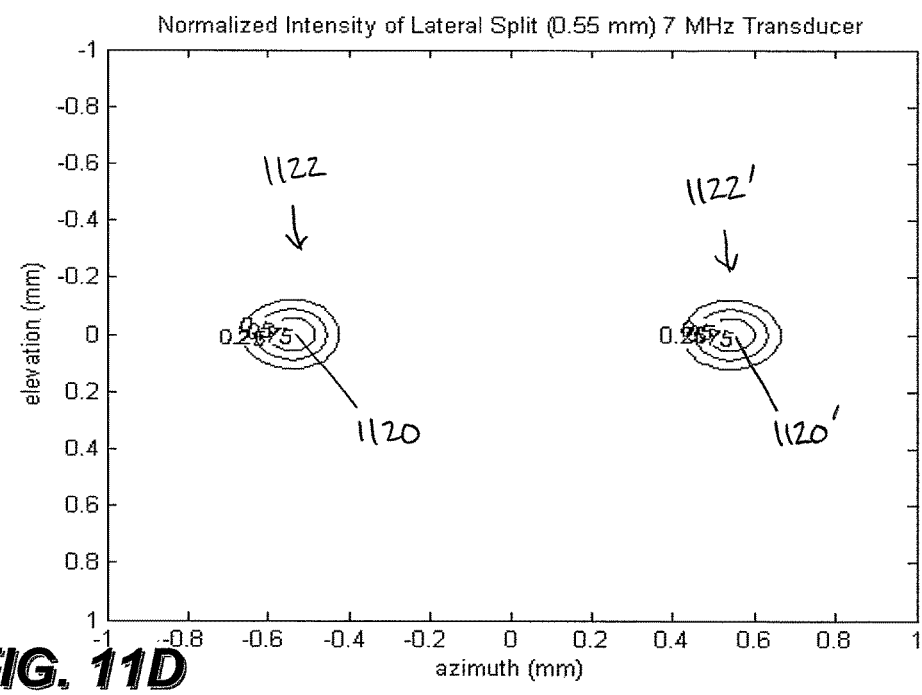
Figure 11E:
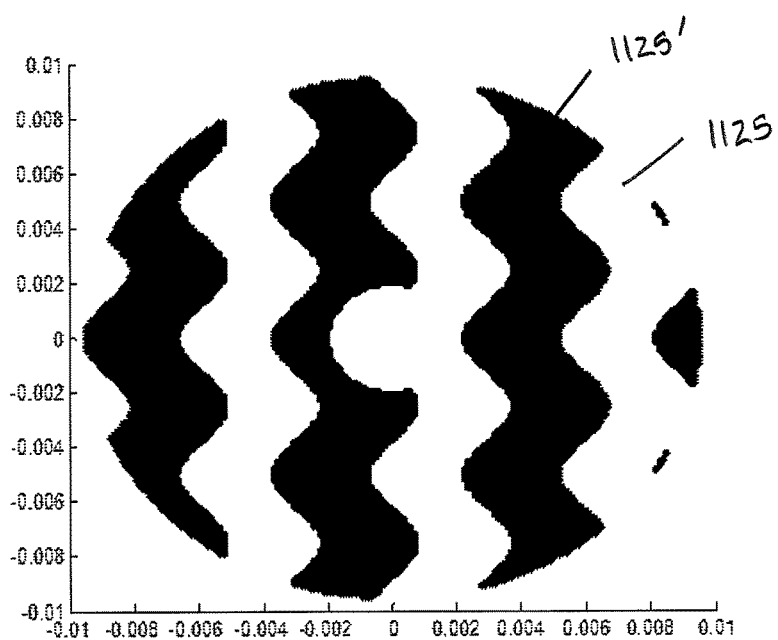
Figure 11F:
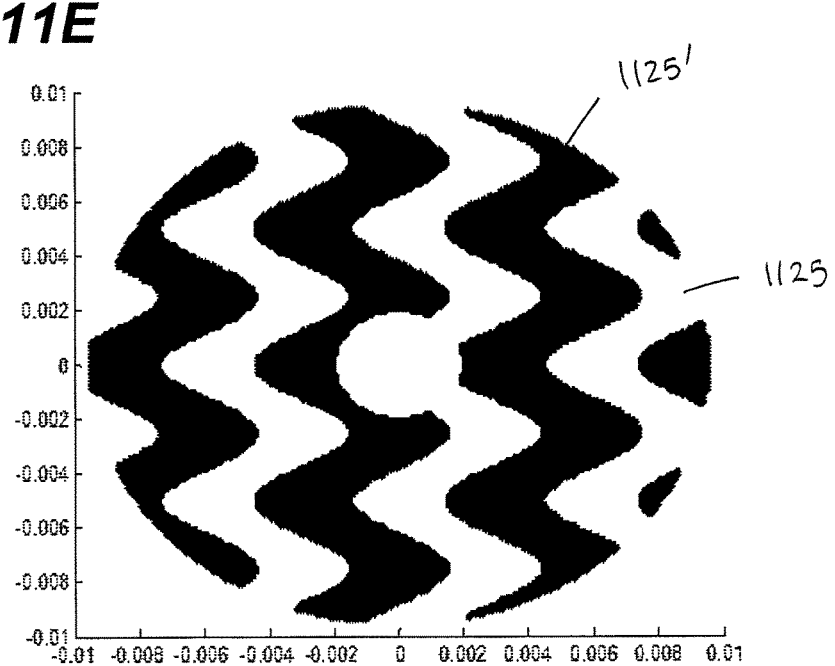
Figure 11G:
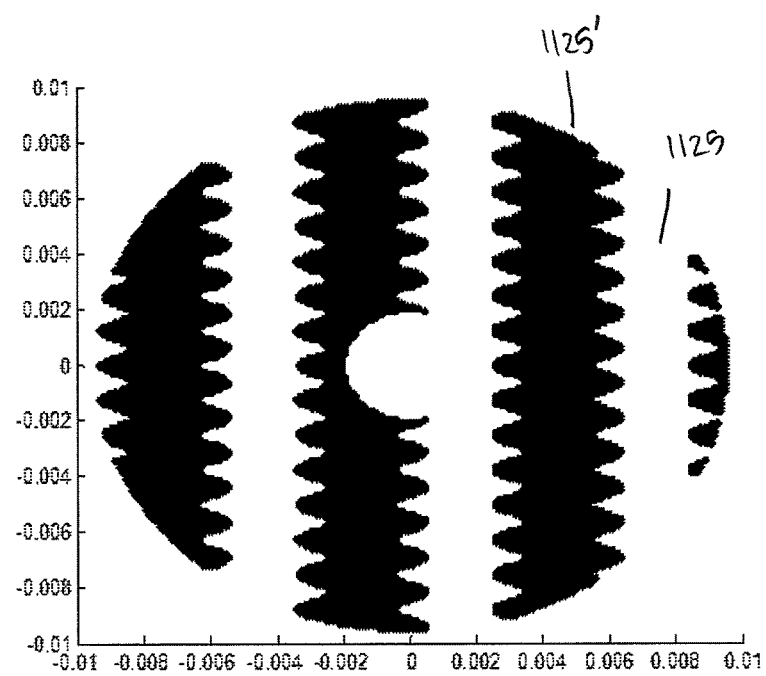
Figure 11H:
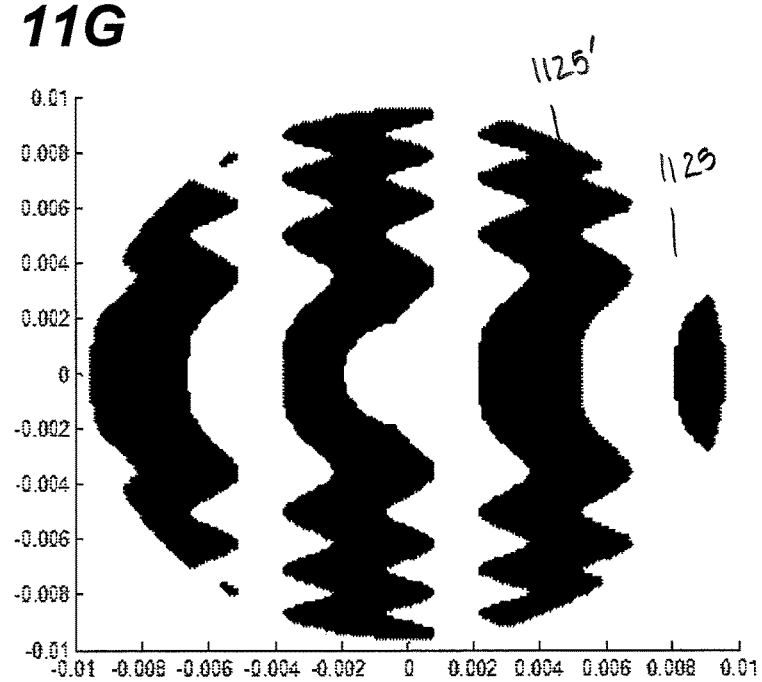

FIGS. 11A-11H illustrate some embodiments of aperture modulation or apodization functions (using two-level poling or three-level poling) and some corresponding normalized intensity distributions of the sound wave pressure at the focus or foci for a transducer excited by a 7 MHz excitation signal according to several embodiments. In one embodiment, transducers illustrated in FIGS. 11A-11H are configured a circular bowls with OD=19 mm and $F_L$=15 mm. FIGS. 11A-11B illustrate apodization profile without splitting the beam and a corresponding intensity distribution according to one embodiment. FIG. 11B illustrates that intensity is concentrated at the focus 1108. FIGS. 11C-11D illustrate apodization profile with laterally splitting the beam by about 1.1 mm between the foci peaks and a corresponding intensity distribution according to one embodiment. As is illustrated by region 1104 in FIG. 11A and region 1114 in FIG. 11C, in several embodiments, part of an aperture of the transducer has an apodization of zero, which represents an inner diameter (ID) of the bowl. In some embodiments, these regions 1104 and 1114, which are illustrated as being about 4 mm in diameter, can correspond to regions where an imaging element can be located. In one embodiment, apodization of the imaging element can be represented by region 1106.

With reference to FIG. 11C, in one embodiment, amplitude modulation for a 1.1 mm split between the foci peaks is illustrated. In one embodiment, if two poling or apodization levels are used, then 8 strips of substantially equal width (except at the edges) are defined on the aperture surface. For example, two such strips are labeled as 1112 and 1112'. In one embodiment, the polarization of the strips alternates from −1 to +1 across the transducer surface. The resulting beam pattern is shown in FIG. 11D. As expected, the ultrasonic beam appears at two foci 1120 and 1120' are located at about −0.55 mm and 0.55 mm. Higher frequency components of the beam are visible in regions 1122 and 1122' at a distance of about 1.65 mm from the beam axis. In one embodiment, these components have lower intensity than foci regions 1120 and 1120'. The higher frequency components can correspond to the third harmonic having a lower intensity, as is expressed in equation (26c). In various embodiments, such as illustrated in FIGS. 11E-11H, polarization of portions 1125, 1125' of the transducer surface can include lines, curves, shapes, waves, patterns, etc. In one embodiment, features of a portions 1125, 1125' can be used to maintain a foci split, and can redistribute energy prefocally and/or post-focally for less heating.

In one embodiment, the split of the beam may occur in both x (azimuth) and y (elevation) dimensions. In one embodiment, x and y axis splits may be treated independently when performing the Fourier transform. In one embodiment, an aperture can be designed for splitting the beam in the x dimension by about 1.0 mm and in the y dimension by about 0.5 mm. The corresponding aperture modulation function can be represented as:

$$f_{aperture}(x, y) = f_{square}\left(\frac{y}{d}\right) f_{square}\left(\frac{x}{c}\right)\left(circ\left(\frac{r}{a}\right) - circ\left(\frac{r}{b}\right)\right) \quad (27)$$

Figure 12A:
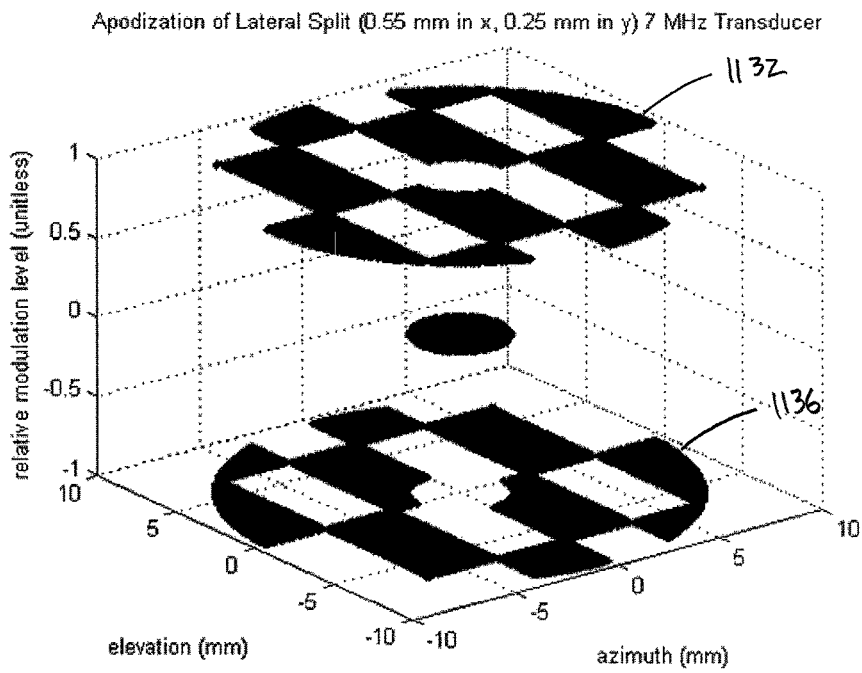
FIGS. 12A-12D are plots illustrating modulation functions and corresponding intensity distributions according to several embodiments of the present invention.
Figure 12B:
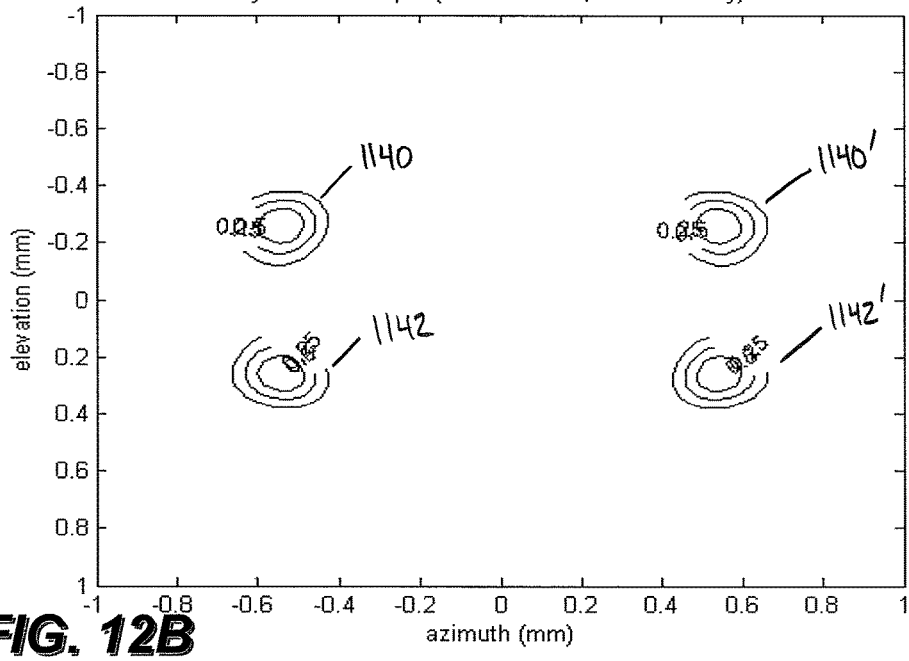

The spatial frequency for alternating amplitude modulation can be calculated as described above in connection with equations 26(a)-(c), with the exception that the calculation is performed for two dimensions. FIGS. 12A-12D illustrate some embodiments of aperture modulation or apodization functions (using two-level poling) and a corresponding normalized intensity distributions of the sound wave pressure at the focus or foci for a transducer excited by a 7 MHz excitation signal according to several embodiments. In one embodiment, transducers illustrated in FIGS. 12A-12D are configured a circular bowls with OD=19 mm and FL=15 mm. FIG. 12A shows an apodization function for the aperture according to one embodiment. As is illustrated, the checkerboard pattern 1132 and 1136 is alternating in amplitude in both x and y directions. As is illustrated in FIG. 12B, the checkerboard pattern produces four substantially distinct ultrasound beams 1140, 1140', 1142, and 1142' separated by the expected distances, namely by about 1.0 mm in x direction and by about 0.5 mm in y direction. In one embodiment, a five point pattern can be achieved by adding a constant to an apex of the aperture, which may have a corresponding intensity distribution at the origin.

Figure 12C:
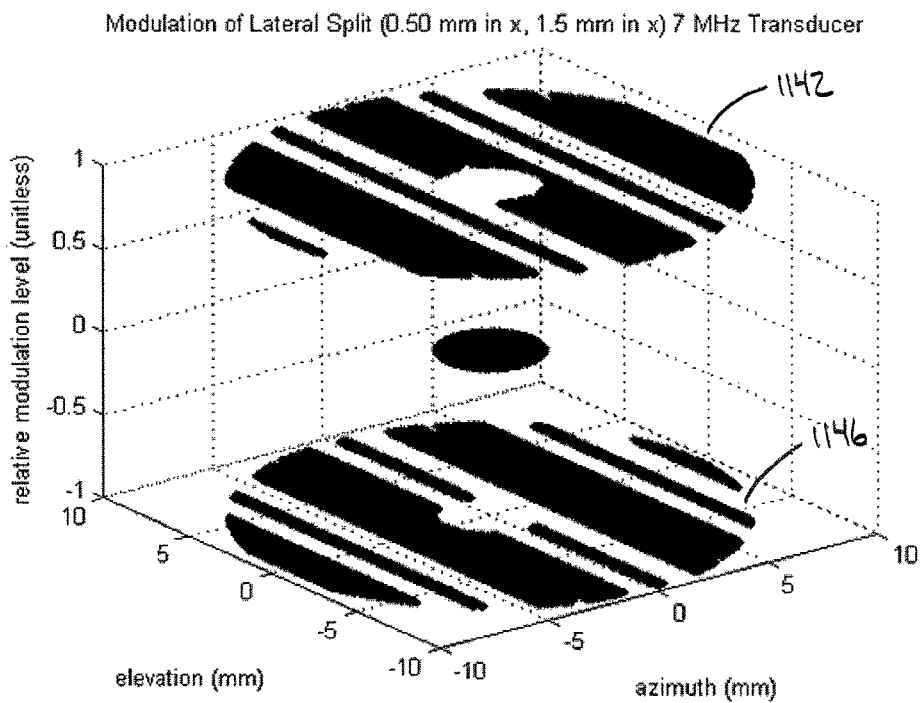
Figure 12D:
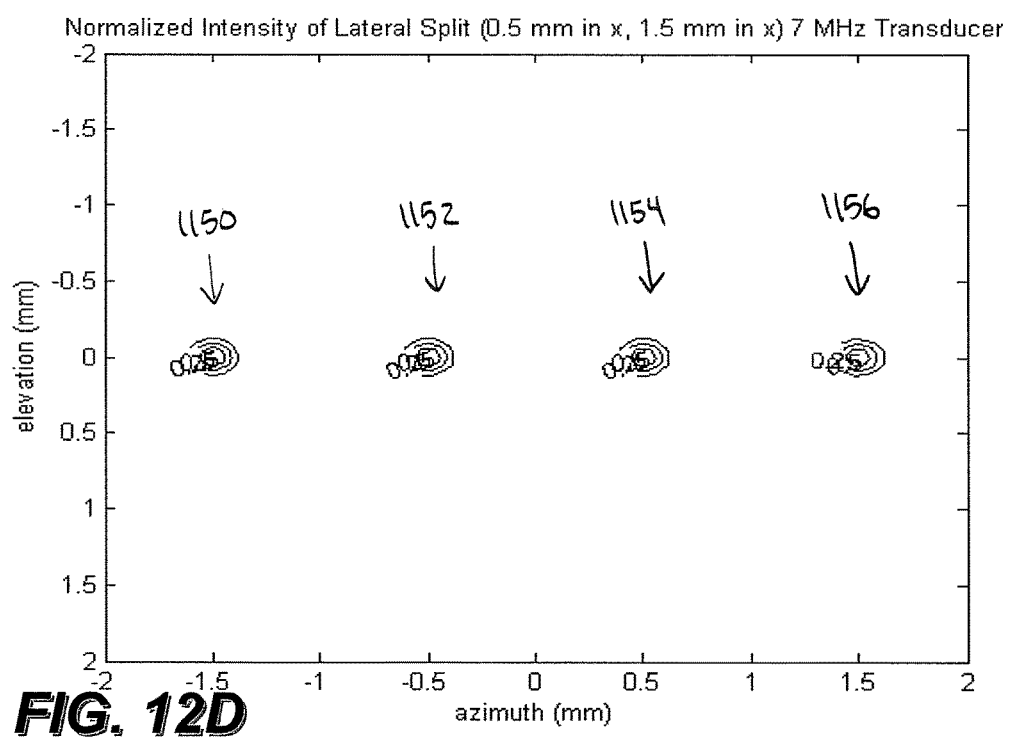

In one embodiment, as is illustrated in FIGS. 12C-12D, a line of four peaks is obtained by placing multiple frequencies along the same dimension (e.g., x dimension). The modulation function can be expressed as:

$$f_{aperture}(x, y) = \left(f_{square}\left(\frac{x}{d}\right) + f_{square}\left(\frac{x}{c}\right)\right)\left(circ\left(\frac{r}{a}\right) - circ\left(\frac{r}{b}\right)\right) \quad (28)$$

FIG. 12C shows an apodization function for the aperture according to one embodiment. As is illustrated, the pattern 1142 and 1146, the polarization of the strips alternates from −1 to +1 across the transducer surface. As is illustrated in FIG. 12D, in one embodiment, the pattern produces four substantially distinct ultrasound beams 1150, 1152, 1154, and 1156 separated by about 1.0 mm and 3.0 mm in an x direction.

In one embodiment, an axial split of the beam or split along one dimension is achieved such that the beam remains axis symmetric. In one embodiment, splitting the beam axially using only two phases from poling can be more difficult than obtaining a lateral split. This can be due to the difficulty of obtaining intensity balance between the two or more peaks. In one embodiment, two phases may produce two simultaneous intensity peaks with one shallower than the other. The deeper intensity peak can be of lower intensity than the shallow peak due to additional diffraction and attenuation in tissue. In one embodiment, more than two phases may be used to achieve an axial split.

Figure 13:
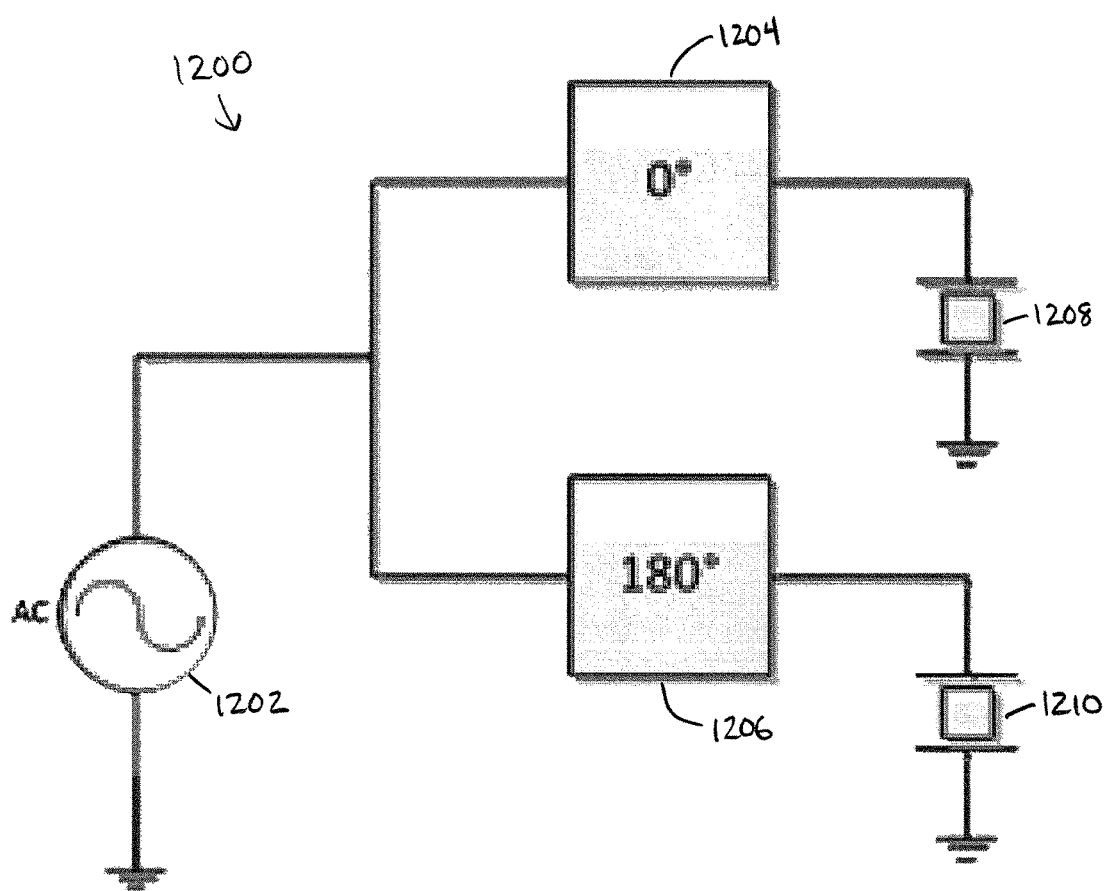
FIG. 13 is a schematic illustration of a two-phase system according to an embodiment of the present invention.

In several embodiments, splitting an ultrasonic beam simultaneously, nearly simultaneously, or sequentially into two or more foci points can be achieved through an application of discrete system phasing. FIG. 13 is a schematic illustration of a two-phase system 1200 according to one embodiment. As is illustrated, block 1202 is a AC voltage (or current) source that drives the discrete phase shifters, blocks 1204 and 1206 are discrete phase shifters by 0° and 180° respectively, and blocks 1208 and 1210 are transducer portions that are phase shifted. In one embodiment, discrete phase shifters 1204 and 1206 can be configured to phase shift the AC voltage (or current) signal supplied by the source 1202, so that the resulting signals are 180° out of phase. In one embodiment, discrete phase shifters 1204 and 1206 can be configured to excite different portions of the transducer. In one embodiment, the system 1200 is configured to mimic two levels of material poling. In one embodiment, it may be desirable to electrically isolate the transducer portions 1208 and 1210. Electrical isolation and corresponding connection scheme can determine a resultant beam pattern at the focus according to one embodiment. In one embodiment, no electrical isolation may be performed. With reference to FIG. 1, in several embodiments, discrete phase shifters may be placed in or on the controller 300, hand wand 100, module 200, and/or transducers of the ultrasound system 20. In one embodiment, continuous phase shifting may be used.

Figure 14:
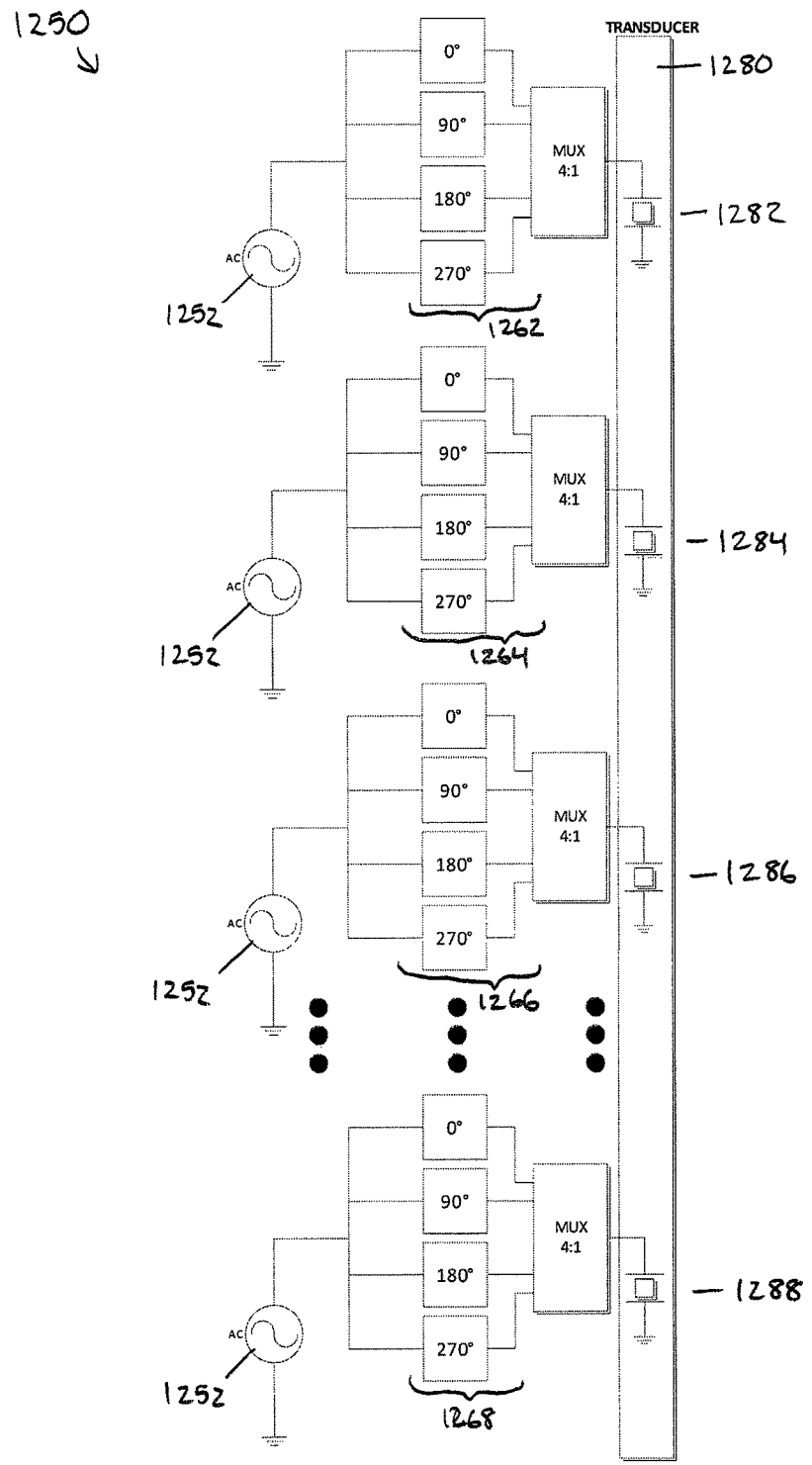
FIG. 14 is a schematic illustration of a selectable, four-phase system according to an embodiment of the present invention.

In several embodiments, more than two discrete phase shifters can be used (e.g., as is shown in Table 4). The increase in the number of phases may result in an improved approximation of the phase delays for steering and/or focus the beam. In one embodiment, four discrete phase shifters can be used. FIG. 14 is a schematic illustration of a selectable, four-phase system 1250 according to one embodiment. As is illustrated, blocks 1252, 1254, 1256, and 1258 are AC voltage (or current) sources that drive the discrete phase shifters 1262, 1264, 1266, and 1268. Each discrete phase shifter block can be configured to provide four different phases 0°, 90°, 180°, and 270°. In one embodiment, multiplexers 1272, 1274, 1276, and 1278 can be included to select a particular phase of a signal. Signal with selected phase can be applied to portions 1282, 1284, 1286, and 1288 of a transducer 1280. In one embodiment a portion is a part of a single transducer with a single transduction element. In one embodiment, a portion can be a transduction element. As is illustrated, each portion 1282, 1284, 1286, and 1288 of the transducer 1280 has a selectable phase (e.g., 0°, 90°, 180°, or 270°). In one embodiment, portions 1282, 1284, 1286, and 1288 can be electrically isolated (e.g., from each other). In one embodiment, if the transducer 1280 is divided or segmented into portions 1282, 1284, 1286, and 1866, the ultrasonic beam could be steered and focused to multiple foci locations.

Figure 15:
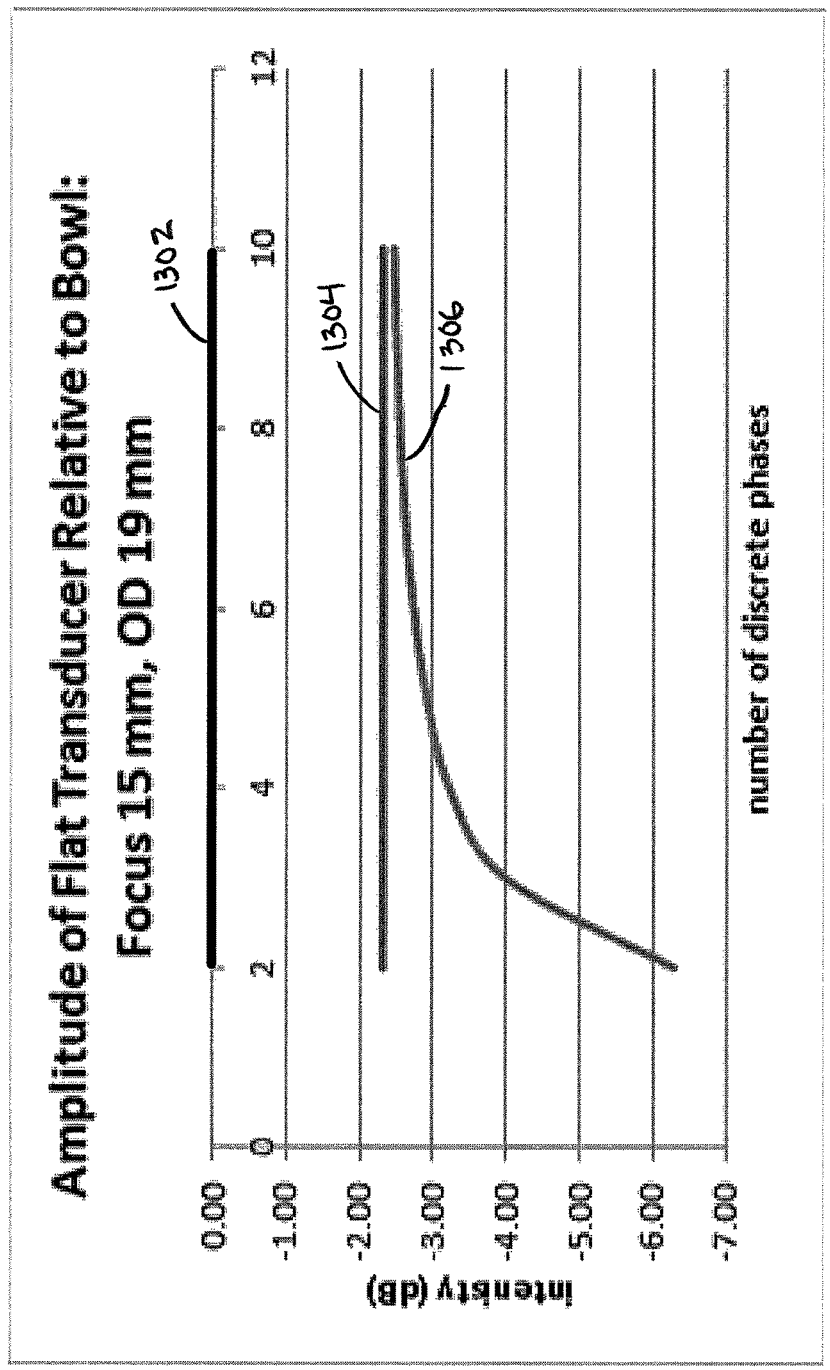
FIG. 15 is a plot illustrating performance of a discrete-phase system according to an embodiment of the present invention.

In one embodiment, an advantage of providing more discrete phase shifters can be illustrated by considering a flat disc or ring transducer and a measured intensity at the focus as compared to a measured intensity at the focus of a substantially perfectly focused circular bowl transducer. FIG. 15 illustrates performance of a discrete-phase system according to one embodiment. In one embodiment, the bowl transducer can be configured to have OD=19 mm and $F_L$=15 mm, and its intensity (in dB) is illustrated by line 1302. Intensity of the flat ring transducer is illustrated by line 1306. As is illustrated, the improvement in the focal intensity produced by the flat ring transducer increases (e.g., exponentially) between about two and 5-6 discrete phase levels, but starts to level off after about 5-6 discrete phases. In one embodiment, the intensity asymptotically approaches about −2.3 dB (line 1304). As is illustrated, in one embodiment flat ring transducer (line 1306) produces a smaller focal gain than the bowl transducer (line 1302). As can be seen, in one embodiment, adding additional discrete phase levels can improve the intensity at the focus and, thereby, improve the transducer performance.

Figure 16A:
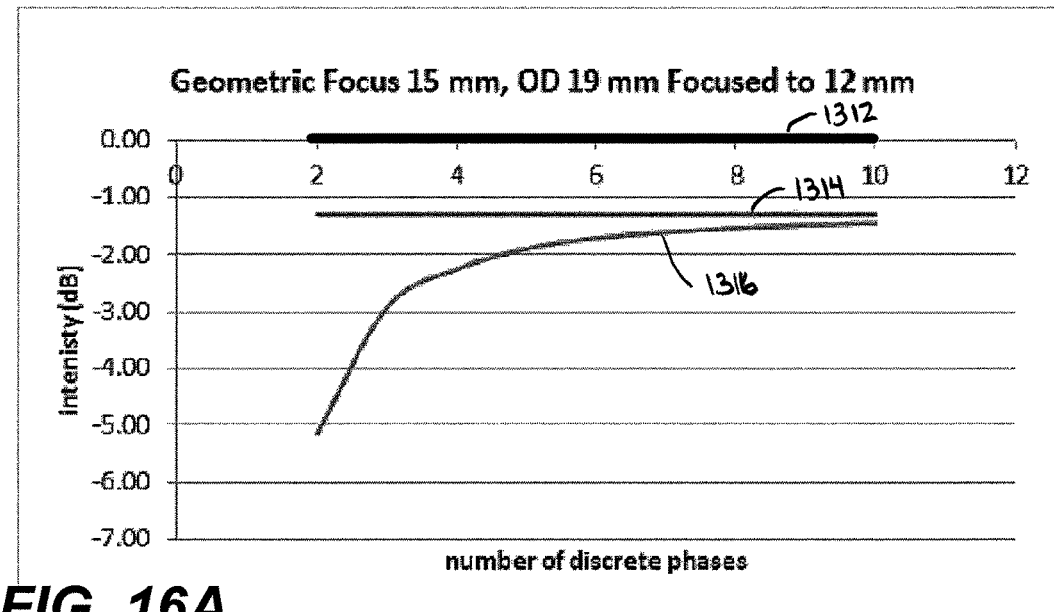
FIGS. 16A-16B are plots illustrating performance of discrete-phase systems at various foci according to several embodiments of the present invention.
Figure 16B:
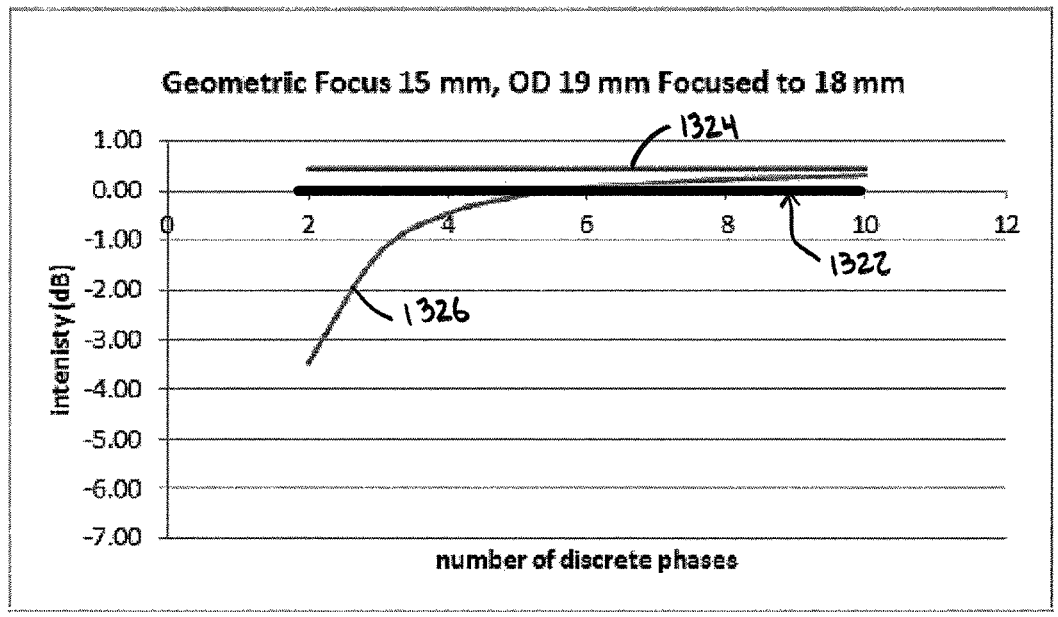

In one embodiment, a difference in intensity between a desired focus point and an ideal focus point can be changed by using a focused bowl. In one embodiment, a circular bowl transducer with OD=19 mm and $F_L$=15 mm can be used initially. Subsequently, in one embodiment, discrete phasing techniques can be used to move the focus to depth of about 12 mm or 18 mm. FIGS. 16A-16B are plots illustrating performance of discrete-phase systems at various foci points according to several embodiments. FIG. 16A illustrates performance 1316 of a bowl transducer (OD=19 mm and $F_L$=15 mm) when the focus is moved to 12 mm using discrete phasing when compared to performance 1312 of a bowl transducer (OD=19 mm bowl and $F_L$=12 mm) according to one embodiment. As is illustrated, line 1316 asymptotically approaches about −1.3 dB (line 1314). In one embodiment, comparing line 1316 with performance of flat disc transducer, which is illustrated by line 1306 in FIG. 15, intensity produced by the bowl transducer has been improved. FIG. 16B illustrates performance 1326 of a bowl transducer (OD=19 mm and $F_L$=15 mm) when the focus is moved to 18 mm using discrete phasing when compared to performance 1322 of a bowl transducer (OD=19 mm bowl and $F_L$=18 mm) according to one embodiment. As is illustrated, line 1326 asymptotically approaches about 0.5 dB (line 1324). As is illustrated, performance of the bowl transducer with discrete phasing (line 1326) can exceed performance of an ideal transducer (line 1322), such as when number of discrete phase levels exceeds about six. In one embodiment, it may be advantageous to use discrete phases to move the focus deeper.

Therapy Delivery Using Amplitude Modulation and Discrete Phase Shifting

In several embodiments, amplitude modulation (e.g., realized via material poling) can be used in addition to discrete phasing. In one embodiment, splitting of an ultrasound beam may cause an increase in transducer power that may be difficult to obtain due to, for example, system or transducer material limitations. It may be desirable to phase shift or tilt the ultrasound beam from one focal position to another focal position. In one embodiment, split of the ultrasound beam may be difficult to achieve due to a possibility of excessive heating of tissue before focus. In one embodiment, linear sequences of TCPs may be created sequentially or substantially sequentially without moving a transducer, which can result in reduction of therapy time. In one embodiment, the transducer can be moved to further distribute treatment points. In one embodiment, a transducer can be a circular bowl transducer excited by 7 MHz excitation signal and having OD of about 19 mm, ID of about 4 mm, and $F_L$ of about 15 mm. Linear TCP sequences can be spaced about 1.0 mm apart. It may be desirable to split the ultrasound beam so two linear TCP sequences are created simultaneously or substantially simultaneously about 1.0 mm apart from each other. However, in one embodiment, as compared to intensity of a beam that is not split, each of the split beams can have intensity that is approximately 2.4 times lower. Due to a potential for excessive heating of tissue located before focus, power delivered to the transducer may not be increased by about 2.4 times to compensate for the reduction in intensity. In one embodiment, quadrature phasing may be used to create linear TCP sequences one at a time. Quadrature phasing can be accomplished by combining material poling with discrete system phasing. In one embodiment, using quadrature phasing may relate to an increase in power of approximately 1.2 times when quadrature phasing is applied to a focused bowl transducer. In one embodiment, such slight increase in power may be desirable.

Figure 17A:
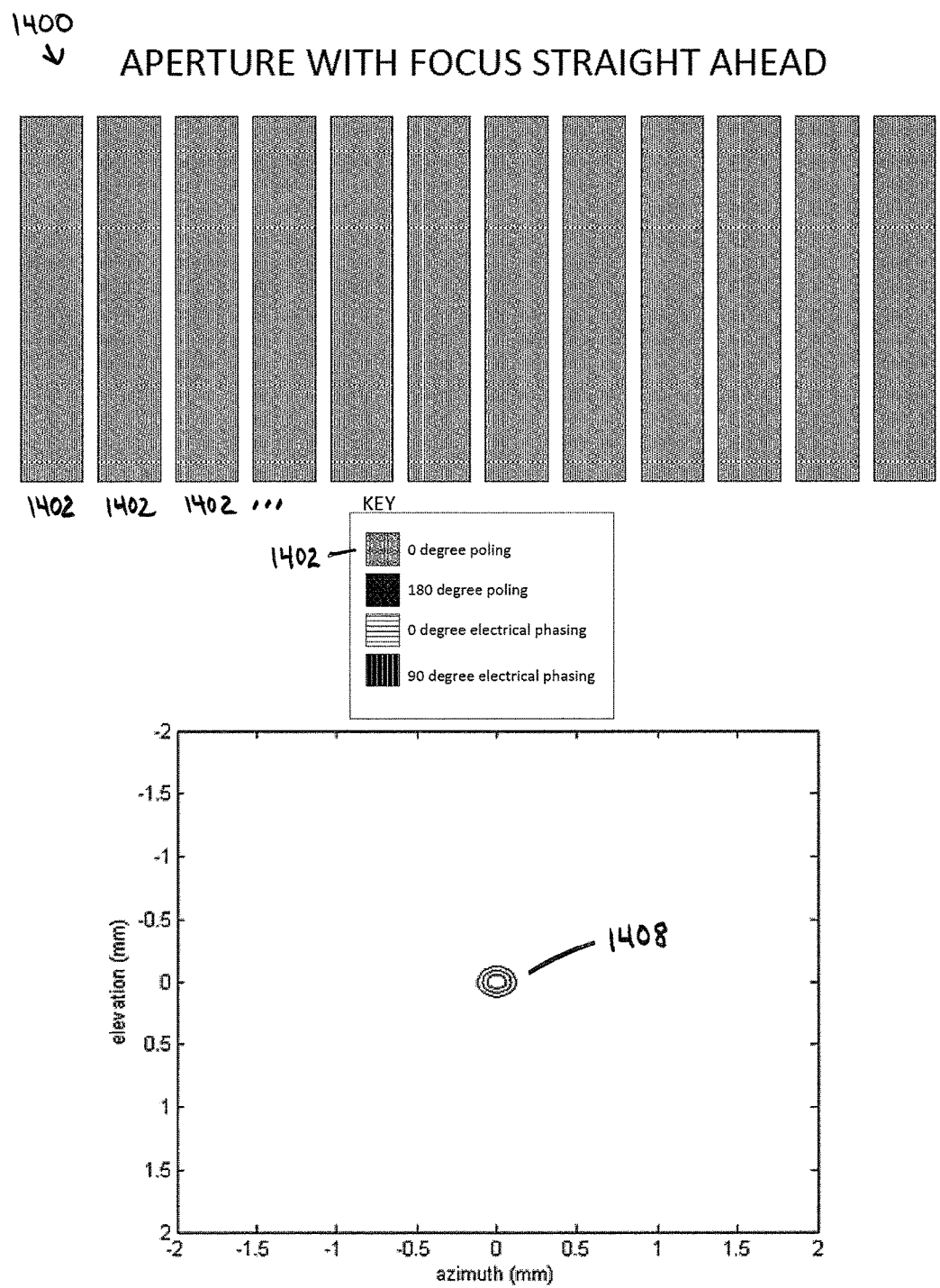
FIGS. 17A-17D are schematic illustrations of hybrid systems and plots illustrating their performance according to several embodiments of the present invention.
Figure 17B:
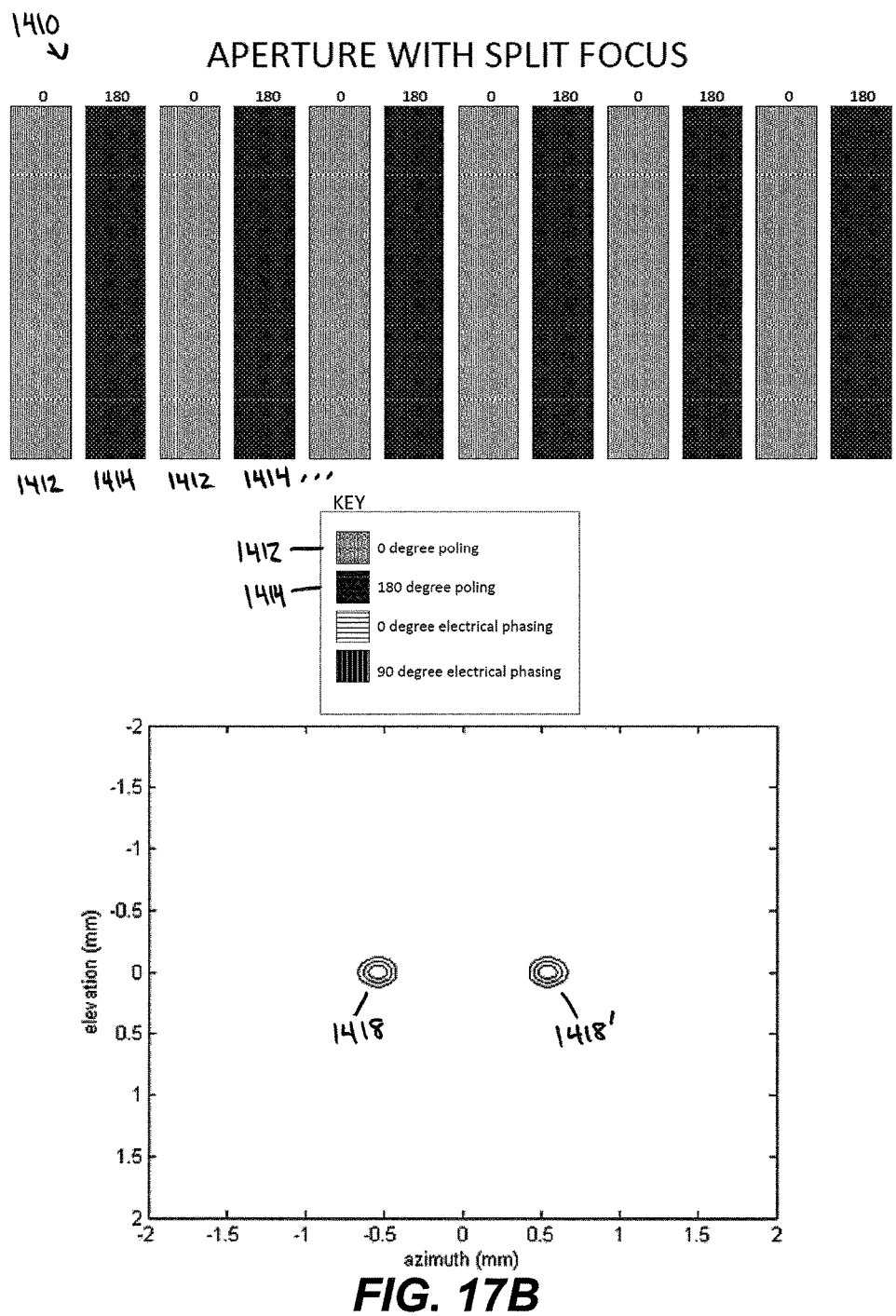

FIGS. 17A-17B illustrate quadrature control of a transducer by combining poling and discrete system phasing according to one embodiment. FIG. 17A illustrates, in one embodiment, individual strips (e.g., 1402, 1404, etc.) defined across a focused circular bowl transducer 1400 at a pitch configured to achieve an about 1.0 mm in the ultrasonic beam produced by the transducer. The focus of the transducer is a single beam 1408 in the plane parallel to the transducer face. Transducer 1400 is not configured with discrete phasing. In one embodiment, as is illustrated in FIG. 17B, strips of transducer 1410 are poled by alternating the phasing direction. For example, strip 1412 has a phase of 0° and strip 1414 has a phase of 180°. As is shown in the intensity plot, two intensity peaks 1418 and 1418' appear substantially along a line at a focal depth.

Figure 17C:
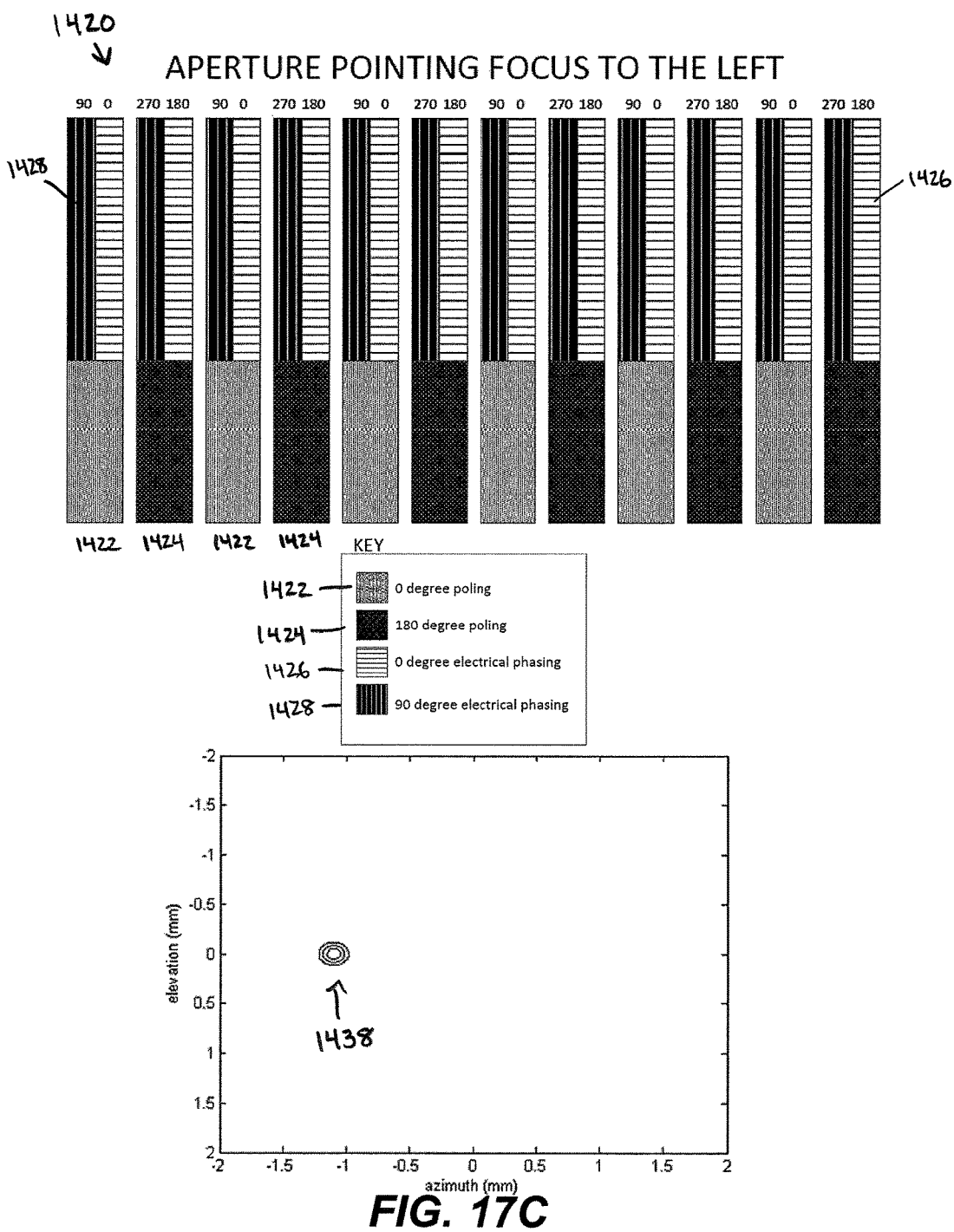
Figure 17D:
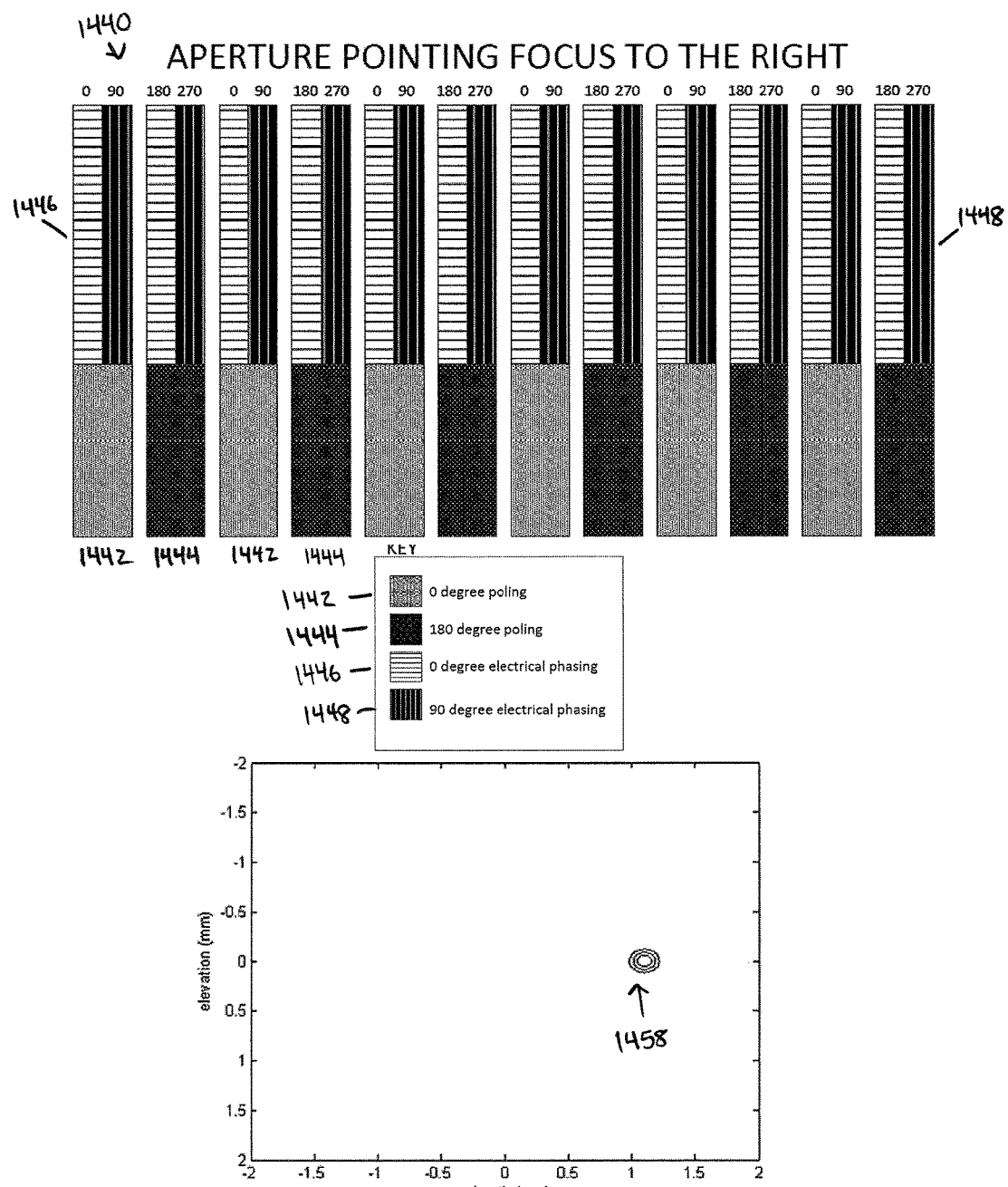

In one embodiment, creating two intensity peaks 1430 and 1432 may be undesirable due to limitations of the system (e.g., power supply) and/or transducer materials. For example, more power may need to be supplied to the transducer to create two TCPs simultaneously or nearly simultaneously. FIG. 17C illustrates modulation of an aperture of a transducer 1420 using an additional phase shift (by 90°) according to one embodiment. As is illustrated, strip 1422 has a phase of 0°, and is further divided into a region or sub-strip 1426 having a phase of 90° and sub-strip 1428 having a phase of 0°. Further, strip 1424 has a phase of 180° (e.g., alternating phase with respect to strip 1422), and is further divided into a region or sub-strip 1430 having a phase of 270° and sub-strip 1432 having a phase of 180°. In one embodiment, these two additional phases (e.g., 1426 and 1428) can be electrically connected to the transducer 1420 through a conductive bond and, optionally, a switch or flex circuit configured to separate the two phases. Similar to the embodiments illustrated in FIGS. 17A-17B, transducer 1420 is poled so that the phase alternates between 0° and 180° between adjacent strips. In one embodiment, one half of the transducer 1420 is excited with 0° phase excitation signal and the other half is excited with 180° phase excitation signal. In one embodiment, a pitch of the phase variation is decreased by two with the additional phasing (e.g., sub-strips 1426 and 1428). In one embodiment, when discrete phasing is combined with poling (e.g., alternating the phase between 0° and 180° between adjacent strips 1422 and 1424), four distinct phases can be provided, namely 0°, 90°, 180°, and 270°. As is illustrated in FIG. 17C, the repeating phase pattern applied across the transducer 1420 from left to right can be 90°, 0°, 270°, and 180°. As is illustrated in the intensity plot, in one embodiment, a peak 1438 about −1 mm away from a beam axis at a focal depth can be created. In one embodiment, as is illustrated in FIG. 17D, if the phase pattern has a reversed order of 0° (sub-strip 1446), 90° (sub-strip 1448), 180° (sub-strip 1450), and 270° (sub-strip 1452), then a peak 1458 moves about +1 mm away from a beam axis. As is illustrated in FIG. 17D, strip 1442 has a phase of 0° and strip 1444 has a phase of 180° (e.g., alternating phase with respect to strip 1442).

Figure 18:
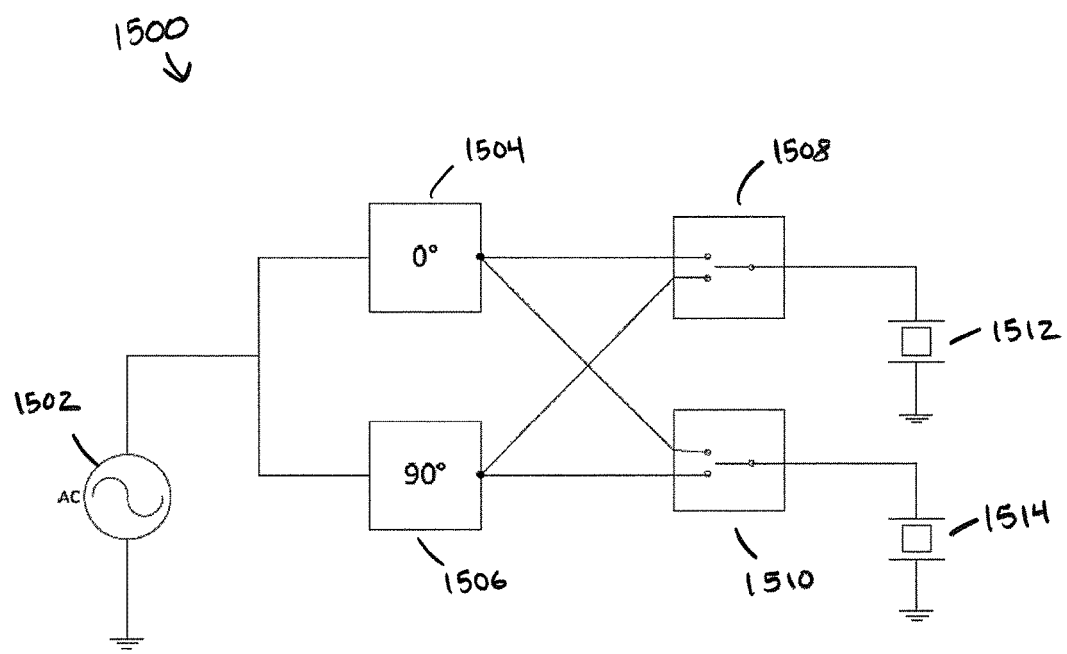
FIG. 18 is a schematic illustration of a two-phase switchable system according to an embodiment of the present invention.

FIG. 18 is a schematic illustration of a two-phase switchable system 1500 according to one embodiment. As is illustrated, the system 1500 includes an AC voltage (or current) source 1502 that drives the discrete phase shifters 1504 (0° phase shifter) and 1506 (90° phase shifter), switches 1508 and 1510, and transducer portions 1512 and 1514. In one embodiment, discrete phase shifters 1504 and 1506 can be configured to phase shift the AC voltage (or current) signal supplied by the source 1502, so that the resulting signals are 90° out of phase. In one embodiment, discrete phase shifters 1504 and 1506 can be configured to excite different portions (e.g., strips) of the transducer. Output of discrete phase shifters 1504 and 1506 can be connected to switches 1508 and 1510 that are connected to different portions 1512 and 1514 of the transducer. On one embodiment, the switches 1508 and 1510 cause the phase of the voltage (or current) signal provided by the source 1502 to toggle between 0° and 90° such that the phase pattern at the transducer reverses the order and causes a focal point to move from one side of the beam axis to another side of the beam axis, as is illustrated in FIGS. 17C-17D. In one embodiment, phase shifters 1504 and 1506 can shift the phase by any suitable value, such as 30°, 45°, 120°, 145°, 180°, etc.

Therapy Delivery Using Amplitude Modulation with Walking

In one embodiment, modulating or splitting an ultrasound beam axially and/or laterally, for example so that multiple linear sequences of TCPs are created simultaneously, substantially simultaneously, or sequentially may necessitate supply of additional power to a transducer in order to achieve substantially same intensity at focal point(s) as an unmodulated beam. In one embodiment, such increase in power can cause a possibility of excessive heating in tissue proximal (pre-focal) and/or distal (post-focal) to the focus. For example, for a given transducer configuration, splitting an ultrasound beam from a focal position of about (0, 0, 15 mm) to focal positions of about (−0.55 mm, 0, 15 mm) and (0.55 mm, 0, 15 mm) may necessitate increasing the supply of power by about 2.2 times in order to produce substantially same intensity at the two focal positions as the intensity in the unmodulated focal position. In one embodiment, such an increase in power may be undesirable. In various embodiments, amplitude modulation can be combined with walking aperture techniques in order to reduce the possibility of excessive heating of tissues in pre-focal and post-focal regions. For example, the maximum intensity measured in the pre-focal and post focal regions may be reduced.

FIGS. 19A-19C are plots of an intensity distribution 1600 in an x-y plane at about 2 mm before focus according to one embodiment. No modulation has been applied to a transducer. The plot 1600 illustrates that the acoustic intensity distribution is axis symmetric about a beam axis. In one embodiment, the symmetry is caused by a circular aperture of the transducer (e.g., a focused circular bowl transducer). The regions of highest intensity 1601, 1602, and 1604 occur along the beam axis at a radius of approximately 0 mm (region 1601), 0.75 mm (region 1602) and 1.0 mm (region 1604). In one embodiment, the maximum intensity is about 101 W/cm$^2$ in the plane provided that the intensity at the aperture is about 1 W/cm$^2$.

FIGS. 20A-20C are plots of an intensity distribution 1620 in an x-y plane at focal depth according to one embodiment. In one embodiment, the focal depth can be about 15 mm. FIGS. 20A-20C show a significant concentration 1622 in acoustic intensity at a focal plane. In one embodiment, the diameter of the acoustic distribution has decreased from an OD of about 3 mm in FIGS. 20A-20C to a diameter of less than about 0.3 mm at a focal depth. The maximum intensity has increased to about 7.73 kW/cm$^2$, which is approximately 77.3 times greater than the maximum intensity about 2 mm before focus.

Figure 21:
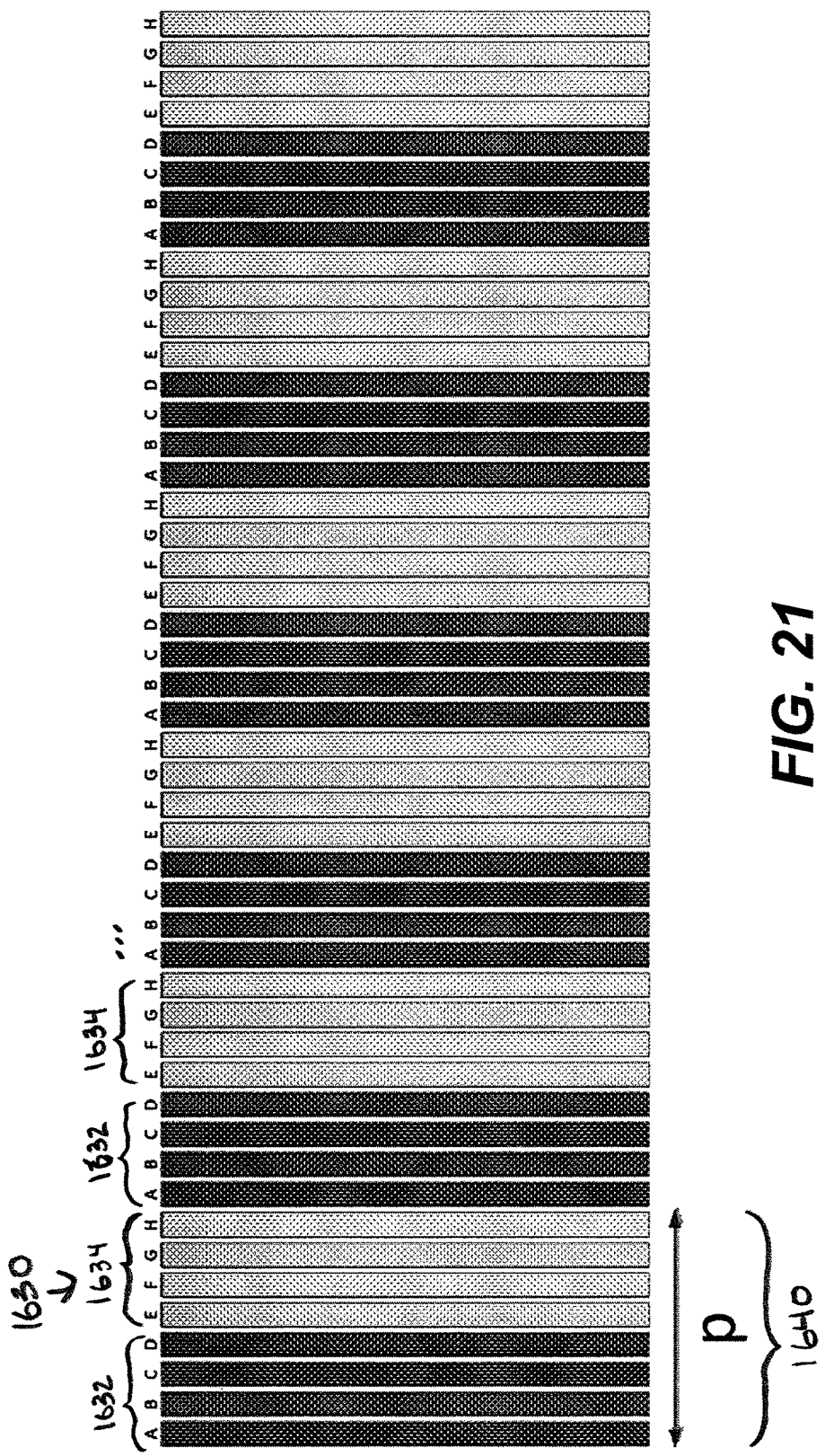
FIG. 21 is a schematic illustration of an amplitude modulation aperture pattern according to an embodiment of the present invention.

FIG. 21 is a schematic illustration of an amplitude modulation aperture pattern 1630 according to one embodiment. The amplitude modulation pattern 1630 can be placed across an aperture. Groups of transducer strips or portions 1632 can represent an amplitude of +1 (e.g., due to expansion of transducer material). Groups of transducer strips or portions 1634 can represent an amplitude of −1 (e.g., due to contraction of transducer material). As is shown, groups 1632 and 1634 can alternate across the aperture. Pitch distance 1640 can correspond to a spatial period of transitions between +1 and −1 transducer material across the aperture. In one embodiment, the pitch distance 1640 along with a focal depth and operating frequency may determine the distance of the split beams in the focal plane. In one embodiment, any number of transducer portions can be grouped into groups 1632 and 1634. In one embodiment, the number of portions in groups 1632 and 1634 may be the same. In one embodiment, the number of portions in groups 1632 and 1634 may be different. In one embodiment, amplitude modulation can include more than two levels, such as three (0 and ±1) or more levels.

FIGS. 22A-22C are plots of an intensity distribution 1650 in an x-y plane from an amplitude modulated aperture pattern of FIG. 21 about 2 mm before focus according to one embodiment. In one embodiment, the pitch distance is approximately 6 mm for an excitation signal frequency of about 7 MHz. In one embodiment, the amplitude modulation pattern 1630 is placed along the y-axis to split the beam by about 1.1 mm, as is demonstrated by foci points 1652 and 1654. In one embodiment, although the energy distribution has an OD of approximately 3 mm in the x-direction, it is increased in the y-direction to about 4 mm. As compared with FIGS. 19A-C, the maximum intensity of intensity distribution 1650 is increased by about 20% to 112 W/cm$^2$, provided that 1 W/cm$^2$ of intensity is placed at the unmodulated focal point. In one embodiment, the amount of power from a split aperture may need to be increased by a factor of about 2.2 to achieve substantially similar intensity at two foci points. At a depth of about 2 mm before focus, the maximum intensity may be about 246 W/cm$^2$ due to the increase in power. However, because in one embodiment temperature increases in a tissue are proportional to increases in intensity, the temperature rise in a pre-focal region can be more than double for a split beam design.

Figure 23A:
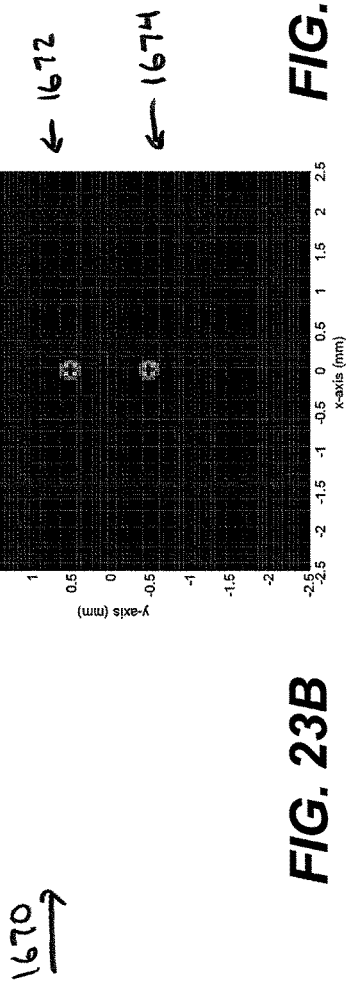
FIGS. 23A-23C are plots of an intensity distribution from an amplitude modulated aperture at focus according to an embodiment of the present invention.
Figure 23C:
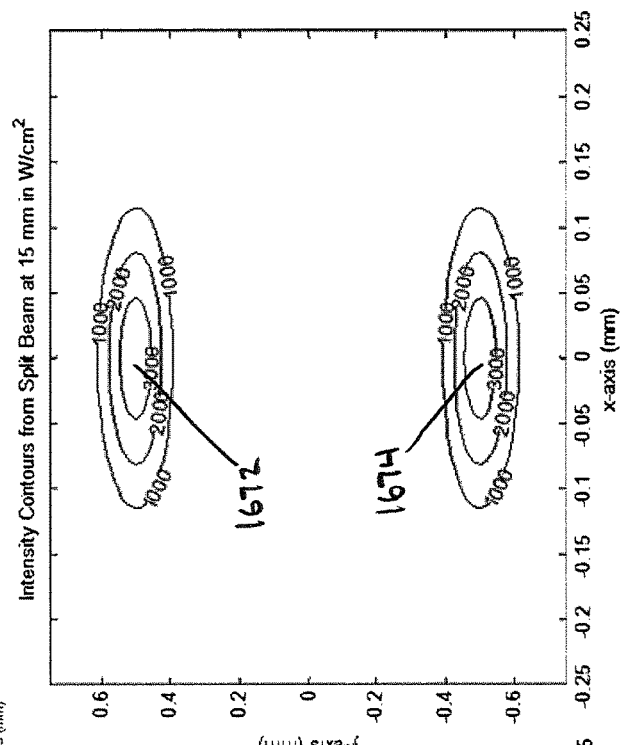
Figure 23B:
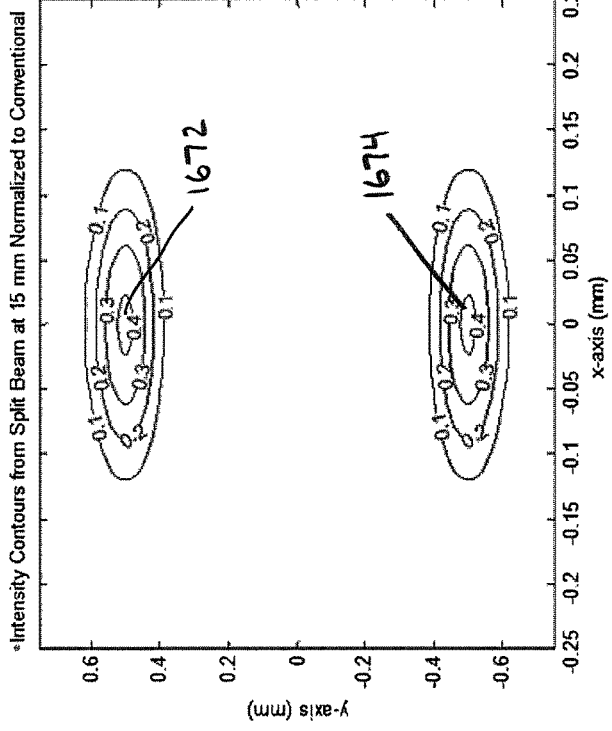

FIGS. 23A-23C are plots of an intensity distribution 1670 in an x-y plane from an amplitude modulated aperture pattern of FIG. 21 at focal depth according to one embodiment. In one embodiment, the focal depth can be about 15 mm. In one embodiment, the intensity of each of the foci 1672 and 1674 can be about 3.45 kW/cm$^2$, provided that 1 W/cm$^2$ of intensity is placed at the unmodulated focal point. As is illustrated, two symmetric beams occur at focal positions 1672 (0.55 mm, 0, 15 mm) and 1674 (−0.55 mm, 0, 15 mm) mm. In one embodiment, the intensity distribution at the focal positions 1672 and 1674 is substantially similar to the intensity distribution illustrated in FIG. 20.

Figure 24:
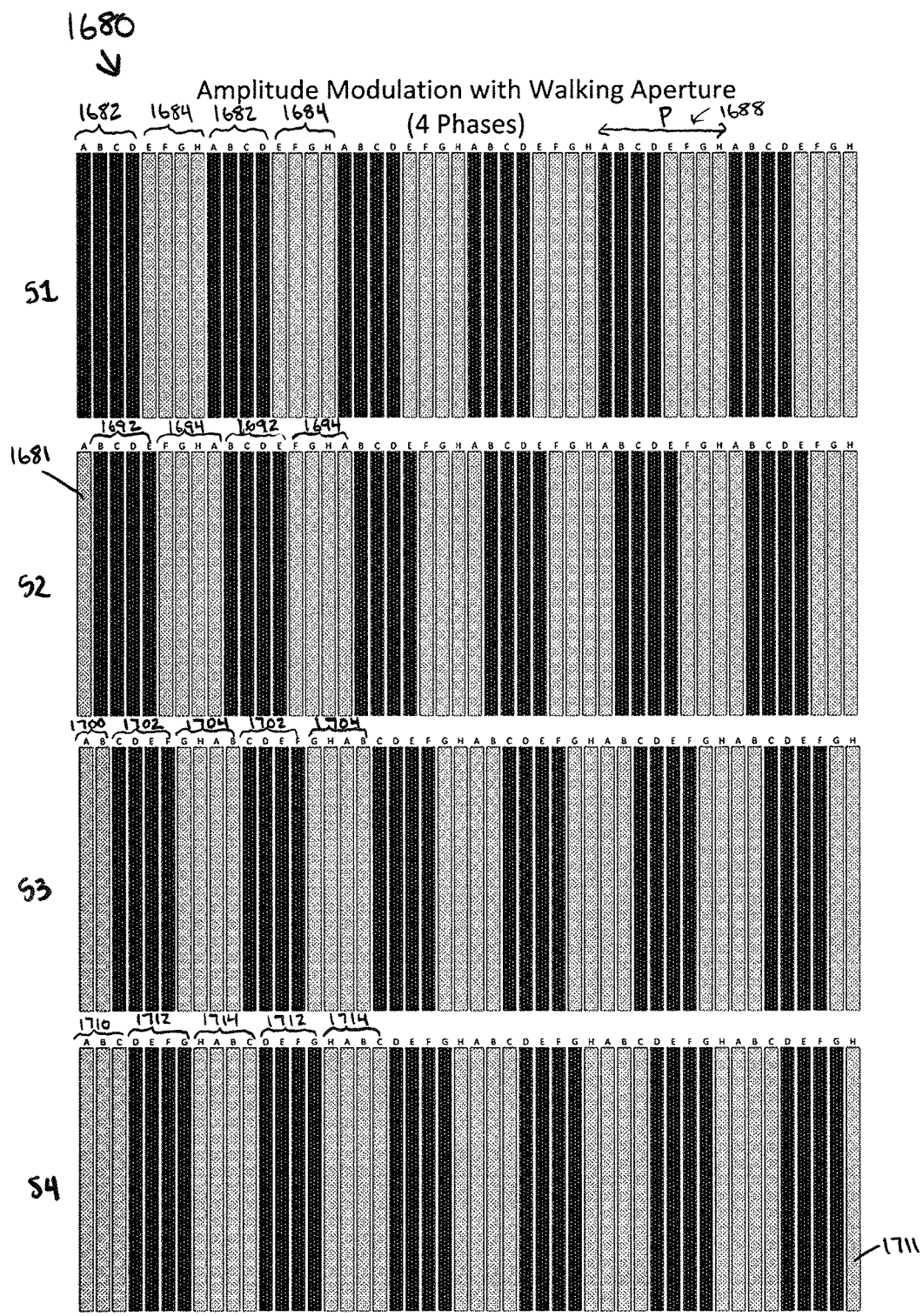
FIG. 24 is a schematic illustration of an amplitude modulated aperture pattern with changing states according to an embodiment of the present invention.
Figure 25B:
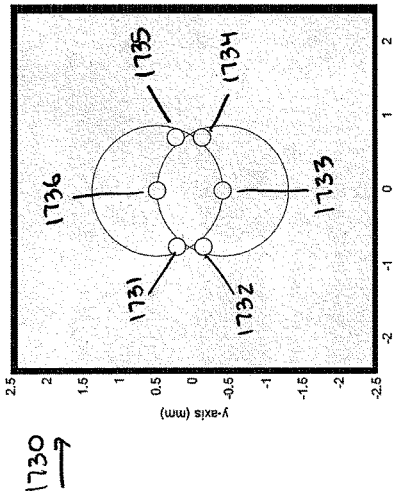
FIGS. 25A-25D are plots of an intensity distribution from an amplitude modulated aperture with changing states before focus according to an embodiment of the present invention.
Figure 25D:
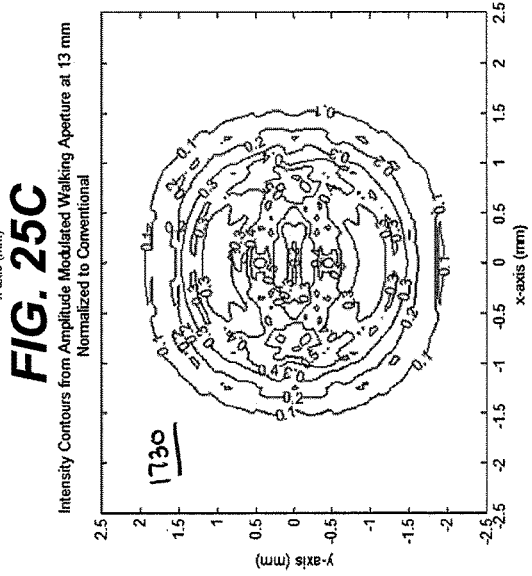
Figure 25A:
Figure 25C:
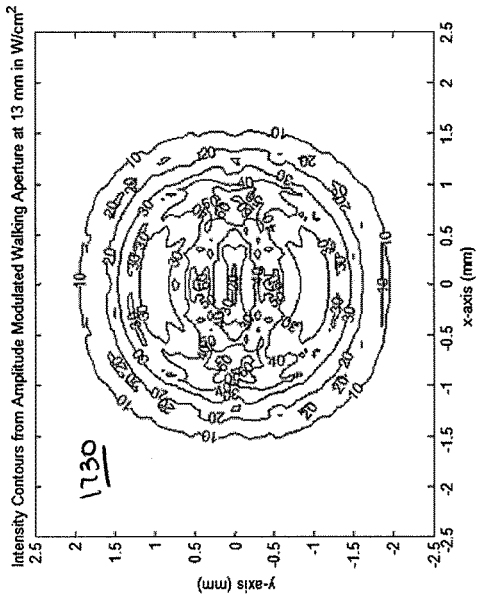

FIG. 24 is a schematic illustration of an amplitude modulation aperture pattern 1680 with walking or changing states according to one embodiment. In one embodiment, the pattern 1680 is the same as the amplitude modulation function 1630 illustrated in FIG. 21 with the exception of state changes. In one embodiment, the amplitude modulation pattern 1680 can be placed across an aperture as follows. Pitch distance 1688 can comprise a plurality of transducer strips or portions. Although eight such portions are shown in FIG. 24, the number of portions can be any suitable number such as less than eight or more than eight. The transducer portions can be individually addressable, and can be configured to represent an amplitude state of −1 and/or +1. As voltage or current is supplied to the transducer, the aperture can change states (or walk) from S1 to S2, then S2 to S3, then S3 to S4, and so on. As is illustrated, in state S1 the plurality of portions across the pitch distance 1688 are divided into two groups 1682 (+1 modulation) and 1684 (−1 modulation). When transition is made from state S1 to state S2, the plurality of portions across the pitch distance 1688 are divided into groups 1692 (+1 modulation) and 1690 and 1694 (−1 modulation). As is illustrated, portion 1681 in state S1 has corresponds to +1 and in state S2 corresponds to −1. When transition is made from state S2 to state S3, the plurality of portions across the pitch distance 1688 are divided into groups 1702 (+1 modulation) and 1700 and 1704 (−1 modulation). When transition is made from state S3 to state S4, the plurality of portions across the pitch distance 1688 are divided into groups 1712 (+1 modulation) and 1710 and 1711 (−1 modulation). Accordingly, the modulation pattern shifts (or walks) across the aperture over time. In one embodiment, there are eight unique states if the aperture walks with the same amplitude modulation pattern across the aperture. In one embodiment, the effective intensity can be determined as a weighted time average of the acoustic intensity distribution from each aperture state. In one embodiment, the aperture changes state (or walks) at a rate sufficient to reduce the possibility of excessive heating of tissues pre-focally and/or post focally. In one embodiment, pitch distance 1688 can include any suitable number of transducer portions. In one embodiment, the number of portions in groups corresponding to modulation of +1 and −1 may be the same. In one embodiment, the number of portions in groups corresponding to modulation of +1 and −1 may be different. In one embodiment, amplitude modulation can include more than two levels, such as three (0 and ±1) or more levels.

FIGS. 25A-25D are plots of an intensity distribution 1730 in an x-y plane from an amplitude modulated aperture pattern with walking of FIG. 24 about 2 mm before focus according to one embodiment. In one embodiment, the maximum intensity is about 71 W/cm$^2$ which is about 37% lower than the maximum intensity from an amplitude modulated aperture pattern without walking (e.g., shown in FIG. 22). In one embodiment, this reduction may be significant. FIGS. 25A-25D illustrate that a number and area of regions experiencing high intensity have been reduced as compared with FIG. 22. Regions receiving significant amount of energy are localized to approximately six locations 1731-1736. Intensity distribution plot 1730 illustrates that the extent of the energy distribution is reduced, as compared to FIG. 22, to about 2 mm OD in the x-dimension and about 3 mm OD in the y-dimension. In one embodiment, this reduction may be significant. In one embodiment, the intensity distribution 1730 appears as acoustic power being emanated from two apertures as the intensity distribution 1730 appears to be a spatially offset summation of the distribution 1600 of FIG. 19. In one embodiment, as is illustrated in FIG. 25, the possibility of excessive heating of tissues located before and after the focus is significantly reduced.

Figure 26A:
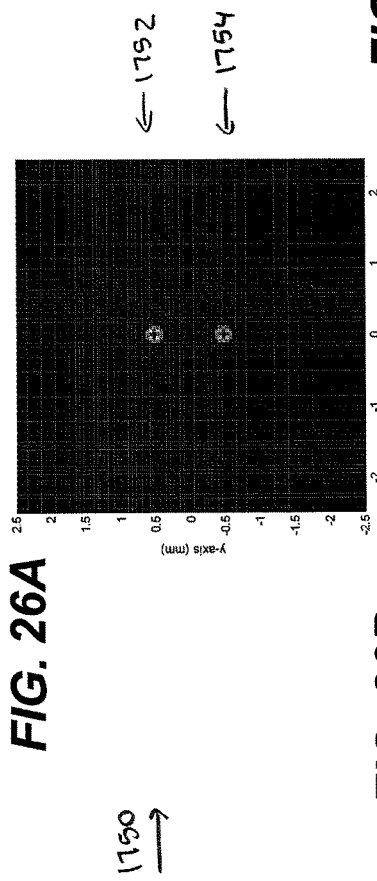
FIGS. 26A-26C are plots of an intensity distribution from an amplitude modulated aperture with changing states at focus according to an embodiment of the present invention.
Figure 26C:
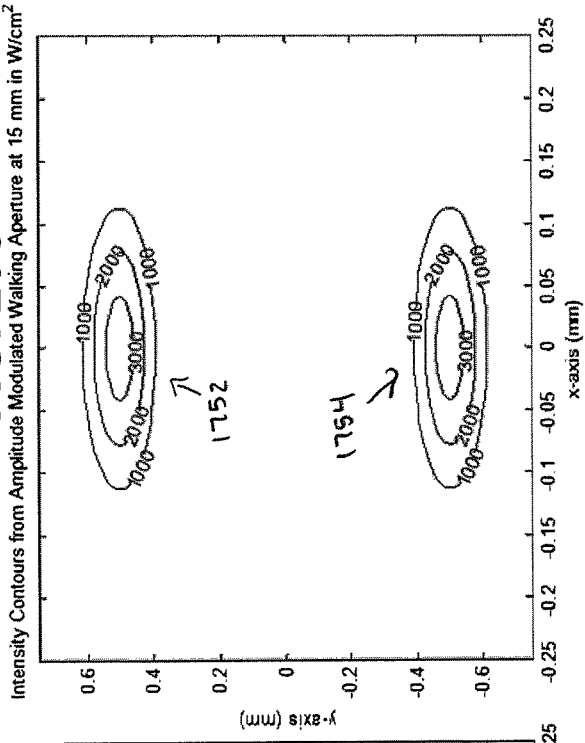
Figure 26B:
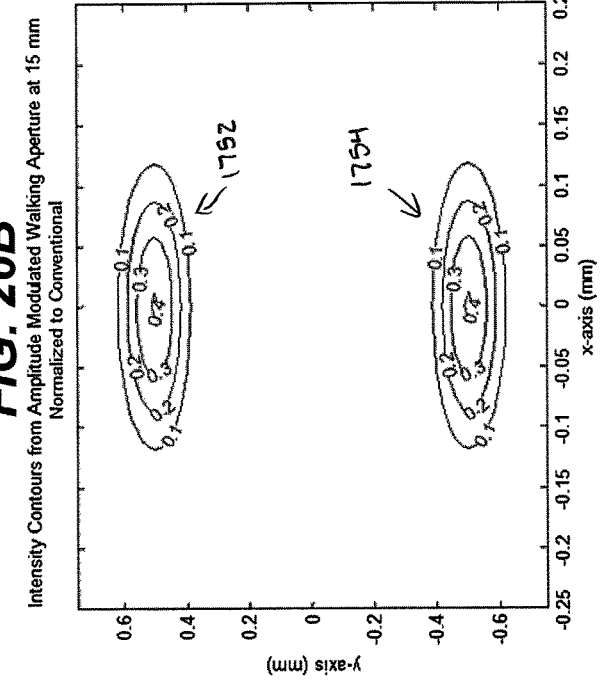

FIGS. 26A-26C are plots of an intensity distribution 1750 in an x-y plane from an amplitude modulated aperture pattern with walking of FIG. 24 at focal depth according to one embodiment. In one embodiment, the focal depth can be about 15 mm. In one embodiment, although intensity distribution before focus changes substantially (compare FIG. 25 with FIG. 22), intensity distribution 1750 at focal is substantially similar to the intensity distribution 1670 at focal depth for amplitude modulated aperture pattern without walking illustrated in FIG. 23. In one embodiment, peak intensity of the intensity distribution 1750 is reduced (e.g., compare 3.34 W/cm$^2$ with 3.45 W/cm$^2$). In one embodiment, to order to get the same intensity at the focal depth, supplied power may need to be increased by a factor of 2.3. The maximum intensity about 2 mm before focus would be 163 W/cm$^2$, which is a substantial reduction over the prediction of 246 W/cm$^2$ (FIG. 22) if the amplitude modulation pattern is not walked across the aperture. In one embodiment, acoustic intensity maximums at foci 1752 and 1754 are substantially concentrated as compared to the intensity distribution 1650 in FIG. 22.

Figure 27A:
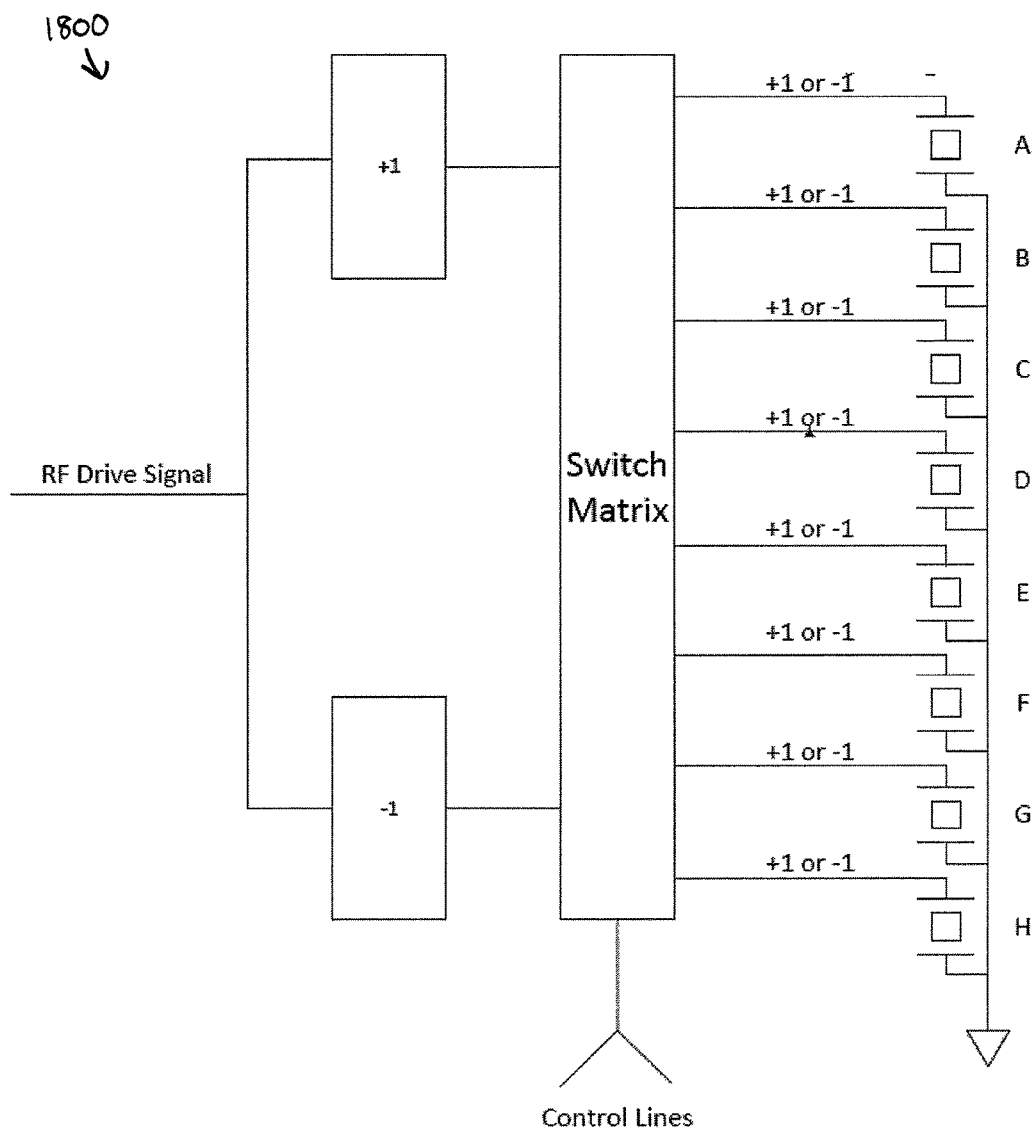
FIG. 27A is a schematic illustration of an amplitude modulated aperture with two changing levels according to an embodiment of the present invention.

FIG. 27A is a schematic illustration of an amplitude modulated aperture with walking (two levels ±1) 1800 according to one embodiment. In one embodiment, the schematic 1800 corresponds to the pattern 1680 illustrated in FIG. 24. FIG. 27B is a state transition table 1850 of the two-state schematic 1800 according to one embodiment.

Figure 28A:
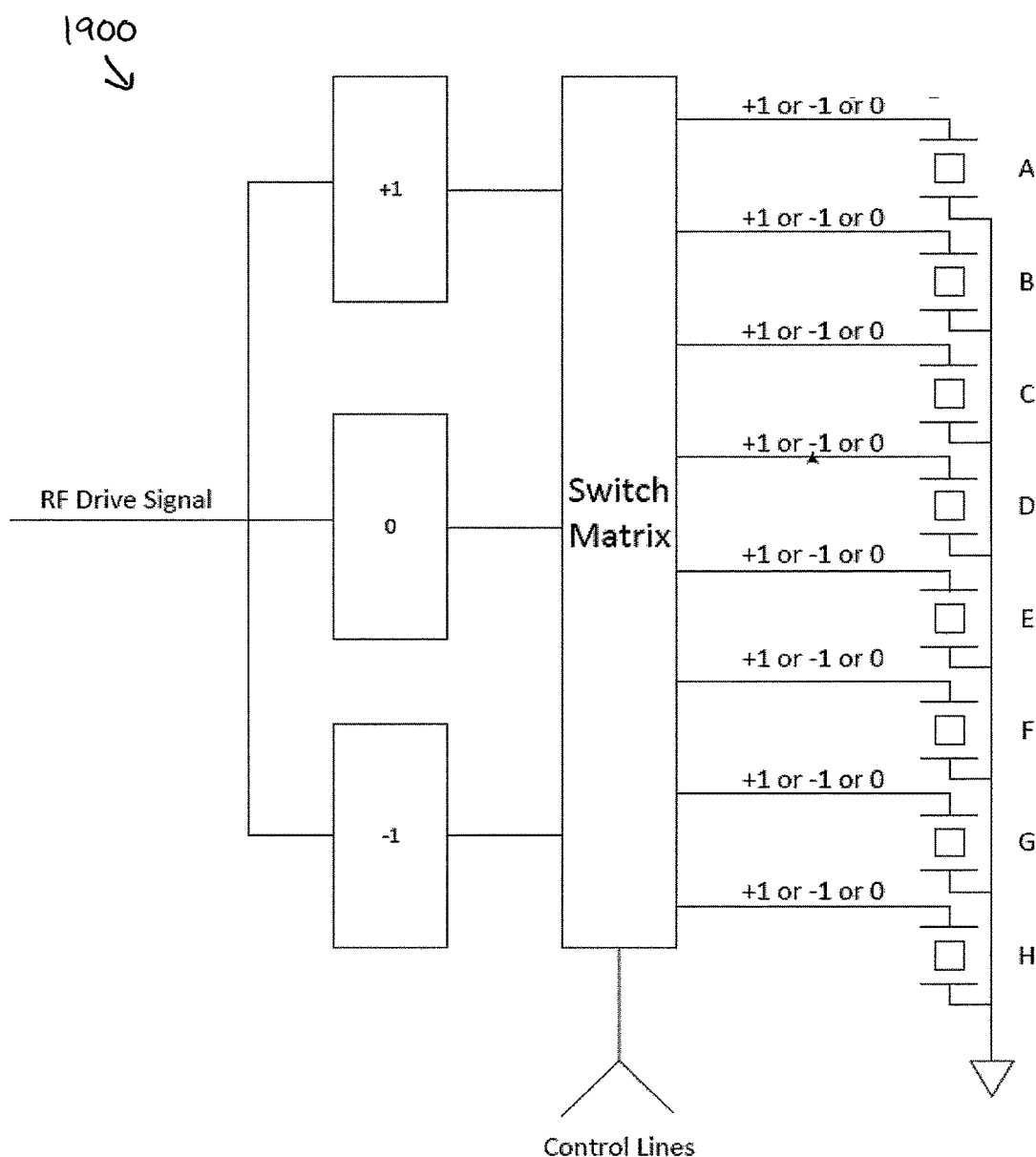
FIG. 28A is a schematic illustration of an amplitude modulated aperture with three changing levels according to an embodiment of the present invention.

FIG. 28A is a schematic illustration of an amplitude modulated aperture with walking (three levels) 1900 according to one embodiment. Schematic 1900 includes a 0 level 1952. In one embodiment, 0 level 1952 can be realized by using a ground terminal or a connecting a resistor to the ground terminal. In one embodiment, 0 level 1952 can reduce an amount of high frequency spatial components in a focal zone (e.g., these components can correspond to grating lobes). In one embodiment, 0 level 1952 can reduces spatial frequency transitions in pre-focal and post focal zones. FIG. 28B is a state transition table 1950 of the three-state schematic 1900 according to one embodiment.

Figure 29A:
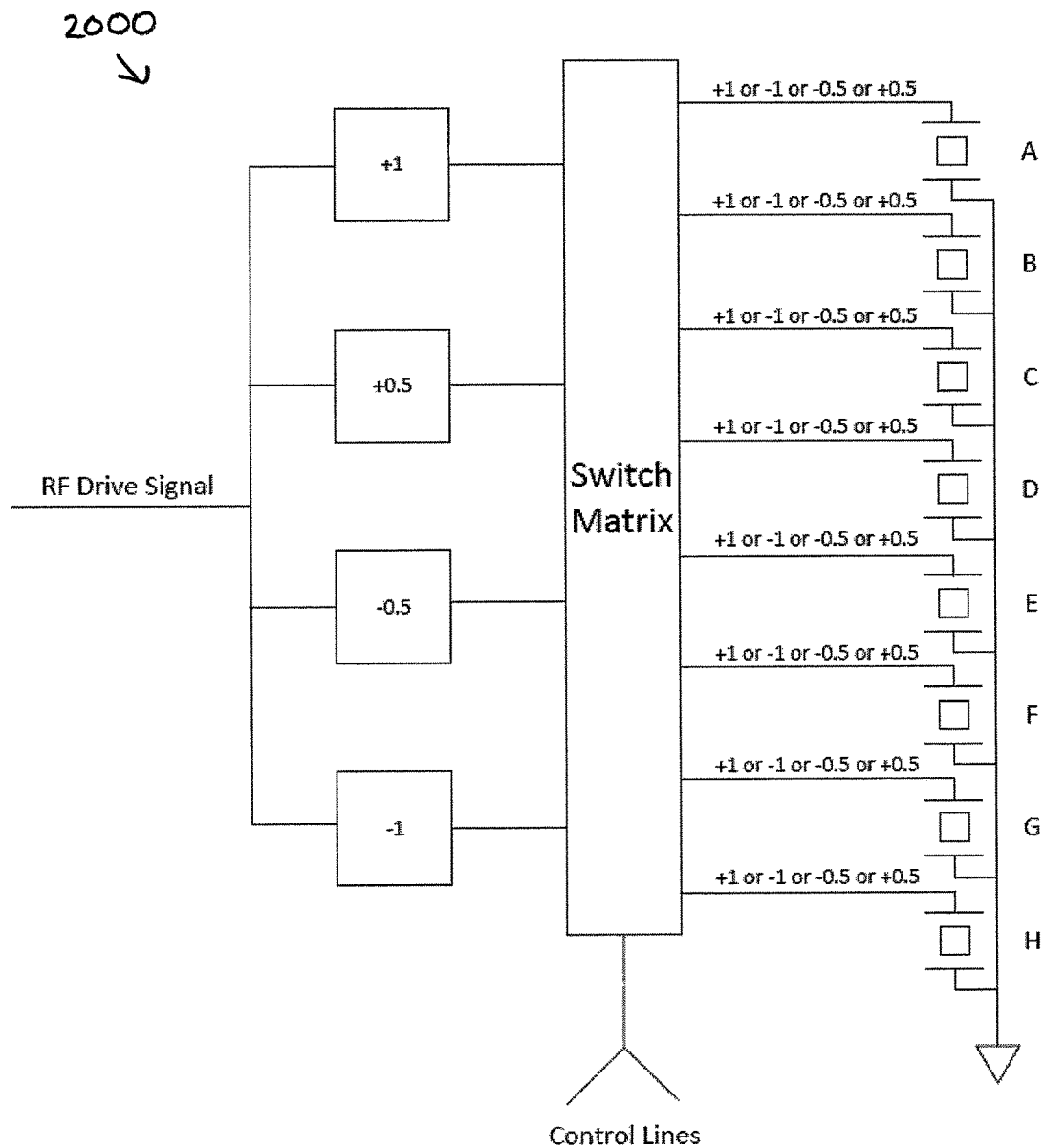
FIG. 29A is a schematic illustration of an amplitude modulated aperture with four changing levels according to an embodiment of the present invention.

FIG. 29A is a schematic illustration of an amplitude modulated aperture with walking (four levels) 2000 according to one embodiment. Schematic 2000 includes two additional levels +0.5 2002 and −0.5 2004. In one embodiment, doing so can provide the similar advantages as adding a 0 level. In one embodiment, amplitude modulation across the aperture provided by schematic 2000 can better approximate a sine wave, such that high frequency spatial components do not occur in the focal plan. FIG. 29B is a state transition table 2050 of the three-state schematic 1900 according to one embodiment.

In several embodiments, number of transducer strips and/or portions in a pitch distance can be less than or greater than eight. The number of portions selected can depend on an amount of heating reduction desired for tissues located before and/or after the focus. In several embodiments, number of amplitude modulation levels can be greater than four, such as six, eight, ten, etc.

There are several advantages to use of embodiments of the systems and methods disclosed herein. In one embodiment, amplitude modulation, particularly with walking, and/or phase shifting techniques can reduce a possibility of excessive pre-focal and post-focal heating. In one embodiment, amplitude modulation, particularly with walking, and/or phase shifting techniques can allow splitting an ultrasound beam into two or more beams. In one embodiment, amplitude modulation, particularly with walking, and/or phase shifting techniques can approximate two or more ultrasound sources by placing ultrasonic energy at two or more foci locations. In one embodiment, amplitude modulation, particularly with walking, and/or phase shifting techniques can reduce pain or discomfort experienced by a patient during ultrasound therapy by redistributing acoustic energy away from a focal point. In one embodiment, amplitude modulation, particularly with walking, and/or phase shifting techniques can reduce therapy time due to the production of multiple TCPs.

Imaging Systems

In one embodiment, a receive ultrasound beamformer can be used as part of an ultrasound imaging system. In one embodiment, an ultrasound imaging system uses a transmit and a receive event to create one line of an ultrasound image. The transmit typically focuses at one location and then the receive processing of the imaging system focuses on the same location. In this case, the response of the imaging system is described as:

$$h(t)=(Tx)*Rx(t) \quad (29)$$

where h(t) is the spatial response of both the transmit and receive apertures, Tx(t) is the response of the transmit aperture, and Rx(t) is the response of the receive aperture.

In one embodiment, an ultrasound imaging systems uses dynamic receive focusing. In this case, although the transmit ultrasound beam focused on one spatial location, the receive system could 'dynamically' change the focus along the beam axis so each spatial location in depth was focused. This system response is represented as:

$$h(t-\delta)=Tx(t)*Rx(t-\delta) \quad (30)$$

The δ represents the time delay between received signals which suggests how the focusing can change for the receive aperture as the signals come from deeper depths.

In one embodiment, a technique to split a transmit therapy beam into multiple foci through aperture amplitude manipulation can include receiving beam(s) as well. In one embodiment, a system can include two transmit foci (or more), and it is possible to focus on either spatial aperture using a receive aperture such as a linear array where delays may be used to steer and focus the received beam along different axes. This method allows the system to obtain two receive beams with just one transmit. This reduces the required time to visually observe the two beam axes from the receive aperture. This system is described as:

$$h_1(t-\delta)=Tx(t)*Rx_1(t-\delta) \quad (31a)$$

$$h_2(t-\delta)=Tx(t)*Rx_2(t-\delta) \quad (31b)$$

For example, suppose the system produces two foci, one at a distance 1.0 mm away from the center axis of the therapy transducer and another −1.0 mm away from the center axis of the therapy transducer each at a depth of 15 mm. The ultrasound receiver would be able to create two receive lines, one constantly focused on the 1.0 mm peak and one constantly focused on the −1.0 mm peak. In one embodiment, a receiver can create two receive lines, one constantly focused on the 1.0 mm peak and one constantly focused on the −1.0 mm peak simultaneously.

In one embodiment, a method 2100 comprises the steps of:

transmitting multiple foci with a therapy aperture gathering a signal from each portion of a receive aperture array creating multiple receive vectors based on the multiple foci, and utilizing the receive vectors to speed up an algorithm for imaging.

In some embodiments, the transmission of multiple foci can be simultaneous or sequential. In some embodiments, the receive vectors can be simultaneously or sequentially utilized.

Some embodiments and the examples described herein are examples and not intended to be limiting in describing the full scope of compositions and methods of these invention. Equivalent changes, modifications and variations of some embodiments, materials, compositions and methods can be made within the scope of the present invention, with substantially similar results.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "coupling a transducer module with an ultrasonic probe" include "instructing the coupling of a transducer module with an ultrasonic probe." The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 25 mm" includes "25 mm."

What is claimed is:

1. An aesthetic ultrasound treatment system for simultaneously creating multiple focus points from a single ultrasound transducer, comprising:

an ultrasonic probe comprising a single ultrasound transducer comprising a single piezoelectric material, the single piezoelectric material comprising a plurality of portions configured to apply ultrasonic therapy to create multiple thermal coagulation points in a tissue simultaneously at a plurality of locations at a focal depth with at least one of the group consisting of amplitude modulation, poling, and phase shifting, wherein the poling comprises different poling moments provided from the plurality of portions of the single piezoelectric material, wherein the phase shifting of the plurality of portions of the single piezoelectric material is excited by corresponding signals applied to the plurality of portions of the single piezoelectric material with different phases, wherein the plurality of portions of the single piezoelectric material are configured to create a plurality of corresponding piezoelectric material variations respectively in response to an electric field applied to the single ultrasound transducer.

2. The aesthetic ultrasound treatment system of claim 1, wherein the plurality of locations are positioned in a linear sequence within a cosmetic treatment zone.

3. The aesthetic ultrasound treatment system of claim 1, wherein a first set of locations is positioned within a first cosmetic treatment zone and a second set of locations is positioned within a second cosmetic treatment zone, the first zone being different from the second zone.

4. The aesthetic ultrasound treatment system of claim 1, wherein the ultrasound transducer is configured to apply ultrasonic therapy using amplitude modulation whereby a plurality of portions of the ultrasound transducer are configured to emit ultrasonic therapy at a plurality of amplitudes of acoustic intensity, wherein a first amplitude is different than a second amplitude.

5. The aesthetic ultrasound treatment system of claim 4, wherein at least one portion of the ultrasonic transducer is configured to emit ultrasonic therapy at two or more amplitudes of acoustic intensity, and wherein the amplitude of ultrasonic therapy emitted by the at least one portion of the single piezoelectric material varies over time.

6. The aesthetic ultrasound treatment system of claim 1, wherein the plurality of piezoelectric material variations comprise at least one of expansion of the piezoelectric material and contraction of the piezoelectric material.

7. The aesthetic ultrasound treatment system of claim 1, wherein the ultrasound transducer is configured to apply ultrasonic therapy phase shifting whereby a plurality of portions of the ultrasound transducer are configured to emit ultrasonic therapy at a plurality of phases of acoustic intensity, wherein a first phase is different than a second phase.

8. The aesthetic ultrasound treatment system of claim 7, wherein the plurality of phases comprises discrete phase values.

9. The aesthetic ultrasound treatment system of claim 1, wherein the ultrasound transducer is configured to:
apply ultrasonic therapy using amplitude modulation whereby a plurality of portions of the ultrasound transducer are configured to emit ultrasonic therapy at a plurality of amplitudes of acoustic intensity, wherein a first amplitude is different than a second amplitude; and
apply ultrasonic therapy phase shifting whereby a plurality of portions of the ultrasound transducer are configured to emit ultrasonic therapy at a plurality of phases of acoustic intensity, wherein a first phase is different than a second phase.

10. The aesthetic ultrasound treatment system of claim 1, wherein the ultrasonic treatment is at least one of a face lift, a brow lift, a chin lift, an eye treatment, a wrinkle reduction, a scar reduction, a burn treatment, a tattoo removal, a skin tightening, a vein removal, a vein reduction, a treatment on a sweat gland, a treatment of hyperhidrosis, a sun spot removal, a fat treatment, a vaginal rejuvenation, and an acne treatment.

11. An aesthetic multi-focus treatment system comprising:
a module comprising a single ultrasound transducer comprising a single piezoelectric material, wherein the single piezoelectric material comprises a plurality of portions
configured to simultaneously apply ultrasonic therapy to tissue at a plurality of locations at a focal depth with at least one of the group consisting of amplitude modulation, poling, and phase shifting,
wherein the poling comprises different poling moments provided from the plurality of portions of the single piezoelectric material,
wherein the phase shifting of the plurality of portions of the single piezoelectric material is excited by corresponding signals applied to the plurality of portions of the single piezoelectric material with different phases,
wherein the module further comprises an interface guide designed for removable coupling to a hand wand to provide electronic communication and power between the module and the hand wand.

12. The aesthetic multi-focus treatment system of claim 11, wherein the ultrasound transducer is configured to apply ultrasonic therapy using amplitude modulation whereby the plurality of portions of the ultrasound transducer are configured to emit ultrasonic therapy at a plurality of amplitudes of acoustic intensity, wherein a first amplitude is different than a second amplitude.

13. The aesthetic multi-focus treatment system of claim 11, wherein the ultrasound transducer is configured to apply ultrasonic therapy phase shifting whereby the plurality of portions of the ultrasound transducer are configured to emit ultrasonic therapy at a plurality of phases of acoustic intensity, wherein a first phase is different than a second phase.

14. The aesthetic multi-focus treatment system of claim 11, wherein at least one portion of the ultrasonic transducer is configured to emit ultrasonic therapy at two or more amplitudes of acoustic intensity, and wherein the amplitude of ultrasonic therapy emitted by the at least one portion of the single piezoelectric varies over time.

15. The aesthetic multi-focus system of claim 11, wherein the ultrasonic treatment is at least one of a face lift, a brow lift, a chin lift, an eye treatment, a wrinkle reduction, a scar reduction, a burn treatment, a tattoo removal, a skin tightening, a vein removal, a vein reduction, a treatment on a sweat gland, a treatment of hyperhidrosis, a sun spot removal, a fat treatment, a vaginal rejuvenation, and an acne treatment.

* * * * *